US008173398B2

(12) United States Patent
Frey et al.

(10) Patent No.: US 8,173,398 B2
(45) Date of Patent: May 8, 2012

(54) HUMANIZED ANTI-IL-6 ANTIBODIES

(75) Inventors: Gerhard Frey, San Diego, CA (US); Hwai Wen Chang, San Marcos, CA (US); Jay Short, Del Mar, CA (US)

(73) Assignee: Femta Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 13/243,915

(22) Filed: Sep. 23, 2011

(65) Prior Publication Data

US 2012/0006716 A1 Jan. 12, 2012

Related U.S. Application Data

(62) Division of application No. 12/617,915, filed on Nov. 13, 2009, now Pat. No. 8,062,866.

(60) Provisional application No. 61/114,295, filed on Nov. 13, 2008.

(51) Int. Cl.
C12P 21/04 (2006.01)
C12P 21/06 (2006.01)
C12N 5/00 (2006.01)
C07K 16/00 (2006.01)
A61K 35/14 (2006.01)

(52) U.S. Cl. . 435/70.1; 435/69.1; 435/325; 530/388.15; 530/388.1; 530/386

(58) Field of Classification Search ........................ None
See application file for complete search history.

(56) References Cited

U.S. PATENT DOCUMENTS

| | | | |
|---|---|---|---|
| 5,530,101 | A | 6/1996 | Queen et al. |
| 5,618,700 | A | 4/1997 | Novick |
| 5,856,135 | A | 1/1999 | Tsuchiya |
| 7,291,721 | B2 | 11/2007 | Giles-Komar et al. |
| 7,560,112 | B2 | 7/2009 | Chen et al. |
| 7,582,298 | B2 | 9/2009 | Stevens et al. |
| 2003/0229208 | A1 | 12/2003 | Queen et al. |
| 2004/0081651 | A1 | 4/2004 | Karpusas et al. |
| 2006/0257407 | A1 | 11/2006 | Chen et al. |
| 2009/0297513 | A1 | 12/2009 | Garcia-Martinez et al. |
| 2009/0317402 | A1 | 12/2009 | Rajpal et al. |

OTHER PUBLICATIONS

Anderson et al. (2000) Hematology 147-165 "Multiple Myeloma: New Insights and Therapeutic Approaches".
Benoy et al. (2002) Clin Breast Cancer 2(4):311-5 "Serum interleukin 6, plasma VEGF, serum VEGF, and VEGF platelet load in breast cancer patients".
Blay et al. (1992) Cancer Research 52:3317-3322 "Serum Level of Interleukin 6 as a Prognosis Factor in Metastatic Renal Cell Carcinoma".
Bock et al. (1993) Cytokine 5(5):480-489 "Characterization of a new IL-6 dependent human B-lymphoma cell line in a long term culture".
Brakenhoff et al. (1990) J. Immunol. 145:561-568 "Structure-function analysis of human IL-6. Epitope Mapping of Neutralizing Monoclonal Antibodies with Amino-and Carboxyl-Terminal Deletion Mutants".
Cahlin et al. (2000) Cancer Research 60:5488-5493 "Experimental Cancer Cachexia: The Role of Host-derived Cytokines Interleukin (IL)-6, IL-12, Interferon-γ, and Tumor Necrosis Factor a Evaluated in Gene Knockout, Tumor-bearing Mice on C57 B1 Background and Eicosanoid-dependent Cachexia".
Campbell et al. (1991) J. Clin. Invest. 87:739-742 "Essential Role for Interferon-gamma. And Interleukin-6 in Autoimmune Insulin-Dependent Diabetes in NOD/Wehi Mice".
Capuron et al. (2001) Psychoneuroendocrinology 26(8):797-808 "Association between immune activation and early depressive symptoms in cancer patients treated with interleukin-2-based therapy".
Conze et al. (2001) Cancer Res 61:8851-8858 "Autocrine Production of Interleukin 6 Causes Multidrug Resistance in Breast Cancer Cells".
Fumagalli et al. (1999) British J. Cancer 80(3-4):407-11 "Pretreatment serum markers and lymphocyte response to interleukin-2 therapy".
Goswami et al. (1998) J. Neurochem 71:1837-1845 "Interleukin-6-mediated autocrine growth promotion in human glioblastoma multiforme cell line U87MG".
Jee et al. (2001) Oncogene 20(2):198-208 "Overexpression of interleukin-6 in human basal cell carcinoma cell lines increases anti-apoptotic activity and tumorigenic potency".
Heinrich et al. (1998) Biochem. J. 334:297-314 "Interleukin-6-type cytokine signaling through the gp130/Jak/STAT pathway".
Heinrich et al. (2003) Biochem. J. 374:1-20 "Principles of interleukin (IL)-6-type cytokine signaling and its regulation".
International Search Report mailed Jun. 1, 2010 re: PCT/US2009/064321.
Klein et al. (1991) Blood 78(5):1198-1204 "Murine Interleukin-6 Monoclonal Antibody Therapy for a Patient with Plasma Cell Leukemia".
Kurebayashi (2000) Breast Cancer 7(2):124-9 "Regulation of interleukin-6 secretion from breast cancer cells and its clinical implications".
Liang et al. (2009) J. of Inflammation 6(10):1-12 "Evaluation of anti-IL-6 monoclonal antibody therapy using murine type II collagen-induced arthritis".
Mauray et al. (2000) Eur J Immunol. 30(7):2065-73 "Epstein-Barr virus-dependent lymphoproliferative disease: critical role of IL-6".
Musselman et al. (2001) Am. J. Psychiatry 158(8):1252-1257 "Higher Than Normal Plasma Interleukin-6 Concentrations in Cancer Patients With Depression: Preliminary Findings".
Okamoto et al. (1997) Cancer Research 57:141-146 "Interleukin-6 as a Paracrine and Autocrine Growth Factor in Human Prostatic Carcinoma Cells in Vitro".
Sandhu et al. (1999) Bone 24(3):217-27 "Effect of interleukin-6 secreted by engineered human stromal cells on osteo clasts in human bone".
Schwantner et al. (2004) J. of Biological Chemistry 279(1):571-576 "Direct Determination of the Interleukin-6 Binding Epitope of the Interleukin-6 Receptor by NMR Spectroscopy".

(Continued)

Primary Examiner — Shulamith H Shafer
(74) Attorney, Agent, or Firm — Akerman Senterfitt LLP

(57) ABSTRACT

The present invention relates to novel chimeric, humanized or CDR-grafted anti-IL-6 antibodies, including isolated nucleic acids that encode at least one such anti-IL-6 antibody, vectors, host cells, transgenic animals or plants, and methods of making and using thereof, including therapeutic compositions, methods and devices.

24 Claims, 44 Drawing Sheets

OTHER PUBLICATIONS

Smith and Keller (2001) Prostate 48(1):47-53 "Anti-interleukin-6 monoclonal antibody induces regression of human prostate cancer xenografts in nude mice".

Smith et al. (2001) Cytokine and Growth Factor Reviews 12:33-40 "Interleukin-6 and prostate cancer progression".

Starnes et al. (1990) J. Immunol. 145(12):4185-4191 "Anti-IL-6 Monoclonal Antibodies Protect Against Lethal *Escherichia coli* Infection and Lethal Tumor Necrosis Factor-alpha. Challenge in Mice".

Strassman et al. (1992) J. Clin. Invest. 89:1681-1684 "Evidence for the Involvement of interleukin 6 in Experimental Cancer Cachexia".

Van Snick (1990) Ann. Rev. Immunol. 8:253-278 "Interleukin-6. An Overview".

Weissglas et al. (1997) Endocrinology 138(5):1879-8 "The role of interleukin-6 in the induction of hypercalcemia in renal cell carcinoma transplanted into nude mice".

Weissglas et al. (1995) The Journal of Urology 153:554-557 "Hypercalcemia and Cosecretion of Interleukin-6 and Parathyroid Hormone Related Peptide by a Human Renal Cell Carcinoma Implanted into Nude Mice".

BA399LC

```
       A  I  Q  L  T  Q  S  P  S  S  L  S  A  S  V  G  D  R  V  T
  1    GCCATCCAGTTGACCCAGTCTCCATCCTCCCTGTCTGCATCTGTAGGAGACAGAGTCACC

I  T  C  S  A  S  S  S  V  S  Y  M  Y  W  Y  Q  Q  K  P  G
 61    ATCACTTGCAGTGCCAGCTCAAGTGTAAGTTACATGTACTGGTACCAGCAGAAACCTGGC

Q  A  P  R  L  L  I  Y  D  T  S  N  L  A  S  G  I  P  P  R
121    CAGGCTCCCAGGCTCCTCATCTATGACACATCCAACCTGGCTTCTGGGATCCCACCTCGA

F  S  G  S  G  Y  G  T  D  F  T  L  T  I  N  N  I  E  S  E
181    TTCAGTGGCAGCGGGTATGGAACAGATTTTACCCTCACAATTAATAACATAGAATCTGAG

D  A  A  Y  Y  F  C  Q  Q  W  S  G  Y  P  Y  T  F  G  Q  G    SEQ ID NO: 1
241    GATGCTGCATATTACTTCTGTCAGCAGTGGAGTGGTTACCCATACACGTTCGGCCAAGGG    SEQ ID NO: 2
```

BA399HC

```
       Q  V  Q  L  V  Q  S  G  A  E  V  K  K  P  G  A  S  V  K  V
  1    CAGGTTCAGCTGGTGCAGTCTGGAGCTGAGGTGAAGAAGCCTGGGGCCTCAGTGAAGGTC

S  C  K  A  S  G  F  T  F  S  S  F  A  M  S  W  I  R  Q  S
 61    TCCTGCAAGGCTTCTGGATTCACCTTCAGTAGCTTTGCCATGTCTTGGATCAGGCAGTCC

P  S  R  G  L  E  W  L  G  E  I  S  S  G  G  S  Y  T  Y  Y
121    CCATCGAGAGGCCTTGAGTGGCTGGGTGAAATTAGTAGTGGTGGAGTTACACCTACTAT

P  D  T  V  T  G  R  F  T  I  S  R  D  N  A  K  N  S  L  Y
181    CCTGACACTGTGACGGGCAGATTCACCATCTCCAGAGACAACGCCAAGAACTCACTGTAT

L  Q  M  N  S  L  R  A  E  D  T  A  V  Y  Y  C  A  R  G  L
241    CTGCAAATGAACAGCCTGAGAGCCGAGGACACGGCTGTGTATTACTGTGCGAGAGGTTTA

W  G  Y  Y  A  L  D  Y  W  G  Q  G    SEQ ID NO: 3
301    TGGGGGTACTATGCTCTTGACTACTGGGGCCAGGGA    SEQ ID NO: 4
```

```
      D   I   Q   M   T   Q   S   P   S   S   L   S   A   S   V   G   D   R   V   T
  1   GACATCCAGATGACCCAGTCTCCATCCTCCCTGTCTGCATCTGTAGGAGACAGAGTCACC

I   T   C   S   A   S   S   S   V   S   Y   M   Y   W   Y   Q   Q   K   P   G
 61   ATCACTTGCAGTGCCAGCTCAAGTGTAAGTTACATGTACTGGTACCAGCAGAAACCTGGC

Q   A   P   R   L   L   I   Y   D   T   S   N   L   A   S   G   I   P   P   R
121   CAGGCTCCCAGGCTCCTCATCTATGACACATCCAACCTGGCTTCTGGGATCCCACCTCGA

F   S   G   S   G   Y   G   T   D   F   T   L   T   I   N   N   I   E   S   E
181   TTCAGTGGCAGCGGGTATGGAACAGATTTTACCCTCACAATTAATAACATAGAATCTGAG

D   A   A   Y   Y   F   C   Q   Q   W   S   G   Y   P   Y   T   F   G   Q   G     SEQ ID NO: 5
241   GATGCTGCATATTACTTCTGTCAGCAGTGGAGTGGTTACCCATACACGTTCGGCCAAGGG     SEQ ID NO: 6
```

BA436HC

```
      Q   V   Q   L   V   Q   S   G   A   E   V   K   K   P   G   A   S   V   K   V
  1   CAGGTTCAGCTGGTGCAGTCTGGAGCTGAGGTGAAGAAGCCTGGGGCCTCAGTGAAGGTC

S   C   K   A   S   G   F   T   F   S   S   F   A   M   S   W   I   R   Q   S
 61   TCCTGCAAGGCTTCTGGATTCACCTTCAGTAGCTTTGCCATGTCTTGGATCAGGCAGTCC

P   S   R   G   L   E   W   L   G   E   I   S   S   G   G   S   Y   T   Y   Y
121   CCATCGAGAGGCCTTGAGTGGCTGGGTGAAATTAGTAGTGGTGGGAGTTACACCTACTAT

P   D   T   V   T   G   R   F   T   I   S   R   D   N   A   K   N   S   L   Y
181   CCTGACACTGTGACGGGCAGATTCACCATCTCCAGAGACAACGCCAAGAACTCACTGTAT

L   Q   M   N   S   L   R   A   E   D   T   A   V   Y   Y   C   A   R   G   L
241   CTGCAAATGAACAGCCTGAGAGCCGAGGACACGGCTGTGTATTACTGTGCGAGAGGTTTA

W   G   Y   Y   A   L   D   Y   W   G   Q   G     SEQ ID NO: 7
301   TGGGGGTACTATGCTCTTGACTACTGGGGCCAGGGA     SEQ ID NO: 8
```

```
      E   I   V   L   T   Q   S   P   D   F   Q   S   V   T   P   K   E   K   V   T
  1   GAAATTGTGCTGACTCAGTCTCCAGACTTTCAGTCTGTGACTCCAAAGGAGAAAGTCACC

I   T   C   S   A   S   S   S   V   S   Y   M   Y   W   Y   L   Q   K   P   G
 61   ATCACCTGCAGTGCCAGCTCAAGTGTAAGTTACATGTACTGGTACCTGCAGAAGCCAGGG

Q   S   P   Q   L   L   I   Y   D   T   S   N   L   A   S   G   V   P   S   R
121   CAGTCTCCACAGCTCCTGATCTATGACACATCCAACCTGGCTTCTGGGGTCCCATCAAGG

F   S   G   S   G   S   G   T   D   F   T   L   T   I   S   S   L   Q   P   E
181   TTCAGCGGCAGTGGATCTGGGACAGATTTCACTCTCACCATCAGCAGCCTGCAGCCTGAA

D   F   A   T   Y   Y   C   Q   Q   W   S   G   Y   P   Y   T   F   G   Q   G      SEQ ID NO: 9
241   GATTTTGCAACTTATTACTGTCAGCAGTGGAGTGGTTACCCATACACGTTCGGCCAAGGG      SEQ ID NO: 10
```

BA802HC

```
      Q   V   Q   L   V   Q   S   G   A   E   V   K   K   P   G   A   S   V   K   V
  1   CAGGTTCAGCTGGTGCAGTCTGGAGCTGAGGTGAAGAAGCCTGGGGCCTCAGTGAAGGTC

S   C   K   A   S   G   F   T   F   S   S   F   A   M   S   W   I   R   Q   S
 61   TCCTGCAAGGCTTCTGGATTCACCTTCAGTAGCTTTGCCATGTCTTGGATCAGGCAGTCC

P   S   R   G   L   E   W   L   G   E   I   S   S   G   G   S   Y   T   Y   Y
121   CCATCGAGAGGCCTTGAGTGGCTGGGTGAAATTAGTAGTGGTGGGAGTTACACCTACTAT

P   D   T   V   T   G   R   F   T   I   S   R   D   N   A   K   N   S   L   Y
181   CCTGACACTGTGACGGGCAGATTCACCATCTCCAGAGACAACGCCAAGAACTCACTGTAT

L   Q   M   N   S   L   R   A   E   D   T   A   V   Y   Y   C   A   R   G   L
241   CTGCAAATGAACAGCCTGAGAGCCGAGGACACGGCTGTGTATTACTGTGCGAGAGGTTTA

W   G   Y   Y   A   L   D   Y   W   G   Q   G      SEQ ID NO: 11
301   TGGGGGTACTATGCTCTTGACTACTGGGGCCAGGGA      SEQ ID NO: 12
```

```
          E  I  V  L  T  Q  S  P  A  T  L  S  V  S  P  G  E  R  A  T
  1   GAAATTGTGTTGACACAGTCTCCAGCCACCCTGTCTGTGTCTCCAGGGGAAAGAGCCACC

L  S  C  S  A  S  S  S  V  S  Y  M  Y  W  Y  L  Q  K  P  G
 61   CTCTCCTGCAGTGCCAGCTCAAGTGTAAGTTACATGTACTGGTACCTGCAGAAGCCAGGG

Q  S  P  Q  L  L  I  Y  D  T  S  N  L  A  S  G  I  P  P  R
121   CAGTCTCCACAGCTCCTGATCTATGACACATCCAACCTGGCTTCTGGGATCCCACCTCGA

F  S  G  S  G  Y  G  T  D  F  T  L  T  I  N  N  I  E  S  E
181   TTCAGTGGCAGCGGGTATGGAACAGATTTTACCCTCACAATTAATAACATAGAATCTGAG

D  A  A  Y  Y  F  C  Q  Q  W  S  G  Y  P  Y  T  F  G  Q  G   SEQ ID NO: 13
241   GATGCTGCATATTACTTCTGTCAGCAGTGGAGTGGTTACCCATACACGTTCGGCCAAGGG  SEQ ID NO: 14
```

BA808HC

```
          Q  V  Q  L  V  Q  S  G  A  E  V  K  K  P  G  A  S  V  K  V
  1   CAGGTTCAGCTGGTGCAGTCTGGAGCTGAGGTGAAGAAGCCTGGGGCCTCAGTGAAGGTC

S  C  K  A  S  G  F  T  F  S  S  F  A  M  S  W  I  R  Q  S
 61   TCCTGCAAGGCTTCTGGATTCACCTTCAGTAGCTTTGCCATGTCTTGGATCAGGCAGTCC

P  S  R  G  L  E  W  L  G  E  I  S  S  G  G  S  Y  T  Y  Y
121   CCATCGAGAGGCCTTGAGTGGCTGGGTGAAATTAGTAGTGGTGGGAGTTACACCTACTAT

P  D  T  V  T  G  R  F  T  I  S  R  D  N  A  K  N  S  L  Y
181   CCTGACACTGTGACGGGCAGATTCACCATCTCCAGAGACAACGCCAAGAACTCACTGTAT

L  Q  M  N  S  L  R  A  E  D  T  A  V  Y  Y  C  A  R  G  L
241   CTGCAAATGAACAGCCTGAGAGCCGAGGACACGGCTGTGTATTACTGTGCGAGAGGTTTA

W  G  Y  Y  A  L  D  Y  W  G  Q  G      SEQ ID NO: 15
301   TGGGGGTACTATGCTCTTGACTACTGGGGCCAGGGA         SEQ ID NO: 16
```

```
        E   I   V   L   T   Q   S   P   D   F   Q   S   V   T   P   K   E   K   V   T
  1   GAAATTGTGCTGACTCAGTCTCCAGACTTTCAGTCTGTGACTCCAAAGGAGAAAGTCACC

I   T   C   S   A   S   S   S   V   S   Y   M   Y   W   Y   L   Q   K   P   G
 61   ATCACCTGCAGTGCCAGCTCAAGTGTAAGTTACATGTACTGGTACCTGCAGAAGCCAGGG

Q   S   P   Q   L   L   I   Y   D   T   S   N   L   A   S   G   I   P   P   R
121   CAGTCTCCACAGCTCCTGATCTATGACACATCCAACCTGGCTTCTGGGATCCCACCTCGA

F   S   G   S   G   Y   G   T   D   F   T   L   T   I   N   N   I   E   S   E
181   TTCAGTGGCAGCGGGTATGGAACAGATTTTACCCTCACAATTAATAACATAGAATCTGAG

D   A   A   Y   Y   F   C   Q   Q   W   S   G   Y   P   Y   T   F   G   Q   G      SEQ ID NO: 17
241   GATGCTGCATATTACTTCTGTCAGCAGTGGAGTGGTTACCCATACACGTTCGGCCAAGGG      SEQ ID NO: 18
```

BA840HC

```
        Q   V   Q   L   V   Q   S   G   A   E   V   K   K   P   G   A   S   V   K   V
  1   CAGGTTCAGCTGGTGCAGTCTGGAGCTGAGGTGAAGAAGCCTGGGGCCTCAGTGAAGGTC

S   C   K   A   S   G   F   T   F   S   S   F   A   M   S   W   I   R   Q   P
 61   TCCTGCAAGGCTTCTGGATTCACCTTCAGTAGCTTTGCCATGTCTTGGATCCGCCAGCCC

P   G   K   G   L   E   W   I   G   E   I   S   S   G   G   S   Y   T   Y   Y
121   CCAGGGAAGGGGCTGGAGTGGATTGGTGAAATTAGTAGTGGTGGGAGTTACACCTACTAT

P   D   T   V   T   G   R   F   T   I   S   R   D   N   A   K   N   S   L   Y
181   CCTGACACTGTGACGGGCAGATTCACCATCTCCAGAGACAACGCCAAGAACTCACTGTAT

L   Q   M   N   S   L   R   A   E   D   T   A   V   Y   Y   C   A   R   G   L
241   CTGCAAATGAACAGCCTGAGAGCCGAGGACACGGCCGTGTATTACTGTGCGAGAGGTTTA

W   G   Y   Y   A   L   D   Y   W   G   Q   G      SEQ ID NO: 19
301   TGGGGGTACTATGCTCTTGACTACTGGGGCCAGGGA      SEQ ID NO: 20
```

```
        A   I   Q   L   T   Q   S   P   S   S   L   S   A   S   V   G   D   R   V   T
  1     GCCATCCAGTTGACCCAGTCTCCATCCTCCCTGTCTGCATCTGTAGGAGACAGAGTCACC

I   T   C   S   A   S   S   S   V   S   Y   M   Y   W   Y   Q   Q   K   P   G
 61     ATCACTTGCAGTGCCAGCTCAAGTGTAAGTTACATGTACTGGTACCAGCAGAAACCTGGC

Q   A   P   R   L   L   I   Y   D   T   S   N   L   A   S   G   I   P   P   R
121     CAGGCTCCCAGGCTCCTCATCTATGACACATCCAACCTGGCTTCTGGGATCCCACCTCGA

F   S   G   S   G   Y   G   T   D   F   T   L   T   I   N   N   I   E   S   E
181     TTCAGTGGCAGCGGGTATGGAACAGATTTTACCCTCACAATTAATAACATAGAATCTGAG

D   A   A   Y   Y   F   C   Q   Q   W   S   G   Y   P   Y   T   F   G   Q   G   SEQ ID NO: 21
241     GATGCTGCATATTACTTCTGTCAGCAGTGGAGTGGTTACCCATACACGTTCGGCCAAGGG  SEQ ID NO: 22
```

BA848HC

```
        E   V   Q   L   V   Q   S   G   A   E   V   K   K   P   G   A   S   V   K   V
  1     GAGGTTCAGCTGGTGCAGTCTGGAGCTGAGGTGAAGAAGCCTGGGGCCTCAGTGAAGGTC

S   C   K   A   S   G   F   T   F   S   S   F   A   M   S   W   V   R   Q   A
 61     TCCTGCAAGGCTTCTGGATTCACCTTCAGTAGCTTTGCCATGTCTTGGGTGCGACAGGCC

P   G   Q   G   L   E   W   M   G   E   I   S   S   G   G   S   Y   T   Y   Y
121     CCTGGACAAGGGCTTGAGTGGATGGGTGAAATTAGTAGTGGTGGGAGTTACACCTACTAT

P   D   T   V   T   G   R   F   T   I   S   R   D   N   A   K   N   S   L   Y
181     CCTGACACTGTGACGGGCAGATTCACCATCTCCAGAGACAACGCCAAGAACTCACTGTAT

L   Q   M   N   S   L   R   A   E   D   T   A   V   Y   Y   C   A   R   G   L
241     CTGCAAATGAACAGCCTGAGAGCCGAGGACACGGCTGTGTATTACTGTGCGAGAGGTTTA

W   G   Y   Y   A   L   D   Y   W   G   Q   G    SEQ ID NO: 23
301     TGGGGGTACTATGCTCTTGACTACTGGGGCCAGGGA    SEQ ID NO: 24
```

```
       A  I  Q  L  T  Q  S  P  S  S  L  S  A  S  V  G  D  R  V  T
  1  GCCATCCAGTTGACCCAGTCTCCATCCTCCCTGTCTGCATCTGTAGGAGACAGAGTCACC

I  T  C  S  A  S  S  S  V  S  Y  M  Y  W  Y  Q  Q  K  P  G
 61  ATCACTTGCAGTGCCAGCTCAAGTGTAAGTTACATGTACTGGTACCAGCAGAAACCTGGC

Q  A  P  R  L  L  I  Y  D  T  S  N  L  A  S  G  I  P  P  R
121  CAGGCTCCCAGGCTCCTCATCTATGACACATCCAACCTGGCTTCTGGGATCCCACCTCGA

F  S  G  S  G  Y  G  T  D  F  T  L  T  I  N  N  I  E  S  E
181  TTCAGTGGCAGCGGGTATGGAACAGATTTTACCCTCACAATTAATAACATAGAATCTGAG

D  A  A  Y  Y  F  C  Q  Q  W  S  G  Y  P  Y  T  F  G  Q  G     SEQ ID NO: 25
241  GATGCTGCATATTACTTCTGTCAGCAGTGGAGTGGTTACCCATACACGTTCGGCCAAGGG     SEQ ID NO: 26
```

BA890HC

```
       Q  V  Q  L  V  Q  S  G  A  E  V  K  K  P  G  A  S  V  K  V
  1  CAGGTTCAGCTGGTGCAGTCTGGAGCTGAGGTGAAGAAGCCTGGGGCCTCAGTGAAGGTC

S  C  K  A  S  G  F  T  F  S  S  F  A  M  S  W  I  R  Q  P
 61  TCCTGCAAGGCTTCTGGATTCACCTTCAGTAGCTTTGCCATGTCTTGGATCCGCCAGCCC

P  G  K  G  L  E  W  I  G  E  I  S  S  G  G  S  Y  T  Y  Y
121  CCAGGGAAGGGGCTGGAGTGGATTGGTGAAATTAGTAGTGGTGGGAGTTACACCTACTAT

P  D  T  V  T  G  R  F  T  I  S  R  D  N  A  K  N  S  L  Y
181  CCTGACACTGTGACGGGCAGATTCACCATCTCCAGAGACAACGCCAAGAACTCACTGTAT

L  Q  M  N  S  L  R  A  E  D  T  A  V  Y  Y  C  A  R  G  L
241  CTGCAAATGAACAGCCTGAGAGCCGAGGACACGGCCGTGTATTACTGTGCGAGAGGTTTA

W  G  Y  Y  A  L  D  Y  W  G  Q  G       SEQ ID NO: 27
301  TGGGGGTACTATGCTCTTGACTACTGGGGCCAGGGA        SEQ ID NO: 28
```

```
      D   I   Q   M   T   Q   S   P   S   S   L   S   A   S   V   G   D   R   V   T
  1   GACATCCAGATGACCCAGTCTCCATCCTCCCTGTCTGCATCTGTAGGAGACAGAGTCACC

I   T   C   S   A   S   S   S   V   S   Y   M   Y   W   Y   Q   Q   K   P   G
 61   ATCACTTGCAGTGCCAGCTCAAGTGTAAGTTACATGTACTGGTACCAGCAGAAACCTGGC

Q   A   P   R   L   L   I   Y   D   T   S   N   L   A   S   G   I   P   P   R
121   CAGGCTCCCAGGCTCCTCATCTATGACACATCCAACCTGGCTTCTGGGATCCCACCTCGA

F   S   G   S   G   Y   G   T   D   F   T   L   T   I   N   N   I   E   S   E
181   TTCAGTGGCAGCGGGTATGGAACAGATTTTACCCTCACAATTAATAACATAGAATCTGAG

D   A   A   Y   Y   F   C   Q   Q   W   S   G   Y   P   Y   T   F   G   Q   G      SEQ ID NO: 29
241   GATGCTGCATATTACTTCTGTCAGCAGTGGAGTGGTTACCCATACACGTTCGGCCAAGGG      SEQ ID NO: 30
```

BA939HC

```
      Q   V   Q   L   V   Q   S   G   A   E   V   K   K   P   G   A   S   V   K   V
  1   CAGGTTCAGCTGGTGCAGTCTGGAGCTGAGGTGAAGAAGCCTGGGGCCTCAGTGAAGGTC

S   C   K   A   S   G   F   T   F   S   S   F   A   M   S   W   V   R   Q   A
 61   TCCTGCAAGGCTTCTGGATTCACCTTCAGTAGCTTTGCCATGTCTTGGGTGCGACAGGCC

P   G   Q   G   L   E   W   M   G   E   I   S   S   G   G   S   Y   T   Y   Y
121   CCTGGACAAGGGCTTGAGTGGATGGGTGAAATTAGTAGTGGTGGGAGTTACACCTACTAT

P   D   T   V   T   G   R   F   T   I   S   R   D   N   A   K   N   S   L   Y
181   CCTGACACTGTGACGGGCAGATTCACCATCTCCAGAGACAACGCCAAGAACTCACTGTAT

L   Q   M   N   S   L   R   A   E   D   T   A   V   Y   Y   C   A   R   G   L
241   CTGCAAATGAACAGCCTGAGAGCCGAGGACACGGCTGTGTATTACTGTGCGAGAGGTTTA

W   G   Y   Y   A   L   D   Y   W   G   Q   G      SEQ ID NO: 31
301   TGGGGGTACTATGCTCTTGACTACTGGGGCCAGGGA         SEQ ID NO: 32
```

```
        Q   I   V   L   I   Q   S   P   A   I   M   S   A   S   P   G   E   K   V   T
  1     CAAATTGTTCTCATACAGTCTCCAGCAATCATGTCTGCATCTCCAGGGGAGAAGGTCACC

M   T   C   S   A   S   S   S   V   S   Y   M   Y   W   Y   Q   Q   K   P   G
 61     ATGACCTGCAGTGCCAGCTCAAGTGTAAGTTACATGTACTGGTACCAGCAGAAGCCAGGA

S   S   P   R   L   L   I   Y   D   T   S   N   L   A   S   G   V   P   V   R
121     TCCTCCCCCAGACTCCTGATTTATGACACATCCAACCTGGCTTCTGGAGTCCCTGTTCGC

F   S   G   S   G   S   G   T   S   Y   S   L   T   I   S   R   M   E   A   E
181     TTCAGTGGCAGTGGGTCTGGGACCTCTTACTCTCTCACAATCAGCCGAATGGAGGCTGAG

D   A   A   T   Y   Y   C   Q   Q   W   S   G   Y   P   Y   T   F   G   Q   G       SEQ ID NO: 33
241     GATGCTGCCACTTATTACTGCCAGCAGTGGAGTGGTTACCCATACACGTTCGGCCAAGGG      SEQ ID NO: 34
```

BA001HC

```
        Q   V   Q   L   V   Q   S   G   A   E   V   K   K   P   G   A   S   V   K   V
  1     CAGGTTCAGCTGGTGCAGTCTGGAGCTGAGGTGAAGAAGCCTGGGGCCTCAGTGAAGGTC

S   C   K   A   S   G   F   T   F   S   S   F   A   M   S   W   I   R   Q   S
 61     TCCTGCAAGGCTTCTGGATTCACCTTCAGTAGCTTTGCCATGTCTTGGATCAGGCAGTCC

P   S   R   G   L   E   W   L   G   E   I   S   S   G   G   S   Y   T   Y   Y
121     CCATCGAGAGGCCTTGAGTGGCTGGGTGAAATTAGTAGTGGTGGGAGTTACACCTACTAT

P   D   T   V   T   G   R   F   T   I   S   R   D   N   A   K   N   S   L   Y
181     CCTGACACTGTGACGGGCAGATTCACCATCTCCAGAGACAACGCCAAGAACTCACTGTAT

L   Q   M   N   S   L   R   A   E   D   T   A   V   Y   Y   C   A   R   G   L
241     CTGCAAATGAACAGCCTGAGAGCCGAGGACACGGCTGTGTATTACTGTGCGAGAGGTTTA

W   G   Y   Y   A   L   D   Y   W   G   Q   G       SEQ ID NO: 35
301     TGGGGGTACTATGCTCTTGACTACTGGGGCCAGGGA      SEQ ID NO: 36
```

FIGURE 9

Binding Affinity of Humanized anti IL6 Hits (before affinity maturation)*

| Clone | $K_a$ (1/Ms) | $K_d$ (1/s) | $K_D$ (M) |
|---|---|---|---|
| CNTO328[1] | 1.1 X$10^6$ | 6.2 X $10^{-5}$ | 57 X $10^{-12}$ |
| BA001[2] | 1.31 X$10^6$ | 3.05 X $10^{-5}$ | 23 X $10^{-12}$ |
| BA399 | 9.73X$10^5$ | 5.21 X $10^{-6}$ | 5.4 X $10^{-12}$ |
| BA436 | 1.20 X$10^6$ | 4.33 X $10^{-5}$ | 36 X $10^{-12}$ |
| BA802 | 1.48 X$10^6$ | 5.88 X $10^{-5}$ | 39.6 X $10^{-12}$ |
| BA808 | 1.31 X$10^6$ | 6.59 X $10^{-5}$ | 50.5 X $10^{-12}$ |
| BA840 | 1.01 X$10^6$ | 2.37 X $10^{-4}$ | 236 X $10^{-12}$ |
| BA848 | 1.25 X$10^6$ | 1.58 X $10^{-4}$ | 127 X $10^{-12}$ |
| BA890 | 7.45X$10^5$ | 6.44 X $10^{-5}$ | 86.5 X $10^{-12}$ |
| BA939 | 1.44 X$10^6$ | 5.76 X $10^{-5}$ | 40 X $10^{-12}$ |

*determined by Biacore; [1]data from US 2006/0257407A1; [2]same molecule as CNTO328

FIGURE 11

>BA399CPS_LC01_DNA
GCCATCCAGTTGACCCAGTCTCCATCCTCCCTGTCTGCATCTGTAGGAGACAGAGTCACC
ATCACTTGCAGTGCCAGCTCAAGTGTAAGTTACATGTACTGGTACCAGCAGAAACCTGGC
CAGGCTCCCAGGCTCCTCATCTATGACACATCCAACCTGGCTTCTGGGATCCCACCTCGA
TTCAGTGGCAGCGGGTATGGAACAGATTTTACCCTCACAATTAATAACATAGAATCTGAG
GATGCTGCATATTACTTCTGTCAGCAGTGGAGTGGTTACCCATACACGTTCGGCCAAGGG
SEQ ID NO: 2

>BA399CPS_LC02_DNA
GCCATCCAGTTGACCCAGTCTCCATCCTCCCTGTCTGCATCTGTAGGAGACAGAGTCACC
ATCACTTGCTATGCCAGCTCAAGTGTAAGTTACATGTACTGGTACCAGCAGAAACCTGGC
CAGGCTCCCAGGCTCCTCATCTATGACACATCCAACCTGGCTTCTGGGATCCCACCTCGA
TTCAGTGGCAGCGGGTATGGAACAGATTTTACCCTCACAATTAATAACATAGAATCTGAG
GATGCTGCATATTACTTCTGTCAGCAGTGGAGTGGTTACCCATACACGTTCGGCCAAGGG
SEQ ID NO: 37

>BA399CPS_LC03_DNA
GCCATCCAGTTGACCCAGTCTCCATCCTCCCTGTCTGCATCTGTAGGAGACAGAGTCACC
ATCACTTGCAGTGCCAGCTCAGATGTAAGTTACATGTACTGGTACCAGCAGAAACCTGGC
CAGGCTCCCAGGCTCCTCATCTATGACACATCCAACCTGGCTTCTGGGATCCCACCTCGA
TTCAGTGGCAGCGGGTATGGAACAGATTTTACCCTCACAATTAATAACATAGAATCTGAG
GATGCTGCATATTACTTCTGTCAGCAGTGGAGTGGTTACCCATACACGTTCGGCCAAGGG
SEQ ID NO: 38

>BA399CPS_LC04_DNA
GCCATCCAGTTGACCCAGTCTCCATCCTCCCTGTCTGCATCTGTAGGAGACAGAGTCACC
ATCACTTGCAGTGCCAGCTCAAGTGTAAGTTACATGTACTGGTACCAGCAGAAACCTGGC
CAGGCTCCCAGGCTCCTCATCTATTCTACATCCAACCTGGCTTCTGGGATCCCACCTCGA
TTCAGTGGCAGCGGGTATGGAACAGATTTTACCCTCACAATTAATAACATAGAATCTGAG
GATGCTGCATATTACTTCTGTCAGCAGTGGAGTGGTTACCCATACACGTTCGGCCAAGGG
SEQ ID NO: 39

>BA399CPS_LC05_DNA
GCCATCCAGTTGACCCAGTCTCCATCCTCCCTGTCTGCATCTGTAGGAGACAGAGTCACC
ATCACTTGCAGTGCCAGCTCAAGTGTAAGTTACATGTACTGGTACCAGCAGAAACCTGGC
CAGGCTCCCAGGCTCCTCATCTATGACACATTGAACCTGGCTTCTGGGATCCCACCTCGA
TTCAGTGGCAGCGGGTATGGAACAGATTTTACCCTCACAATTAATAACATAGAATCTGAG
GATGCTGCATATTACTTCTGTCAGCAGTGGAGTGGTTACCCATACACGTTCGGCCAAGGG
SEQ ID NO: 40

>BA399CPS_LC06_DNA
GCCATCCAGTTGACCCAGTCTCCATCCTCCCTGTCTGCATCTGTAGGAGACAGAGTCACC
ATCACTTGCAGTGCCAGCTCAAGTGTAAGTTACATGTACTGGTACCAGCAGAAACCTGGC
CAGGCTCCCAGGCTCCTCATCTATGACACATCCAACCTGGCTTCTGGGATCCCACCTCGA
TTCAGTGGCAGCGGGTATGGAACAGATTTTACCCTCACAATTAATAACATAGAATCTGAG
GATGCTGCATATTACTTCTGTCAGGATTGGAGTGGTTACCCATACACGTTCGGCCAAGGG
SEQ ID NO: 41

FIGURE 12

>BA399CPS_LC07_DNA
GCCATCCAGTTGACCCAGTCTCCATCCTCCCTGTCTGCATCTGTAGGAGACAGAGTCACC
ATCACTTGCTATGCCAGCTCAGATGTAAGTTACATGTACTGGTACCAGCAGAAACCTGGC
CAGGCTCCCAGGCTCCTCATCTATGACACATCCAACCTGGCTTCTGGGATCCCACCTCGA
TTCAGTGGCAGCGGGTATGGAACAGATTTTACCCTCACAATTAATAACATAGAATCTGAG
GATGCTGCATATTACTTCTGTCAGCAGTGGAGTGGTTACCCATACACGTTCGGCCAAGGG
SEQ ID NO: 42

>BA399CPS_LC08_DNA
GCCATCCAGTTGACCCAGTCTCCATCCTCCCTGTCTGCATCTGTAGGAGACAGAGTCACC
ATCACTTGCTATGCCAGCTCAAGTGTAAGTTACATGTACTGGTACCAGCAGAAACCTGGC
CAGGCTCCCAGGCTCCTCATCTATTCTACATCCAACCTGGCTTCTGGGATCCCACCTCGA
TTCAGTGGCAGCGGGTATGGAACAGATTTTACCCTCACAATTAATAACATAGAATCTGAG
GATGCTGCATATTACTTCTGTCAGCAGTGGAGTGGTTACCCATACACGTTCGGCCAAGGG
SEQ ID NO: 43

>BA399CPS_LC09_DNA
GCCATCCAGTTGACCCAGTCTCCATCCTCCCTGTCTGCATCTGTAGGAGACAGAGTCACC
ATCACTTGCTATGCCAGCTCAAGTGTAAGTTACATGTACTGGTACCAGCAGAAACCTGGC
CAGGCTCCCAGGCTCCTCATCTATGACACATTGAACCTGGCTTCTGGGATCCCACCTCGA
TTCAGTGGCAGCGGGTATGGAACAGATTTTACCCTCACAATTAATAACATAGAATCTGAG
GATGCTGCATATTACTTCTGTCAGCAGTGGAGTGGTTACCCATACACGTTCGGCCAAGGG
SEQ ID NO: 44

>BA399CPS_LC10_DNA
GCCATCCAGTTGACCCAGTCTCCATCCTCCCTGTCTGCATCTGTAGGAGACAGAGTCACC
ATCACTTGCTATGCCAGCTCAAGTGTAAGTTACATGTACTGGTACCAGCAGAAACCTGGC
CAGGCTCCCAGGCTCCTCATCTATGACACATCCAACCTGGCTTCTGGGATCCCACCTCGA
TTCAGTGGCAGCGGGTATGGAACAGATTTTACCCTCACAATTAATAACATAGAATCTGAG
GATGCTGCATATTACTTCTGTCAGGATTGGAGTGGTTACCCATACACGTTCGGCCAAGGG
SEQ ID NO: 45

>BA399CPS_LC11_DNA
GCCATCCAGTTGACCCAGTCTCCATCCTCCCTGTCTGCATCTGTAGGAGACAGAGTCACC
ATCACTTGCAGTGCCAGCTCAGATGTAAGTTACATGTACTGGTACCAGCAGAAACCTGGC
CAGGCTCCCAGGCTCCTCATCTATTCTACATCCAACCTGGCTTCTGGGATCCCACCTCGA
TTCAGTGGCAGCGGGTATGGAACAGATTTTACCCTCACAATTAATAACATAGAATCTGAG
GATGCTGCATATTACTTCTGTCAGCAGTGGAGTGGTTACCCATACACGTTCGGCCAAGGG
SEQ ID NO: 46

>BA399CPS_LC12_DNA
GCCATCCAGTTGACCCAGTCTCCATCCTCCCTGTCTGCATCTGTAGGAGACAGAGTCACC
ATCACTTGCAGTGCCAGCTCAGATGTAAGTTACATGTACTGGTACCAGCAGAAACCTGGC
CAGGCTCCCAGGCTCCTCATCTATGACACATTGAACCTGGCTTCTGGGATCCCACCTCGA
TTCAGTGGCAGCGGGTATGGAACAGATTTTACCCTCACAATTAATAACATAGAATCTGAG
GATGCTGCATATTACTTCTGTCAGCAGTGGAGTGGTTACCCATACACGTTCGGCCAAGGG
SEQ ID NO: 47

FIGURE 13

>BA399CPS_LC13_DNA
GCCATCCAGTTGACCCAGTCTCCATCCTCCCTGTCTGCATCTGTAGGAGACAGAGTCACC
ATCACTTGCAGTGCCAGCTCAGATGTAAGTTACATGTACTGGTACCAGCAGAAACCTGGC
CAGGCTCCCAGGCTCCTCATCTATGACACATCCAACCTGGCTTCTGGGATCCCACCTCGA
TTCAGTGGCAGCGGGTATGGAACAGATTTTACCCTCACAATTAATAACATAGAATCTGAG
GATGCTGCATATTACTTCTGTCAGGATTGGAGTGGTTACCCATACACGTTCGGCCAAGGG
SEQ ID NO: 48

>BA399CPS_LC14_DNA
GCCATCCAGTTGACCCAGTCTCCATCCTCCCTGTCTGCATCTGTAGGAGACAGAGTCACC
ATCACTTGCAGTGCCAGCTCAAGTGTAAGTTACATGTACTGGTACCAGCAGAAACCTGGC
CAGGCTCCCAGGCTCCTCATCTATTCTACATTGAACCTGGCTTCTGGGATCCCACCTCGA
TTCAGTGGCAGCGGGTATGGAACAGATTTTACCCTCACAATTAATAACATAGAATCTGAG
GATGCTGCATATTACTTCTGTCAGCAGTGGAGTGGTTACCCATACACGTTCGGCCAAGGG
SEQ ID NO: 49

>BA399CPS_LC15_DNA
GCCATCCAGTTGACCCAGTCTCCATCCTCCCTGTCTGCATCTGTAGGAGACAGAGTCACC
ATCACTTGCAGTGCCAGCTCAAGTGTAAGTTACATGTACTGGTACCAGCAGAAACCTGGC
CAGGCTCCCAGGCTCCTCATCTATTCTACATCCAACCTGGCTTCTGGGATCCCACCTCGA
TTCAGTGGCAGCGGGTATGGAACAGATTTTACCCTCACAATTAATAACATAGAATCTGAG
GATGCTGCATATTACTTCTGTCAGGATTGGAGTGGTTACCCATACACGTTCGGCCAAGGG
SEQ ID NO: 50

>BA399CPS_LC16_DNA
GCCATCCAGTTGACCCAGTCTCCATCCTCCCTGTCTGCATCTGTAGGAGACAGAGTCACC
ATCACTTGCAGTGCCAGCTCAAGTGTAAGTTACATGTACTGGTACCAGCAGAAACCTGGC
CAGGCTCCCAGGCTCCTCATCTATGACACATTGAACCTGGCTTCTGGGATCCCACCTCGA
TTCAGTGGCAGCGGGTATGGAACAGATTTTACCCTCACAATTAATAACATAGAATCTGAG
GATGCTGCATATTACTTCTGTCAGGATTGGAGTGGTTACCCATACACGTTCGGCCAAGGG
SEQ ID NO: 51

>BA399CPS_LC17_DNA
GCCATCCAGTTGACCCAGTCTCCATCCTCCCTGTCTGCATCTGTAGGAGACAGAGTCACC
ATCACTTGCTATGCCAGCTCAGATGTAAGTTACATGTACTGGTACCAGCAGAAACCTGGC
CAGGCTCCCAGGCTCCTCATCTATTCTACATCCAACCTGGCTTCTGGGATCCCACCTCGA
TTCAGTGGCAGCGGGTATGGAACAGATTTTACCCTCACAATTAATAACATAGAATCTGAG
GATGCTGCATATTACTTCTGTCAGCAGTGGAGTGGTTACCCATACACGTTCGGCCAAGGG
SEQ ID NO: 52

>BA399CPS_LC18_DNA
GCCATCCAGTTGACCCAGTCTCCATCCTCCCTGTCTGCATCTGTAGGAGACAGAGTCACC
ATCACTTGCTATGCCAGCTCAGATGTAAGTTACATGTACTGGTACCAGCAGAAACCTGGC
CAGGCTCCCAGGCTCCTCATCTATGACACATTGAACCTGGCTTCTGGGATCCCACCTCGA
TTCAGTGGCAGCGGGTATGGAACAGATTTTACCCTCACAATTAATAACATAGAATCTGAG
GATGCTGCATATTACTTCTGTCAGCAGTGGAGTGGTTACCCATACACGTTCGGCCAAGGG
SEQ ID NO: 53

FIGURE 14

>BA399CPS_LC19_DNA
GCCATCCAGTTGACCCAGTCTCCATCCTCCCTGTCTGCATCTGTAGGAGACAGAGTCACC
ATCACTTGCTATGCCAGCTCAGATGTAAGTTACATGTACTGGTACCAGCAGAAACCTGGC
CAGGCTCCCAGGCTCCTCATCTATGACACATCCAACCTGGCTTCTGGGATCCCACCTCGA
TTCAGTGGCAGCGGGTATGGAACAGATTTTACCCTCACAATTAATAACATAGAATCTGAG
GATGCTGCATATTACTTCTGTCAGGATTGGAGTGGTTACCCATACACGTTCGGCCAAGGG
SEQ ID NO: 54

>BA399CPS_LC20_DNA
GCCATCCAGTTGACCCAGTCTCCATCCTCCCTGTCTGCATCTGTAGGAGACAGAGTCACC
ATCACTTGCTATGCCAGCTCAAGTGTAAGTTACATGTACTGGTACCAGCAGAAACCTGGC
CAGGCTCCCAGGCTCCTCATCTATTCTACATTGAACCTGGCTTCTGGGATCCCACCTCGA
TTCAGTGGCAGCGGGTATGGAACAGATTTTACCCTCACAATTAATAACATAGAATCTGAG
GATGCTGCATATTACTTCTGTCAGCAGTGGAGTGGTTACCCATACACGTTCGGCCAAGGG
SEQ ID NO: 55

>BA399CPS_LC21_DNA
GCCATCCAGTTGACCCAGTCTCCATCCTCCCTGTCTGCATCTGTAGGAGACAGAGTCACC
ATCACTTGCTATGCCAGCTCAAGTGTAAGTTACATGTACTGGTACCAGCAGAAACCTGGC
CAGGCTCCCAGGCTCCTCATCTATTCTACATCCAACCTGGCTTCTGGGATCCCACCTCGA
TTCAGTGGCAGCGGGTATGGAACAGATTTTACCCTCACAATTAATAACATAGAATCTGAG
GATGCTGCATATTACTTCTGTCAGGATTGGAGTGGTTACCCATACACGTTCGGCCAAGGG
SEQ ID NO: 56

>BA399CPS_LC22_DNA
GCCATCCAGTTGACCCAGTCTCCATCCTCCCTGTCTGCATCTGTAGGAGACAGAGTCACC
ATCACTTGCTATGCCAGCTCAAGTGTAAGTTACATGTACTGGTACCAGCAGAAACCTGGC
CAGGCTCCCAGGCTCCTCATCTATGACACATTGAACCTGGCTTCTGGGATCCCACCTCGA
TTCAGTGGCAGCGGGTATGGAACAGATTTTACCCTCACAATTAATAACATAGAATCTGAG
GATGCTGCATATTACTTCTGTCAGGATTGGAGTGGTTACCCATACACGTTCGGCCAAGGG
SEQ ID NO: 57

>BA399CPS_LC23_DNA
GCCATCCAGTTGACCCAGTCTCCATCCTCCCTGTCTGCATCTGTAGGAGACAGAGTCACC
ATCACTTGCAGTGCCAGCTCAGATGTAAGTTACATGTACTGGTACCAGCAGAAACCTGGC
CAGGCTCCCAGGCTCCTCATCTATTCTACATTGAACCTGGCTTCTGGGATCCCACCTCGA
TTCAGTGGCAGCGGGTATGGAACAGATTTTACCCTCACAATTAATAACATAGAATCTGAG
GATGCTGCATATTACTTCTGTCAGCAGTGGAGTGGTTACCCATACACGTTCGGCCAAGGG
SEQ ID NO: 58

>BA399CPS_LC24_DNA
GCCATCCAGTTGACCCAGTCTCCATCCTCCCTGTCTGCATCTGTAGGAGACAGAGTCACC
ATCACTTGCAGTGCCAGCTCAGATGTAAGTTACATGTACTGGTACCAGCAGAAACCTGGC
CAGGCTCCCAGGCTCCTCATCTATTCTACATCCAACCTGGCTTCTGGGATCCCACCTCGA
TTCAGTGGCAGCGGGTATGGAACAGATTTTACCCTCACAATTAATAACATAGAATCTGAG
GATGCTGCATATTACTTCTGTCAGGATTGGAGTGGTTACCCATACACGTTCGGCCAAGGG
SEQ ID NO: 59

FIGURE 15

>BA399CPS_LC25_DNA
GCCATCCAGTTGACCCAGTCTCCATCCTCCCTGTCTGCATCTGTAGGAGACAGAGTCACC
ATCACTTGCAGTGCCAGCTCAGATGTAAGTTACATGTACTGGTACCAGCAGAAACCTGGC
CAGGCTCCCAGGCTCCTCATCTATGACACATTGAACCTGGCTTCTGGGATCCCACCTCGA
TTCAGTGGCAGCGGGTATGGAACAGATTTTACCCTCACAATTAATAACATAGAATCTGAG
GATGCTGCATATTACTTCTGTCAGGATTGGAGTGGTTACCCATACACGTTCGGCCAAGGG
SEQ ID NO: 60

>BA399CPS_LC26_DNA
GCCATCCAGTTGACCCAGTCTCCATCCTCCCTGTCTGCATCTGTAGGAGACAGAGTCACC
ATCACTTGCAGTGCCAGCTCAAGTGTAAGTTACATGTACTGGTACCAGCAGAAACCTGGC
CAGGCTCCCAGGCTCCTCATCTATTCTACATTGAACCTGGCTTCTGGGATCCCACCTCGA
TTCAGTGGCAGCGGGTATGGAACAGATTTTACCCTCACAATTAATAACATAGAATCTGAG
GATGCTGCATATTACTTCTGTCAGGATTGGAGTGGTTACCCATACACGTTCGGCCAAGGG
SEQ ID NO: 61

>BA399CPS_LC27_DNA
GCCATCCAGTTGACCCAGTCTCCATCCTCCCTGTCTGCATCTGTAGGAGACAGAGTCACC
ATCACTTGCTATGCCAGCTCAGATGTAAGTTACATGTACTGGTACCAGCAGAAACCTGGC
CAGGCTCCCAGGCTCCTCATCTATTCTACATTGAACCTGGCTTCTGGGATCCCACCTCGA
TTCAGTGGCAGCGGGTATGGAACAGATTTTACCCTCACAATTAATAACATAGAATCTGAG
GATGCTGCATATTACTTCTGTCAGCAGTGGAGTGGTTACCCATACACGTTCGGCCAAGGG
SEQ ID NO: 62

>BA399CPS_LC28_DNA
GCCATCCAGTTGACCCAGTCTCCATCCTCCCTGTCTGCATCTGTAGGAGACAGAGTCACC
ATCACTTGCTATGCCAGCTCAGATGTAAGTTACATGTACTGGTACCAGCAGAAACCTGGC
CAGGCTCCCAGGCTCCTCATCTATTCTACATCCAACCTGGCTTCTGGGATCCCACCTCGA
TTCAGTGGCAGCGGGTATGGAACAGATTTTACCCTCACAATTAATAACATAGAATCTGAG
GATGCTGCATATTACTTCTGTCAGGATTGGAGTGGTTACCCATACACGTTCGGCCAAGGG
SEQ ID NO: 63

>BA399CPS_LC29_DNA
GCCATCCAGTTGACCCAGTCTCCATCCTCCCTGTCTGCATCTGTAGGAGACAGAGTCACC
ATCACTTGCTATGCCAGCTCAGATGTAAGTTACATGTACTGGTACCAGCAGAAACCTGGC
CAGGCTCCCAGGCTCCTCATCTATGACACATTGAACCTGGCTTCTGGGATCCCACCTCGA
TTCAGTGGCAGCGGGTATGGAACAGATTTTACCCTCACAATTAATAACATAGAATCTGAG
GATGCTGCATATTACTTCTGTCAGGATTGGAGTGGTTACCCATACACGTTCGGCCAAGGG
SEQ ID NO: 64

>BA399CPS_LC30_DNA
GCCATCCAGTTGACCCAGTCTCCATCCTCCCTGTCTGCATCTGTAGGAGACAGAGTCACC
ATCACTTGCTATGCCAGCTCAAGTGTAAGTTACATGTACTGGTACCAGCAGAAACCTGGC
CAGGCTCCCAGGCTCCTCATCTATTCTACATTGAACCTGGCTTCTGGGATCCCACCTCGA
TTCAGTGGCAGCGGGTATGGAACAGATTTTACCCTCACAATTAATAACATAGAATCTGAG
GATGCTGCATATTACTTCTGTCAGGATTGGAGTGGTTACCCATACACGTTCGGCCAAGGG
SEQ ID NO: 65

FIGURE 16

>BA399CPS_LC31_DNA
GCCATCCAGTTGACCCAGTCTCCATCCTCCCTGTCTGCATCTGTAGGAGACAGAGTCACC
ATCACTTGCAGTGCCAGCTCAGATGTAAGTTACATGTACTGGTACCAGCAGAAACCTGGC
CAGGCTCCCAGGCTCCTCATCTATTCTACATTGAACCTGGCTTCTGGGATCCCACCTCGA
TTCAGTGGCAGCGGGTATGGAACAGATTTTACCCTCACAATTAATAACATAGAATCTGAG
GATGCTGCATATTACTTCTGTCAGGATTGGAGTGGTTACCCATACACGTTCGGCCAAGGG
SEQ ID NO: 66

>BA399CPS_LC32_DNA
GCCATCCAGTTGACCCAGTCTCCATCCTCCCTGTCTGCATCTGTAGGAGACAGAGTCACC
ATCACTTGCTATGCCAGCTCAGATGTAAGTTACATGTACTGGTACCAGCAGAAACCTGGC
CAGGCTCCCAGGCTCCTCATCTATTCTACATTGAACCTGGCTTCTGGGATCCCACCTCGA
TTCAGTGGCAGCGGGTATGGAACAGATTTTACCCTCACAATTAATAACATAGAATCTGAG
GATGCTGCATATTACTTCTGTCAGGATTGGAGTGGTTACCCATACACGTTCGGCCAAGGG
SEQ ID NO: 67

>BA399CPS_LC01_PRO
AIQLTQSPSSLSASVGDRVTITCSASSSVSYMYWYQQKPGQAPRLLIYDTSNLASGIPPR
FSGSGYGTDFTLTINNIESEDAAYYFCQQWSGYPYTFGQG SEQ ID NO: 1

>BA399CPS_LC02_PRO
AIQLTQSPSSLSASVGDRVTITCYASSSVSYMYWYQQKPGQAPRLLIYDTSNLASGIPPR
FSGSGYGTDFTLTINNIESEDAAYYFCQQWSGYPYTFGQG    SEQ ID NO: 68

>BA399CPS_LC03_PRO
AIQLTQSPSSLSASVGDRVTITCSASSDVSYMYWYQQKPGQAPRLLIYDTSNLASGIPPR
FSGSGYGTDFTLTINNIESEDAAYYFCQQWSGYPYTFGQG    SEQ ID NO: 69

>BA399CPS_LC04_PRO
AIQLTQSPSSLSASVGDRVTITCSASSSVSYMYWYQQKPGQAPRLLIYSTSNLASGIPPR
FSGSGYGTDFTLTINNIESEDAAYYFCQQWSGYPYTFGQG    SEQ ID NO: 70

>BA399CPS_LC05_PRO
AIQLTQSPSSLSASVGDRVTITCSASSSVSYMYWYQQKPGQAPRLLIYDTLNLASGIPPR
FSGSGYGTDFTLTINNIESEDAAYYFCQQWSGYPYTFGQG    SEQ ID NO: 71

>BA399CPS_LC06_PRO
AIQLTQSPSSLSASVGDRVTITCSASSSVSYMYWYQQKPGQAPRLLIYDTSNLASGIPPR
FSGSGYGTDFTLTINNIESEDAAYYFCQDWSGYPYTFGQG    SEQ ID NO: 72

>BA399CPS_LC07_PRO
AIQLTQSPSSLSASVGDRVTITCYASSDVSYMYWYQQKPGQAPRLLIYDTSNLASGIPPR
FSGSGYGTDFTLTINNIESEDAAYYFCQQWSGYPYTFGQG    SEQ ID NO: 73

>BA399CPS_LC08_PRO
AIQLTQSPSSLSASVGDRVTITCYASSSVSYMYWYQQKPGQAPRLLIYSTSNLASGIPPR
FSGSGYGTDFTLTINNIESEDAAYYFCQQWSGYPYTFGQG    SEQ ID NO: 74

FIGURE 17

>BA399CPS_LC09_PRO
AIQLTQSPSSLSASVGDRVTITCYASSSVSYMYWYQQKPGQAPRLLIYDTLNLASGIPPR
FSGSGYGTDFTLTINNIESEDAAYYFCQQWSGYPYTFGQG   SEQ ID NO: 75

>BA399CPS_LC10_PRO
AIQLTQSPSSLSASVGDRVTITCYASSSVSYMYWYQQKPGQAPRLLIYDTSNLASGIPPR
FSGSGYGTDFTLTINNIESEDAAYYFCQDWSGYPYTFGQG   SEQ ID NO: 76

>BA399CPS_LC11_PRO
AIQLTQSPSSLSASVGDRVTITCSASSDVSYMYWYQQKPGQAPRLLIYSTSNLASGIPPR
FSGSGYGTDFTLTINNIESEDAAYYFCQQWSGYPYTFGQG   SEQ ID NO: 77

>BA399CPS_LC12_PRO
AIQLTQSPSSLSASVGDRVTITCSASSDVSYMYWYQQKPGQAPRLLIYDTLNLASGIPPR
FSGSGYGTDFTLTINNIESEDAAYYFCQQWSGYPYTFGQG   SEQ ID NO: 78

>BA399CPS_LC13_PRO
AIQLTQSPSSLSASVGDRVTITCSASSDVSYMYWYQQKPGQAPRLLIYDTSNLASGIPPR
FSGSGYGTDFTLTINNIESEDAAYYFCQDWSGYPYTFGQG   SEQ ID NO: 79

>BA399CPS_LC14_PRO
AIQLTQSPSSLSASVGDRVTITCSASSSVSYMYWYQQKPGQAPRLLIYSTLNLASGIPPR
FSGSGYGTDFTLTINNIESEDAAYYFCQQWSGYPYTFGQG   SEQ ID NO: 80

>BA399CPS_LC15_PRO
AIQLTQSPSSLSASVGDRVTITCSASSSVSYMYWYQQKPGQAPRLLIYSTSNLASGIPPR
FSGSGYGTDFTLTINNIESEDAAYYFCQDWSGYPYTFGQG   SEQ ID NO: 81

>BA399CPS_LC16_PRO
AIQLTQSPSSLSASVGDRVTITCSASSSVSYMYWYQQKPGQAPRLLIYDTLNLASGIPPR
FSGSGYGTDFTLTINNIESEDAAYYFCQDWSGYPYTFGQG   SEQ ID NO: 82

>BA399CPS_LC17_PRO
AIQLTQSPSSLSASVGDRVTITCYASSDVSYMYWYQQKPGQAPRLLIYSTSNLASGIPPR
FSGSGYGTDFTLTINNIESEDAAYYFCQQWSGYPYTFGQG   SEQ ID NO: 83

>BA399CPS_LC18_PRO
AIQLTQSPSSLSASVGDRVTITCYASSDVSYMYWYQQKPGQAPRLLIYDTLNLASGIPPR
FSGSGYGTDFTLTINNIESEDAAYYFCQQWSGYPYTFGQG   SEQ ID NO: 84

>BA399CPS_LC19_PRO
AIQLTQSPSSLSASVGDRVTITCYASSDVSYMYWYQQKPGQAPRLLIYDTSNLASGIPPR
FSGSGYGTDFTLTINNIESEDAAYYFCQDWSGYPYTFGQG   SEQ ID NO: 85

>BA399CPS_LC20_PRO
AIQLTQSPSSLSASVGDRVTITCYASSSVSYMYWYQQKPGQAPRLLIYSTLNLASGIPPR
FSGSGYGTDFTLTINNIESEDAAYYFCQQWSGYPYTFGQG   SEQ ID NO: 86

FIGURE 18

>BA399CPS_LC21_PRO
AIQLTQSPSSLSASVGDRVTITCYASSSVSYMYWYQQKPGQAPRLLIYSTSNLASGIPPR
FSGSGYGTDFTLTINNIESEDAAYYFCQDWSGYPYTFGQG   SEQ ID NO: 87

>BA399CPS_LC22_PRO
AIQLTQSPSSLSASVGDRVTITCYASSSVSYMYWYQQKPGQAPRLLIYDTLNLASGIPPR
FSGSGYGTDFTLTINNIESEDAAYYFCQDWSGYPYTFGQG   SEQ ID NO: 88

>BA399CPS_LC23_PRO
AIQLTQSPSSLSASVGDRVTITCSASSDVSYMYWYQQKPGQAPRLLIYSTLNLASGIPPR
FSGSGYGTDFTLTINNIESEDAAYYFCQQWSGYPYTFGQG   SEQ ID NO: 89

>BA399CPS_LC24_PRO
AIQLTQSPSSLSASVGDRVTITCSASSDVSYMYWYQQKPGQAPRLLIYSTSNLASGIPPR
FSGSGYGTDFTLTINNIESEDAAYYFCQDWSGYPYTFGQG   SEQ ID NO: 90

>BA399CPS_LC25_PRO
AIQLTQSPSSLSASVGDRVTITCSASSDVSYMYWYQQKPGQAPRLLIYDTLNLASGIPPR
FSGSGYGTDFTLTINNIESEDAAYYFCQDWSGYPYTFGQG   SEQ ID NO: 91

>BA399CPS_LC26_PRO
AIQLTQSPSSLSASVGDRVTITCSASSSVSYMYWYQQKPGQAPRLLIYSTLNLASGIPPR
FSGSGYGTDFTLTINNIESEDAAYYFCQDWSGYPYTFGQG   SEQ ID NO: 92

>BA399CPS_LC27_PRO
AIQLTQSPSSLSASVGDRVTITCYASSDVSYMYWYQQKPGQAPRLLIYSTLNLASGIPPR
FSGSGYGTDFTLTINNIESEDAAYYFCQQWSGYPYTFGQG   SEQ ID NO: 93

>BA399CPS_LC28_PRO
AIQLTQSPSSLSASVGDRVTITCYASSDVSYMYWYQQKPGQAPRLLIYSTSNLASGIPPR
FSGSGYGTDFTLTINNIESEDAAYYFCQDWSGYPYTFGQG   SEQ ID NO: 94

>BA399CPS_LC29_PRO
AIQLTQSPSSLSASVGDRVTITCYASSDVSYMYWYQQKPGQAPRLLIYDTLNLASGIPPR
FSGSGYGTDFTLTINNIESEDAAYYFCQDWSGYPYTFGQG   SEQ ID NO: 95

>BA399CPS_LC30_PRO
AIQLTQSPSSLSASVGDRVTITCYASSSVSYMYWYQQKPGQAPRLLIYSTLNLASGIPPR
FSGSGYGTDFTLTINNIESEDAAYYFCQDWSGYPYTFGQG   SEQ ID NO: 96

>BA399CPS_LC31_PRO
AIQLTQSPSSLSASVGDRVTITCSASSDVSYMYWYQQKPGQAPRLLIYSTLNLASGIPPR
FSGSGYGTDFTLTINNIESEDAAYYFCQDWSGYPYTFGQG   SEQ ID NO: 97

>BA399CPS_LC32_PRO
AIQLTQSPSSLSASVGDRVTITCYASSDVSYMYWYQQKPGQAPRLLIYSTLNLASGIPPR
FSGSGYGTDFTLTINNIESEDAAYYFCQDWSGYPYTFGQG   SEQ ID NO: 98

FIGURE 19

>BA399CPS_HC01_DNA
CAGGTTCAGCTGGTGCAGTCTGGAGCTGAGGTGAAGAAGCCTGGGGCCTCAGTGAAGGTC
TCCTGCAAGGCTTCTGGATTCACCTTCAGTAGCTTTGCCATGTCTTGGATCAGGCAGTCC
CCATCGAGAGGCCTTGAGTGGCTGGGTGAAATTAGTAGTGGTGGGAGTTACACCTACTAT
CCTGACACTGTGACGGGCAGATTCACCATCTCCAGAGACAACGCCAAGAACTCACTGTAT
CTGCAAATGAACAGCCTGAGAGCCGAGGACACGGCTGTGTATTACTGTGCGAGAGGTTTA
TGGGGGTACTATGCTCTTGACTACTGGGGCCAGGGA    SEQ ID NO: 4

>BA399CPS_HC02_DNA
CAGGTTCAGCTGGTGCAGTCTGGAGCTGAGGTGAAGAAGCCTGGGGCCTCAGTGAAGGTC
TCCTGCAAGGCTTCTCATTTCACCTTCAGTAGCTTTGCCATGTCTTGGATCAGGCAGTCC
CCATCGAGAGGCCTTGAGTGGCTGGGTGAAATTAGTAGTGGTGGGAGTTACACCTACTAT
CCTGACACTGTGACGGGCAGATTCACCATCTCCAGAGACAACGCCAAGAACTCACTGTAT
CTGCAAATGAACAGCCTGAGAGCCGAGGACACGGCTGTGTATTACTGTGCGAGAGGTTTA
TGGGGGTACTATGCTCTTGACTACTGGGGCCAGGGA    SEQ ID NO: 99

>BA399CPS_HC03_DNA
CAGGTTCAGCTGGTGCAGTCTGGAGCTGAGGTGAAGAAGCCTGGGGCCTCAGTGAAGGTC
TCCTGCAAGGCTTCTGGATTCACCTTCAGTAGCTTTTCGATGTCTTGGATCAGGCAGTCC
CCATCGAGAGGCCTTGAGTGGCTGGGTGAAATTAGTAGTGGTGGGAGTTACACCTACTAT
CCTGACACTGTGACGGGCAGATTCACCATCTCCAGAGACAACGCCAAGAACTCACTGTAT
CTGCAAATGAACAGCCTGAGAGCCGAGGACACGGCTGTGTATTACTGTGCGAGAGGTTTA
TGGGGGTACTATGCTCTTGACTACTGGGGCCAGGGA    SEQ ID NO: 100

>BA399CPS_HC04_DNA
CAGGTTCAGCTGGTGCAGTCTGGAGCTGAGGTGAAGAAGCCTGGGGCCTCAGTGAAGGTC
TCCTGCAAGGCTTCTGGATTCACCTTCAGTAGCTTTGCCATGTCTTGGATCAGGCAGTCC
CCATCGAGAGGCCTTGAGTGGCTGGGTGAAATTAGTAGTGGTGGGAGTTACCATTACTAT
CCTGACACTGTGACGGGCAGATTCACCATCTCCAGAGACAACGCCAAGAACTCACTGTAT
CTGCAAATGAACAGCCTGAGAGCCGAGGACACGGCTGTGTATTACTGTGCGAGAGGTTTA
TGGGGGTACTATGCTCTTGACTACTGGGGCCAGGGA    SEQ ID NO: 101

>BA399CPS_HC05_DNA
CAGGTTCAGCTGGTGCAGTCTGGAGCTGAGGTGAAGAAGCCTGGGGCCTCAGTGAAGGTC
TCCTGCAAGGCTTCTGGATTCACCTTCAGTAGCTTTGCCATGTCTTGGATCAGGCAGTCC
CCATCGAGAGGCCTTGAGTGGCTGGGTGAAATTAGTAGTGGTGGGAGTTACACCTACTAT
CCTGACACTAAGACGGGCAGATTCACCATCTCCAGAGACAACGCCAAGAACTCACTGTAT
CTGCAAATGAACAGCCTGAGAGCCGAGGACACGGCTGTGTATTACTGTGCGAGAGGTTTA
TGGGGGTACTATGCTCTTGACTACTGGGGCCAGGGA    SEQ ID NO: 102

>BA399CPS_HC06_DNA
CAGGTTCAGCTGGTGCAGTCTGGAGCTGAGGTGAAGAAGCCTGGGGCCTCAGTGAAGGTC
TCCTGCAAGGCTTCTGGATTCACCTTCAGTAGCTTTGCCATGTCTTGGATCAGGCAGTCC
CCATCGAGAGGCCTTGAGTGGCTGGGTGAAATTAGTAGTGGTGGGAGTTACACCTACTAT
CCTGACACTGTGACGGGCAGATTCACCATCTCCAGAGACAACGCCAAGAACTCACTGTAT
CTGCAAATGAACAGCCTGAGAGCCGAGGACACGGCTGTGTATTACTGTGCGAGAGGTCAG
TGGGGGTACTATGCTCTTGACTACTGGGGCCAGGGA    SEQ ID NO: 103

FIGURE 20

>BA399CPS_HC07_DNA
CAGGTTCAGCTGGTGCAGTCTGGAGCTGAGGTGAAGAAGCCTGGGGCCTCAGTGAAGGTC
TCCTGCAAGGCTTCTCATTTCACCTTCAGTAGCTTTTCGATGTCTTGGATCAGGCAGTCC
CCATCGAGAGGCCTTGAGTGGCTGGGTGAAATTAGTAGTGGTGGGAGTTACACCTACTAT
CCTGACACTGTGACGGGCAGATTCACCATCTCCAGAGACAACGCCAAGAACTCACTGTAT
CTGCAAATGAACAGCCTGAGAGCCGAGGACACGGCTGTGTATTACTGTGCGAGAGGTTTA
TGGGGGTACTATGCTCTTGACTACTGGGGCCAGGGA    SEQ ID NO: 104

>BA399CPS_HC08_DNA
CAGGTTCAGCTGGTGCAGTCTGGAGCTGAGGTGAAGAAGCCTGGGGCCTCAGTGAAGGTC
TCCTGCAAGGCTTCTCATTTCACCTTCAGTAGCTTTGCCATGTCTTGGATCAGGCAGTCC
CCATCGAGAGGCCTTGAGTGGCTGGGTGAAATTAGTAGTGGTGGGAGTTACCATTACTAT
CCTGACACTGTGACGGGCAGATTCACCATCTCCAGAGACAACGCCAAGAACTCACTGTAT
CTGCAAATGAACAGCCTGAGAGCCGAGGACACGGCTGTGTATTACTGTGCGAGAGGTTTA
TGGGGGTACTATGCTCTTGACTACTGGGGCCAGGGA    SEQ ID NO: 105

>BA399CPS_HC09_DNA
CAGGTTCAGCTGGTGCAGTCTGGAGCTGAGGTGAAGAAGCCTGGGGCCTCAGTGAAGGTC
TCCTGCAAGGCTTCTCATTTCACCTTCAGTAGCTTTGCCATGTCTTGGATCAGGCAGTCC
CCATCGAGAGGCCTTGAGTGGCTGGGTGAAATTAGTAGTGGTGGGAGTTACACCTACTAT
CCTGACACTAAGACGGGCAGATTCACCATCTCCAGAGACAACGCCAAGAACTCACTGTAT
CTGCAAATGAACAGCCTGAGAGCCGAGGACACGGCTGTGTATTACTGTGCGAGAGGTTTA
TGGGGGTACTATGCTCTTGACTACTGGGGCCAGGGA    SEQ ID NO: 106

>BA399CPS_HC10_DNA
CAGGTTCAGCTGGTGCAGTCTGGAGCTGAGGTGAAGAAGCCTGGGGCCTCAGTGAAGGTC
TCCTGCAAGGCTTCTCATTTCACCTTCAGTAGCTTTGCCATGTCTTGGATCAGGCAGTCC
CCATCGAGAGGCCTTGAGTGGCTGGGTGAAATTAGTAGTGGTGGGAGTTACACCTACTAT
CCTGACACTGTGACGGGCAGATTCACCATCTCCAGAGACAACGCCAAGAACTCACTGTAT
CTGCAAATGAACAGCCTGAGAGCCGAGGACACGGCTGTGTATTACTGTGCGAGAGGTCAG
TGGGGGTACTATGCTCTTGACTACTGGGGCCAGGGA    SEQ ID NO: 107

>BA399CPS_HC11_DNA
CAGGTTCAGCTGGTGCAGTCTGGAGCTGAGGTGAAGAAGCCTGGGGCCTCAGTGAAGGTC
TCCTGCAAGGCTTCTGGATTCACCTTCAGTAGCTTTTCGATGTCTTGGATCAGGCAGTCC
CCATCGAGAGGCCTTGAGTGGCTGGGTGAAATTAGTAGTGGTGGGAGTTACCATTACTAT
CCTGACACTGTGACGGGCAGATTCACCATCTCCAGAGACAACGCCAAGAACTCACTGTAT
CTGCAAATGAACAGCCTGAGAGCCGAGGACACGGCTGTGTATTACTGTGCGAGAGGTTTA
TGGGGGTACTATGCTCTTGACTACTGGGGCCAGGGA    SEQ ID NO: 108

>BA399CPS_HC12_DNA
CAGGTTCAGCTGGTGCAGTCTGGAGCTGAGGTGAAGAAGCCTGGGGCCTCAGTGAAGGTC
TCCTGCAAGGCTTCTGGATTCACCTTCAGTAGCTTTTCGATGTCTTGGATCAGGCAGTCC
CCATCGAGAGGCCTTGAGTGGCTGGGTGAAATTAGTAGTGGTGGGAGTTACACCTACTAT
CCTGACACTAAGACGGGCAGATTCACCATCTCCAGAGACAACGCCAAGAACTCACTGTAT
CTGCAAATGAACAGCCTGAGAGCCGAGGACACGGCTGTGTATTACTGTGCGAGAGGTTTA
TGGGGGTACTATGCTCTTGACTACTGGGGCCAGGGA    SEQ ID NO: 109

FIGURE 21

>BA399CPS_HC13_DNA
CAGGTTCAGCTGGTGCAGTCTGGAGCTGAGGTGAAGAAGCCTGGGGCCTCAGTGAAGGTC
TCCTGCAAGGCTTCTGGATTCACCTTCAGTAGCTTTTCGATGTCTTGGATCAGGCAGTCC
CCATCGAGAGGCCTTGAGTGGCTGGGTGAAATTAGTAGTGGTGGGAGTTACACCTACTAT
CCTGACACTGTGACGGGCAGATTCACCATCTCCAGAGACAACGCCAAGAACTCACTGTAT
CTGCAAATGAACAGCCTGAGAGCCGAGGACACGGCTGTGTATTACTGTGCGAGAGGTCAG
TGGGGGTACTATGCTCTTGACTACTGGGGCCAGGGA    SEQ ID NO: 110

>BA399CPS_HC14_DNA
CAGGTTCAGCTGGTGCAGTCTGGAGCTGAGGTGAAGAAGCCTGGGGCCTCAGTGAAGGTC
TCCTGCAAGGCTTCTGGATTCACCTTCAGTAGCTTTGCCATGTCTTGGATCAGGCAGTCC
CCATCGAGAGGCCTTGAGTGGCTGGGTGAAATTAGTAGTGGTGGGAGTTACCATTACTAT
CCTGACACTAAGACGGGCAGATTCACCATCTCCAGAGACAACGCCAAGAACTCACTGTAT
CTGCAAATGAACAGCCTGAGAGCCGAGGACACGGCTGTGTATTACTGTGCGAGAGGTTTA
TGGGGGTACTATGCTCTTGACTACTGGGGCCAGGGA    SEQ ID NO: 111

>BA399CPS_HC15_DNA
CAGGTTCAGCTGGTGCAGTCTGGAGCTGAGGTGAAGAAGCCTGGGGCCTCAGTGAAGGTC
TCCTGCAAGGCTTCTGGATTCACCTTCAGTAGCTTTGCCATGTCTTGGATCAGGCAGTCC
CCATCGAGAGGCCTTGAGTGGCTGGGTGAAATTAGTAGTGGTGGGAGTTACCATTACTAT
CCTGACACTGTGACGGGCAGATTCACCATCTCCAGAGACAACGCCAAGAACTCACTGTAT
CTGCAAATGAACAGCCTGAGAGCCGAGGACACGGCTGTGTATTACTGTGCGAGAGGTCAG
TGGGGGTACTATGCTCTTGACTACTGGGGCCAGGGA    SEQ ID NO: 112

>BA399CPS_HC16_DNA
CAGGTTCAGCTGGTGCAGTCTGGAGCTGAGGTGAAGAAGCCTGGGGCCTCAGTGAAGGTC
TCCTGCAAGGCTTCTGGATTCACCTTCAGTAGCTTTGCCATGTCTTGGATCAGGCAGTCC
CCATCGAGAGGCCTTGAGTGGCTGGGTGAAATTAGTAGTGGTGGGAGTTACACCTACTAT
CCTGACACTAAGACGGGCAGATTCACCATCTCCAGAGACAACGCCAAGAACTCACTGTAT
CTGCAAATGAACAGCCTGAGAGCCGAGGACACGGCTGTGTATTACTGTGCGAGAGGTCAG
TGGGGGTACTATGCTCTTGACTACTGGGGCCAGGGA    SEQ ID NO: 113

>BA399CPS_HC17_DNA
CAGGTTCAGCTGGTGCAGTCTGGAGCTGAGGTGAAGAAGCCTGGGGCCTCAGTGAAGGTC
TCCTGCAAGGCTTCTCATTTCACCTTCAGTAGCTTTTCGATGTCTTGGATCAGGCAGTCC
CCATCGAGAGGCCTTGAGTGGCTGGGTGAAATTAGTAGTGGTGGGAGTTACCATTACTAT
CCTGACACTGTGACGGGCAGATTCACCATCTCCAGAGACAACGCCAAGAACTCACTGTAT
CTGCAAATGAACAGCCTGAGAGCCGAGGACACGGCTGTGTATTACTGTGCGAGAGGTTTA
TGGGGGTACTATGCTCTTGACTACTGGGGCCAGGGA    SEQ ID NO: 114

>BA399CPS_HC18_DNA
CAGGTTCAGCTGGTGCAGTCTGGAGCTGAGGTGAAGAAGCCTGGGGCCTCAGTGAAGGTC
TCCTGCAAGGCTTCTCATTTCACCTTCAGTAGCTTTTCGATGTCTTGGATCAGGCAGTCC
CCATCGAGAGGCCTTGAGTGGCTGGGTGAAATTAGTAGTGGTGGGAGTTACACCTACTAT
CCTGACACTAAGACGGGCAGATTCACCATCTCCAGAGACAACGCCAAGAACTCACTGTAT
CTGCAAATGAACAGCCTGAGAGCCGAGGACACGGCTGTGTATTACTGTGCGAGAGGTTTA
TGGGGGTACTATGCTCTTGACTACTGGGGCCAGGGA    SEQ ID NO: 115

FIGURE 22

>BA399CPS_HC19_DNA
CAGGTTCAGCTGGTGCAGTCTGGAGCTGAGGTGAAGAAGCCTGGGGCCTCAGTGAAGGTC
TCCTGCAAGGCTTCTCATTTCACCTTCAGTAGCTTTTCGATGTCTTGGATCAGGCAGTCC
CCATCGAGAGGCCTTGAGTGGCTGGGTGAAATTAGTAGTGGTGGGAGTTACACCTACTAT
CCTGACACTGTGACGGGCAGATTCACCATCTCCAGAGACAACGCCAAGAACTCACTGTAT
CTGCAAATGAACAGCCTGAGAGCCGAGGACACGGCTGTGTATTACTGTGCGAGAGGTCAG
TGGGGGTACTATGCTCTTGACTACTGGGGCCAGGGA        SEQ ID NO: 116

>BA399CPS_HC20_DNA
CAGGTTCAGCTGGTGCAGTCTGGAGCTGAGGTGAAGAAGCCTGGGGCCTCAGTGAAGGTC
TCCTGCAAGGCTTCTCATTTCACCTTCAGTAGCTTTGCCATGTCTTGGATCAGGCAGTCC
CCATCGAGAGGCCTTGAGTGGCTGGGTGAAATTAGTAGTGGTGGGAGTTACCATTACTAT
CCTGACACTAAGACGGGCAGATTCACCATCTCCAGAGACAACGCCAAGAACTCACTGTAT
CTGCAAATGAACAGCCTGAGAGCCGAGGACACGGCTGTGTATTACTGTGCGAGAGGTTTA
TGGGGGTACTATGCTCTTGACTACTGGGGCCAGGGA        SEQ ID NO: 117

>BA399CPS_HC21_DNA
CAGGTTCAGCTGGTGCAGTCTGGAGCTGAGGTGAAGAAGCCTGGGGCCTCAGTGAAGGTC
TCCTGCAAGGCTTCTCATTTCACCTTCAGTAGCTTTGCCATGTCTTGGATCAGGCAGTCC
CCATCGAGAGGCCTTGAGTGGCTGGGTGAAATTAGTAGTGGTGGGAGTTACCATTACTAT
CCTGACACTGTGACGGGCAGATTCACCATCTCCAGAGACAACGCCAAGAACTCACTGTAT
CTGCAAATGAACAGCCTGAGAGCCGAGGACACGGCTGTGTATTACTGTGCGAGAGGTCAG
TGGGGGTACTATGCTCTTGACTACTGGGGCCAGGGA        SEQ ID NO: 118

>BA399CPS_HC22_DNA
CAGGTTCAGCTGGTGCAGTCTGGAGCTGAGGTGAAGAAGCCTGGGGCCTCAGTGAAGGTC
TCCTGCAAGGCTTCTCATTTCACCTTCAGTAGCTTTGCCATGTCTTGGATCAGGCAGTCC
CCATCGAGAGGCCTTGAGTGGCTGGGTGAAATTAGTAGTGGTGGGAGTTACACCTACTAT
CCTGACACTAAGACGGGCAGATTCACCATCTCCAGAGACAACGCCAAGAACTCACTGTAT
CTGCAAATGAACAGCCTGAGAGCCGAGGACACGGCTGTGTATTACTGTGCGAGAGGTCAG
TGGGGGTACTATGCTCTTGACTACTGGGGCCAGGGA        SEQ ID NO: 119

>BA399CPS_HC23_DNA
CAGGTTCAGCTGGTGCAGTCTGGAGCTGAGGTGAAGAAGCCTGGGGCCTCAGTGAAGGTC
TCCTGCAAGGCTTCTGGATTCACCTTCAGTAGCTTTTCGATGTCTTGGATCAGGCAGTCC
CCATCGAGAGGCCTTGAGTGGCTGGGTGAAATTAGTAGTGGTGGGAGTTACCATTACTAT
CCTGACACTAAGACGGGCAGATTCACCATCTCCAGAGACAACGCCAAGAACTCACTGTAT
CTGCAAATGAACAGCCTGAGAGCCGAGGACACGGCTGTGTATTACTGTGCGAGAGGTTTA
TGGGGGTACTATGCTCTTGACTACTGGGGCCAGGGA        SEQ ID NO: 120

>BA399CPS_HC24_DNA
CAGGTTCAGCTGGTGCAGTCTGGAGCTGAGGTGAAGAAGCCTGGGGCCTCAGTGAAGGTC
TCCTGCAAGGCTTCTGGATTCACCTTCAGTAGCTTTTCGATGTCTTGGATCAGGCAGTCC
CCATCGAGAGGCCTTGAGTGGCTGGGTGAAATTAGTAGTGGTGGGAGTTACCATTACTAT
CCTGACACTGTGACGGGCAGATTCACCATCTCCAGAGACAACGCCAAGAACTCACTGTAT
CTGCAAATGAACAGCCTGAGAGCCGAGGACACGGCTGTGTATTACTGTGCGAGAGGTCAG
TGGGGGTACTATGCTCTTGACTACTGGGGCCAGGGA        SEQ ID NO: 121

FIGURE 23

>BA399CPS_HC25_DNA
CAGGTTCAGCTGGTGCAGTCTGGAGCTGAGGTGAAGAAGCCTGGGGCCTCAGTGAAGGTC
TCCTGCAAGGCTTCTGGATTCACCTTCAGTAGCTTTTCGATGTCTTGGATCAGGCAGTCC
CCATCGAGAGGCCTTGAGTGGCTGGGTGAAATTAGTAGTGGTGGGAGTTACACCTACTAT
CCTGACACTAAGACGGGCAGATTCACCATCTCCAGAGACAACGCCAAGAACTCACTGTAT
CTGCAAATGAACAGCCTGAGAGCCGAGGACACGGCTGTGTATTACTGTGCGAGAGGTCAG
TGGGGGTACTATGCTCTTGACTACTGGGGCCAGGGA    SEQ ID NO: 122

>BA399CPS_HC26_DNA
CAGGTTCAGCTGGTGCAGTCTGGAGCTGAGGTGAAGAAGCCTGGGGCCTCAGTGAAGGTC
TCCTGCAAGGCTTCTGGATTCACCTTCAGTAGCTTTGCCATGTCTTGGATCAGGCAGTCC
CCATCGAGAGGCCTTGAGTGGCTGGGTGAAATTAGTAGTGGTGGGAGTTACCATTACTAT
CCTGACACTAAGACGGGCAGATTCACCATCTCCAGAGACAACGCCAAGAACTCACTGTAT
CTGCAAATGAACAGCCTGAGAGCCGAGGACACGGCTGTGTATTACTGTGCGAGAGGTCAG
TGGGGGTACTATGCTCTTGACTACTGGGGCCAGGGA    SEQ ID NO: 123

>BA399CPS_HC27_DNA
CAGGTTCAGCTGGTGCAGTCTGGAGCTGAGGTGAAGAAGCCTGGGGCCTCAGTGAAGGTC
TCCTGCAAGGCTTCTCATTTCACCTTCAGTAGCTTTTCGATGTCTTGGATCAGGCAGTCC
CCATCGAGAGGCCTTGAGTGGCTGGGTGAAATTAGTAGTGGTGGGAGTTACCATTACTAT
CCTGACACTAAGACGGGCAGATTCACCATCTCCAGAGACAACGCCAAGAACTCACTGTAT
CTGCAAATGAACAGCCTGAGAGCCGAGGACACGGCTGTGTATTACTGTGCGAGAGGTTTA
TGGGGGTACTATGCTCTTGACTACTGGGGCCAGGGA    SEQ ID NO: 124

>BA399CPS_HC28_DNA
CAGGTTCAGCTGGTGCAGTCTGGAGCTGAGGTGAAGAAGCCTGGGGCCTCAGTGAAGGTC
TCCTGCAAGGCTTCTCATTTCACCTTCAGTAGCTTTTCGATGTCTTGGATCAGGCAGTCC
CCATCGAGAGGCCTTGAGTGGCTGGGTGAAATTAGTAGTGGTGGGAGTTACCATTACTAT
CCTGACACTGTGACGGGCAGATTCACCATCTCCAGAGACAACGCCAAGAACTCACTGTAT
CTGCAAATGAACAGCCTGAGAGCCGAGGACACGGCTGTGTATTACTGTGCGAGAGGTCAG
TGGGGGTACTATGCTCTTGACTACTGGGGCCAGGGA    SEQ ID NO: 125

>BA399CPS_HC29_DNA
CAGGTTCAGCTGGTGCAGTCTGGAGCTGAGGTGAAGAAGCCTGGGGCCTCAGTGAAGGTC
TCCTGCAAGGCTTCTCATTTCACCTTCAGTAGCTTTTCGATGTCTTGGATCAGGCAGTCC
CCATCGAGAGGCCTTGAGTGGCTGGGTGAAATTAGTAGTGGTGGGAGTTACACCTACTAT
CCTGACACTAAGACGGGCAGATTCACCATCTCCAGAGACAACGCCAAGAACTCACTGTAT
CTGCAAATGAACAGCCTGAGAGCCGAGGACACGGCTGTGTATTACTGTGCGAGAGGTCAG
TGGGGGTACTATGCTCTTGACTACTGGGGCCAGGGA    SEQ ID NO: 126

>BA399CPS_HC30_DNA
CAGGTTCAGCTGGTGCAGTCTGGAGCTGAGGTGAAGAAGCCTGGGGCCTCAGTGAAGGTC
TCCTGCAAGGCTTCTCATTTCACCTTCAGTAGCTTTGCCATGTCTTGGATCAGGCAGTCC
CCATCGAGAGGCCTTGAGTGGCTGGGTGAAATTAGTAGTGGTGGGAGTTACCATTACTAT
CCTGACACTAAGACGGGCAGATTCACCATCTCCAGAGACAACGCCAAGAACTCACTGTAT
CTGCAAATGAACAGCCTGAGAGCCGAGGACACGGCTGTGTATTACTGTGCGAGAGGTCAG
TGGGGGTACTATGCTCTTGACTACTGGGGCCAGGGA    SEQ ID NO: 127

FIGURE 24

>BA399CPS_HC31_DNA
CAGGTTCAGCTGGTGCAGTCTGGAGCTGAGGTGAAGAAGCCTGGGGCCTCAGTGAAGGTC
TCCTGCAAGGCTTCTGGATTCACCTTCAGTAGCTTTTCGATGTCTTGGATCAGGCAGTCC
CCATCGAGAGGCCTTGAGTGGCTGGGTGAAATTAGTAGTGGTGGGAGTTACCATTACTAT
CCTGACACTAAGACGGGCAGATTCACCATCTCCAGAGACAACGCCAAGAACTCACTGTAT
CTGCAAATGAACAGCCTGAGAGCCGAGGACACGGCTGTGTATTACTGTGCGAGAGGTCAG
TGGGGGTACTATGCTCTTGACTACTGGGGCCAGGGA       SEQ ID NO: 128

>BA399CPS_HC32_DNA
CAGGTTCAGCTGGTGCAGTCTGGAGCTGAGGTGAAGAAGCCTGGGGCCTCAGTGAAGGTC
TCCTGCAAGGCTTCTCATTTCACCTTCAGTAGCTTTTCGATGTCTTGGATCAGGCAGTCC
CCATCGAGAGGCCTTGAGTGGCTGGGTGAAATTAGTAGTGGTGGGAGTTACCATTACTAT
CCTGACACTAAGACGGGCAGATTCACCATCTCCAGAGACAACGCCAAGAACTCACTGTAT
CTGCAAATGAACAGCCTGAGAGCCGAGGACACGGCTGTGTATTACTGTGCGAGAGGTCAG
TGGGGGTACTATGCTCTTGACTACTGGGGCCAGGGA       SEQ ID NO: 129

>BA399CPS_HC01_PRO
QVQLVQSGAEVKKPGASVKVSCKASGFTFSSFAMSWIRQSPSRGLEWLGEISSGGSYTYY
PDTVTGRFTISRDNAKNSLYLQMNSLRAEDTAVYYCARGLWGYYALDYWGQG
SEQ ID NO: 3

>BA399CPS_HC02_PRO
QVQLVQSGAEVKKPGASVKVSCKASHFTFSSFAMSWIRQSPSRGLEWLGEISSGGSYTYY
PDTVTGRFTISRDNAKNSLYLQMNSLRAEDTAVYYCARGLWGYYALDYWGQG
SEQ ID NO: 130

>BA399CPS_HC03_PRO
QVQLVQSGAEVKKPGASVKVSCKASGFTFSSFSMSWIRQSPSRGLEWLGEISSGGSYTYY
PDTVTGRFTISRDNAKNSLYLQMNSLRAEDTAVYYCARGLWGYYALDYWGQG
SEQ ID NO: 131

>BA399CPS_HC04_PRO
QVQLVQSGAEVKKPGASVKVSCKASGFTFSSFAMSWIRQSPSRGLEWLGEISSGGSYHYY
PDTVTGRFTISRDNAKNSLYLQMNSLRAEDTAVYYCARGLWGYYALDYWGQG
SEQ ID NO: 132

>BA399CPS_HC05_PRO
QVQLVQSGAEVKKPGASVKVSCKASGFTFSSFAMSWIRQSPSRGLEWLGEISSGGSYTYY
PDTKTGRFTISRDNAKNSLYLQMNSLRAEDTAVYYCARGLWGYYALDYWGQG
SEQ ID NO: 133

>BA399CPS_HC06_PRO
QVQLVQSGAEVKKPGASVKVSCKASGFTFSSFAMSWIRQSPSRGLEWLGEISSGGSYTYY
PDTVTGRFTISRDNAKNSLYLQMNSLRAEDTAVYYCARGQWGYYALDYWGQG
SEQ ID NO: 134

FIGURE 25

>BA399CPS_HC07_PRO
QVQLVQSGAEVKKPGASVKVSCKASHFTFSSFSMSWIRQSPSRGLEWLGEISSGGSYTYY
PDTVTGRFTISRDNAKNSLYLQMNSLRAEDTAVYYCARGLWGYYALDYWGQG
SEQ ID NO: 135

>BA399CPS_HC08_PRO
QVQLVQSGAEVKKPGASVKVSCKASHFTFSSFAMSWIRQSPSRGLEWLGEISSGGSYHYY
PDTVTGRFTISRDNAKNSLYLQMNSLRAEDTAVYYCARGLWGYYALDYWGQG
SEQ ID NO: 136

>BA399CPS_HC09_PRO
QVQLVQSGAEVKKPGASVKVSCKASHFTFSSFAMSWIRQSPSRGLEWLGEISSGGSYTYY
PDTKTGRFTISRDNAKNSLYLQMNSLRAEDTAVYYCARGLWGYYALDYWGQG
SEQ ID NO: 137

>BA399CPS_HC10_PRO
QVQLVQSGAEVKKPGASVKVSCKASHFTFSSFAMSWIRQSPSRGLEWLGEISSGGSYTYY
PDTVTGRFTISRDNAKNSLYLQMNSLRAEDTAVYYCARGQWGYYALDYWGQG
SEQ ID NO: 138

>BA399CPS_HC11_PRO
QVQLVQSGAEVKKPGASVKVSCKASGFTFSSFSMSWIRQSPSRGLEWLGEISSGGSYHYY
PDTVTGRFTISRDNAKNSLYLQMNSLRAEDTAVYYCARGLWGYYALDYWGQG
SEQ ID NO: 139

>BA399CPS_HC12_PRO
QVQLVQSGAEVKKPGASVKVSCKASGFTFSSFSMSWIRQSPSRGLEWLGEISSGGSYTYY
PDTKTGRFTISRDNAKNSLYLQMNSLRAEDTAVYYCARGLWGYYALDYWGQG
SEQ ID NO: 140

>BA399CPS_HC13_PRO
QVQLVQSGAEVKKPGASVKVSCKASGFTFSSFSMSWIRQSPSRGLEWLGEISSGGSYTYY
PDTVTGRFTISRDNAKNSLYLQMNSLRAEDTAVYYCARGQWGYYALDYWGQG
SEQ ID NO: 141

>BA399CPS_HC14_PRO
QVQLVQSGAEVKKPGASVKVSCKASGFTFSSFAMSWIRQSPSRGLEWLGEISSGGSYHYY
PDTKTGRFTISRDNAKNSLYLQMNSLRAEDTAVYYCARGLWGYYALDYWGQG
SEQ ID NO: 142

>BA399CPS_HC15_PRO
QVQLVQSGAEVKKPGASVKVSCKASGFTFSSFAMSWIRQSPSRGLEWLGEISSGGSYHYY
PDTVTGRFTISRDNAKNSLYLQMNSLRAEDTAVYYCARGQWGYYALDYWGQG
SEQ ID NO: 143

FIGURE 26

>BA399CPS_HC16_PRO
QVQLVQSGAEVKKPGASVKVSCKASGFTFSSFAMSWIRQSPSRGLEWLGEISSGGSYTYY
PDTKTGRFTISRDNAKNSLYLQMNSLRAEDTAVYYCARGQWGYYALDYWGQG
SEQ ID NO: 144

>BA399CPS_HC17_PRO
QVQLVQSGAEVKKPGASVKVSCKASHFTFSSFSMSWIRQSPSRGLEWLGEISSGGSYHYY
PDTVTGRFTISRDNAKNSLYLQMNSLRAEDTAVYYCARGLWGYYALDYWGQG
SEQ ID NO: 145

>BA399CPS_HC18_PRO
QVQLVQSGAEVKKPGASVKVSCKASHFTFSSFSMSWIRQSPSRGLEWLGEISSGGSYTYY
PDTKTGRFTISRDNAKNSLYLQMNSLRAEDTAVYYCARGLWGYYALDYWGQG
SEQ ID NO: 146

>BA399CPS_HC19_PRO
QVQLVQSGAEVKKPGASVKVSCKASHFTFSSFSMSWIRQSPSRGLEWLGEISSGGSYTYY
PDTVTGRFTISRDNAKNSLYLQMNSLRAEDTAVYYCARGQWGYYALDYWGQG
SEQ ID NO: 147

>BA399CPS_HC20_PRO
QVQLVQSGAEVKKPGASVKVSCKASHFTFSSFAMSWIRQSPSRGLEWLGEISSGGSYHYY
PDTKTGRFTISRDNAKNSLYLQMNSLRAEDTAVYYCARGLWGYYALDYWGQG
SEQ ID NO: 148

>BA399CPS_HC21_PRO
QVQLVQSGAEVKKPGASVKVSCKASHFTFSSFAMSWIRQSPSRGLEWLGEISSGGSYHYY
PDTVTGRFTISRDNAKNSLYLQMNSLRAEDTAVYYCARGQWGYYALDYWGQG
SEQ ID NO: 149

>BA399CPS_HC22_PRO
QVQLVQSGAEVKKPGASVKVSCKASHFTFSSFAMSWIRQSPSRGLEWLGEISSGGSYTYY
PDTKTGRFTISRDNAKNSLYLQMNSLRAEDTAVYYCARGQWGYYALDYWGQG
SEQ ID NO: 150

>BA399CPS_HC23_PRO
QVQLVQSGAEVKKPGASVKVSCKASGFTFSSFSMSWIRQSPSRGLEWLGEISSGGSYHYY
PDTKTGRFTISRDNAKNSLYLQMNSLRAEDTAVYYCARGLWGYYALDYWGQG
SEQ ID NO: 151

>BA399CPS_HC24_PRO
QVQLVQSGAEVKKPGASVKVSCKASGFTFSSFSMSWIRQSPSRGLEWLGEISSGGSYHYY
PDTVTGRFTISRDNAKNSLYLQMNSLRAEDTAVYYCARGQWGYYALDYWGQG
SEQ ID NO: 152

>BA399CPS_HC25_PRO
QVQLVQSGAEVKKPGASVKVSCKASGFTFSSFSMSWIRQSPSRGLEWLGEISSGGSYTYY
PDTKTGRFTISRDNAKNSLYLQMNSLRAEDTAVYYCARGQWGYYALDYWGQG
SEQ ID NO: 153

FIGURE 27

>BA399CPS_HC26_PRO
QVQLVQSGAEVKKPGASVKVSCKASGFTFSSFAMSWIRQSPSRGLEWLGEISSGGSYHYY
PDTKTGRFTISRDNAKNSLYLQMNSLRAEDTAVYYCARGQWGYYALDYWGQG
SEQ ID NO: 154

>BA399CPS_HC27_PRO
QVQLVQSGAEVKKPGASVKVSCKASHFTFSSFSMSWIRQSPSRGLEWLGEISSGGSYHYY
PDTKTGRFTISRDNAKNSLYLQMNSLRAEDTAVYYCARGLWGYYALDYWGQG
SEQ ID NO: 155

>BA399CPS_HC28_PRO
QVQLVQSGAEVKKPGASVKVSCKASHFTFSSFSMSWIRQSPSRGLEWLGEISSGGSYHYY
PDTVTGRFTISRDNAKNSLYLQMNSLRAEDTAVYYCARGQWGYYALDYWGQG
SEQ ID NO: 156

>BA399CPS_HC29_PRO
QVQLVQSGAEVKKPGASVKVSCKASHFTFSSFSMSWIRQSPSRGLEWLGEISSGGSYTYY
PDTKTGRFTISRDNAKNSLYLQMNSLRAEDTAVYYCARGQWGYYALDYWGQG
SEQ ID NO: 157

>BA399CPS_HC30_PRO
QVQLVQSGAEVKKPGASVKVSCKASHFTFSSFAMSWIRQSPSRGLEWLGEISSGGSYHYY
PDTKTGRFTISRDNAKNSLYLQMNSLRAEDTAVYYCARGQWGYYALDYWGQG
SEQ ID NO: 158

>BA399CPS_HC31_PRO
QVQLVQSGAEVKKPGASVKVSCKASGFTFSSFSMSWIRQSPSRGLEWLGEISSGGSYHYY
PDTKTGRFTISRDNAKNSLYLQMNSLRAEDTAVYYCARGQWGYYALDYWGQG
SEQ ID NO: 159

>BA399CPS_HC32_PRO
QVQLVQSGAEVKKPGASVKVSCKASHFTFSSFSMSWIRQSPSRGLEWLGEISSGGSYHYY
PDTKTGRFTISRDNAKNSLYLQMNSLRAEDTAVYYCARGQWGYYALDYWGQG
SEQ ID NO: 160

FIGURE 28

Top 10 CPS hits – Sapidyne Analysis

| | $K_d$ | $K_d$ Range (95% Confidence Interval) |
|---|---|---|
| BA003 (cnto136) | 4.37 pM | 5.66pM to 3.28pM |
| BAP001 clone 1 | 9.48 pM | 17.16 pM to 3.69 pM |
| BAP001 clone 2 | 2.15 pM | 4.33 pM to 680.84 fM |
| BAP001 clone 3 | 36.07 pM | 115.1pM to 4.45pM |
| BAP001 clone 4 | 14.85 pM | 25.45pM to 7.57pM |
| BAP001 clone 5 | 1.8 pM | 4.36pM to 261.66 fM |
| BAP001 clone 6 | 14.23 pM | 21.8 pM to 8.64 pM |
| BAP001 clone 7 | 16.72 pM | 33.76pM to 6.28 pM |
| BAP001 clone 8 | 8.98 pM | 20.61pM to 2.55pM |
| BAP001 clone 9 | 17.8 pM | 31.58pM to 9.04pM |
| BAP001 clone 10 | 9.8 pM | 14.69pM to 6.08pM |

FIGURE 33

BA399 Affinity Maturation Biacore analysis

| | ka (1/Ms) | kd (1/s) | KA (1/M) | KD (M) |
|---|---|---|---|---|
| Clone BA399-2 | $7.42 \times 10^5$ | $9.11 \times 10^{-9}$ | $8.14 \times 10^{13}$ | $1.23 \times 10^{-14}$ |
| Clone BA399-5 | $1.01 \times 10^6$ | $2.86 \times 10^{-5}$ | $3.52 \times 10^{10}$ | $2.84 \times 10^{-11}$ |
| Clone BA399-9 | $6.48 \times 10^5$ | $5.07 \times 10^{-8}$ | $1.28 \times 10^{13}$ | $7.83 \times 10^{-14}$ |
| Clone BA399-10 | $6.43 \times 10^5$ | $1.82 \times 10^{-7}$ | $3.52 \times 10^{12}$ | $2.84 \times 10^{-13}$ |

FIGURE 34

Data normalized based on Western for total Stat3

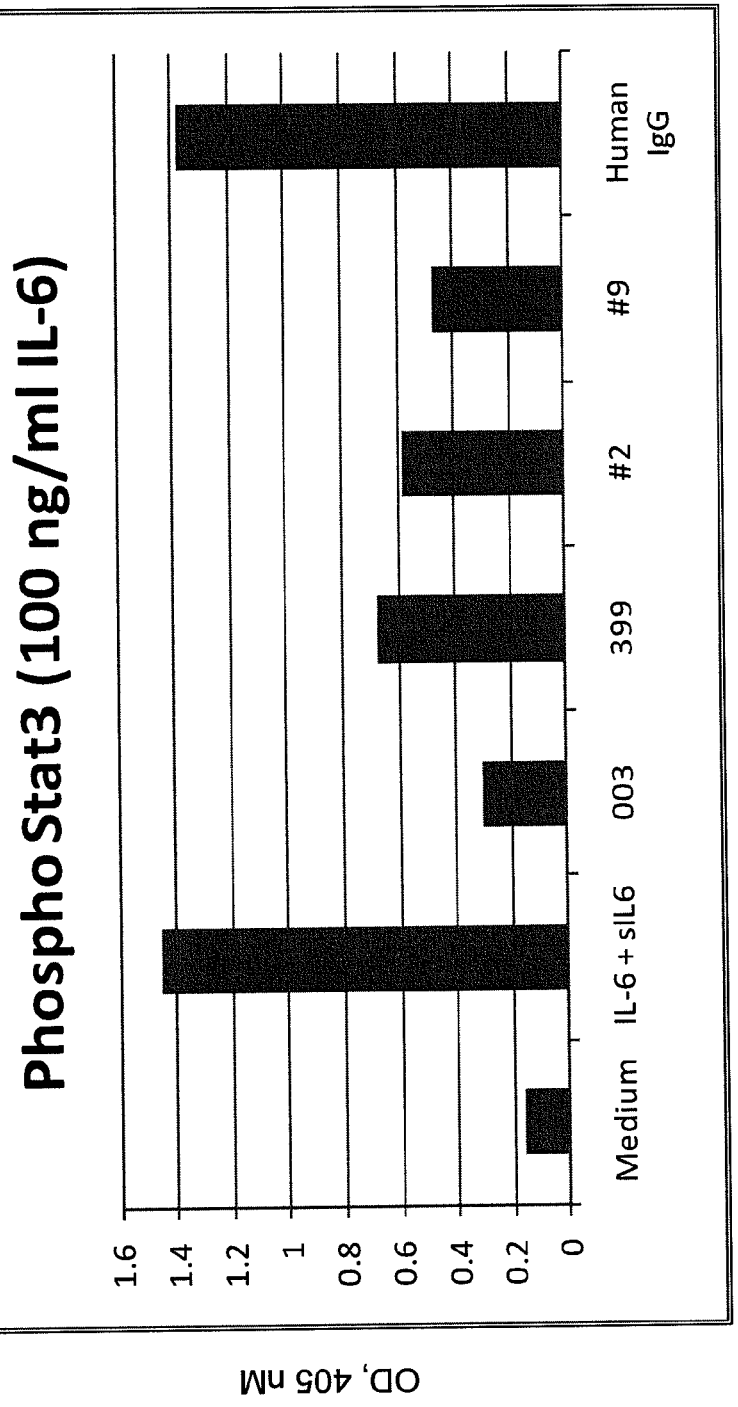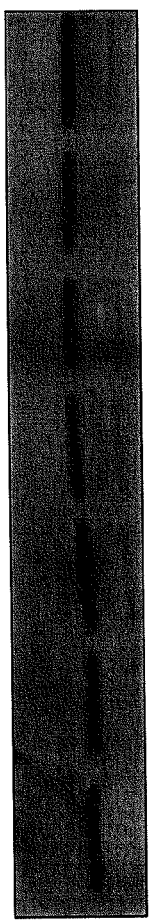
FIGURE 36

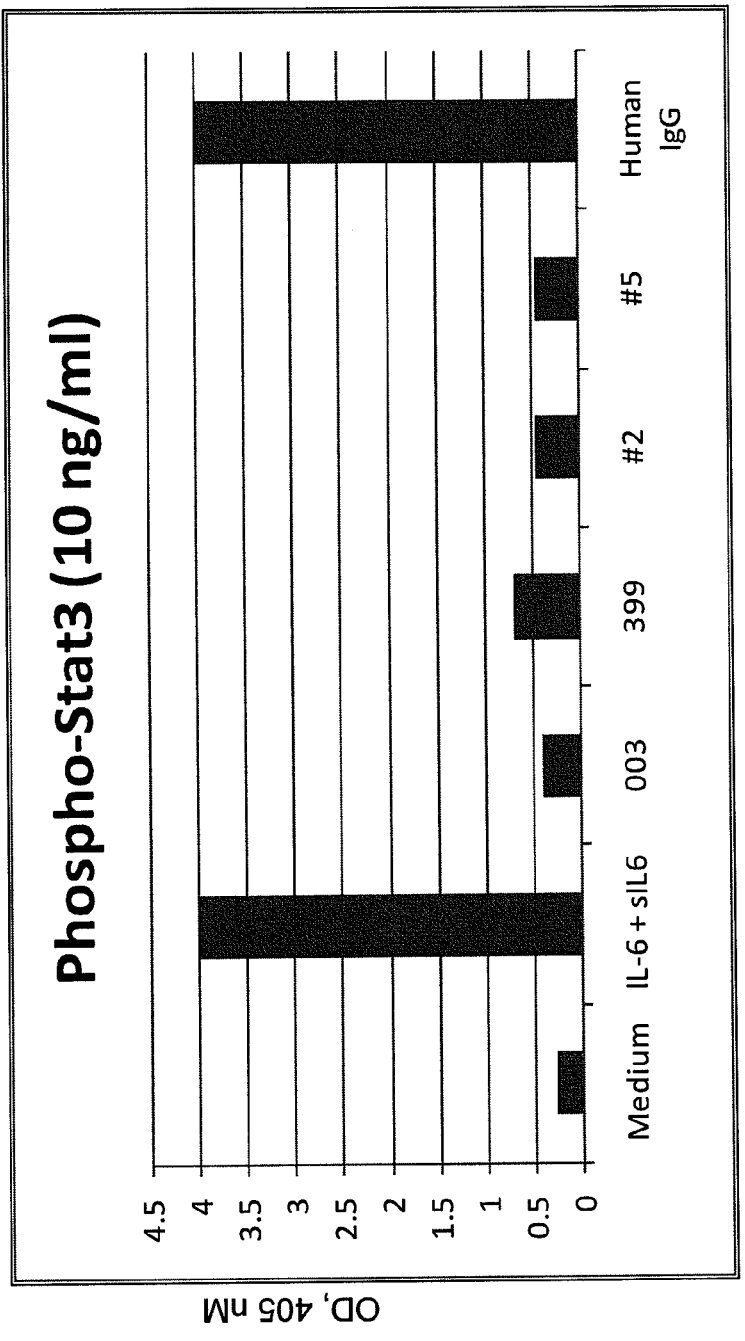
FIGURE 37

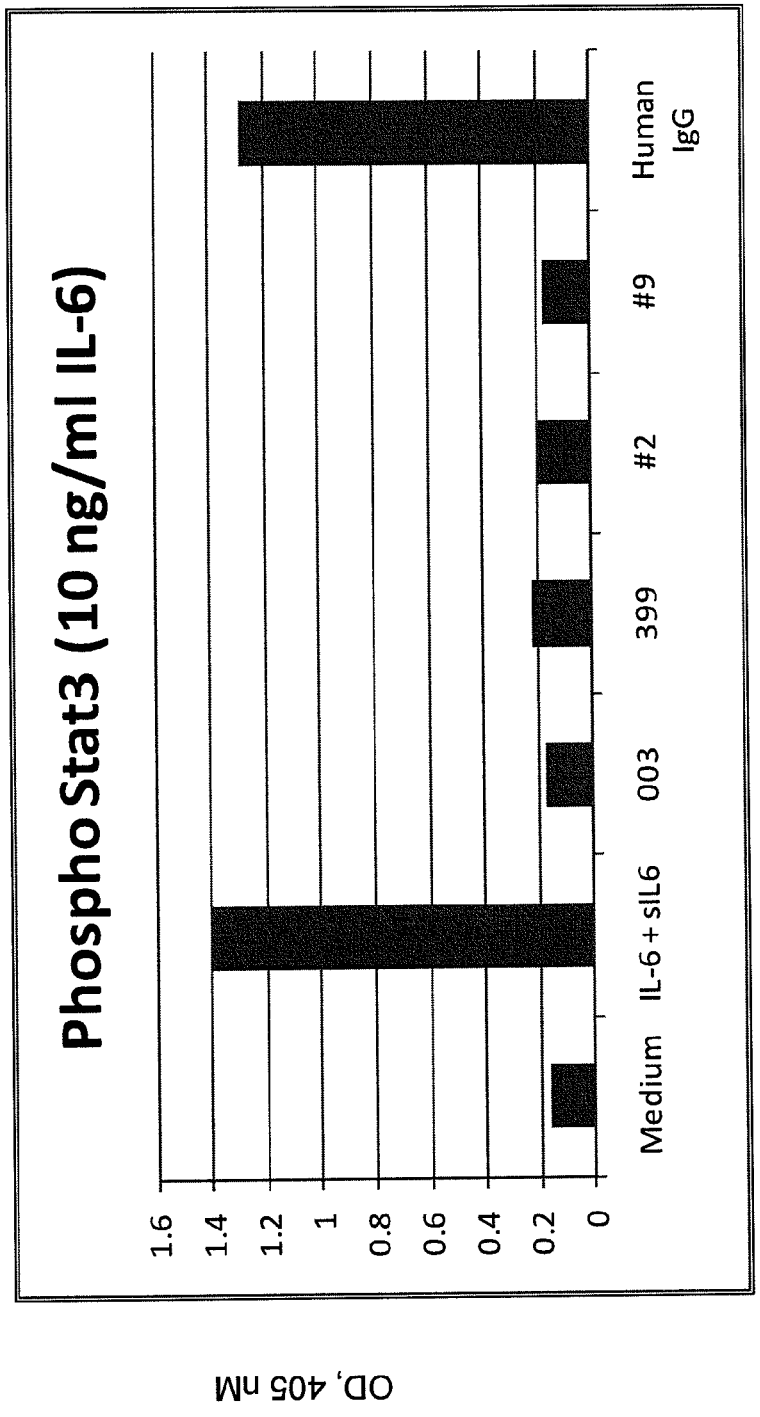
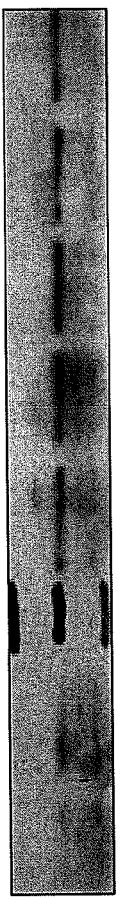
FIGURE 38

| Clone | Light chain | Heavy Chain |
|---|---|---|
| BA399_01 | BA399CPS_LC06 | BA399CPS_HC06 |
| BA399_02 | BA399CPS_LC02 | BA399CPS_HC25 |
| BA399_03 | BA399CPS_LC05 | BA399CPS_HC21 |
| BA399_04 | BA399CPS_LC06 | BA399CPS_HC13 |
| BA399_05 | BA399CPS_LC10 | BA399CPS_HC16 |
| BA399_06 | BA399CPS_LC22 | BA399CPS_HC24 |
| BA399_07 | BA399CPS_LC14 | BA399CPS_HC19 |
| BA399_08 | BA399CPS_LC10 | BA399CPS_HC12 |
| BA399_09 | BA399CPS_LC09 | BA399CPS_HC24 |
| BA399_10 | BA399CPS_LC09 | BA399CPS_HC28 |

FIGURE 44

HUMANIZED ANTI-IL-6 ANTIBODIES

RELATED APPLICATION INFORMATION

This application is a divisional of U.S. patent application Ser. No. 12/617,915, filed Nov. 13, 2009, which claims the benefit of U.S. Provisional Application Ser. No. 61/114,295, filed Nov. 13, 2008, entitled "Humanized IL-6 Antibodies," the entire contents of which are incorporated herein by this reference.

SEQUENCE LISTING INFORMATION

The sequence listing for this application is contained in the ASCII text file submitted herewith having the name of 10438-1A_ST25.txt, created Sep. 23, 2011, with a size of 121 kilobytes and is hereby incorporated by reference.

BACKGROUND OF THE INVENTION

1. Field of the Invention

The present invention relates to antibodies, including specified portions or variants, specific for at least one Interleukin-6 (IL-6 also known as Interferon β2) protein or fragment thereof, as well as nucleic acids encoding such anti-IL-6 antibodies, complementary nucleic acids, vectors, host cells, and methods of making and using thereof, including therapeutic formulations, administration and devices.

2. Related Art

Interleukin-6 (IL-6) is a pro-inflammatory cytokine that is produced by many different cell types. In vivo, stimulated monocytes, fibroblasts, and endothelial cells represent the main sources of IL-6. Other cells such as macrophages, T and B lymphocytes, granulocytes, keratinocytes, mast cells, osteoblasts, chrondrocytes, glial cells, and smooth muscle cells also produce IL-6 after stimulation. Several tumor cells also produce IL-6 and IL-6 has been implicated as a prognostic factor for prostate cancer progression. IL-6 production can be regulated by IL-6 itself and depending upon cell type, IL-6 can stimulate or inhibit its own synthesis.

IL-6 can bind to the IL-6 receptor expressed on mitogen-activated B cells, T cells, peripheral monocytes, and certain tumors. The IL-6 receptor has at least two different components and is composed of an alpha chain called gp80 that is responsible for IL-6 binding and a beta chain designated gp130 that is needed for signal transduction. The cytokine family which includes IL-6, LIF, Oncostatin M, IL-11, CNTF, and CT-1 all signal through gp130 after binding to their cognate receptors. In addition, all members of the IL-6 cytokine family can induce hepatic expression of acute phase proteins.

There are at least two major biological functions of IL-6: mediation of acute phase proteins and acting as a differentiation and activation factor. Acute phase proteins are known to regulate immune responses, mediate inflammation, and play a role in tissue remodeling. As a differentiation and activation factor, IL-6 induces B cells to differentiate and secrete antibody, it induces T cells to differentiate into cytotoxic T cells, activates cell signaling factors, and promotes hematopoiesis. IL-6 is prominently involved in many critical bodily functions and processes. As a result, physiological processes including bone metabolism, neoplastic transformation, and immune and inflammatory responses can be enhanced, suppressed, or prevented by manipulation of the biological activity of IL-6 in vivo by means of an antibody.

There is a need to provide high affinity, neutralizing chimeric or human antibodies to IL-6 or fragments thereof for use in preventing, treating, ameliorating, or diagnosing conditions related to the IL-6.

SUMMARY OF THE INVENTION

The present invention provides isolated humanized anti-IL-6 antibodies, having at least one antigen binding region derived from the high affinity BA399, BA436, BA802, BA808, BA840, BA848, BA890 or BA939 anti-IL-6 antibodies, as well as anti-IL-6 antibody compositions, encoding or complementary nucleic acids, vectors, host cells, compositions, formulations, devices, transgenic animals, transgenic plants related thereto, and methods of making and using thereof, as described and enabled herein, in combination with what is known in the art. The antibody of the invention specifically neutralizes human IL-6 with high affinity.

The present invention provides at least one isolated humanized anti-IL-6 antibody as described herein. The antibody according to the present invention includes any one of BA399, BA436, BA802, BA808, BA840, BA848, BA890 or BA939 or any protein or peptide molecule that comprises at least one complementarity determining region (CDR) of a heavy or light chain or a ligand binding portion thereof, derived from one of BA399, BA436, BA802, BA808, BA840, BA848, BA890 or BA939 antibody, in combination with a heavy chain or light chain constant region, a framework region, or any portion thereof, that can be incorporated into an antibody of the present invention. In one embodiment the invention is directed to an anti-IL-6 antibody comprising a light chain and a heavy chain, each of the chains comprising at least part of a human constant region and at least part of a variable region (v) derived from one or more of BA399, BA436, BA802, BA808, BA840, BA848, BA890 or BA939 each of which has specificity to human IL-6, said antibody binding with high affinity to an inhibiting and/or neutralizing epitope of human IL-6. The invention also includes fragments or a derivative of such an antibody, such as one or more portions of the antibody chain, such as the heavy chain constant, joining, diversity or variable regions, or the light chain constant, joining or variable regions.

The antibody can comprise at least one specified portion of at least one complementarily determining region (CDR) (e.g., CDR1, CDR2 or CDR3 of the heavy or light chain variable region) derived from an anti-IL-6 antibody (as such term is defined herein), and/or at least one constant or variable framework region or any portion thereof. The antibody amino acid sequence can further optionally comprise at least one specified substitution, insertion or deletion as described herein or as known in the art.

Preferred antibodies of the present invention include BA399, BA436, BA802, BA808, BA840, BA848, BA890, BA939, BA399-01, BA399-02, BA399-03, BA399-04, BA399-05, BA399-06, BA399-07, BA399-08, BA399-09, and BA399-10, as well as fragments and regions thereof.

In one embodiment, the disclosure provides an isolated antibody or antibody fragment that binds to human IL-6, comprising a heavy chain variable region having the amino acid sequence of SEQ ID NO: 3, 7, 11, 15, 19, 23, 27, 31, 134, 140, 141, 144, 147, 149, 152, 153 or 156; a light chain variable region having the amino acid sequence of SEQ ID NO: 1, 5, 9, 13, 17, 21, 25, 29, 68, 71, 72, 75, 76, 80 or 88; and a constant region derived from one or more human antibodies. In one aspect, the disclosure provides an isolated antibody or antibody fragment that binds to human IL-6, comprising a heavy chain and light chain complementarity determining regions (CDRs) derived from the variable regions from one or more of BA399, BA436, BA802, BA808, BA840, BA848, BA890 and BA939, and a constant region derived from one or more human antibodies. In another aspect, the disclosure provides an antibody or fragment according to claim 1, wherein said antibody or fragment competitively inhibits in vivo the binding to human IL-6 of an anti IL-6 murine antibody.

Preferred antibodies of the present invention are those that bind human IL-6 and block receptor binding, which include epitopes as described by Brackenhoff et al. (supra). Preferred methods for determining monoclonal antibody specificity and affinity by competitive inhibition can be found in Harlow, et al, Antibodies: A Laboratory Manual, Cold Spring Harbor Laboratory Press, Cold Spring Harbor, N.Y., 1988), hereby incorporated by reference into the present application. At least one antibody of the invention binds at least one specified epitope specific to human IL-6 protein, subunit, fragment, portion or any combination thereof, for example as described by Brackenhoff et al. (supra). The epitope can comprise at least one antibody binding region, which epitope is preferably comprised of at least 1-5 amino acids of at least one portion thereof, such as but not limited to, at least one functional, extracellular, soluble, hydrophillic, external or cytoplasmic domain of human IL-6 protein, or any portion thereof.

In one aspect, the present invention provides at least one isolated mammalian anti-IL-6 antibody, comprising at least one variable region from one of BA399, BA436, BA802, BA808, BA840, BA848, BA890, BA939, BA399-01, BA399-02, BA399-03, BA399-04, BA399-05, BA399-06, BA399-07, BA399-08, BA399-09 and BA399-10, and the nucleic acid sequences encoding them.

In another aspect, the present invention provides at least one isolated mammalian anti-IL-6 antibody, comprising either (i) all of the heavy chain complementarity determining regions (CDR) amino acid sequences derived from BA399, BA436, BA802, BA808, BA840, BA848, BA890, BA939, BA399-01, BA399-02, BA399-03, BA399-04, BA399-05, BA399-06, BA399-07, BA399-08, BA399-09 and BA399-10, and the nucleic acid sequences encoding them; or (ii) all of the light chain CDR amino acids sequences from one of BA399, BA436, BA802, BA808, BA840, BA848, BA890, BA939, BA399-01, BA399-02, BA399-03, BA399-04, BA399-05, BA399-06, BA399-07, BA399-08, BA399-09 and BA399-10, and the nucleic acid sequences encoding them.

In another aspect, the present invention provides at least one isolated mammalian anti-IL-6 antibody, comprising at least one heavy chain or light chain CDR having the amino acid sequence derived from BA399, BA436, BA802, BA808, BA840, BA848, BA890, BA939, BA399-01, BA399-02, BA399-03, BA399-04, BA399-05, BA399-06, BA399-07, BA399-08, BA399-09 and BA399-10, and the nucleic acid sequences encoding them.

In other aspect the present invention provides at least one isolated mammalian chimeric, humanized or CDR-grafted anti-IL-6 antibody, comprising at least one human CDR, wherein the antibody specifically binds at least one epitope comprising at least 1-3 amino acids of an epitope of human IL-6.

At least one antibody can optionally further bind IL-6 with an affinity ($K_d$) of at least $10^{-9}$ M, preferably at least $10^{-10}$ M, and/or substantially neutralize at least one activity of at least one IL-6 protein. In a preferred embodiment, the antibody binds IL-6 with an affinity ($K_{ds}$) of at least $5 \times 10^{-10}$ M, preferably $5 \times 10^{-11}$, more preferably $5 \times 10^{-12}$ and neutralizes human IL-6.

The present invention provides, in one aspect, isolated nucleic acid molecules comprising, complementary, or hybridizing to, a polynucleotide encoding the aforementioned specific anti-IL-6 antibodies, comprising at least one specified sequence, domain, portion or variant thereof. The present invention further provides recombinant vectors comprising said anti-IL-6 antibody nucleic acid molecules, host cells containing such nucleic acids and/or recombinant vectors, as well as methods of making and/or using such antibody nucleic acids, vectors and/or host cells. Thus, the invention comprises isolated nucleic acid encoding at least one isolated mammalian anti-IL-6 antibody; an isolated nucleic acid vector comprising the isolated nucleic acid, and/or a prokaryotic or eukaryotic host cell comprising the isolated nucleic acid. The host cell can optionally be at least one selected from COS-1, COS-7, HEK293, BHK21, CHO, BSC-1, Hep G2, 653, SP2/0, 293, HeLa, PER.C6®, myeloma, or lymphoma cells, or any derivative, immortalized or transformed cell thereof. Also provided is a method for producing at least one anti-IL-6 antibody, comprising translating the antibody encoding nucleic acid under conditions in vitro, in vivo or in situ, such that the IL-6 antibody is expressed in detectable or recoverable amounts.

The present invention also provides at least one method for expressing at least one aforementioned anti-IL-6 antibody in a host cell, comprising culturing a host cell as described herein under conditions wherein at least one anti-IL-6 antibody is expressed in detectable and/or recoverable amounts.

The present invention also provides at least one composition comprising (a) an isolated anti-IL-6 antibody encoding nucleic acid and/or antibody as described herein; and (b) a suitable carrier or diluent. The carrier or diluent can optionally be pharmaceutically acceptable, according to known carriers or diluents. The composition can optionally further comprise at least one further compound, protein or composition.

The present invention further provides at least one anti-IL-6 antibody method or composition, for administering a therapeutically effective amount to modulate or treat at least one IL-6 related condition in a cell, tissue, organ, animal or patient and/or, prior to, subsequent to, or during a related condition, as known in the art and/or as described herein. Thus, the invention provides a method for diagnosing or treating an IL-6 related condition in a cell, tissue, organ or animal, comprising contacting or administering a composition comprising an effective amount of at least one isolated anti-IL-6 antibody of the invention with, or to, the cell, tissue, organ or animal. The method can optionally further comprise using an effective amount of 0.001-50 mg/kilogram of an anti-IL-6 antibody of the invention to the cells, tissue, organ or animal. The method can optionally further comprise using the contacting or the administrating by at least one mode selected from parenteral, subcutaneous, intramuscular, intravenous, intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, or transdermal. The method can optionally further comprise administering, prior, concurrently, or after the antibody contacting or administering at least one composition comprising an effective amount of at least one compound or protein selected from at least one of a detectable label or reporter, a TNF antagonist, an antirheumatic, a muscle relaxant, a narcotic, a non-steroid anti-inflammatory drug (NSAID), an analgesic, an anesthetic, a sedative, a local anesthetic, a neuromuscular blocker, an antimicrobial, an antipsoriatic, a corticosteriod, an anabolic steroid, an erythropoietin, an immunization, an immunoglobulin, an immunosuppressive, a growth hormone, a hormone replacement drug, a radiopharmaceutical, an antidepressant, an antipsychotic, a stimulant, an asthma medication, a beta agonist, an inhaled steroid, an epinephrine or analog thereof, a cytotoxic or other anti-cancer agent, an anti-metabolite such as methotrexate, an anti-proliferative agent, a cytokine, a cytokine antagonist, and an anti-TNFα or IL-12/IL-23 monoclonal antibody.

The present invention further provides at least one anti-IL-6 antibody method for diagnosing at least one IL-6 related condition in a cell, tissue, organ, animal or patient and/or, prior to, subsequent to, or during a related condition, as known in the art and/or as described herein.

The present invention also provides at least one composition, device and/or method of delivery for diagnosing of at least one anti-IL-6 antibody, according to the present invention.

Also provided is a composition comprising at least one isolated humanized anti-IL-6 antibody and at least one pharmaceutically acceptable carrier or diluent. The composition can optionally further comprise an effective amount of at least one compound or protein selected from at least one of a detectable label or reporter, a cytotoxic or other anti-cancer agent, an anti-metabolite such as methotrexate, an anti-proliferative agent, a cytokine, or a cytokine antagonist, a TNF antagonist, an antirheumatic, a muscle relaxant, a narcotic, a non-steroid anti-inflammatory drug (NTHE), an analgesic, an anesthetic, a sedative, a local anethetic, a neuromuscular blocker, an antimicrobial, an antipsoriatic, a corticosteriod, an anabolic steroid, an erythropoietin, an immunization, an immunoglobulin, an immunosuppressive, a growth hormone, a hormone replacement drug, a radiopharmaceutical, an antidepressant, an antipsychotic, a stimulant, an asthma medication, a beta agonist, an inhaled steroid, an epinephrine or analog.

Also provided is a medical device, comprising at least one isolated mammalian anti-IL-6 antibody of the invention, wherein the device is suitable to contacting or administering the at least one anti-IL-6 antibody by at least one mode selected from parenteral, subcutaneous, intramuscular, intravenous, intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, or transdermal.

In a further aspect, the disclosure provides a kit comprising at least one anti-IL-6 antibody or fragment of the disclosure in lyophilized form in a first container, and an optional second container comprising sterile water, sterile buffered water, or at least one preservative selected from the group consisting of phenol, m-cresol, p-cresol, o-cresol, chlorocresol, benzyl alcohol, phenylmercuric nitrite, phenoxyethanol, formaldehyde, chlorobutanol, magnesium chloride, alkylparaben, benzalkonium chloride, benzethonium chloride, sodium dehydroacetate and thimerosal, or mixtures thereof in an aqueous diluent. In one aspect, in the kit, the concentration of anti-IL-6 antibody or specified portion or variant in the first container is reconstituted to a concentration of about 0.1 mg/ml to about 500 mg/ml with the contents of the second container. In another aspect, the second container further comprises an isotonicity agent. In another aspect, the second container further comprises a physiologically acceptable buffer. In one aspect, the disclosure provides a method of treating at least one anti-IL-6 mediated condition, comprising administering to a patient in need thereof a formulation provided in a kit and reconstituted prior to administration.

Also provided is an article of manufacture for human pharmaceutical or diagnostic use, comprising packaging material and a container comprising a solution or a lyophilized form of at least one isolated mammalian anti-IL-6 antibody of the present invention. The article of manufacture can optionally comprise having the container as a component of a parenteral, subcutaneous, intramuscular, intravenous, intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, or transdermal delivery device or system.

The present invention further provides any invention described herein.

DESCRIPTION OF THE FIGURES

FIG. 1 shows the amino acid sequences and nucleic acid sequences, respectively, for the light chain (SEQ ID NOs: 1, 2) and heavy chain (SEQ ID NOs: 3, 4) variable region of Anti-IL-6 Ab BA399.

FIG. 2 shows the amino acid sequences and nucleic acid sequences, respectively, for the light chain (SEQ ID NOs: 5, 6) and heavy chain (SEQ ID NOs: 7, 8) variable region of Anti-IL-6 Ab BA436.

FIG. 3 shows the amino acid sequences and nucleic acid sequences, respectively, for the light chain (SEQ ID NOs: 9, 10) and heavy chain (SEQ ID NOs: 11, 12) variable region of Anti-IL-6 Ab BA802.

FIG. 4 shows the amino acid sequences and nucleic acid sequences, respectively, for the light chain (SEQ ID NOs: 13, 14) and heavy chain (SEQ ID NOs: 15, 16) variable region of Anti-IL-6 Ab BA808.

FIG. 5 shows the amino acid sequences and nucleic acid sequences, respectively, for the light chain (SEQ ID NOs: 17, 18) and heavy chain (SEQ ID NOs: 19, 20) variable region of Anti-IL-6 Ab BA840.

FIG. 6 shows the amino acid sequences and nucleic acid sequences, respectively, for the light chain (SEQ ID NOs: 21, 22) and heavy chain (SEQ ID NOs: 23, 24) variable region of Anti-IL-6 Ab BA848.

FIG. 7 shows the amino acid sequences and nucleic acid sequences, respectively, for the light chain (SEQ ID NOs: 25, 26) and heavy chain (SEQ ID NOs: 27, 28) variable region of Anti-IL-6 Ab BA890.

FIG. 8 shows the amino acid sequences and nucleic acid sequences, respectively, for the light chain (SEQ ID NOs: 29, 30) and heavy chain (SEQ ID NOs: 31, 32) variable region of Anti-IL-6 Ab BA939.

FIG. 9 shows the amino acid sequences and nucleic acid sequences, respectively, for the light chain (SEQ ID NOs: 33, 34) and heavy chain (SEQ ID NOs: 35, 36) variable region of Anti-IL-6 Ab BA001.

FIG. 11 shows BiaCore and ELISA analysis of BA001 and Anti-IL-6 Antibodies of the invention.

FIG. 12 shows nucleic acid sequences for the BA399 CPS light chain variable region of Anti-IL-6 Ab BA399 LC01 DNA to LC06 DNA (SEQ ID NOs: 2, 37, 38, 39, 40 and 41, respectively).

FIG. 13 shows nucleic acid sequences for the BA399 CPS light chain variable region of Anti-IL-6 Ab BA399 LC07 DNA to LC12 DNA (SEQ ID NOs: 42, 43, 44, 45, 46 and 47, respectively).

FIG. 14 shows nucleic acid sequences for the BA399 CPS light chain variable region of Anti-IL-6 Ab BA399 LC13 DNA to LC18 DNA (SEQ ID NOs: 48, 49, 50, 51, 52 and 53, respectively).

FIG. 15 shows nucleic acid sequences for the BA399 CPS light chain variable region of Anti-IL-6 Ab BA399 LC19 DNA to LC24 DNA (SEQ ID NOs: 54, 55, 56, 57, 58 and 59, respectively).

FIG. 16 shows nucleic acid sequences for the BA399 CPS light chain variable region of Anti-IL-6 Ab BA399 LC25 DNA to LC30 DNA (SEQ ID NOs: 60, 61, 62, 63, 64 and 65, respectively).

FIG. 17 shows nucleic acid sequences for the BA399 CPS light chain variable region of Anti-IL-6 Ab BA399 LC31 DNA and LC32 DNA (SEQ ID NOs: 66 and 67, respectively); and amino acid sequences for the light chain variable region of Anti-IL-6 Ab BA399 LC01 PRO to LC08 PRO(SEQ ID NOs: 1, 68, 69, 70, 71, 72, 73, and 74, respectively).

FIG. 18 shows amino acid sequences for the BA399 CPS light chain variable region of Anti-IL-6 Ab BA399 LC09 PRO to LC20 PRO (SEQ ID NOs: 75, 76, 77, 78, 79, 80, 81, 82, 83, 84, 85 and 86, respectively).

FIG. 19 shows amino acid sequences for the BA399 CPS light chain variable region of Anti-IL-6 Ab BA399 LC21 PRO to LC32 PRO (SEQ ID NOs: 87, 88, 89, 90, 91, 92, 93, 94, 95, 96, 97 and 98, respectively).

FIG. 20 shows nucleic acid sequences for the BA BA399 CPS heavy chain variable region of Anti-IL-6 Ab BA399 HC01 DNA to HC06 DNA (SEQ ID NOs: 4, 99, 100, 101, 102 and 103, respectively).

FIG. 21 shows nucleic acid sequences for the BA399 CPS heavy chain variable region of Anti-IL-6 Ab BA399 HC07 DNA to HC12 DNA (SEQ ID NOs: 104, 105, 106, 107, 108 and 109, respectively).

FIG. 22 shows nucleic acid sequences for the BA399 CPS heavy chain variable region of Anti-IL-6 Ab BA399 HC13 DNA to HC18 DNA (SEQ ID NOs: 110. 111, 112, 113, 114 and 115, respectively).

FIG. 23 shows nucleic acid sequences for the BA399 CPS heavy chain variable region of Anti-IL-6 Ab BA399 HC19 DNA to HC24 DNA (SEQ ID NOs: 116, 117, 118, 119, 120 and 121, respectively).

FIG. 24 shows nucleic acid sequences for the BA399 CPS heavy chain variable region of Anti-IL-6 Ab BA399 HC25 DNA to HC30 DNA (SEQ ID NOs: 122, 123, 124, 125, 126 and 127, respectively).

FIG. 25 shows nucleic acid sequences for the BA399 CPS heavy chain variable region of Anti-IL-6 Ab BA399 HC31 DNA and HC32 DNA (SEQ ID NOs: 128 and 129, respectively); and amino acid sequences for the heavy chain variable region of Anti-IL-6 Ab BA399 HC01 PRO to HC06 PRO (SEQ ID NOs: 3, 130, 131, 132, 133 and 134, respectively).

FIG. 26 shows amino acid sequences for the BA399 CPS heavy chain variable region of Anti-IL-6 Ab BA399 HC07 PRO to HC15 PRO (SEQ ID NOs: 135, 136, 137, 138, 139, 140, 141, 142 and 143, respectively).

FIG. 27 shows amino acid sequences for the BA399 CPS heavy chain variable region of Anti-IL-6 Ab BA399 HC16 PRO to HC25 PRO (SEQ ID NOs: 144, 145, 146, 147, 148, 149, 150, 151, 152 and 153 respectively).

FIG. 28 shows amino acid sequences for the BA399 CPS heavy chain variable region of Anti-IL-6 Ab BA399 HC26 PRO to HC32 PRO (SEQ ID NOs: 154, 155, 156, 157, 158, 159 and 160 respectively).

FIG. 33 shows a table with dissociation constants ($K_d$) from Sapidyne KinExA® kinetic exclusion analysis of Anti-IL-6 Mab clones BA003(CNTO136), and BAP001 clone 1 to BAP001 clone 10 which were produced by affinity maturation of Anti-IL-6 Ab BA399.

FIG. 34 shows a table with binding data from BiaCore analysis of Anti-IL-6 Ab clones BA399-2, BA399-5, BA399-9 and BA399-10 which were produced by affinity maturation of Anti-IL-6 Ab BA399.

FIG. 36 shows inhibition of Stat3 phosphorylation in THP-1 cells stimulated by IL-6/sIL-6R by various anti-IL6 Mabs including 003, BA399, BA399-2 and BA399-9(A) using 100 ng/mL IL-6. A Western blot for total Stat3 for each condition is shown in (B).

FIG. 37 shows inhibition of Stat3 phosphorylation in THP-1 cells stimulated by IL-6/sIL-6R by various anti-IL6 Mabs including 003, BA399, BA399-2 and BA399-5 in (A) using 10 ng/mL IL-6. A Western blot for total Stat3 for each condition is shown in (B).

FIG. 38 shows inhibition of Stat3 phosphorylation in THP-1 cells stimulated by IL-6/sIL-6R by various anti-IL6 Mabs including BA003, BA399, BA399-2 and BA399-9 in (A) using 10 ng/mL IL-6. A Western blot for total Stat3 for each condition is shown in (B).

FIG. 44 shows the combinations of light chains and heavy chains utilized in the top 10 clones from CPS affinity maturation of BA399 anti-IL-6 Mab. Corresponding amino acid sequences and SEQ ID NOs for the light chains and heavy chains can be found in FIGS. 17-19 and FIGS. 25-28, respectively.

DETAILED DESCRIPTION OF THE INVENTION

Citations

Figure 10:
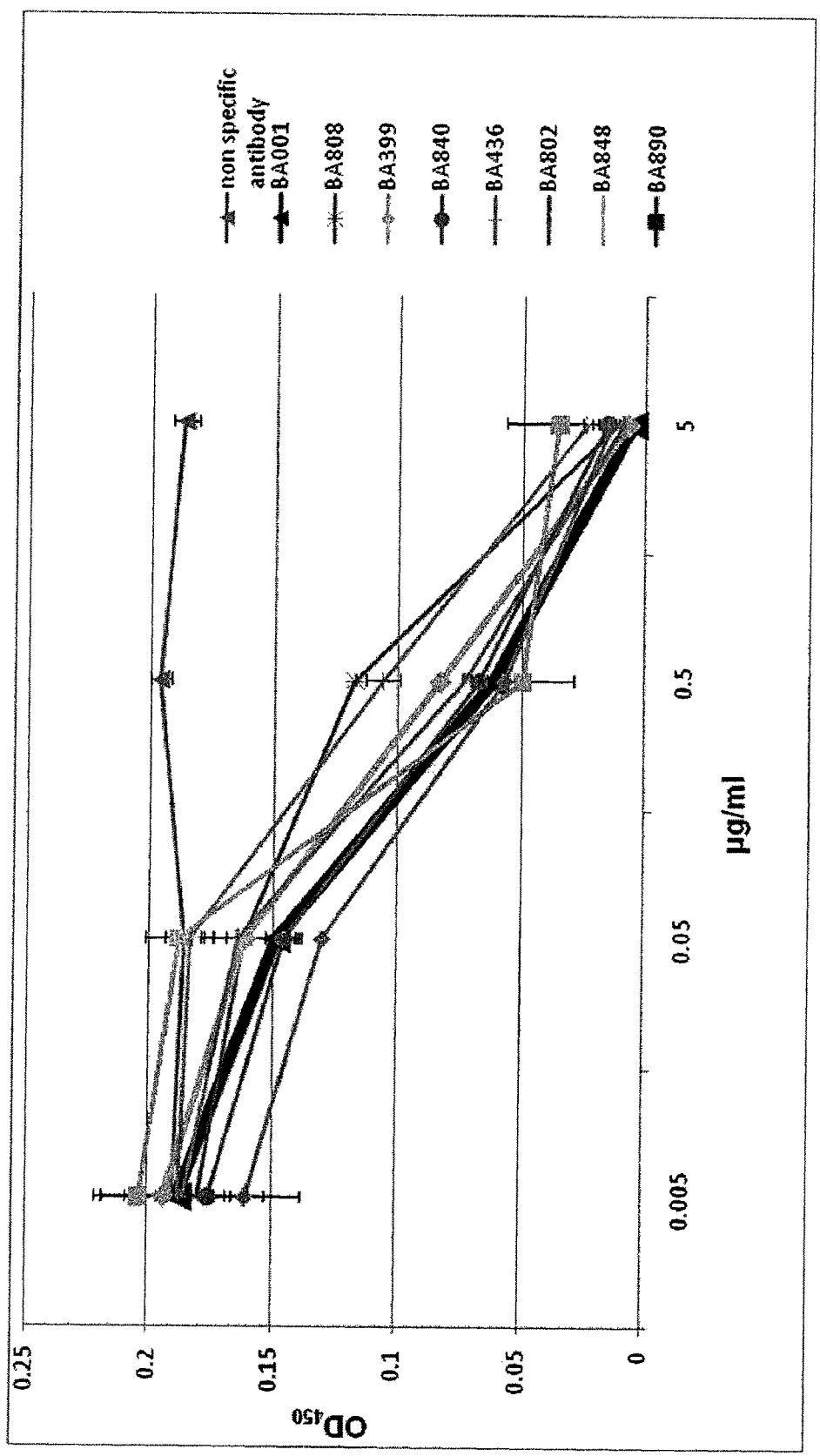
FIG. 10 shows competition ELISA analysis of BA001 and Anti-IL-6 Antibodies of the invention.

All publications or patents cited herein are entirely incorporated herein by reference as they show the state of the art at the time of the present invention and/or to provide description and enablement of the present invention. Publications refer to any scientific or patent publications, or any other information available in any media format, including all recorded, electronic or printed formats. The following references are entirely incorporated herein by reference: Ausubel, et al., ed., Current Protocols in lecular Biology, John Wiley & Sons, Inc., NY, N.Y. (1987-2001); Sambrook, et al., Molecular Cloning: A Laboratory Manual, 2.sup.nd Edition, Cold Spring Harbor, N.Y. (1989); Harlow and Lane, Antibodies, a Laboratory Manual, Cold Spring Harbor, N.Y. (1989); Colligan, et al., eds., Current Protocols in Immunology, John Wiley & Sons, Inc., NY (1994-2001); Colligan et al., Current Protocols in Protein Science, John Wiley & Sons, NY, N.Y., (1997-2001).

Amino Acid Codes

The amino acids that make up anti-IL-6 antibodies of the present invention are often abbreviated. The amino acid designations can be indicated by designating the amino acid by its single letter code, its three letter code, name, or three nucleotide codon(s) as is well understood in the art (see Alberts, B., et al., Molecular Biology of The Cell, Third Ed., Garland Publishing, Inc., New York, 1994).

Definitions

As used herein, an "Anti-Interleukin-6 antibody," "Anti-IL-6 antibody," "Anti-IL-6 antibody portion," or "Anti-IL-6 antibody fragment" and/or "Anti-IL-6 antibody variant" and the like include any protein or peptide containing molecule that comprises at least a portion of an immunoglobulin molecule, containing at least one complementarity determining region (CDR) of a heavy or light chain or a ligand binding portion thereof derived from at least one of the BA399, BA436, BA802, BA808, BA840, BA848, BA890 or BA939 humanized monoclonal antibodies, in combination with a heavy chain or light chain variable region, a heavy chain or light chain constant region, a framework region, or any portion thereof, of non-murine origin, preferably of human origin, which can be incorporated into an antibody of the present invention. Alternatively, the term "Anti-IL-6 antibody" shall refer collectively or individually to the humanized monoclonal antibodies BA399, BA436, BA802, BA808, BA840, BA848, BA890 and BA939. Such antibody is capable of modulating, decreasing, antagonizes, mitigates, alleviates, blocks, inhibits, abrogates and/or interferes with at least one IL-6 activity or binding, or with IL-6 receptor activity or binding, in vitro, in situ and/or in vivo. As a non-limiting example, a suitable Anti-IL-6 antibody, specified portion or variant of the present invention can bind with high affinity to an inhibiting and/or neutralizing epitope of human IL-6 recognized by at least one of BA399, BA436, BA802, BA808, BA840, BA848, BA890 or BA939 monoclonal antibody. A suitable Anti-IL-6 antibody, specified portion, or variant can also optionally affect at least one of IL-6 activity or function, such as but not limited to, RNA, DNA or protein synthesis, IL-6 release, IL-6 receptor signaling, membrane IL-6 cleavage, IL-6 activity, IL-6 production and/or synthesis.

The term "antibody" is further intended to encompass antibodies, digestion fragments, specified portions and variants thereof, including antibody mimetics or comprising portions of antibodies that mimic the structure and/or function of an antibody or specified fragment or portion thereof, including single chain antibodies and fragments thereof, each containing at least one CDR derived from an Anti-IL-6. Functional fragments include antigen-binding fragments that bind to a mammalian IL-6. For example, antibody fragments capable of binding to IL-6 or portions thereof, including, but not limited to Fab (e.g., by papain digestion), Fab' (e.g., by pepsin digestion and partial reduction) and F(ab')$_2$ (e.g., by pepsin digestion), facb (e.g., by plasmin digestion), pFc' (e.g., by pepsin or plasmin digestion), Fd (e.g., by pepsin digestion, partial reduction and reaggregation), Fv or scFv (e.g., by molecular biology techniques) fragments, are encompassed by the invention (see, e.g., Colligan, Immunology, supra).

Antibody fragments can be produced by enzymatic cleavage, synthetic or recombinant techniques, as known in the art and/or as described herein. Antibodies can also be produced in a variety of truncated forms using antibody genes in which one or more stop codons have been introduced upstream of the natural stop site. For example, a combination gene encoding a F(ab')$_2$ heavy chain portion can be designed to include DNA sequences encoding the $CH_1$ domain and/or hinge region of the heavy chain. The various portions of antibodies can be joined together chemically by conventional techniques, or can be prepared as a contiguous protein using genetic engineering techniques.

As used herein "chimeric" antibodies or "humanized" antibodies or "CDR-grafted" include any combination of the herein described Anti-IL-6 Abs, or any CDR derived therefrom combined with one or more proteins or peptides derived from a non-murine, preferably, human antibody. In accordance with the invention, chimeric or humanized antibodies include those wherein the CDR's are derived from one or more of the Anti-IL-6 Abs described herein and at least a portion, or the remainder of the antibody is derived from one or more human antibodies. Thus, the human part of the antibody may include the framework, $C_L$, $C_H$ domains (e.g., $C_{H1}$, $C_{H2}$, $C_{H3}$), hinge, ($V_L$, $V_H$)) regions which are substantially non-immunogenic in humans. The regions of the antibody that are derived from human antibodies need not have 100% identity with human antibodies. In a preferred embodiment, as many of the human amino acid residues as possible are retained in order for the immunogenicity to be negligible, but the human residues may be modified as necessary to support the antigen binding site formed by the CDR's while simultaneously maximizing the humanization of the antibody. Such changes or variations optionally and preferably retain or reduce the immunogenicity in humans or other species relative to non-modified antibodies. It is pointed out that a humanized antibody can be produced by a non-human animal or prokaryotic or eukaryotic cell that is capable of expressing functionally rearranged human immunoglobulin (e.g., heavy chain and/or light chain) genes. Further, when the antibody is a single chain antibody, it can comprise a linker peptide that is not found in native human antibodies. For example, an Fv can comprise a linker peptide, such as two to about eight glycine or other amino acid residues, which connects the variable region of the heavy chain and the variable region of the light chain. Such linker peptides are considered to be of human origin.

Antibody humanization can be performed by, for example, synthesizing a combinatorial library comprising the six CDRs of a non-human target monoclonal antibody fused in frame to a pool of individual human frameworks. A human framework library that contains genes representative of all known heavy and light chain human germline genes can be utilized. The resulting combinatorial libraries can then be screened for binding to antigens of interest. This approach can allow for the selection of the most favorable combinations of fully human frameworks in terms of maintaining the binding activity to the parental antibody. Humanized antibodies can then be further optimized by a variety of techniques.

Antibody Humanization can be used to evolve mouse or other non-human antibodies into "fully human" antibodies. The resulting antibody contains only human sequence and no mouse or non-human antibody sequence, while maintaining similar binding affinity and specificity as the starting antibody.

The term "Comprehensive Positional Evolution" (CPE™) is used to describe an antibody evolution technology platform that can be used to combine comprehensive mutagenesis, shuffling and synthesis technologies to enhance single or multiple antibody properties and binding characteristics. The CPE platform allows for the comprehensive mapping of the in vivo effects of every individual codon change within the protein for all 63 potential codon changes at each position within the protein. This comprehensive mutagenesis technology rapidly generates antibody variants by testing amino acid changes at every position along an antibody variable domain's sequence.

The term "Combinatorial Protein Synthesis" (CPS™) is used to describe combinatorial protein synthesis technologies that can be used to optimize the desired characteristics of antibodies by combining their best properties into a new, high-performance antibody. CPS™ can be used following CPE™ and can allow for the subsequent generation and in vivo selection of all permutations of improved individual codons for identification of the optimal combination or set of codon changes within a protein or antibody. The combination of these technologies can significantly expand the pool of antibody variants available to be screened and it significantly increases the probability of finding antibodies with single or multiple enhanced characteristics such as binding affinity, specificity, thermo-stability, expression level, effector function, glycosylation, and solubility.

For full length antibody molecules, the immunoglobulin genes can be obtained from genomic DNA or mRNA of hybridoma cell lines. Antibody heavy and light chains are cloned in a mammalian vector system. Assembly is documented with double strand sequence analysis. The antibody construct can be expressed in other human or mammalian host cell lines. The construct can then be validated by transient transfection assays and Western blot analysis of the expressed antibody of interest. Stable cell lines with the highest productivity can be isolated and screened using rapid assay methods.

The term "affinity maturation" refers to the increase in average affinity of an immune response for an antigen. In nature, it can occur after repeated exposure to an antigen. A particularly preferred type of substitutional variant involves substituting one or more hypervariable region residues of a parent antibody (e.g. human antibody). Generally, the resulting variant(s) selected for further development will have improved biological properties relative to the parent antibody from which they are generated. A convenient way for generating such substitutional variants involves affinity maturation using techniques described herein or other techniques known to one of skill in the art, for example, phage display (Schier R., J. Mol. Biol., 263:551-67, 1996). The variants are then screened for their biological activity (e.g. binding affinity) as described herein, e.g. Biacore analysis. In order to identify hypervariable region residues which would be good candidates for modification, alanine scanning mutagenesis can be performed to identify hypervariable region residues contributing significantly to antigen binding. Antibodies with superior properties in one or more relevant assays can undergo further development.

An "effective amount" is an amount of anti-IL6 antibody or fragment which is effective to treat or prevent a condition in a living organism to whom it is administered over some period of time, e.g., provides a therapeutic effect during a desired dosing interval.

The term "treating" includes: (1) preventing or delaying the appearance of clinical symptoms of the state, disorder or condition developing in an animal that may be afflicted with or predisposed to the state, disorder or condition but does not yet experience or display clinical or subclinical symptoms of the state, disorder or condition; (2) inhibiting the state, disorder or condition (i.e., arresting, reducing or delaying the development of the disease, or a relapse thereof in case of maintenance treatment, of at least one clinical or subclinical symptom thereof); and/or (3) relieving the condition (i.e., causing regression of the state, disorder or condition or at least one of its clinical or subclinical symptoms). The benefit to a patient to be treated is either statistically significant or at least perceptible to the patient or to the physician.

As used herein in connection with a measured quantity, the term "about" refers to the normal variation in that measured quantity that would be expected by the skilled artisan making the measurement and exercising a level of care commensurate with the objective of the measurement and the precision of the measuring equipment used. Unless otherwise indicated, "about" refers to a variation of +/−10% of the value provided.

Antibodies of the Present Invention

In accordance with the present invention, the Anti-IL-6 antibodies comprise any one of BA399, BA436, BA802, BA808, BA840, BA848, BA890 or BA939 antibodies or an antibody in which the variable region or CDRs are derived from any one of BA399, BA436, BA802, BA808, BA840, BA848, BA890 or BA939 antibody and the framework and constant regions of the antibody are derived from one or more human antibodies. The variable region or CDRs derived from the antibody preferably have from about 90% to about 100% identity with the variable region or CDRs of any one of BA399, BA436, BA802, BA808, BA840, BA848, BA890 or BA939 antibody, although any and all modifications, including substitutions, insertions and deletions, are contemplated so long as the chimeric antibody maintains the ability to bind to and inhibit IL-6. The regions of the chimeric, humanized or CDR-grafted antibodies that are derived from human antibodies need not have 100% identity with the human antibodies. In a preferred embodiment, as many of the human amino acid residues as possible are retained in order that immunogenicity is negligible, but the human residues, in particular residues of the framework region, are substituted as required and as taught herein below in accordance with the present invention. Such modifications as disclosed herein are necessary to support the antigen binding site formed by the CDRs while simultaneously maximizing the humanization of the antibody.

Figure 30:
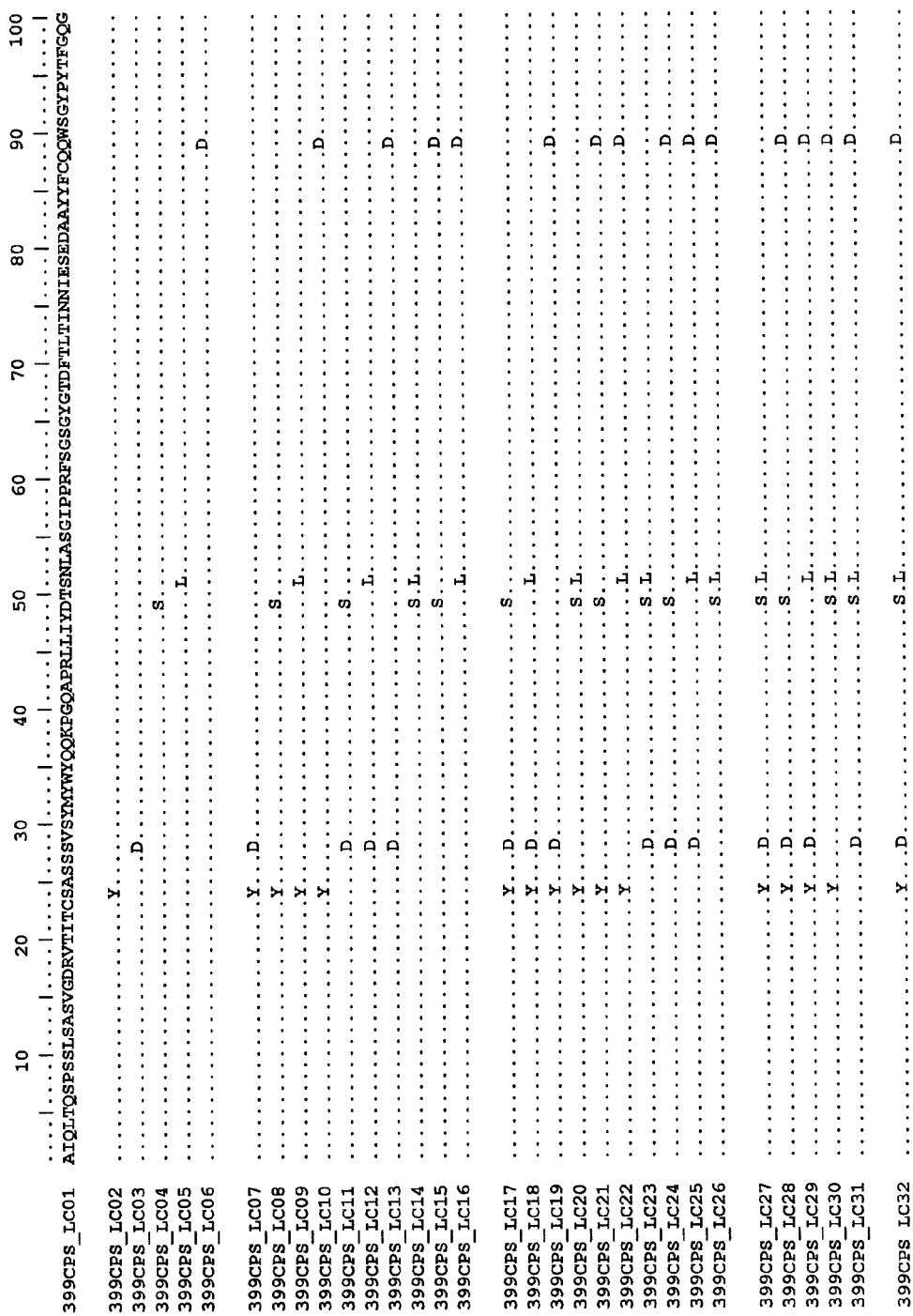
FIG. 30 shows a comparison of the amino acid sequences of 399CPS LC01 to 399CPS LC32 (SEQ ID NOs: 1, 68, 69, 70 . . . 98, respectively) from affinity maturation by combinatorial protein synthesis (CPS) of the light chain variable region of Anti-IL-6 Ab BA399. Full sequences and corresponding SEQ ID NOs are shown in FIGS. 17-19.
Figure 31:
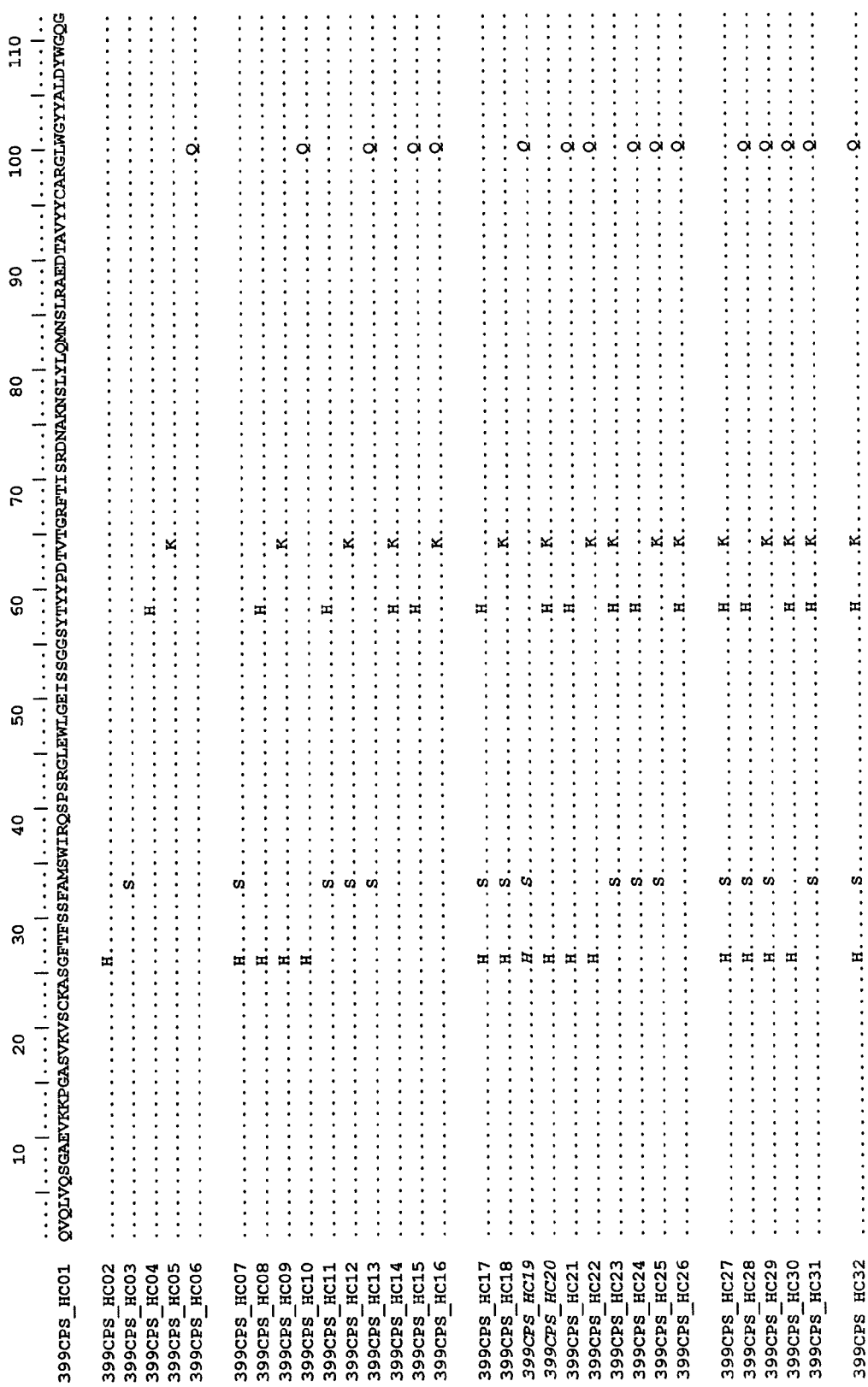
FIG. 31 shows a comparison of the amino acid sequences of 399CPS HC01 to 399CPS HC32 (SEQ ID NOs: 3, 130, 131, 132 . . . 160, respectively) from affinity maturation by combinatorial protein synthesis (CPS) of the heavy chain variable region of Anti-IL-6 Ab BA399. Full sequences and corresponding SEQ ID NOs are shown in FIGS. 25-28.

In accordance with the present invention, the nucleic acid sequences and the deduced amino acid sequences of the variable regions (light and heavy chain) of the Anti-IL-6 Abs are set forth in FIGS. 1-8. The sequences of BA001 light and heavy chain variable regions are set forth in FIG. 9. The nucleic acid and amino acid sequences of light and heavy chain variable regions from affinity maturation of BA399 are shown in FIGS. 12-28, The sequences of light and heavy chain variable regions are compared in FIGS. 30 and 31, respectively. Each of the heavy and light chain variable regions contain three CDRs that combine to form the antigen binding site. The three CDRs are surrounded by four FR regions that primarily function to support the CDRs. The sequences of the CDRs within the sequences of the variable regions of the heavy and light chains can be identified by computer-assisted alignment according to Kabat et al. (1987) in Sequences of Proteins of Immunological Interest, 4$^{th}$ ed., United States Department of Health and Human Services, U.S. Government Printing Office, Washington, D.C., or by molecular modeling of the variable regions, for example utilizing the ENCAD program as described by Levitt (1983) J. Mol. Biol. 168:595.

In a preferred embodiment the CDRs are derived from any one of BA399, BA436, BA802, BA808, BA840, BA848, BA890 or BA939. Determination of the heavy chain CDRs and light chain CDRs is well within the skill of one in the art. See, for example, the website of bioinf.org.uk/abs/.

The sequences of the CDRs of the Anti-IL-6 antibody may be modified by insertions, substitutions and deletions to the extent that the CDR-grafted antibody maintains the ability to bind to and inhibit human Il-6. The ordinarily skilled artisan can ascertain the maintenance of this activity by performing the functional assays described herein below.

Alternatively, the entire heavy chain variable region and light chain variable region of any one of BA399, BA436, BA802, BA808, BA840, BA848, BA890 or BA939 may be combined with the human constant and framework regions to form the chimeric antibody of the present invention. In one aspect, the variable light chain and heavy chain amino acid sequences utilized for the top ten clones of anti-IL6 Mab BA399 from affinity maturation are disclosed in FIG. 44. Clone BA399-01 comprises light chain BA399CPS-LC06 (SEQ ID NO: 72) and heavy chain BA399CPS-HC-06 (SEQ ID NO: 134). Clone BA399-02 comprises light chain BA399CPS-LC02 (SEQ ID NO: 68) and heavy chain BA399CPS-25 (SEQ ID NO: 153). Clone BA399-03 comprises light chain BA399CPS-LC05 (SEQ ID NO: 71) and heavy chain BA399CPS-HC21 (SEQ ID NO: 149). Clone BA399-04 comprises light chain BA399CPS-LC06 (SEQ ID NO: 72) and heavy chain BA399CPS-HC13 (SEQ ID NO: 141). Clone BA399-05 comprises light chain BA399CPS-LC10 (SEQ ID NO: 76) and heavy chain BA399CPS-HC16 (SEQ ID NO: 144). Clone BA399-06 comprises light chain BA399CPS-LC22 (SEQ ID NO: 88) and heavy chain BA399CPS-HC24 (SEQ ID NO:152). Clone BA399-07 comprises light chain BA399CPS-LC14 (SEQ ID NO: 80) and heavy chain BA399CPS-HC19 (SEQ ID NO: 147). Clone BA399-08 comprises light chain BA399CPS-LC10 (SEQ ID NO: 76) and heavy chain BA399CPS-HC12 (SEQ ID NO: 140). Clone BA399-09 comprises light chain BA399CPS-LC09 (SEQ ID NO: 75) and heavy chain BA399CPS-HC24 (SEQ ID NO: 152). Clone BA399-10 comprises light chain BA399CPS-LC09 (SEQ ID NO: 75) and heavy chain BA399CPS-HC28 (SEQ ID NO: 156).

Human genes which encode the constant (C) regions of the humanized antibodies, fragments and regions of the present invention can be derived from a human fetal liver library, by known methods. Human C region genes can be derived from any human cell including those which express and produce human immunoglobulins. The human $C_H$ region can be derived from any of the known classes or isotypes of human H chains, including y, a, δ, ε, and subtypes thereof, such as G1, G2, G3 and G4. Since the H chain isotype is responsible for the various effector functions of an antibody, the choice of $C_H$ region will be guided by the desired effector functions, such as complement fixation, or activity in antibody-dependent cellular cytotoxicity (ADCC). Preferably, the $C_H$ region is derived from gamma 1 (IgG1).

The human $C_L$ region can be derived from either human L chain isotype, kappa or lambda, preferably kappa.

Genes encoding human immunoglobulin C regions are obtained from human cells by standard cloning techniques (Sambrook, et al. (Molecular Cloning: A Laboratory Manual, 2$^{nd}$ Edition, Cold Spring Harbor Press, Cold Spring Harbor, N.Y. (1989) and Ausubel et al., eds. Current Protocols in Molecular Biology (1987-1993)). Human C region genes are readily available from known clones containing genes representing the two classes of L chains, the five classes of H chains and subclasses thereof. Chimeric antibody fragments, such as F(ab$^1$)$_2$ and Fab, can be prepared by designing a chimeric H chain gene which is appropriately truncated. For example, a chimeric gene encoding an H chain portion of an F(ab$^1$)$_2$ fragment would include DNA sequences encoding the CH1 domain and hinge region of the H chain, followed by a translational stop codon to yield the truncated molecule.

Generally, in one example, humanized antibodies, fragments and regions of the present invention are produced by cloning DNA segments encoding the H and L chain antigen-binding regions of the Anti IL-6 specific antibody, and joining these DNA segments to DNA segments including $C_H$ and $C_L$ regions, respectively, to produce full length chimeric immunoglobulin-encoding genes.

The sequences of the variable regions of the antibody may be modified by insertions, substitutions and deletions to the extent that the chimeric antibody maintains the ability to bind to and inhibit human IL-6. The ordinarily skilled artisan can ascertain the maintenance of this activity by performing the functional assays described hereinbelow. The variable regions can have, for example, from about 50% to about 100% homology to the variable regions of SEQ ID NOS: 1-32. In a preferred embodiment, the variable regions of the antibody have from about 80% to about 100% homology to the variable regions of SEQ ID NOS: 1-32 and 37-160. In a more preferred embodiment the variable regions have from about 90% to about 100% homology to the variable regions of SEQ ID NOS: 1-32 and 37-160.

In one specific aspect, preferred anti-IL-6 Mabs of the disclosure comprise variable light chain regions having 95%, 96%, 97%, 98% or 99% amino acid sequence homology to SEQ ID NO: 1 and further comprise variable heavy chain regions having 95%, 96%, 97%, 98% or 99% amino acid sequence homology to SEQ ID NO: 3.

In one specific aspect, preferred anti-IL-6 Mabs of the disclosure comprise a variable light chain region selected from one of SEQ ID NO: 68-98. In a further specific aspect, preferred anti-IL-6 Mabs of the disclosure comprise a variable light chain region selected from one of SEQ ID NO: 68, 71, 72, 75, 76, 80 and 88.

In another specific aspect, preferred anti-IL-6 Mabs of the disclosure comprise a variable heavy chain region selected from one of SEQ ID NO: 130-160. In a further specific aspect, preferred anti-IL-6 Mabs of the disclosure comprise a variable heavy chain region selected from one of SEQ ID NO: 134, 140, 141, 144, 147, 149, 152, 153 and 156.

Methods for engineering or humanizing non-human or human antibodies can be used and are well known in the art. Generally, a humanized or engineered antibody has one or more amino acid residues from a source which is non-human, e.g., but not limited to mouse, rat, rabbit, non-human primate or other mammal. These human amino acid residues are often referred to as "import" residues, which are typically taken from an "import" variable, constant or other domain of a known human sequence. Known human Ig sequences are disclosed, e.g., at the following websites of the following: ncbi.nlm.nih.gov/entrez/query.fcgi; atcc.org/phage/hdb.html; sciquest.com/; abcam.com/; antibodyresource. com/onlinecomp.html; public.iastate.eduLabout.pedro/research_tools.html; mgen.uni-heidelberg.de/SD/IT/IT.html; whfreeman.com/immunology/CH05/kuby05.htm; library.thinkquest.org/12429/Immune/Antibody.html; hhmi.org/grants/lectures/1996/vlab/; path.cam.ac. uk/.about.mrc7/mikeimages.html; antibodyresource.com/; mcb.harvard.edu/BioLinks/Immunology.html. immunolo-gylink.com/; pathbox.wustl.edu/.about.hcenter/index.html; biotech.ufl.eduLabout.hcl/; pebio.com/pa/340913/ 340913.html; nal.usda.gov/awic/pubs/antibody/; m.ehime-u.ac.jp/.about.yasuhito/Elisa.html; biodesign.com/table.asp; icnet.uk/axp/facs/davies/links.html; biotech.ufl. edu/.about.fccl/protocol.html; isac-net.org/sites_geo.html; aximtLimtuni-marburg.deLaboutrek/AEPStart.html; baser-v.uci.kun.nl/.about.jraats/linksl.html; recab.uni-hd.de/immuno.bme.nwvu.edu/; mrc-cpe.cam.ac.uk/imt-doc/public/IN-TRO.html; ibt.unam.mx/vir/V_mice.html; imgt.cnusc.fr: 8104/; biochem.ucl.ac.uk/.about.martin/abs/index.html; antibody.bath.ac.uk/; abgen.cvm.tamu.edu/lab/wwwab-gen.html; unizh.chLabouthonegger/AHOseminar/ Slide01.html; cryst.bbk.ac.uk/.aboutubcg07s/; nimr.mr-c.ac.uk/CC/ccaewg/ccaewg.htm; path.cam.ac.uk/.about. mrc7/humanisation/TAHHP.html; ibt.unam.mx/vir/structure/stat_aim.html; biosci.missouri.edu/smithgp/index.html; cryst.bioc.cam.ac.uk/.about.fmolina/Web-pages/Pept/spot-tech.html; jerini.de/fr_products.htm; patents.ibm.con/ ibm.html. Kabat et al. Sequences of Proteins of Immunological Interest, U.S. Dept. Health (1983), each entirely incorporated herein by reference.

Such imported sequences can be used to reduce immunogenicity or reduce, enhance or modify binding, affinity, on-rate, off-rate, avidity, specificity, half-life, or any other suitable characteristic, as known in the art. Generally part or all of the non-human or human CDR sequences are maintained while the non-human sequences of the variable and constant regions are replaced with human or other amino acids. Antibodies can also optionally be humanized with retention of high affinity for the antigen and other favorable biological properties. To achieve this goal, humanized antibodies can be optionally prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immuno- globulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen(s), is achieved. In general, the CDR residues are directly and most substantially involved in influencing antigen binding. Humanization or engineering of antibodies of the present invention can be performed using any known method, such as but not limited to those described in, Winter (Jones et al., Nature 321:522 (1986); Riechmann et al., Nature 332:323 (1988); Verhoeyen et al., Science 239:1534 (1988)), Sims et al., J. Immunol. 151: 2296 (1993); Chothia and Lesk, J. Mol. Biol. 196:901 (1987), Carter et al., Proc. Natl. Acad. Sci. U.S.A. 89:4285 (1992); Presta et al., J. Immunol. 151:2623 (1993), U.S. Pat. Nos. 5,723,323, 5,976, 862, 5,824,514, 5,817,483, 5,814,476, 5,763,192, 5,723,323, 5,766,886, 5,714,352, 6,204,023, 6,180,370, 5,693,762, 5,530,101, 5,585,089, 5,225,539; 4,816,567, PCT/: US98/ 16280, US96/18978, US91/09630, US91/05939, US94/ 01234, GB89/01334, GB91/01134, GB92/01755; WO90/ 14443, WO90/14424, WO90/14430, EP 229246, each entirely incorporated herein by reference, included references cited therein.

The human constant region of the humanized antibody of the invention can be of any class (IgG, IgA, IgM, IgE, IgD, etc.) or isotype and can comprise a kappa or lambda light chain. In one embodiment, the human constant region comprises an IgG heavy chain or defined fragment, for example, at least one of isotypes, IgG1, IgG2, IgG3 or IgG4. In another embodiment, the anti-human IL-6 human antibody comprises an IgG1 heavy chain and a IgG1 K light chain. The isolated anti-IL-6 antibodies of the present invention comprise antibody amino acid sequences disclosed herein encoded by any suitable polynucleotide as well as. Preferably, the antibody or antigen-binding fragment binds human IL-6 and, thereby partially or substantially neutralizes at least one biological activity of the protein. The antibody, or specified portion or variant thereof, partially or preferably substantially neutralizes at least one biological activity of at least one IL-6 protein or fragment and thereby inhibit activities mediated through the binding of IL-6 to the IL-6 receptor or through other IL-6-dependent or mediated mechanisms. As used herein, the term "neutralizing antibody" refers to an antibody that can inhibit an IL-6-dependent activity by about 20-120%, preferably by at least about 10, 20, 30, 40, 50, 55, 60, 65, 70, 75, 80, 85, 90, 91, 92, 93, 94, 95, 96, 97, 98, 99, 100% or more depending on the assay. The capacity of an Anti-IL-6 antibody to inhibit an IL-6-dependent activity is preferably assessed by at least one suitable IL-6 protein or receptor assay, as described herein and/or as known in the art.

At least one antibody of the invention binds at least one specified epitope specific to at least one IL-6 protein, subunit, fragment, portion or any combination thereof. The at least one epitope can comprise at least one antibody binding region that comprises at least one portion of the protein, which epitope is preferably comprised of at least one extracellular, soluble, hydrophillic, external or cytoplasmic portion of the protein. Generally, the human antibody or antigen-binding fragment of the present invention will comprise an antigen-binding region that comprises at least one human complementarity determining region (CDR1, CDR2 and CDR3) or variant of at least one heavy chain variable region and at least one human complementarity determining region (CDR4, CDR5 and CDR6) or variant of at least one light chain variable region, derived from an anti-IL-6 Ab described herein. In a particular embodiment, the antibody or antigen-binding fragment can have an antigen-binding region that comprises at least a portion of at least one heavy chain CDR (i.e., CDR1, CDR2 and/or CDR3) having the amino acid sequence of the corresponding CDRs 1, 2 and/or 3. In another particular embodiment, the antibody or antigen-binding portion or variant can have an antigen-binding region that comprises at least a portion of at least one light chain CDR (i.e., CDR4, CDR5 and/or CDR6) having the amino acid sequence of the corresponding CDRs 4, 5 and/or 6. In a preferred embodiment the three heavy chain CDRs and the three light chain CDRs of the antibody or antigen-binding fragment have the amino acid sequence of the corresponding CDR of at least one of BA399, BA436, BA802, BA808, BA840, BA848, BA890 or BA939. Such antibodies can be prepared by chemically joining together the various portions (e.g., CDRs, framework) of the antibody using conventional techniques, by preparing and expressing a (i.e., one or more) nucleic acid molecule that encodes the antibody using conventional techniques of recombinant DNA technology or by using any other suitable method and using any of the possible redundant codons that will result in expression of a polypeptide of the invention.

Liquid phase synthesis of combinatorial variable domain humanized libraries for the light chain and the heavy chain can be employed. The assembly of a humanized light chain (LC) variable domain library, for example, contains human light chain frameworks (FW) and non-human complementarity determining regions (CDR). The library is assembled by, for example, by using stepwise liquid phase ligation of FW and CDR DNA fragments. The libraries are assembled by using stepwise liquid phase ligation of FW and CDR DNA fragments in the order of FW1—CDR1—FW2—CDR2—FW3—CDR3 by techniques known to one of skill in the art. For example, by the techniques of one or more of the following references, each of which is incorporated herein by reference. Lo, B. K., 2003, Antibody humanization by CDR grafting. Antibody Engineering, Methods and protocols. Edit by Benny K. C. Lo, Methods in Molecular Biology, 248, 135-159; Kashmiri et al., 2003, Developing a minimally immunogenic humanized antibody by SDR grafting. Antibody Engineering, Methods and protocols. Edit by Benny K. C. Lo, Methods in Molecular Biology, 248, 361-376; Bassette, P. H., et al., 2003, Construction of Designed Protein Libraries Using Gene Assembly Mutagenesis. Directed Evolution Library Creation, Methods and protocols. Edit. Arnold and Georgiou, Methods in Molecular Biology, 231, 29-37; Chames, P., et al., 2001, Selections on Biotinylated antigens. Antibody Engineering, Edit by R. Kontermann and S. Dubel, Springer Lab Manual, 149-166; O'Brien S., and Jones, T., 2001, Humanising antibodies by CDR grafting. Antibody Engineering, Edit by R. Kontermann and S. Dubel, Springer Lab Manual, 567-590.

Antibodies that bind to human IL-6 and that comprise the defined heavy or light chain variable region or CDR regions can be prepared using suitable methods, such as phage display (Katsube, Y., et al., Int J. Mol. Med, 1(5):863-868 (1998)) or methods that employ transgenic animals, as known in the art and/or as described herein. For example, the antibody, specified portion or variant can be expressed using the encoding nucleic acid or portion thereof in a suitable host cell.

As stated, the invention also relates to antibodies, antigen-binding fragments, immunoglobulin chains and CDRs comprising amino acids in a sequence that is substantially the same as an amino acid sequence described herein. Such Anti-IL-6 antibodies can include one or more amino acid substitutions, deletions or additions, either from natural mutations or human manipulation, as specified herein. Preferably, such antibodies or antigen-binding fragments and antibodies comprising such chains or CDRs can bind human IL-6 with high affinity (e.g., $K_D$ less than or equal to about $10^{-9}$ M). Amino acid sequences that are substantially the same as the sequences described herein include sequences comprising conservative amino acid substitutions, as well as amino acid deletions and/or insertions. A conservative amino acid substitution refers to the replacement of a first amino acid by a second amino acid that has chemical and/or physical properties (e.g., charge, structure, polarity, hydrophobicity/hydrophilicity) that are similar to those of the first amino acid. Conservative substitutions include replacement of one amino acid by another within the following groups: lysine (K), arginine (R) and histidine (H); aspartate (D) and glutamate (E); asparagine (N), glutamine (Q), serine (S), threonine (T), tyrosine (Y), K, R, H, D and E; alanine (A), valine (V), leucine (L), isoleucine (I), proline (P), phenylalanine (F), tryptophan (W), methionine (M), cysteine (C) and glycine (G); F, W and Y; C, S and T.

Of course, the number of amino acid substitutions a skilled artisan would make depends on many factors, including those described above. Generally speaking, the number of amino acid substitutions, insertions or deletions for any given Anti-IL-6 antibody, fragment or variant will not be more than 40, 30, 20, 19, 18, 17, 16, 15, 14, 13, 12, 11, 10, 9, 8, 7, 6, 5, 4, 3, 2, 1, such as 1-30 or any range or value therein, as specified herein.

Amino acids in an Anti-IL-6 antibody of the present invention that are essential for function can be identified by methods known in the art, such as site-directed mutagenesis or alanine-scanning mutagenesis (e.g., Ausubel, supra, Chapters 8, 15; Cunningham and Wells, Science 244:1081-1085 (1989)). The latter procedure introduces single alanine mutations at every residue in the molecule. The resulting mutant molecules are then tested for biological activity, such as, but not limited to at least one IL-6 neutralizing activity. Sites that are critical for antibody binding can also be identified by structural analysis such as crystallization, nuclear magnetic resonance or photoaffinity labeling (Smith, et al., J. Mol. Biol. 224:899-904 (1992) and de Vos, et al., Science 255:306-312 (1992)).

Anti-IL-6 antibodies of the present invention can include, but are not limited to, at least one portion, sequence or combination selected from 5 to all of the contiguous amino acids of at least one of CDRs derived from SEQ ID NOS: 1, 3, 5, 7, 9, 11, 13, 15, 17, 19, 21, 23, 25, 27, 29, 31, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, or 160.

An Anti-IL-6 antibody can further optionally comprise a polypeptide of at least one of 70-100% of the contiguous amino acids of the CDRs derived from at least one of SEQ ID NOS: 1, 3, 5, . . . 31. In one specific aspect, the anti-IL-6 antibody comprises a polypeptide of 95-99% sequence homology to SEQ ID NO: 1; preferably a CDR comprising one of SEQ ID NO: 68-98. In another specific aspect, the anti-IL-6 antibody comprises a polypeptide of 95-99% sequence homology to SEQ ID NO: 3; preferably a CDR comprising one of SEQ ID NO: 130-160.

In one embodiment, the amino acid sequence of an immunoglobulin chain, or portion thereof (e.g., variable region, CDR) has about 70-100% identity (e.g., 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or any range or value therein) to the amino acid sequence of at least one of SEQ ID NOS: 1, 3, 5, . . . 31. For example, the amino acid sequence of a light chain variable region can be compared with the sequence of SEQ ID NO: 1, 5, 9, 13, 17, 21, 25, 29. Preferably, 70-100% amino acid identity (i.e., 90, 91, 92, 93, 94, 95, 96, 97, 98, 99, 100 or any range or value therein) is determined using a suitable computer algorithm, as known in the art. In one specific aspect, the anti-IL-6 antibody comprises a polypeptide of 95-99% sequence homology to SEQ ID NO: 1; preferably a variable region comprising one of SEQ ID NO: 68-98. In another specific aspect, the anti-IL-6 antibody comprises a polypeptide of 95-99% sequence homology to SEQ ID NO: 3; preferably a variable region comprising one of SEQ ID NO: 130-160.

Exemplary heavy chain and light chain variable regions sequences are provided in SEQ ID NOS: 1, 3, 5, ... 31, 68-98, or 130-160. The antibodies of the present invention, or specified variants thereof, can comprise any number of contiguous amino acid residues from an antibody of the present invention, wherein that number is selected from the group of integers consisting of from 10-100% of the number of contiguous residues in an Anti-IL-6 antibody. Optionally, this subsequence of contiguous amino acids is at least about 10, 20, 30, 40, 50, 60, 70, 80, 90, 100, 110, 120, 130, 140, 150, 160, 170, 180, 190, 200, 210, 220, 230, 240, 250 or more amino acids in length, or any range or value therein. Further, the number of such subsequences can be any integer selected from the group consisting of from 1 to 20, such as at least 2, 3, 4, or 5.

As those of skill will appreciate, the present invention includes at least one biologically active antibody of the present invention. Biologically active antibodies have a specific activity at least 20%, 30%, or 40%, and preferably at least 50%, 60%, or 70%, and most preferably at least 80%, 90%, or 95%-100% of that of the native (non-synthetic), endogenous or related and known antibody. Methods of assaying and quantifying measures of enzymatic activity and substrate specificity, are well known to those of skill in the art.

In another aspect, the invention relates to human antibodies and antigen-binding fragments, as described herein, which are modified by the covalent attachment of an organic moiety. Such modification can produce an antibody or antigen-binding fragment with improved pharmacokinetic properties (e.g., increased in vivo serum half-life). The organic moiety can be a linear or branched hydrophilic polymeric group, fatty acid group, or fatty acid ester group. In particular embodiments, the hydrophilic polymeric group can have a molecular weight of about 800 to about 120,000 Daltons and can be a polyalkane glycol (e.g., polyethylene glycol (PEG), polypropylene glycol (PPG)), carbohydrate polymer, amino acid polymer or polyvinyl pyrolidone, and the fatty acid or fatty acid ester group can comprise from about eight to about forty carbon atoms.

The modified antibodies and antigen-binding fragments of the invention can comprise one or more organic moieties that are covalently bonded, directly or indirectly, to the antibody. Each organic moiety that is bonded to an antibody or antigen-binding fragment of the invention can independently be a hydrophilic polymeric group, a fatty acid group or a fatty acid ester group. As used herein, the term "fatty acid" encompasses mono-carboxylic acids and di-carboxylic acids. A "hydrophilic polymeric group," as the term is used herein, refers to an organic polymer that is more soluble in water than in octane. For example, polylysine is more soluble in water than in octane. Thus, an antibody modified by the covalent attachment of polylysine is encompassed by the invention. Hydrophilic polymers suitable for modifying antibodies of the invention can be linear or branched and include, for example, polyalkane glycols (e.g., PEG, monomethoxy-polyethylene glycol (mPEG), PPG and the like), carbohydrates (e.g., dextran, cellulose, oligosaccharides, polysaccharides and the like), polymers of hydrophilic amino acids (e.g., polylysine, polyarginine, polyaspartate and the like), polyalkane oxides (e.g., polyethylene oxide, polypropylene oxide and the like) and polyvinyl pyrolidone. Preferably, the hydrophilic polymer that modifies the antibody of the invention has a molecular weight of about 800 to about 150,000 Daltons as a separate molecular entity. For example $PEG_{5000}$ and $PEG_{20,000}$, wherein the subscript is the average molecular weight of the polymer in Daltons, can be used. The hydrophilic polymeric group can be substituted with one to about six alkyl, fatty acid or fatty acid ester groups. Hydrophilic polymers that are substituted with a fatty acid or fatty acid ester group can be prepared by employing suitable methods. For example, a polymer comprising an amine group can be coupled to a carboxylate of the fatty acid or fatty acid ester, and an activated carboxylate (e.g., activated with N,N-carbonyl diimidazole) on a fatty acid or fatty acid ester can be coupled to a hydroxyl group on a polymer.

Fatty acids and fatty acid esters suitable for modifying antibodies of the invention can be saturated or can contain one or more units of unsaturation. Fatty acids that are suitable for modifying antibodies of the invention include, for example, n-dodecanoate ($C_{12}$, laurate), n-tetradecanoate ($C_{14}$, myristate), n-octadecanoate ($C_{18}$, stearate), n-eicosanoate ($C_{20}$, arachidate), n-docosanoate ($C_{22}$, behenate), n-triacontanoate ($C_{30\text{-}}$), n-tetracontanoate ($C_{40\text{-}}$), cis-δ 9-octadecanoate ($C_{18}$, oleate), all cis-δ 5,8,11,14-eicosatetraenoate ($C_{20}$, arachidonate), octanedioic acid, tetradecanedioic acid, octadecanedioic acid, docosanedioic acid, and the like. Suitable fatty acid esters include mono-esters of dicarboxylic acids that comprise a linear or branched lower alkyl group. The lower alkyl group can comprise from one to about twelve, preferably one to about six, carbon atoms.

The modified human antibodies and antigen-binding fragments can be prepared using suitable methods, such as by reaction with one or more modifying agents. A "modifying agent" as the term is used herein, refers to a suitable organic group (e.g., hydrophilic polymer, a fatty acid, a fatty acid ester) that comprises an activating group. An "activating group" is a chemical moiety or functional group that can, under appropriate conditions, react with a second chemical group thereby forming a covalent bond between the modifying agent and the second chemical group. For example, amine-reactive activating groups include electrophilic groups such as tosylate, mesylate, halo (chloro, bromo, fluoro, iodo), N-hydroxysuccinimidyl esters (NHS), and the like. Activating groups that can react with thiols include, for example, maleimide, iodoacetyl, acrylolyl, pyridyl disulfides, 5-thiol-2-nitrobenzoic acid thiol (TNB-thiol), and the like. An aldehyde functional group can be coupled to amine- or hydrazide-containing molecules, and an azide group can react with a trivalent phosphorous group to form phosphoramidate or phosphorimide linkages. Suitable methods to introduce activating groups into molecules are known in the art (see for example, Hernanson, G. T., Bioconjugate Techniques, Academic Press: San Diego, Calif. (1996)). An activating group can be bonded directly to the organic group (e.g., hydrophilic polymer, fatty acid, fatty acid ester), or through a linker moiety, for example a divalent $C_1$-$C_{12}$ group wherein one or more carbon atoms can be replaced by a heteroatom such as oxygen, nitrogen or sulfur. Suitable linker moieties include, for example, tetraethylene glycol, $—(CH_2)_3—$, $—NH—(CH_2)_6—NH—$, $—(CH_2)_2—NH—$ and $—CH_2—O—CH_2—CH_2—O—CH_2—CH_2—O—CH—NH—$. Modifying agents that comprise a linker moiety can be produced, for example, by reacting a mono-Boc-alkyldiamine (e.g., mono-Boc-ethylenediamine, mono-Boc-diaminohexane) with a fatty acid in the presence of 1-ethyl-3-(3-dimethylaminopropyl) carbodiimide (EDC) to form an amide bond between the free amine and the fatty acid carboxylate. The Boc protecting group can be removed from the product by treatment with trifluoroacetic acid (TFA) to expose a primary amine that can be coupled to another carboxylate as described, or can be reacted with maleic anhydride and the resulting product cyclized to produce an activated maleimido derivative of the fatty acid. (See, for example, Thompson, et al., WO 92/16221 the entire teachings of which are incorporated herein by reference.)

The modified antibodies of the invention can be produced by reacting a human antibody or antigen-binding fragment with a modifying agent. For example, the organic moieties can be bonded to the antibody in a non-site specific manner by employing an amine-reactive modifying agent, for example, an NHS ester of PEG. Modified human antibodies or antigen-binding fragments can also be prepared by reducing disulfide bonds (e.g., intra-chain disulfide bonds) of an antibody or antigen-binding fragment. The reduced antibody or antigen-binding fragment can then be reacted with a thiol-reactive modifying agent to produce the modified antibody of the invention. Modified human antibodies and antigen-binding fragments comprising an organic moiety that is bonded to specific sites of an antibody of the present invention can be prepared using suitable methods, such as reverse proteolysis (Fisch et al., Bioconjugate Chem., 3:147-153 (1992); Werlen et al., Bioconjugate Chem., 5:411-417 (1994); Kumaran et al., Protein Sci. 6(10):2233-2241 (1997); Itoh et al., Bioorg. Chem., 24(1): 59-68 (1996); Capellas et al., Biotechnol. Bioeng., 56(4):456-463 (1997)), and the methods described in Hermanson, G. T., Bioconjugate Techniques, Academic Press: San Diego, Calif. (1996).

The antibodies of the invention can bind human IL-6 with a wide range of affinities ($K_D$). In a preferred embodiment at least one human mAb of the present invention can optionally bind human IL-6 with high affinity. For example, a mAb can bind human IL-6 with a $K_D$ equal to or less than about $10^{-7}$ M, such as but not limited to, 0.1-9.9 (or any range or value therein) X $10^{-7}$, $10^{-8}$, $10^{-9}$, $10^{-10}$, $10^{-11}$, $10^{-12}$, $10^{-13}$ or any range or value therein.

The affinity or avidity of an antibody for an antigen can be determined experimentally using any suitable method. (See, for example, Berzofsky, et al., "Antibody-Antigen Interactions," In Fundamental Immunology, Paul, W. E., Ed., Raven Press: New York, N.Y. (1984); Kuby, Janis Immunology, W. H. Freeman and Company: New York, N.Y. (1992); and methods described herein). The measured affinity of a particular antibody-antigen interaction can vary if measured under different conditions (e.g., salt concentration, pH). Thus, measurements of affinity and other antigen-binding parameters (e.g., $K_D$, $K_a$, $K_d$) are preferably made with standardized solutions of antibody and antigen, and a standardized buffer, such as the buffer described herein.

Anti-IL-6 antibodies useful in the methods and compositions of the present invention are characterized by high affinity binding to IL-6 and optionally and preferably having low toxicity. In particular, an antibody, specified fragment or variant of the invention, where the individual components, such as the variable region, constant region and framework, individually and/or collectively, optionally and preferably possess low immunogenicity, is useful in the present invention. The antibodies that can be used in the invention are optionally characterized by their ability to treat patients for extended periods with measurable alleviation of symptoms and low and/or acceptable toxicity. Low or acceptable immunogenicity and/or high affinity, as well as other suitable properties, can contribute to the therapeutic results achieved. "Low immunogenicity" is defined herein as raising significant HAHA, HACA or HAMA responses in less than about 75%, or preferably less than about 50% of the patients treated and/or raising low titres in the patient treated (less than about 300, preferably less than about 100 measured with a double antigen enzyme immunoassay) (Elliott et al., Lancet 344: 1125-1127 (1994), entirely incorporated herein by reference).

Bispecific, heterospecific, heteroconjugate or similar antibodies can also be used that are monoclonal, humanized, antibodies that have binding specificities for at least two different antigens. In the present case, one of the binding specificities is for at least one IL-6 protein, the other one is for any other antigen. Methods for making bispecific antibodies are known in the art. Traditionally, the recombinant production of bispecific antibodies is based on the co-expression of two immunoglobulin heavy chain-light chain pairs, where the two heavy chains have different specificities (Milstein and Cuello, Nature 305:537 (1983)). Because of the random assortment of immunoglobulin heavy and light chains, these hybridomas (quadromas) produce a potential mixture of 10 different antibody molecules, of which only one has the correct bispecific structure. The purification of the correct molecule, which is usually done by affinity chromatography steps, is rather cumbersome, and the product yields are low. Similar procedures are disclosed, e.g., in WO 93/08829, U.S. Pat. Nos. 6,210,668, 6,193,967, 6,132,992, 6,106,833, 6,060,285, 6,037,453, 6,010,902, 5,989,530, 5,959,084, 5,959,083, 5,932,448, 5,833,985, 5,821,333, 5,807,706, 5,643,759, 5,601,819, 5,582,996, 5,496,549, 4,676,980, WO 91/00360, WO 92/00373, EP 03089, Traunecker et al., EMBO J. 10:3655 (1991), Suresh et al., Methods in Enzymology 121: 210 (1986), each entirely incorporated herein by reference.

Nucleic Acid Molecules

Using the information provided herein, such as the nucleotide sequences encoding at least 70-100% of the contiguous amino acids of at least one of SEQ ID NOS: 1, 3, 5, . . . 31, 68-98, or 130-160 specified fragments, variants or consensus sequences thereof, or a deposited vector comprising at least one of these sequences, a nucleic acid molecule of the present invention encoding at least one Anti-IL-6 antibody can be obtained using methods described herein or as known in the art.

Nucleic acid molecules of the present invention can be in the form of RNA, such as mRNA, hnRNA, tRNA or any other form, or in the form of DNA, including, but not limited to, cDNA and genomic DNA obtained by cloning or produced synthetically, or any combinations thereof. The DNA can be triple-stranded, double-stranded or single-stranded, or any combination thereof. Any portion of at least one strand of the DNA or RNA can be the coding strand, also known as the sense strand, or it can be the non-coding strand, also referred to as the anti-sense strand.

Isolated nucleic acid molecules of the present invention can include nucleic acid molecules comprising an open reading frame (ORF), optionally with one or more introns, e.g., but not limited to, at least one specified portion of at least one CDR, as CDR1, CDR2 and/or CDR3 of at least one heavy chain (e.g., SEQ ID NOS: 4, 8, 12, 16, 20, 24, 28, 32, or 99-129) or light chain (e.g., SEQ ID NOS: 2, 6, 10, 14, 18, 22, 26, 30 or 37-67); nucleic acid molecules comprising the coding sequence for an anti-IL-6 antibody or variable region (e.g., SEQ ID NOS: 2, 4, 6 . . . 32, 37-67 or 99-129); and nucleic acid molecules which comprise a nucleotide sequence substantially different from those described above but which, due to the degeneracy of the genetic code, still encode at least one Anti-IL-6 antibody as described herein and/or as known in the art. Of course, the genetic code is well known in the art. Thus, it would be routine for one skilled in the art to generate such degenerate nucleic acid variants that code for specific Anti-IL-6 antibodies of the present invention. See, e.g., Ausubel, et al., supra, and such nucleic acid variants are included in the present invention. Non-limiting examples of isolated nucleic acid molecules of the present invention include SEQ ID NOS: 2, 4, 6 . . . 32, 37-67 or 99-129; corresponding to non-limiting examples of a nucleic acid encoding, respectively, HC CDR1, HC CDR2, HC CDR3, LC CDR1, LC CDR2, LC CDR3, HC variable region and LC variable region.

As indicated herein, nucleic acid molecules of the present invention which comprise a nucleic acid encoding an Anti-IL-6 antibody can include, but are not limited to, those encoding the amino acid sequence of an antibody fragment, by itself, the coding sequence for the entire antibody or a portion thereof, the coding sequence for an antibody, fragment or portion, as well as additional sequences, such as the coding sequence of at least one signal leader or fusion peptide, with or without the aforementioned additional coding sequences, such as at least one intron, together with additional, non-coding sequences, including but not limited to, non-coding 5' and 3' sequences, such as the transcribed, non-translated sequences that play a role in transcription, mRNA processing, including splicing and polyadenylation signals (for example—ribosome binding and stability of mRNA); an additional coding sequence that codes for additional amino acids, such as those that provide additional functionalities. Thus, the sequence encoding an antibody can be fused to a marker sequence, such as a sequence encoding a peptide that facilitates purification of the fused antibody comprising an antibody fragment or portion.

Polynucleotides which Selectively Hybridize to a Polynucleotide as Described Herein The present invention provides isolated nucleic acids that hybridize under selective hybridization conditions to a polynucleotide disclosed herein. Thus, the polynucleotides of this embodiment can be used for isolating, detecting, and/or quantifying nucleic acids comprising such polynucleotides. For example, polynucleotides of the present invention can be used to identify, isolate, or amplify partial or full-length clones in a deposited library. In some embodiments, the polynucleotides are genomic or cDNA sequences isolated, or otherwise complementary to, a cDNA from a human or mammalian nucleic acid library.

Preferably, the cDNA library comprises at least 80% full-length sequences, preferably at least 85% or 90% full-length sequences, and more preferably at least 95% full-length sequences. The cDNA libraries can be normalized to increase the representation of rare sequences. Low or moderate stringency hybridization conditions are typically, but not exclusively, employed with sequences having a reduced sequence identity relative to complementary sequences. Moderate and high stringency conditions can optionally be employed for sequences of greater identity. Low stringency conditions allow selective hybridization of sequences having about 70% sequence identity and can be employed to identify orthologous or paralogous sequences.

Optionally, polynucleotides of this invention will encode at least a portion of an antibody encoded by the polynucleotides described herein. The polynucleotides of this invention embrace nucleic acid sequences that can be employed for selective hybridization to a polynucleotide encoding an antibody of the present invention. See, e.g., Ausubel, supra; Colligan, supra, each entirely incorporated herein by reference.

Construction of Nucleic Acids

The isolated nucleic acids of the present invention can be made using (a) recombinant methods, (b) synthetic techniques, (c) purification techniques, or combinations thereof, as well-known in the art.

The nucleic acids can conveniently comprise sequences in addition to a polynucleotide of the present invention. For example, a multi-cloning site comprising one or more endonuclease restriction sites can be inserted into the nucleic acid to aid in isolation of the polynucleotide. Also, translatable sequences can be inserted to aid in the isolation of the translated polynucleotide of the present invention. For example, a hexa-histidine marker sequence provides a convenient means to purify the proteins of the present invention. The nucleic acid of the present invention—excluding the coding sequence—is optionally a vector, adapter, or linker for cloning and/or expression of a polynucleotide of the present invention.

Additional sequences can be added to such cloning and/or expression sequences to optimize their function in cloning and/or expression, to aid in isolation of the polynucleotide, or to improve the introduction of the polynucleotide into a cell. Use of cloning vectors, expression vectors, adapters, and linkers is well known in the art. (See, e.g., Ausubel, supra; or Sambrook, supra).

Recombinant Methods for Constructing Nucleic Acids

The isolated nucleic acid compositions of this invention, such as RNA, cDNA, genomic DNA, or any combination thereof, can be obtained from biological sources using any number of cloning methodologies known to those of skill in the art. In some embodiments, oligonucleotide probes that selectively hybridize, under stringent conditions, to the polynucleotides of the present invention are used to identify the desired sequence in a cDNA or genomic DNA library. The isolation of RNA, and construction of cDNA and genomic libraries, is well known to those of ordinary skill in the art. (See, e.g., Ausubel, supra; or Sambrook, supra).

Nucleic Acid Screening and Isolation Methods

A cDNA or genomic library can be screened using a probe based upon the sequence of a polynucleotide of the present invention, such as those disclosed herein. Probes can be used to hybridize with genomic DNA or cDNA sequences to isolate homologous genes in the same or different organisms. Those of skill in the art will appreciate that various degrees of stringency of hybridization can be employed in the assay; and either the hybridization or the wash medium can be stringent. As the conditions for hybridization become more stringent, there must be a greater degree of complementarity between the probe and the target for duplex formation to occur. The degree of stringency can be controlled by one or more of temperature, ionic strength, pH and the presence of a partially denaturing solvent such as formamide. For example, the stringency of hybridization is conveniently varied by changing the polarity of the reactant solution through, for example, manipulation of the concentration of formamide within the range of 0% to 50%. The degree of complementarity (sequence identity) required for detectable binding will vary in accordance with the stringency of the hybridization medium and/or wash medium. The degree of complementarity will optimally be 100%, or 70-100%, or any range or value therein. However, it should be understood that minor sequence variations in the probes and primers can be compensated for by reducing the stringency of the hybridization and/or wash medium.

Methods of amplification of RNA or DNA are well known in the art and can be used according to the present invention without undue experimentation, based on the teaching and guidance presented herein.

Known methods of DNA or RNA amplification include, but are not limited to, polymerase chain reaction (PCR) and related amplification processes (see, e.g., U.S. Pat. Nos. 4,683,195, 4,683,202, 4,800,159, 4,965,188, to Mullis, et al.; 4,795,699 and 4,921,794 to Tabor, et al; 5,142,033 to Innis; 5,122,464 to Wilson, et al.; 5,091,310 to Innis; 5,066,584 to Gyllensten, et al; 4,889,818 to Gelfand, et al; 4,994,370 to Silver, et al; 4,766,067 to Biswas; 4,656,134 to Ringold) and RNA mediated amplification that uses anti-sense RNA to the target sequence as a template for double-stranded DNA synthesis (U.S. Pat. No. 5,130,238 to Malek, et al., with the tradename NASBA), the entire contents of which references are incorporated herein by reference. (See, e.g., Ausubel, supra; or Sambrook, supra.)

For instance, polymerase chain reaction (PCR) technology can be used to amplify the sequences of polynucleotides of the present invention and related genes directly from genomic DNA or cDNA libraries. PCR and other in vitro amplification methods can also be useful, for example, to clone nucleic acid sequences that code for proteins to be expressed, to make nucleic acids to use as probes for detecting the presence of the desired mRNA in samples, for nucleic acid sequencing, or for other purposes. Examples of techniques sufficient to direct persons of skill through in vitro amplification methods are found in Berger, supra, Sambrook, supra, and Ausubel, supra, as well as Mullis, et al., U.S. Pat. No. 4,683,202 (1987); and Innis, et al., PCR Protocols A Guide to Methods and Applications, Eds., Academic Press Inc., San Diego, Calif. (1990). Commercially available kits for genomic PCR amplification are known in the art. See, e.g., Advantage-GC Genomic PCR Kit (Clontech). Additionally, e.g., the T4 gene 32 protein (Boehringer Mannheim) can be used to improve yield of long PCR products.

Synthetic Methods for Constructing Nucleic Acids

The isolated nucleic acids of the present invention can also be prepared by direct chemical synthesis by known methods (see, e.g., Ausubel, et al., supra). Chemical synthesis generally produces a single-stranded oligonucleotide, which can be converted into double-stranded DNA by hybridization with a complementary sequence, or by polymerization with a DNA polymerase using the single strand as a template. One of skill in the art will recognize that while chemical synthesis of DNA can be limited to sequences of about 100 or more bases, longer sequences can be obtained by the ligation of shorter sequences.

Recombinant Expression Cassettes

The present invention further provides recombinant expression cassettes comprising a nucleic acid of the present invention. A nucleic acid sequence of the present invention, for example a cDNA or a genomic sequence encoding an antibody of the present invention, can be used to construct a recombinant expression cassette that can be introduced into at least one desired host cell. A recombinant expression cassette will typically comprise a polynucleotide of the present invention operably linked to transcriptional initiation regulatory sequences that will direct the transcription of the polynucleotide in the intended host cell. Both heterologous and non-heterologous (i.e., endogenous) promoters can be employed to direct expression of the nucleic acids of the present invention.

In some embodiments, isolated nucleic acids that serve as promoter, enhancer, or other elements can be introduced in the appropriate position (upstream, downstream or in intron) of a non-heterologous form of a polynucleotide of the present invention so as to up or down regulate expression of a polynucleotide of the present invention. For example, endogenous promoters can be altered in vivo or in vitro by mutation, deletion and/or substitution.

Vectors And Host Cells

The present invention also relates to vectors that include isolated nucleic acid molecules of the present invention, host cells that are genetically engineered with the recombinant vectors, and the production of at least one anti-IL-6 antibody by recombinant techniques, as is well known in the art. See, e.g., Sambrook, et al., supra; Ausubel, et al., supra, each entirely incorporated herein by reference.

The polynucleotides can optionally be joined to a vector containing a selectable marker for propagation in a host. Generally, a plasmid vector is introduced in a precipitate, such as a calcium phosphate precipitate, or in a complex with a charged lipid. If the vector is a virus, it can be packaged in vitro using an appropriate packaging cell line and then transduced into host cells.

The DNA insert should be operatively linked to an appropriate promoter. The expression constructs will further contain sites for transcription initiation, termination and, in the transcribed region, a ribosome binding site for translation. The coding portion of the mature transcripts expressed by the constructs will preferably include a translation initiating at the beginning and a termination codon (e.g., UAA, UGA or UAG) appropriately positioned at the end of the mRNA to be translated, with UAA and UAG preferred for mammalian or eukaryotic cell expression.

Expression vectors will preferably but optionally include at least one selectable marker. Such markers include, e.g., but not limited to, methotrexate (MTX), dihydrofolate reductase (DHFR, U.S. Pat. Nos. 4,399,216; 4,634,665; 4,656,134; 4,956,288; 5,149,636; 5,179,017, ampicillin, neomycin (G418), mycophenolic acid, or glutamine synthetase (GS, U.S. Pat. Nos. 5,122,464; 5,770,359; 5,827,739) resistance for eukaryotic cell culture, and tetracycline or ampicillin resistance genes for culturing in E. coli and other bacteria or prokaryotics (the above patents are entirely incorporated hereby by reference). Appropriate culture mediums and conditions for the above-described host cells are known in the art. Suitable vectors will be readily apparent to the skilled artisan. Introduction of a vector construct into a host cell can be effected by calcium phosphate transfection, DEAE-dextran mediated transfection, cationic lipid-mediated transfection, electroporation, transduction, infection or other known methods. Such methods are described in the art, such as Sambrook, supra, Chapters 1-4 and 16-18; Ausubel, supra, Chapters 1, 9, 13, 15, 16.

At least one antibody of the present invention can be expressed in a modified form, such as a fusion protein, and can include not only secretion signals, but also additional heterologous functional regions. For instance, a region of additional amino acids, particularly charged amino acids, can be added to the N-terminus of an antibody to improve stability and persistence in the host cell, during purification, or during subsequent handling and storage. Also, peptide moieties can be added to an antibody of the present invention to facilitate purification. Such regions can be removed prior to final preparation of an antibody or at least one fragment thereof. Such methods are described in many standard laboratory manuals, such as Sambrook, supra, Chapters 17.29-17.42 and 18.1-18.74; Ausubel, supra, Chapters 16, 17 and 18.

Those of ordinary skill in the art are knowledgeable in the numerous expression systems available for expression of a nucleic acid encoding a protein of the present invention.

Alternatively, nucleic acids of the present invention can be expressed in a host cell by turning on (by manipulation) in a host cell that contains endogenous DNA encoding an antibody of the present invention. Such methods are well known in the art, e.g., as described in U.S. Pat. Nos. 5,580,734, 5,641,670, 5,733,746, and 5,733,761, entirely incorporated herein by reference.

Illustrative of cell cultures useful for the production of the antibodies, specified portions or variants thereof, are mammalian cells. Mammalian cell systems often will be in the form of monolayers of cells although mammalian cell suspensions or bioreactors can also be used. A number of suitable host cell lines capable of expressing intact glycosylated proteins have been developed in the art, and include the COS-1 (e.g., ATCC CRL 1650), COS-7 (e.g., ATCC CRL-1651), HEK293, BHK21 (e.g., ATCC CRL-10), CHO (e.g., ATCC CRL 1610) and BSC-1 (e.g., ATCC CRL-26) cell lines, Cos-7 cells, CHO cells, hep G2 cells, P3X63Ag8.653, SP2/0-Ag14, 293 cells, HeLa cells and the like, which are readily available from, for example, American Type Culture Collection, Manassas, Va. (www.atcc.org). Preferred host cells include cells of lymphoid origin such as myeloma and lymphoma cells. Particularly preferred host cells are P3X63Ag8.653 cells (ATCC Accession Number CRL-1580) and SP2/0-Ag14 cells (ATCC Accession Number CRL-1851). In a particularly preferred embodiment, the recombinant cell is a P3X63Ab8.653 or a SP2/0-Ag14 cell.

Expression vectors for these cells can include one or more of the following expression control sequences, such as, but not limited to an origin of replication; a promoter (e.g., late or early SV40 promoters, the CMV promoter (U.S. Pat. Nos. 5,168,062; 5,385,839), an HSV tk promoter, a pgk (phosphoglycerate kinase) promoter, an EF-1 alpha promoter (U.S. Pat. No. 5,266,491), at least one human immunoglobulin promoter; an enhancer, and/or processing information sites, such as ribosome binding sites, RNA splice sites, polyadenylation sites (e.g., an SV40 large T Ag poly A addition site), and transcriptional terminator sequences. See, e.g., Ausubel et al., supra; Sambrook, et al., supra. Other cells useful for production of nucleic acids or proteins of the present invention are known and/or available, for instance, from the American Type Culture Collection Catalogue of Cell Lines and Hybridomas (www.atcc.org) or other known or commercial sources.

When eukaryotic host cells are employed, polyadenlyation or transcription terminator sequences are typically incorporated into the vector. An example of a terminator sequence is the polyadenlyation sequence from the bovine growth hormone gene. Sequences for accurate splicing of the transcript can also be included. An example of a splicing sequence is the VP1 intron from SV40 (Sprague, et al., J. Virol. 45:773-781 (1983)). Additionally, gene sequences to control replication in the host cell can be incorporated into the vector, as known in the art.

Production of an Antibody

At least one Anti-IL-6 antibody of the present invention can be optionally produced by a cell line, a mixed cell line, an immortalized cell or clonal population of immortalized cells, as well known in the art. See, e.g., Ausubel, et al., ed., Current Protocols in Molecular Biology, John Wiley & Sons, Inc., NY, N.Y. (1987-2001); Sambrook, et al., Molecular Cloning: A Laboratory Manual, 2.sup.nd Edition, Cold Spring Harbor, N.Y. (1989); Harlow and Lane, antibodies, a Laboratory Manual, Cold Spring Harbor, N.Y. (1989). Colligan, et al., eds., Current Protocols in Immunology, John Wiley & Sons, Inc., NY (1994-2001); Colligan et al., Current Protocols in Protein Science, John Wiley & Sons, NY, N.Y., (1997-2001), each entirely incorporated herein by reference.

In one approach, a hybridoma is produced by fusing a suitable immortal cell line (e.g., a myeloma cell line such as, but not limited to, Sp2/0, Sp2/0-AG14, NSO, NS1, NS2, AE-1, L.5, >243, P3X63Ag8.653, Sp2 SA3, Sp2 MAI, Sp2 SS1, Sp2 SA5, U937, MLA 144, ACT IV, MOLT4, DA-1, JURKAT, WEHI, K-562, COS, RAJI, NIH 3T3, HL-60, MLA 144, NAMAIWA, NEURO 2A), or the like, or heteromylomas, fusion products thereof, or any cell or fusion cell derived therefrom, or any other suitable cell line as known in the art. See, e.g., www.atcc.org, www.lifetech.com., and the like, with antibody producing cells, such as, but not limited to, isolated or cloned spleen, peripheral blood, lymph, tonsil, or other immune or B cell containing cells, or any other cells expressing heavy or light chain constant or variable or framework or CDR sequences, either as endogenous or heterologous nucleic acid, as recombinant or endogenous, viral, bacterial, algal, prokaryotic, amphibian, insect, reptilian, fish, mammalian, rodent, equine, ovine, goat, sheep, primate, eukaryotic, genomic DNA, cDNA, rDNA, mitochondrial DNA or RNA, chloroplast DNA or RNA, hnRNA, mRNA, tRNA, single, double or triple stranded, hybridized, and the like or any combination thereof. See, e.g., Ausubel, supra, and Colligan, Immunology, supra, chapter 2, entirely incorporated herein by reference.

Any other suitable host cell can also be used for expressing heterologous or endogenous nucleic acid encoding an antibody, specified fragment or variant thereof, of the present invention. The fused cells (hybridomas) or recombinant cells can be isolated using selective culture conditions or other suitable known methods, and cloned by limiting dilution or cell sorting, or other known methods. Cells which produce antibodies with the desired specificity can be selected by a suitable assay (e.g., ELISA).

Antibodies of the present invention can also be prepared using at least one anti-IL-6 antibody encoding nucleic acid to provide transgenic animals or mammals, such as goats, cows, horses, sheep, and the like, that produce such antibodies in their milk. Such animals can be provided using known methods. See, e.g., but not limited to, U.S. Pat. Nos. 5,827,690; 5,849,992; 4,873,316; 5,849,992; 5,994,616, 5,565,362; 5,304,489, and the like, each of which is entirely incorporated herein by reference.

Antibodies of the present invention can additionally be prepared using at least one Anti-IL-6 antibody encoding nucleic acid to provide transgenic plants and cultured plant cells (e.g., but not limited to tobacco and maize) that produce such antibodies, specified portions or variants in the plant parts or in cells cultured therefrom. As a non-limiting example, transgenic tobacco leaves expressing recombinant proteins have been successfully used to provide large amounts of recombinant proteins, e.g., using an inducible promoter. See, e.g., Cramer et al., Curr. Top. Microbol. Immunol. 240:95-118 (1999) and references cited therein. Also, transgenic maize have been used to express mammalian proteins at commercial production levels, with biological activities equivalent to those produced in other recombinant systems or purified from natural sources. See, e.g., Hood et al., Adv. Exp. Med. Biol. 464:127-147 (1999) and references cited therein. Antibodies have also been produced in large amounts from transgenic plant seeds including antibody fragments, such as single chain antibodies (scFv's), including tobacco seeds and potato tubers. See, e.g., Conrad et al., Plant Mol. Biol. 38:101-109 (1998) and references cited therein. Thus, antibodies of the present invention can also be produced using transgenic plants, according to known methods. See also, e.g., Fischer et al., Biotechnol. Appl. Biochem. 30:99-108 (October, 1999), Ma et al., Trends Biotechnol.

13:522-7 (1995); Ma et al., Plant Physiol. 109:341-6 (1995); Whitelam et al., Biochem Soc. Trans. 22:940-944 (1994); and references cited therein. Each of the above references is entirely incorporated herein by reference.

Purification of an Antibody

An Anti-IL-6 antibody can be recovered and purified from recombinant cell cultures by well-known methods including, but not limited to, protein A purification, protein G purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be employed for purification. See, e.g., Colligan, Current Protocols in Immunology, or Current Protocols in Protein Science, John Wiley & Sons, NY, N.Y., (1997-2001), e.g., chapters 1, 4, 6, 8, 9, and 10, each entirely incorporated herein by reference.

Antibodies of the present invention include naturally purified products, products of chemical synthetic procedures, and products produced by recombinant techniques from a eukaryotic host, including, for example, yeast, higher plant, insect and mammalian cells. Depending upon the host employed in a recombinant production procedure, the antibody of the present invention can be glycosylated or can be non-glycosylated, with glycosylated preferred. Such methods are described in many standard laboratory manuals, such as Sambrook, supra, Sections 17.37-17.42; Ausubel, supra, Chapters 10, 12, 13, 16, 18 and 20, Colligan, Protein Science, supra, Chapters 12-14, all entirely incorporated herein by reference.

Purified antibodies can be characterized by, for example, ELISA, ELISPOT, flow cytometry, immunocytology, Biacore® analysis, Sapidyne KinExA™ kinetic exclusion assay, SDS-PAGE and Western blot, or by HPLC analysis as well as by a number of other functional assays disclosed herein.

Cloning and Expression of IL-6 antibody in Mammalian Cells

A typical mammalian expression vector contains at least one promoter element, which mediates the initiation of transcription of mRNA, the antibody coding sequence, and signals required for the termination of transcription and polyadenylation of the transcript. Additional elements include enhancers, Kozak sequences and intervening sequences flanked by donor and acceptor sites for RNA splicing. Highly efficient transcription can be achieved with the early and late promoters from SV40, the long terminal repeats (LTRS) from retroviruses, e.g., RSV, HTLVI, HIVI and the early promoter of the cytomegalovirus (CMV). However, cellular elements can also be used (e.g., the human actin promoter). Suitable expression vectors for use in practicing the present invention include, for example, vectors such as pIRES1neo, pRetro-Off, pRetro-On, PLXSN, or pLNCX (Clonetech Labs, Palo Alto, Calif.), pcDNA3.1 (+/−), pcDNA/Zeo (+/−) or pcDNA3.1/Hygro (+/−) (Invitrogen), PSVL and PMSG (Pharmacia, Uppsala, Sweden), pRSVcat (ATCC 37152), pSV2dhfr (ATCC 37146) and pBC12MI (ATCC 67109). Mammalian host cells that could be used include human Hela 293, H9 and Jurkat cells, mouse NIH3T3 and C127 cells, Cos 1, Cos 7 and CV 1, quail QC1-3 cells, mouse L cells and Chinese hamster ovary (CHO) cells.

Alternatively, the gene can be expressed in stable cell lines that contain the gene integrated into a chromosome. The co-transfection with a selectable marker such as dhfr, gpt, neomycin, or hygromycin allows the identification and isolation of the transfected cells.

The transfected gene can also be amplified to express large amounts of the encoded antibody. The DHFR (dihydrofolate reductase) marker is useful to develop cell lines that carry several hundred or even several thousand copies of the gene of interest. Another useful selection marker is the enzyme glutamine synthase (GS) (Murphy, et al., Biochem. J. 227: 277-279 (1991); Bebbington, et al., Bio/Technology 10:169-175 (1992)). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of antibodies.

Cloning and Expression in CHO Cells

The isolated variable and constant region encoding DNA and the dephosphorylated vector are ligated with T4 DNA ligase. E. coli HB101 or XL-1 Blue cells are then transformed and bacteria are identified that contain the fragment inserted into plasmid pC4 using, for instance, restriction enzyme analysis.

Chinese hamster ovary (CHO) cells lacking an active DHFR gene are used for transfection. 5 μg of the expression plasmid pC4 is cotransfected with 0.5 μg of the plasmid pSV2-neo using lipofectin. The plasmid pSV2neo contains a dominant selectable marker, the neo gene from Tn5 encoding an enzyme that confers resistance to a group of antibiotics including G418. The cells are seeded in alpha minus MEM supplemented with 1 μg/ml G418. After 2 days, the cells are trypsinized and seeded in hybridoma cloning plates (Greiner, Germany) in alpha minus MEM supplemented with 10, 25, or 50 ng/ml of methotrexate plus 1 μg/ml G418. After about 10-14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 mM, 2 mM, 5 mM, 10 mM, 20 mM). The same procedure is repeated until clones are obtained that grow at a concentration of 100-200 mM. Expression of the desired gene product is analyzed, for instance, by SDS-PAGE and Western blot, ELISA, or by reverse phase HPLC analysis.

Anti-Il-6 Antibody Compositions

The present invention also provides at least one Anti-IL-6 antibody composition comprising at least one, at least two, at least three, at least four, at least five, at least six or more Anti-IL-6 antibodies thereof, as described herein and/or as known in the art that are provided in a non-naturally occurring composition, mixture or form. Such compositions comprise non-naturally occurring compositions comprising at least one or two full length, C- and/or N-terminally deleted variants, domains, fragments, or specified variants, of the anti-IL-6 antibody amino acid sequence selected from the group consisting of 70-100% of the contiguous amino acids of the CDR regions of the antibodies described herein, or specified fragments, domains or variants thereof. Preferred Anti-IL-6 antibody compositions include at least one or two full length, fragments, domains or variants as at least one CDR or LBR containing portions of the anti-IL-6 antibody sequences described herein. Further preferred compositions comprise 40-99% of at least one of 70-100% of a CDR region of an Anti-IL-6 Ab described herein. Such composition percentages are by weight, volume, concentration, molarity, or molality as liquid or dry solutions, mixtures, suspension, emulsions or colloids, as known in the art or as described herein.

Anti-IL-6 antibody compositions of the present invention can further comprise at least one of any suitable and effective amount of a composition or pharmaceutical composition comprising at least one Anti-IL-6 antibody to a cell, tissue, organ, animal or patient in need of such modulation, treatment or therapy, optionally further comprising at least one selected from at least one TNF antagonist (e.g., but not limited to a TNF antibody or fragment a soluble TNF receptor or fragment, fusion proteins thereof, or a small molecule TNF antagonist), an antirheumatic (e.g., methotrexate, auranofin, aurothioglucose, azathioprine, etanercept, gold sodium thiomalate, hydroxychloroquine sulfate, leflunomide, sulfasalzine), a muscle relaxant, a narcotic, a non-steroid anti-inflammatory drug (NSAID), an analgesic, an anesthetic, a sedative, a local anethetic, a neuromuscular blocker, an antimicrobial (e.g., aminoglycoside, an antifungal, an antiparasitic, an antiviral, a carbapenem, cephalosporin, a fluororquinolone, a macrolide, a penicillin, a sulfonamide, a tetracycline, another antimicrobial), an antipsoriatic, a corticosteriod, an anabolic steroid, a diabetes related agent, a mineral, a nutritional, a thyroid agent, a vitamin, a calcium related hormone, an antidiarrheal, an antitussive, an antiemetic, an antiulcer, a laxative, an anticoagulant, an erythropieitin (e.g., epoetin alpha), a filgrastim (e.g., G-CSF, Neupogen), a sargramostim (GM-CSF, Leukine), an immunization, an immunoglobulin, an immunosuppressive (e.g., basiliximab, cyclosporine, daclizumab), a growth hormone, a hormone replacement drug, an estrogen receptor modulator, a mydriatic, a cycloplegic, an alkylating agent, an antimetabolite, a mitotic inhibitor, a radiopharmaceutical, an antidepressant, antimanic agent, an antipsychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog, domase alpha (Pulmozyme), a cytokine or a cytokine antagonist. Non-limiting examples of such cytokines include, but are not limited to, any of IL-1 to IL-34. Suitable dosages are well known in the art. See, e.g., Wells et al., eds., Pharmacotherapy Handbook, 2.sup.nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are entirely incorporated herein by reference.

Such anti-cancer or anti-infectives can also include toxin molecules that are associated, bound, co-formulated or co-administered with at least one antibody of the present invention. The toxin can optionally act to selectively kill the pathologic cell or tissue. The pathologic cell can be a cancer or other cell. Such toxins can be, but are not limited to, purified or recombinant toxin or toxin fragment comprising at least one functional cytotoxic domain of toxin, e.g., selected from at least one of ricin, diphtheria toxin, a venom toxin, or a bacterial toxin. The term toxin also includes both endotoxins and exotoxins produced by any naturally occurring, mutant or recombinant bacteria or viruses which may cause any pathological condition in humans and other mammals, including toxin shock, which can result in death. Such toxins may include, but are not limited to, enterotoxigenic *E. coli* heat-labile enterotoxin (LT), heat-stable enterotoxin (ST), *Shigella cytotoxin*, *Aeromonas* enterotoxins, toxic shock syndrome toxin-1 (TSST-1), Staphylococcal enterotoxin A (SEA), B (SEB), or C (SEC), Streptococcal enterotoxins and the like. Such bacteria include, but are not limited to, strains of a species of enterotoxigenic *E. coli* (ETEC), enterohemorrhagic *E. coli* (e.g., strains of serotype 0157:H7), *Staphylococcus* species (e.g., *Staphylococcus aureus, Staphylococcus pyogenes*), *Shigella* species (e.g., *Shigella dysenteriae, Shigella flexneri, Shigella boydii*, and *Shigella sonnei*), *Salmonella* species (e.g., *Salmonella typhi, Salmonella cholerasuis, Salmonella enteritidis*), *Clostridium* species (e.g., *Clostridium perfringens. Clostridium dificile, Clostridium botulinum*), *Camphlobacter* species (e.g., *Camphlobacter jejuni, Camphlobacter fetus*), *Heliobacter* species, (e.g., *Heliobacter pylori*), *Aeromonas* species (e.g., *Aeromonas sobria, Aeromonas hydrophila, Aeromonas caviae*), *Pleisomonas shigelloides, Yersina enterocolitica, Vibrios* species (e.g., *Vibrios cholerae, Vibrios parahemolyticus*), *Klebsiella* species, *Pseudomonas aeruginosa*, and Streptococci. See, e.g., Stein, ed., INTERNAL MEDICINE, 3rd ed., pp 1-13, Little, Brown and Co., Boston, (1990); Evans et al., eds., Bacterial Infections of Humans: Epidemiology and Control, 2d. Ed., pp 239-254, Plenum Medical Book Co., New York (1991); Mandell et al, Principles and Practice of Infectious Diseases, 3d. Ed., Churchill Livingstone, N.Y. (1990); Berkow et al, eds., The Merck Manual, 16th edition, Merck and Co., Rahway, N.J., 1992; Wood et al, FEMS Microbiology Immunology, 76:121-134 (1991); Marrack et al, Science, 248:705-711 (1990), the contents of which references are incorporated entirely herein by reference.

Anti-IL-6 antibody compounds, compositions or combinations of the present invention can further comprise at least one of any suitable auxiliary, such as, but not limited to, diluent, binder, stabilizer, buffers, salts, lipophilic solvents, preservative, adjuvant or the like. Pharmaceutically acceptable auxiliaries are preferred. Non-limiting examples of, and methods of preparing such sterile solutions are well known in the art, such as, but limited to, Gennaro, Ed., Remington's Pharmaceutical Sciences, $18^{th}$ Edition, Mack Publishing Co. (Easton, Pa.) 1990. Pharmaceutically acceptable carriers can be routinely selected that are suitable for the mode of administration, solubility and/or stability of the anti-IL-6 antibody, fragment or variant composition as well known in the art or as described herein.

Pharmaceutical excipients and additives useful in the present composition include but are not limited to proteins, peptides, amino acids, lipids, and carbohydrates (e.g., sugars, including monosaccharides, di-, tri-, tetra-, and oligosaccharides; derivatized sugars such as alditols, aldonic acids, esterified sugars and the like; and polysaccharides or sugar polymers), which can be present singly or in combination, comprising alone or in combination 1-99.99% by weight or volume. Exemplary protein excipients include serum albumin such as human serum albumin (HSA), recombinant human albumin (rHA), gelatin, casein, and the like. Representative amino acid/antibody components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like. One preferred amino acid is glycine.

Carbohydrate excipients suitable for use in the invention include, for example, monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol), myoinositol and the like. Preferred carbohydrate excipients for use in the present invention are mannitol, trehalose, and raffinose.

Anti-IL-6 antibody compositions can also include a buffer or a pH adjusting agent; typically, the buffer is a salt prepared from an organic acid or base. Representative buffers include organic acid salts such as salts of citric acid, ascorbic acid, gluconic acid, carbonic acid, tartaric acid, succinic acid, acetic acid, or phthalic acid; Tris, tromethamine hydrochloride, or phosphate buffers. Preferred buffers for use in the present compositions are organic acid salts such as citrate.

Additionally, Anti-IL-6 antibody compositions of the invention can include polymeric excipients/additives such as polyvinylpyrrolidones, ficolls (a polymeric sugar), dextrates (e.g., cyclodextrins, such as 2-hydroxypropyl-.beta.-cyclodextrin), polyethylene glycols, flavoring agents, antimicrobial agents, sweeteners, antioxidants, antistatic agents, surfactants (e.g., polysorbates such as "TWEEN 20" and "TWEEN 80"), lipids (e.g., phospholipids, fatty acids), steroids (e.g., cholesterol), and chelating agents (e.g., EDTA).

These and additional known pharmaceutical excipients and/or additives suitable for use in the Anti-IL-6 antibody, portion or variant compositions according to the invention are known in the art, e.g., as listed in "Remington: The Science & Practice of Pharmacy", 19.sup.th ed., Williams & Williams, (1995), and in the "Physician's Desk Reference", $52^{nd}$ ed., Medical Economics, Montvale, N.J. (1998), the disclosures of which are entirely incorporated herein by reference. Preferred carrier or excipient materials are carbohydrates (e.g., saccharides and alditols) and buffers (e.g., citrate) or polymeric agents.

Formulations

As noted above, the invention provides for stable formulations, which is preferably a phosphate buffer with saline or a chosen salt, as well as preserved solutions and formulations containing a preservative as well as multi-use preserved formulations suitable for pharmaceutical or veterinary use, comprising at least one Anti-IL-6 antibody in a pharmaceutically acceptable formulation. Preserved formulations contain at least one known preservative or optionally selected from the group consisting of at least one phenol, m-cresol, p-cresol, o-cresol, chlorocresol, benzyl alcohol, phenylmercuric nitrite, phenoxyethanol, formaldehyde, chlorobutanol, magnesium chloride (e.g., hexahydrate), alkylparaben (methyl, ethyl, propyl, butyl and the like), benzalkonium chloride, benzethonium chloride, sodium dehydroacetate and thimerosal, or mixtures thereof in an aqueous diluent. Any suitable concentration or mixture can be used as known in the art, such as 0.001-5%, or any range or value therein, such as, but not limited to 0.001, 0.003, 0.005, 0.009, 0.01, 0.02, 0.03, 0.05, 0.09, 0.1, 0.2, 0.3, 0.4., 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.3, 4.5, 4.6, 4.7, 4.8, 4.9, or any range or value therein. Non-limiting examples include, no preservative, 0.1-2% m-cresol (e.g., 0.2, 0.3. 0.4, 0.5, 0.9, 1.0%), 0.1-3% benzyl alcohol (e.g., 0.5, 0.9, 1.1., 1.5, 1.9, 2.0, 2.5%), 0.001-0.5% thimerosal (e.g., 0.005, 0.01), 0.001-2.0% phenol (e.g., 0.05, 0.25, 0.28, 0.5, 0.9, 1.0%), 0.0005-1.0% alkylparaben(s) (e.g., 0.00075, 0.0009, 0.001, 0.002, 0.005, 0.0075, 0.009, 0.01, 0.02, 0.05, 0.075, 0.09, 0.1, 0.2, 0.3, 0.5, 0.75, 0.9, 1.0%), and the like.

As noted above, the invention provides an article of manufacture, comprising packaging material and at least one vial comprising a solution of at least one Anti-IL-6 antibody with the prescribed buffers and/or preservatives, optionally in an aqueous diluent, wherein said packaging material comprises a label that indicates that such solution can be held over a period of 1, 2, 3, 4, 5, 6, 9, 12, 18, 20, 24, 30, 36, 40, 48, 54, 60, 66, 72 hours or greater. The invention further comprises an article of manufacture, comprising packaging material, a first vial comprising lyophilized at least one Anti-IL-6 antibody, and a second vial comprising an aqueous diluent of prescribed buffer or preservative, wherein said packaging material comprises a label that instructs a patient to reconstitute the at least one Anti-IL-6 antibody in the aqueous diluent to form a solution that can be held over a period of twenty-four hours or greater.

The at least one Anti-IL-6 antibody used in accordance with the present invention can be produced by recombinant means, including from mammalian cell or transgenic preparations, or can be purified from other biological sources, as described herein or as known in the art.

The range of at least one Anti-IL-6 antibody in the product of the present invention includes amounts yielding upon reconstitution, if in a wet/dry system, concentrations from about 1.0 microgram/ml to about 1000 mg/ml, although lower and higher concentrations are operable and are dependent on the intended delivery vehicle, e.g., solution formulations will differ from transdermal patch, pulmonary, transmucosal, or osmotic or micro pump methods.

Preferably, the aqueous diluent optionally further comprises a pharmaceutically acceptable preservative. Preferred preservatives include those selected from the group consisting of phenol, m-cresol, p-cresol, o-cresol, chlorocresol, benzyl alcohol, alkylparaben (methyl, ethyl, propyl, butyl and the like), benzalkonium chloride, benzethonium chloride, sodium dehydroacetate and thimerosal, or mixtures thereof. The concentration of preservative used in the formulation is a concentration sufficient to yield an anti-microbial effect. Such concentrations are dependent on the preservative selected and are readily determined by the skilled artisan.

Other excipients, e.g. isotonicity agents, buffers, antioxidants, preservative enhancers, can be optionally and preferably added to the diluent. An isotonicity agent, such as glycerin, is commonly used at known concentrations. A physiologically tolerated buffer is preferably added to provide improved pH control. The formulations can cover a wide range of pHs, such as from about pH 4 to about pH 10, and preferred ranges from about pH 5 to about pH 9, and a most preferred range of about 6.0 to about 8.0. Preferably the formulations of the present invention have pH between about 6.8 and about 7.8. Preferred buffers include phosphate buffers, most preferably sodium phosphate, particularly phosphate buffered saline (PBS).

Other additives, such as a pharmaceutically acceptable solubilizers like Tween 20 (polyoxyethylene (20) sorbitan monolaurate), Tween 40 (polyoxyethylene (20) sorbitan monopalmitate), Tween 80 (polyoxyethylene (20) sorbitan monooleate), Pluronic F68 (polyoxyethylene polyoxypropylene block copolymers), and PEG (polyethylene glycol) or non-ionic surfactants such as polysorbate 20 or 80 or poloxamer 184 or 188, Pluronic® polyls, other block co-polymers, and chelators such as EDTA and EGTA can optionally be added to the formulations or compositions to reduce aggregation. These additives are particularly useful if a pump or plastic container is used to administer the formulation. The presence of pharmaceutically acceptable surfactant mitigates the propensity for the protein to aggregate.

The formulations of the present invention can be prepared by a process which comprises mixing at least one anti-IL-6 antibody and a preservative selected from the group consisting of phenol, m-cresol, p-cresol, o-cresol, chlorocresol, benzyl alcohol, alkylparaben, (methyl, ethyl, propyl, butyl and the like), benzalkonium chloride, benzethonium chloride, sodium dehydroacetate and thimerosal or mixtures thereof in an aqueous diluent. Mixing the at least one anti-IL-6 antibody and preservative in an aqueous diluent is carried out using conventional dissolution and mixing procedures. To prepare a suitable formulation, for example, a measured amount of at least one anti-IL-6 antibody in buffered solution is combined with the desired preservative in a buffered solution in quantities sufficient to provide the protein and preservative at the desired concentrations. Variations of this process would be recognized by one of ordinary skill in the art. For example, the order the components are added, whether additional additives are used, the temperature and pH at which the formulation is prepared, are all factors that can be optimized for the concentration and means of administration used.

The claimed formulations can be provided to patients as clear solutions or as dual vials comprising a vial of lyophilized at least one Anti-IL-6 antibody that is reconstituted with a second vial containing water, a preservative and/or excipients, preferably a phosphate buffer and/or saline and a chosen salt, in an aqueous diluent. Either a single solution vial or dual vial requiring reconstitution can be reused multiple times and can suffice for a single or multiple cycles of patient treatment and thus can provide a more convenient treatment regimen than currently available.

The present claimed articles of manufacture are useful for administration over a period of immediately to twenty-four hours or greater. Accordingly, the presently claimed articles of manufacture offer significant advantages to the patient. Formulations of the invention can optionally be safely stored at temperatures of from about 2° C. to about 40° C. and retain the biologically activity of the protein for extended periods of time, thus, allowing a package label indicating that the solution can be held and/or used over a period of 6, 12, 18, 24, 36, 48, 72, or 96 hours or greater. If preserved diluent is used, such label can include use up to 1-12 months, one-half, one and a half, and/or two years.

The solutions of at least one Anti-IL-6 antibody in the invention can be prepared by a process that comprises mixing at least one antibody in an aqueous diluent. Mixing is carried out using conventional dissolution and mixing procedures. To prepare a suitable diluent, for example, a measured amount of at least one antibody in water or buffer is combined in quantities sufficient to provide the protein and optionally a preservative or buffer at the desired concentrations. Variations of this process would be recognized by one of ordinary skill in the art. For example, the order the components are added, whether additional additives are used, the temperature and pH at which the formulation is prepared, are all factors that can be optimized for the concentration and means of administration used.

The claimed products can be provided to patients as clear solutions or as dual vials comprising a vial of lyophilized at least one Anti-IL-6 antibody that is reconstituted with a second vial containing the aqueous diluent. Either a single solution vial or dual vial requiring reconstitution can be reused multiple times and can suffice for a single or multiple cycles of patient treatment and thus provides a more convenient treatment regimen than currently available.

The claimed products can be provided indirectly to patients by providing to pharmacies, clinics, or other such institutions and facilities, clear solutions or dual vials comprising a vial of lyophilized at least one Anti-IL-6 antibody that is reconstituted with a second vial containing the aqueous diluent. The clear solution in this case can be up to one liter or even larger in size, providing a large reservoir from which smaller portions of the at least one antibody solution can be retrieved one or multiple times for transfer into smaller vials and provided by the pharmacy or clinic to their customers and/or patients.

Recognized devices comprising these single vial systems include those pen-injector devices for delivery of a solution such as BD Pens, BD Autojector®, Humaject®, NovoPen®, B-D®Pen, AutoPen®, and OptiPen®, GenotropinPen®, Genotronorm Pen®, Humatro Pen®, Reco-Pen®, Roferon Pen®, Biojector®, Iject®, J-tip Needle-Free Injector®, Intraject®, Medi-Ject®, e.g., as made or developed by Becton Dickensen (Franklin Lakes, N.J., www.bectondickenson.com), Disetronic (Burgdorf, Switzerland, www.disetronic.com; Bioject, Portland, Oreg. (www.bioject.com); National Medical Products, Weston Medical (Peterborough, UK, www.weston-medical.com), Medi-Ject Corp (Minneapolis, Minn., www.mediject.com). Recognized devices comprising a dual vial system include those pen-injector systems for reconstituting a lyophilized drug in a cartridge for delivery of the reconstituted solution such as the Humatro-Pen®.

The products presently claimed include packaging material. The packaging material provides, in addition to the information required by the regulatory agencies, the conditions under which the product can be used. The packaging material of the present invention provides instructions to the patient to reconstitute the at least one Anti-IL-6 antibody in the aqueous diluent to form a solution and to use the solution over a period of 2-24 hours or greater for the two vial, wet/dry, product. For the single vial, solution product, the label indicates that such solution can be used over a period of 2-24 hours or greater. The presently claimed products are useful for human pharmaceutical product use.

The formulations of the present invention can be prepared by a process that comprises mixing at least one Anti-IL-6 antibody and a selected buffer, preferably a phosphate buffer containing saline or a chosen salt. Mixing the at least one antibody and buffer in an aqueous diluent is carried out using conventional dissolution and mixing procedures. To prepare a suitable formulation, for example, a measured amount of at least one antibody in water or buffer is combined with the desired buffering agent in water in quantities sufficient to provide the protein and buffer at the desired concentrations. Variations of this process would be recognized by one of ordinary skill in the art. For example, the order the components are added, whether additional additives are used, the temperature and pH at which the formulation is prepared, are all factors that can be optimized for the concentration and means of administration used.

The claimed stable or preserved formulations can be provided to patients as clear solutions or as dual vials comprising a vial of lyophilized at least one Anti-IL-6 antibody that is reconstituted with a second vial containing a preservative or buffer and excipients in an aqueous diluent. Either a single solution vial or dual vial requiring reconstitution can be reused multiple times and can suffice for a single or multiple cycles of patient treatment and thus provides a more convenient treatment regimen than currently available.

At least one Anti-IL-6 antibody in either the stable or presented formulations or solutions described herein, can be administered to a patient in accordance with the present invention via a variety of delivery methods including SC or IM injection; transdermal, pulmonary, transmucosal, implant, osmotic pump, cartridge, micro pump, or other means appreciated by the skilled artisan, as well-known in the art.

Therapeutic Applications

In one embodiment of the present invention, the pharmaceutical compositions comprising an anti-IL-6 antibody of the disclosure facilitate administration of humanized antibodies to an organism, preferably an animal, preferably a mammal. Particular mammals include bovine, canine, equine, feline, ovine, and porcine animals, non-human primates, and humans. Humans are particularly preferred.

IL-6, due to its pleiotropic activity, is implicated in the pathology of a variety of diseases. Therefore, a high affinity, neutralizing chimeric or human antibody to IL-6 would be desirable to be used in IL-6 related diseases such as cancer, cachexia, SLE, rheumatoid arthritis, osteoporosis, brain trauma, cerebral edema, depression, and CHF. In one preferred aspect, an anti-IL-6 antibody of the disclosure can be used to treat rheumatoid arthritis. Anti-IL-6 Abs or any derivatives of these mAbs including chimeric or humanized, or fragments can be used in alleviating bone pain, inhibiting growth of tumors such as melanoma, renal, prostate, breast, lung, colon cancer and multiple myeloma, lymphoproliferative disorders and other diseases in which IL-6 has been implicated. These antibodies can be used either as a single agent or in combination with other therapeutic agents. In addition, these Mabs can be used as a chemosensitizer whereby it can increase therapeutic efficacy of cytotoxic agents. These antibodies can be used as a radiosensitizer whereby it can improve efficacy of radiation. They can also be used in combination with other tumor-immunomodulating agents such as IL-2, IL-12 and/or IFNalpha. Additionally, the Anti-IL-6 antibodies can be used in combination with other monoclonal antibodies such as anti-TNF-α, IL-12/IL-23, IL-2, GpIIb/IIIa receptor, CD52, CD20, RSV proteins, HER2/neu receptor, and the like; as well as with commercially approved antibodies including Rituxan, Herceptin, Mylotarg, Campath, Zevalin, Bexxar, Erbitux, Avastin and Vectibix.

Thus, the present invention also provides a method for modulating or treating at least one IL-6 related disease, in a cell, tissue, organ, animal, or patient, as known in the art or as described herein, using at least one anti-IL-6 antibody of the present invention.

IL-6 is known to enhance proliferation, differentiation and survival of malignant plasma cells in multiple myeloma (MM) through an autocrine or a paracrine mechanism that involves the inhibition of apoptosis of the malignant cells. MM is an incurable malignant plasma cell disorder where, blocking IL-6 has been postulated to be an effective therapy (Anderson et al., Multiple Myeloma: New Insights and Therapeutic Approaches. Hematology: 147-165, 2000). IL-6 also has a tumorigenic effect in basal cell carcinoma where IL-6 transfected cells showed increased tumor growth rate by both suppressing apoptosis and actively promoting (Jee et al., Overexpression of interleukin-6 in human basal cell carcinoma cell lines increases anti-apoptotic activity and tumorigenic potency. Oncogene, Vol. 20, No. 2 pp. 198-208, 2001). IL-6 can also promote resistance of breast cancer cells to chemotherapy by inducing mdr1 gene expression (mdr1 and metallothionein pathways) (Conze et al, Autocrine Production of Interleukin 6 Causes Multidrug Resistance in Breast Cancer Cells. Cancer Res 61: 8851-8858, 2001).

The ability, of IL-6 to mediate tumor cell survival and disease progression was confirmed by the inhibitory effects of an anti-IL-6 mAb on tumor growth both in vitro and in vivo. It was reported that blockade of IL-6 can inhibit growth of human brain tumors (glioblastoma) in vitro (Goswami et al., interleukin-6-mediated autocrine growth promotion in human glioblastoma multiforme cell line U87MG. J Neurochem 71: 1837-1845, 1998). Using the same approach it was shown that injection of murine CLB8 anti-IL-6 antibody prolonged the survival of human tumor bearing mice (Mauray et al., Epstein-Ban virus-dependent lymphoproliferative disease: critical role of IL-6. Eur J Immunol; 30(7):2065-73, 2000). It was also reported that mCLB8 anti-IL-6 antibody regressed growth of human renal carcinoma tumors and decreased serum calcium concentrations in nude mice (Weisglass et al., The role of interleukin-6 in the induction of hypercalcemia in renal cell carcinoma transplanted into nude mice. Endocrinology 138(5):1879-8., 1995). CLB-8 antibody also regressed established human hormone refractory prostate tumor xenografts in mice (Smith et al. 2001). Anti-interleukin-6 monoclonal antibody induces regression of human prostate cancer xenografts in nude mice (Smith and Keller, Prostate; 48(1):47-53).

IL-6 can also be a prognostic factor and a marker for malignancies. In renal cell carcinoma (RCC) high levels of IL-6 were reported to correlate with tumor metastasis and eventually to poor prognosis and short survival (Jean-Yves Blay et al. 1992). Moreover, in RCC, elevated serum IL-6 is associated with poor response to IL-2 therapy (Fumagalli et al. 1999) Pretreatment serum markers and lymphocyte response to interleukin-2 therapy. Br J Cancer 80(3-4):407-11 and correlated with the degree of IL-2 associated toxicity (Capuron et al. 2001) Association between immune activation and early depressive symptoms in cancer patients treated with interleukin-2-based therapy. Psychoneuroendocrinology; 26(8):797-808.

Elevated levels of IL-6 also correlated with poor prognosis and the presence of metastatic disease in breast cancer (Kurebayashi 2000 and Benoy 2002) Regulation of interleukin-6 secretion from breast cancer cells and its clinical implications. Breast Cancer; 7(2):124-9. Serum interleukin 6, plasma VEGF, serum VEGF, and VEGF platelet load in breast cancer patients. Clin Breast Cancer; 2(4):311-5.

IL-6 is hypothesized to be a causative factor in cancer-related morbidity such as asthenia/cachexia and bone resorption. Tumor-induced cachexia (Cahlin et al. 2000) and bone resorption (subsequent hypercalcemia) (Sandhu et al. 1999) were found to be diminished in IL-6 knockout mice. Cancer-associated depression and cerebral edema secondary to brain tumors have also been associated with high levels of IL-6 (Musselman et al. 2001). Anti-IL-6 antibodies of the invention also can inhibit human melanoma and human prostate carcinoma induced cachexia in nude mice.

The present invention includes a method for modulating or treating at least one malignant disease in a cell, tissue, organ, animal or patient, including, but not limited to, at least one of: multiple myeloma, leukemia, acute leukemia, acute lymphoblastic leukemia (ALL), B-cell, T-cell or FAB ALL, acute myeloid leukemia (AML), chromic myelocytic leukemia (CML), chronic lymphocytic leukemia (CLL), hairy cell leukemia, myelodyplastic syndrome (MDS), a lymphoma, Hodgkin's disease, a malignamt lymphoma, non-hodgkin's lymphoma, Burkitt's lymphoma, multiple myeloma, Kaposi's sarcoma, colorectal carcinoma, renal cell carcinoma, pancreatic carcinoma, prostatic carcinoma, nasopharyngeal carcinoma, malignant histiocytosis, paraneoplastic syndrome/hypercalcemia of malignancy, solid tumors, adenocarcinomas, sarcomas, malignant melanoma, hemangioma, metastatic disease, cancer related bone resorption, cancer related bone pain; the suppression of cancer metastasis; the amelioration of cancer cachexia; and the treatment of inflammatory diseases such as mesangial proliferative glomerulonephritis and the like. Such a method can optionally be used in combination with, by administering before, concurrently or after administration of such IL-6 antibody, radiation therapy, an anti-angiogenic agent, a chemotherapeutic agent, a farnesyl transferase inhibitor or the like.

The present invention also provides a method for modulating or treating at least one IL-6 mediated immune related disease, in a cell, tissue, organ, animal, or patient including, but not limited to, at least one of rheumatoid arthritis, juvenile rheumatoid arthritis, systemic onset juvenile rheumatoid arthritis, psoriatic arthritis, ankylosing spondilitis, gastric ulcer, seronegative arthropathies, asteoarthritis, inflammatory bowel disease, ulverative colitis, systemic lupus erythematosis, antiphospholipid syndrome, iridocyclitis/uveitis/optic neuritis, idiopathic pulmonary fibrosis, systemic vasculitis/wegener's granulomatosis, sarcoidosis, orchitis/vasectomy reversal procedures, allergic/atopic diseases, asthma, allergic rhinitis, eczema, allergic contact dermatitis, allergic conjunctivitis, hypersensitivity pneumonitis, transplants, organ transplant rejection, graft-versus-host disease, systemic inflammatory response syndrome, sepsis syndrome, gram positive sepsis, gram negative sepsis, culture negative sepsis, fungal sepsis, neutropenic fever, urosepsis, meningococcemia, trauma/hemorrhage, burns, ionizing radiation exposure, acute pancreatitis, adult respiratory distress syndrome, rheumatoid arthritis, alcohol-induced hepatitis, chronic inflammatory pathologies, sarcoidosis, Crohn's pathology, sickle cell anemia, diabetes, nephrosis, atopic diseases, hypersensitivity reactions, allergic rhinitis, hay fever, perennial rhinitis, conjunctivitis, endometriosis, asthma, urticaria, systemic anaphalaxis, dermatitis, pernicious anemia, hemolytic disease, thrombocytopenia, graft rejection of any organ or tissue, kidney transplant rejection, heart transplant rejection, liver transplant rejection, pancreas transplant rejection, lung transplant rejection, bone marrow transplant (BMT) rejection, skin allograft rejection, cartilage transplant rejection, hone graft rejection, small bowel transplant rejection, fetal thymus implant rejection, parathyroid transplant rejection, xenograft rejection of any organ or tissue, allograft rejection, anti-receptor hypersensitivity reactions, Graves disease, Raynoud's disease, type B insulin-resistant diabetes, asthma, myasthenia gravis, antibody-meditated cytotoxicity, type III hypersensitivity reactions, systemic lupus erythematosus, POEMS syndrome (polyneuropathy, organomegaly, endocrinopathy, monoclonal gammopathy, and skin changes syndrome), polyneuropathy, organomegaly, endocrinopathy, monoclonal gammopathy, skin changes syndrome, antiphospholipid syndrome, pemphigus, scleroderma, mixed connective tissue disease, idiopathic Addison's disease, diabetes mellitus, chronic active hepatitis, primary billiary cirrhosis, vitiligo, vasculitis, post-MI cardiotomy syndrome, type IV hypersensitivity, contact dermatitis, hypersensitivity pneumonitis, allograft rejection, granulomas due to intracellular organisms, drug sensitivity, metabolic/idiopathic, Wilson's disease, hemachromatosis, alpha-1-antitrypsin deficiency, diabetic retinopathy, hashimoto's thyroiditis, osteoporosis, hypothalamic-pituitary-adrenal axis evaluation, primary biliary cirrhosis, thyroiditis, encephalomyelitis, cachexia, cystic fibrosis, neonatal chronic lung disease, chronic obstructive pulmonary disease (COPD), familial hematophagocytic lymphohistiocytosis, dermatologic conditions, psoriasis, alopecia, nephrotic syndrome, nephritis, glomerular nephritis, acute renal failure, hemodialysis, uremia, toxicity, preeclampsia, okt3 therapy, anti-cd3 therapy, cytokine therapy, chemotherapy, radiation therapy (e.g., including but not limited to asthenia, anemia, cachexia, and the like), chronic salicylate intoxication, sleep apnea, obesity, heart failure, sinusitis, inflammatory bowel disease, and the like. See, e.g., the Merck Manual, 12th-17th Editions, Merck & Company, Rahway, N.J. (1972, 1977, 1982, 1987, 1992, 1999), Pharmacotherapy Handbook, Wells et al., eds., Second Edition, Appleton and Lange, Stamford, Conn. (1998, 2000), each entirely incorporated by reference.

The present invention also provides a method for modulating or treating at least one infectious disease in a cell, tissue, organ, animal or patient, including, but not limited to, at least one of: acute or chronic bacterial infection, acute and chronic parasitic or infectious processes, including bacterial, viral and fungal infections, HIV infection/HIV neuropathy, meningitis, hepatitis (A, B or C, or the like), septic arthritis, peritonitis, pneumonia, epiglottitis, *E. coli* 0157:h7, hemolytic uremic syndrome/thrombolytic thrombocytopenic purpura, malaria, dengue hemorrhagic fever, leishmaniasis, leprosy, toxic shock syndrome, streptococcal myositis, gas gangrene, *mycobacterium tuberculosis, mycobacterium avium* intracellulare, *pneumocystis carinii* pneumonia, pelvic inflammatory disease, orchitis/epidydimitis, *legionella*, lyme disease, influenza a, epstein-barr virus, vital-associated hemaphagocytic syndrome, vital encephalitis/aseptic meningitis, and the like;

Any of such methods can optionally comprise administering an effective amount of at least one composition or pharmaceutical composition comprising at least one anti-IL-6 antibody to a cell, tissue, organ, animal or patient in need of such modulation, treatment or therapy. Indications for treatment with ant-IL-6 therapy are disclosed in the following references, hereby incorporated by reference into the present application: Van Snick, "Interleukin-6: An Overview," Ann. Rev. Immunol., 8:253-278 (1990); Campbell et al., "Essential Role for Interferon-gamma. And Interleukin-6 in Autoimmune Insulin-Dependent Diabetes in NOD/Wehi Mice," J. Clin. Invest, 87:739-742 (1991); Heinrich et al., "Interleukin-6 Monoclonal Antibody Therapy for a Patient with Plasma Cell Leukemia," Blood, 78(5):1198-1204 (1991); Starnes et al., "Anti-IL-6 Monoclonal Antibodies Protect Against Lethal *Escherichia coli* Infection and Lethal Tumor Necrosis Factor-alpha. Challenge in Mice," J. Immunol., 145(12):4185-4191 (1990); Strassman et al., "Evidence for the Involvement of interleukin 6 in Experimental Cancer Cachexia," J. Clin. Invest., 89:1681-1684 (1992).

Any method of the present invention can comprise administering an effective amount of a composition or pharmaceutical composition comprising at least one anti-IL-6 antibody to a cell, tissue, organ, animal or patient in need of such modulation, treatment or therapy. Such a method can optionally further comprise co-administration or combination therapy for treating such immune diseases or malignant diseases, wherein the administering of said at least one anti-IL-6 antibody, specified portion or variant thereof, further comprises administering, before concurrently, and/or after, at least one selected from at least one TNF antagonist (e.g., but not limited to a TNF antibody or fragment, a soluble TNF receptor or fragment, fusion proteins thereof, or a small molecule TNF antagonist), an IL-18 antibody or fragment, small molecule IL-18 antagonist or IL-18 receptor binding protein, an IL-1 antibody (including both IL-1 alpha and IL-1 beta) or fragment, a soluble IL-1 receptor antagonist, an antirheumatic (e.g., methotrexate, auranofin, aurothioglucose, azathioprine, etanercept, gold sodium thiomalate, hydroxychloroquine sulfate, leflunomide, sulfasalazine, radiation therapy, an anti-angiogenic agent, a chemotherapeutic agent, Thalidomidea muscle relaxant, a narcotic, a non-steroid anti-inflammatory drug (NSAID), an analgesic, an anesthetic, a sedative, a local anethetic, a neuromuscular blocker, an antimicrobial (e.g., aminoglycoside, an antifungal, an antiparasitic, an antiviral, a carbapenem, cephalosporin, a fluororquinolone, a macrolide, a penicillin, a sulfonamide, a tetracycline, another antimicrobial), an antipsoriatic, a corticosteriod, an anabolic steroid, a diabetes related agent, a mineral, a nutritional, a thyroid agent, a vitamin, a calcium related hormone, an erythropieitin (e.g., epoetin alpha), a filgrastim (e.g., G-CSF, Neupogen), a sargramostim (GM-CSF, Leukine), an immunization, an immunoglobulin, an immunosuppressive (e.g., basiliximab, cyclosporine, daclizumab), a growth hormone, a hormone replacement drug, an estrogen receptor modulator, a mydriatic, a cycloplegic, an alkylating agent, an antimetabolite, a mitotic inhibitor, a radiopharmaceutical, an antidepressant, antimanic agent, an antipsychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog, domase alpha (Pulmozyme), a cytokine or a cytokine antagonist. Suitable dosages are well known in the art. See, e.g., Wells et al., eds., Pharmacotherapy Handbook, $2^{nd}$ Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which is entirely incorporated herein by reference.

TNF antagonists suitable for compositions, combination therapy, co-administration, devices and/or methods of the present invention (further comprising at least one anti body, specified portion and variant thereof, of the present invention), include, but are not limited to, anti-TNF antibodies, antigen-binding fragments thereof, and receptor molecules which bind specifically to TNF; compounds which prevent and/or inhibit TNF synthesis, TNF release or its action on target cells, such as thalidomide, tenidap, phosphodiesterase inhibitors (e.g., pentoxifylline and rolipram), A2b adenosine receptor agonists and A2b adenosine receptor enhancers; compounds which prevent and/or inhibit TNF receptor signalling, such as mitogen activated protein (MAP) kinase inhibitors; compounds which block and/or inhibit membrane TNF cleavage, such as metalloproteinase inhibitors; compounds which block and/or inhibit TNF activity, such as angiotensin converting enzyme (ACE) inhibitors (e.g., captopril); and compounds which block and/or inhibit TNF production and/or synthesis, such as MAP kinase inhibitors.

Therapeutic Treatments

Any method of the present invention can comprise a method for treating an IL-6 mediated disorder, comprising administering an effective amount of a composition or pharmaceutical composition comprising at least one Anti-IL-6 antibody to a cell, tissue, organ, animal or patient in need of such modulation, treatment or therapy. Such a method can optionally further comprise co-administration or combination therapy for treating such immune diseases, wherein the administering of said at least one Anti-IL-6 antibody, specified portion or variant thereof, further comprises administering, before concurrently, and/or after, at least one agent as described above.

Typically, treatment of pathologic conditions is effected by administering an effective amount or dosage of at least one Anti-IL-6 antibody composition that total, on average, a range from at least about 0.01 to 500 milligrams of at least one Anti-IL-6 antibody per kilogram of patient per dose, and preferably from at least about 0.1 to 100 milligrams antibody/kilogram of patient per single or multiple administration, depending upon the specific activity of contained in the composition. Alternatively, the effective serum concentration can comprise 0.1-5000 .mu.g/ml serum concentration per single or multiple administration. Suitable dosages are known to medical practitioners and will, of course, depend upon the particular disease state, specific activity of the composition being administered, and the particular patient undergoing treatment in some instances, to achieve the desired therapeutic amount, it can be necessary to provide for repeated administration, i.e., repeated individual administrations of a particular monitored or metered dose, where the individual administrations are repeated until the desired daily dose or effect is achieved.

Preferred doses can optionally include 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 and/or 100-500 mg/kg/administration, or any range, value or fraction thereof, or to achieve a serum concentration of 0.1, 0.5, 0.9, 1.0, 1.1, 1.2, 1.5, 1.9, 2.0, 2.5, 2.9, 3.0, 3.5, 3.9, 4.0, 4.5, 4.9, 5.0, 5.5, 5.9, 6.0, 6.5, 6.9, 7.0, 7.5, 7.9, 8.0, 8.5, 8.9, 9.0, 9.5, 9.9, 10, 10.5, 10.9, 11, 11.5, 11.9, 20, 12.5, 12.9, 13.0, 13.5, 13.9, 14.0, 14.5, 4.9, 5.0, 5.5., 5.9, 6.0, 6.5, 6.9, 7.0, 7.5, 7.9, 8.0, 8.5, 8.9, 9.0, 9.5, 9.9, 10, 10.5, 10.9, 11, 11.5, 11.9, 12, 12.5, 12.9, 13.0, 13.5, 13.9, 14, 14.5, 15, 15.5, 15.9, 1.6, 16.5, 16.9, 17, 17.5, 17.9, 18, 18.5, 18.9, 19, 19.5, 19.9, 20, 20.5, 20.9, 21, 22, 23, 24, 25, 26, 27, 28, 29, 30, 35, 40, 45, 50, 55, 60, 65, 70, 75, 80, 85, 90, 96, 100, 200, 300, 400, 500, 600, 700, 800, 900, 1000, 1500, 2000, 2500, 3000, 3500, 4000, 4500, and/or 5000 µg/ml serum concentration per single or multiple administration, or any range, value or fraction thereof.

Alternatively, the dosage administered can vary depending upon known factors, such as the pharmacodynamic characteristics of the particular agent, and its mode and route of administration; age, health, and weight of the recipient; nature and extent of symptoms, kind of concurrent treatment, frequency of treatment, and the effect desired. Usually a dosage of active ingredient can be about 0.1 to 100 milligrams per kilogram of body weight. Ordinarily 0.1 to 50, and preferably 0.1 to 10 milligrams per kilogram per administration or in sustained release form is effective to obtain desired results.

As a non-limiting example, treatment of humans or animals can be provided as a one-time or periodic dosage of at least one antibody of the present invention 0.1 to 100 mg/kg, such as 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively or additionally, at least one of week 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or 52, or alternatively or additionally, at least one of 1, 2, 3, 4, 5, 6, 7, 8, 9, 10, 11, 12, 13, 14, 15, 16, 17, 18, 19, or 20 years, or any combination thereof, using single, infusion or repeated doses.

Dosage forms (composition) suitable for internal administration generally contain from about 0.1 milligram to about 500 milligrams of active ingredient per unit or container. In these pharmaceutical compositions the active ingredient will ordinarily be present in an amount of about 0.5-99.999% by weight based on the total weight of the composition.

Parenteral Formulations and Administration

For parenteral administration, the antibody can be formulated as a solution, suspension, emulsion or lyophilized powder in association, or separately provided, with a pharmaceutically acceptable parenteral vehicle. Examples of such vehicles are water, saline, Ringer's solution, dextrose solution, and 1-10% human serum albumin. Liposomes and nonaqueous vehicles such as fixed oils can also be used. The vehicle or lyophilized powder can contain additives that maintain isotonicity (e.g., sodium chloride, mannitol) and chemical stability (e.g., buffers and preservatives). The formulation is sterilized by known or suitable techniques.

Suitable pharmaceutical carriers are described in the most recent edition of Remington's Pharmaceutical Sciences, A. Osol, a standard reference text in this field.

Formulations for parenteral administration can contain as common excipients sterile water or saline, polyalkylene glycols such as polyethylene glycol, oils of vegetable origin, hydrogenated naphthalenes and the like. Aqueous or oily suspensions for injection can be prepared by using an appropriate emulsifier or humidifier and a suspending agent, according to known methods. Agents for injection can be a non-toxic, non-orally administrable diluting agent such as aqueous solution or a sterile injectable solution or suspension in a solvent. As the usable vehicle or solvent, water, Ringer's solution, isotonic saline, etc. are allowed; as an ordinary solvent, or suspending solvent, sterile involatile oil can be used. For these purposes, any kind of involatile oil and fatty acid can be used, including natural or synthetic or semisynthetic fatty oils or fatty acids; natural or synthetic or semisynthetic mono- or di- or tri-glycerides. Parental administration is known in the art and includes, but is not limited to, conventional means of injections, a gas pressured needle-less injection device as described in U.S. Pat. No. 5,851,198, and a laser perforator device as described in U.S. Pat. No. 5,839,446 entirely incorporated herein by reference.

Alternative Delivery

The invention further relates to the administration of at least one Anti-IL-6 antibody by parenteral, subcutaneous, intramuscular, intravenous, intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, or transdermal means. At least one Anti-IL-6 antibody composition can be prepared for use for parenteral (subcutaneous, intramuscular or intravenous) or any other administration particularly in the form of liquid solutions or suspensions; for use in vaginal or rectal administration particularly in semisolid forms such as, but not limited to, creams and suppositories; for buccal, or sublingual administration such as, but not limited to, in the form of tablets or capsules; or intranasally such as, but not limited to, the form of powders, nasal drops or aerosols or certain agents; or transdermally such as not limited to a gel, ointment, lotion, suspension or patch delivery system with chemical enhancers such as dimethyl sulfoxide to either modify the skin structure or to increase the drug concentration in the transdermal patch (Junginger, et al. In "Drug Permeation Enhancement"; Hsieh, D. S., Eds., pp. 59-90, Marcel Dekker, Inc. New York 1994, entirely incorporated herein by reference), or with oxidizing agents that enable the application of formulations containing proteins and peptides onto the skin (WO 98/53847), or applications of electric fields to create transient transport pathways such as electroporation, or to increase the mobility of charged drugs through the skin such as iontophoresis, or application of ultrasound such as sonophoresis (U.S. Pat. Nos. 4,309,989 and 4,767,402) (the above publications and patents being entirely incorporated herein by reference).

Pulmonary/Nasal Administration

For pulmonary administration, preferably at least one Anti-IL-6 antibody composition is delivered in a particle size effective for reaching the lower airways of the lung or sinuses. According to the invention, at least one Anti-IL-6 antibody can be delivered by any of a variety of inhalation or nasal devices known in the art for administration of a therapeutic agent by inhalation. These devices capable of depositing aerosolized formulations in the sinus cavity or alveoli of a patient include metered dose inhalers, nebulizers, dry powder generators, sprayers, and the like. Other devices suitable for directing the pulmonary or nasal administration of antibodies are also known in the art. All such devices can use of formulations suitable for the administration for the dispensing of antibody in an aerosol. Such aerosols can be comprised of either solutions (both aqueous and non aqueous) or solid particles. Metered dose inhalers like the Ventolin® metered dose inhaler, typically use a propellant gas and require actuation during inspiration (See, e.g., WO 94/16970, WO 98/35888). Dry powder inhalers like Turbuhaler™ (Astra), Rotahaler® (Glaxo), Diskus® (Glaxo), Spiros™ inhaler (Dura), devices marketed by Inhale Therapeutics, and the Spinhaler® powder inhaler (Fisons), use breath-actuation of a mixed powder (U.S. Pat. No. 4,668,218 Astra, EP 237507 Astra, WO 97/25086 Glaxo, WO 94/08552 Dura, U.S. Pat. No. 5,458,135 Inhale, WO 94/06498 Fisons, entirely incorporated herein by reference). Nebulizers like AERx™ Aradigm, the Ultravent® nebulizer (Mallinckrodt), and the Acorn II® nebulizer (Marquest Medical Products) (U.S. Pat. No. 5,404,871 Aradigm, WO 97/22376), the above references entirely incorporated herein by reference, produce aerosols from solutions, while metered dose inhalers, dry powder inhalers, etc. generate small particle aerosols. These specific examples of commercially available inhalation devices are intended to be a representative of specific devices suitable for the practice of this invention, and are not intended as limiting the scope of the invention. Preferably, a composition comprising at least one Anti-IL-6 antibody is delivered by a dry powder inhaler or a sprayer. There are several desirable features of an inhalation device for administering at least one antibody of the present invention. For example, delivery by the inhalation device is advantageously reliable, reproducible, and accurate. The inhalation device can optionally deliver small dry particles, e.g. less than about 10 µm, preferably about 1-5 µm, for good respirability.

Administration of IL-6 Antibody Compositions as a Spray

A spray including IL-6 antibody composition protein can be produced by forcing a suspension or solution of at least one Anti-IL-6 antibody through a nozzle under pressure. The nozzle size and configuration, the applied pressure, and the liquid feed rate can be chosen to achieve the desired output and particle size. An electrospray can be produced, for example, by an electric field in connection with a capillary or nozzle feed. Advantageously, particles of at least one Anti-IL-6 antibody composition protein delivered by a sprayer have a particle size less than about 10 µm, preferably in the range of about 1 µm to about 5 µm, and most preferably about 2 µm to about 3 µm.

Formulations of at least one Anti-IL-6 antibody composition protein suitable for use with a sprayer typically include antibody composition protein in an aqueous solution at a concentration of about 0.1 mg to about 100 mg of at least one Anti-IL-6 antibody composition protein per ml of solution or mg/gm, or any range or value therein, e.g., but not limited to, 0.1, 0.2., 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/ml or mg/gm. The formulation can include agents such as an excipient, a buffer, an isotonicity agent, a preservative, a surfactant, and, preferably, zinc. The formulation can also include an excipient or agent for stabilization of the antibody composition protein, such as a buffer, a reducing agent, a bulk protein, or a carbohydrate. Bulk proteins useful in formulating antibody composition proteins include albumin, protamine, or the like. Typical carbohydrates useful in formulating antibody composition proteins include sucrose, mannitol, lactose, trehalose, glucose, or the like. The antibody composition protein formulation can also include a surfactant, which can reduce or prevent surface-induced aggregation of the antibody composition protein caused by atomization of the solution in forming an aerosol. Various conventional surfactants can be employed, such as polyoxyethylene fatty acid esters and alcohols, and polyoxy ethylene sorbitol fatty acid esters. Amounts will generally range between 0.001 and 14% by weight of the formulation. Especially preferred surfactants for purposes of this invention are polyoxyethylene sorbitan monooleate, polysorbate 80, polysorbate 20, or the like. Additional agents known in the art for formulation of a protein such as IL-6 antibodies, or specified portions, or variants, can also be included in the formulation.

Administration of IL-6 Antibody Compositions by a Nebulizer

Antibody composition protein can be administered by a nebulizer, such as jet nebulizer or an ultrasonic nebulizer. Typically, in a jet nebulizer, a compressed air source is used to create a high-velocity air jet through an orifice. As the gas expands beyond the nozzle, a low-pressure region is created, which draws a solution of antibody composition protein through a capillary tube connected to a liquid reservoir. The liquid stream from the capillary tube is sheared into unstable filaments and droplets as it exits the tube, creating the aerosol. A range of configurations, flow rates, and baffle types can be employed to achieve the desired performance characteristics from a given jet nebulizer. In an ultrasonic nebulizer, high-frequency electrical energy is used to create vibrational, mechanical energy, typically employing a piezoelectric transducer. This energy is transmitted to the formulation of antibody composition protein either directly or through a coupling fluid, creating an aerosol including the antibody composition protein. Advantageously, particles of antibody composition protein delivered by a nebulizer have a particle size less than about 10 µm, preferably in the range of about 1 µm to about 5 µm, and most preferably about 2 µm to about 3 µm.

Formulations of at least one Anti-IL-6 antibody suitable for use with a nebulizer, either jet or ultrasonic, typically include a concentration of about 0.1 mg to about 100 mg of at least one Anti-IL-6 antibody protein per ml of solution. The formulation can include agents such as an excipient, a buffer, an isotonicity agent, a preservative, a surfactant, and, preferably, zinc. The formulation can also include an excipient or agent for stabilization of the at least one Anti-IL-6 antibody composition protein, such as a buffer, a reducing agent, a bulk protein, or a carbohydrate. Bulk proteins useful in formulating at least one Anti-IL-6 antibody composition proteins include albumin, protamine, or the like. Typical carbohydrates useful in formulating at least one anti-IL-6 antibody include sucrose, mannitol, lactose, trehalose, glucose, or the like. The at least one Anti-IL-6 antibody formulation can also include a surfactant, which can reduce or prevent surface-induced aggregation of the at least one Anti-IL-6 antibody caused by atomization of the solution in forming an aerosol. Various conventional surfactants can be employed, such as polyoxyethylene fatty acid esters and alcohols, and polyoxyethylene sorbital fatty acid esters. Amounts will generally range between 0.001 and 4% by weight of the formulation. Especially preferred surfactants for purposes of this invention are polyoxyethylene sorbitan mono-oleate, polysorbate 80, polysorbate 20, or the like. Additional agents known in the art for formulation of a protein such as antibody protein can also be included in the formulation.

Administration of IL-6 Antibody Compositions by a Metered Dose Inhaler

In a metered dose inhaler (MDI), a propellant, at least one Anti-IL-6 antibody, and any excipients or other additives are contained in a canister as a mixture including a liquefied compressed gas. Actuation of the metering valve releases die mixture as an aerosol, preferably containing particles in the size range of less than about 10 µm, preferably about 1 µm to about 5 µm, and most preferably about 2 µm to about 3 µm. The desired aerosol particle size can be obtained by employing a formulation of antibody composition protein produced by various methods known to those of skill in the art, including jet-milling, spray drying, critical point condensation, or the like. Preferred metered dose inhalers include those manufactured by 3M or Glaxo and employing a hydrofluorocarbon propellant.

Formulations of at least one Anti-IL-6 antibody for use with a metered-dose inhaler device will generally include a finely divided powder containing at least one Anti-IL-6 antibody as a suspension in a non-aqueous medium, for example, suspended in a propellant with the aid of a surfactant. The propellant can be any conventional material employed for this purpose, such as chlorofluorocarbon, a hydrochlorofluorocarbon, a hydrofluorocarbon, or a hydrocarbon, including trichlorofluoromethane, dichlorodifluoromethane, dichlorotetrafluoroethanol and 1,1,1,2-tetrafluoroethane, HFA-134a (hydrofluoroalkane-134a), HFA-227 (hydrofluoroalkane-227), or the like. Preferably the propellant is a hydrofluorocarbon. The surfactant can be chosen to stabilize the at least one anti-IL-6 antibody as a suspension in the propellant, to protect the active agent against chemical degradation, and the like. Suitable surfactants include sorbitan trioleate, soya lecithin, oleic acid, or the like. In some cases solution aerosols are preferred using solvents such as ethanol. Additional agents known in the art for formulation of a protein can also be included in the formulation.

One of ordinary skill in the art will recognize that the methods of the current invention can be achieved by pulmonary administration of at least one Anti-IL-6 antibody compositions via devices not described herein.

Oral Formulations and Administration

Formulations for oral administration rely on the co-administration of adjuvants (e.g., resorcinols and nonionic surfactants such as polyoxyethylene oleyl ether and n-hexadecylpolyethylene ether) to increase artificially the permeability of the intestinal walls, as well as the co-administration of enzymatic inhibitors (e.g., pancreatic trypsin inhibitors, diisopropylfluorophosphate (DFF) and trasylol) to inhibit enzymatic degradation. The active constituent compound of the solid-type dosage form for oral administration can be mixed with at least one additive, including sucrose, lactose, cellulose, mannitol, trehalose, raffinose, maltitol, dextran, starches, agar, arginates, chitins, chitosans, pectins, gum tragacanth, gum arabic, gelatin, collagen, casein, albumin, synthetic or semisynthetic polymer, and glyceride. These dosage forms can also contain other type(s) of additives, e.g., inactive diluting agent, lubricant such as magnesium stearate, paraben, preserving agent such as sorbic acid, ascorbic acid, alpha.-tocopherol, antioxidant such as cysteine, disintegrator, binder, thickener, buffering agent, sweetening agent, flavoring agent, perfuming agent, etc.

Tablets and pills can be further processed into enteric-coated preparations. The liquid preparations for oral administration include emulsion, syrup, elixir, suspension and solution preparations allowable for medical use. These preparations can contain inactive diluting agents ordinarily used in said field, e.g., water. Liposomes have also been described as drug deliver systems for insulin and heparin (U.S. Pat. No. 4,239,754). More recently, microspheres of artificial polymers of mixed amino acids (proteinoids) have been used to deliver pharmaceuticals (U.S. Pat. No. 4,925, 673). Furthermore, carrier compounds described in U.S. Pat.

No. 5,879,681 and U.S. Pat. No. 5,5,871,753 are used to deliver biologically active agents orally are known in the art.

Mucosal Formulations and Administration

For absorption through mucosal surfaces, compositions and methods of administering at least one Anti-IL-6 antibody include an emulsion comprising a plurality of submicron particles, a mucoadhesive macromolecule, a bioactive peptide, and an aqueous continuous phase, which promotes absorption through mucosal surfaces by achieving mucoadhesion of the emulsion particles (U.S. Pat. No. 5,514,670). Mucous surfaces suitable for application of the emulsions of the present invention can include corneal, conjunctival, buccal, sublingual, nasal, vaginal, pulmonary, stomachic, intestinal, and rectal routes of administration. Formulations for vaginal or rectal administration, e.g. suppositories, can contain as excipients, for example, polyalkyleneglycols, vaseline, cocoa butter, and the like. Formulations for intranasal administration can be solid and contain as excipients, for example, lactose or can be aqueous or oily solutions of nasal drops. For buccal administration excipients include sugars, calcium stearate, magnesium stearate, pregelinatined starch, and the like (U.S. Pat. No. 5,849,695).

Transdermal Formulations and Administration

For transdermal administration, the at least one Anti-IL-6 antibody is encapsulated in a delivery device such as a liposome or polymeric nanoparticles, microparticle, microcapsule, or microspheres (referred to collectively as microparticles unless otherwise stated). A number of suitable devices are known, including microparticles made of synthetic polymers such as polyhydroxy acids such as polylactic acid, polyglycolic acid and copolymers thereof, polyorthoesters, polyanhydrides, and polyphosphazenes, and natural polymers such as collagen, polyamino acids, albumin and other proteins, alginate and other polysaccharides, and combinations thereof (U.S. Pat. No. 5,814,599).

Prolonged Administration and Formulations

It can be sometimes desirable to deliver the compounds of the present invention to the subject over prolonged periods of time, for example, for periods of one week to one year from a single administration. Various slow release, depot or implant dosage forms can be utilized. For example, a dosage form can contain a pharmaceutically acceptable non-toxic salt of the compounds that has a low degree of solubility in body fluids, for example, (a) an acid addition salt with a polybasic acid such as phosphoric acid, sulfuric acid, citric acid, tartaric acid, tannic acid, pamoic acid, alginic acid, polyglutamic acid, naphthalene mono- or di-sulfonic acids, polygalacturonic acid, and the like; (b) a salt with a polyvalent metal cation such as zinc, calcium, bismuth, barium, magnesium, aluminum, copper, cobalt, nickel, cadmium and the like, or with an organic cation formed from e.g., N,N'-dibenzyl-ethylenediamine or ethylenediamine; or (c) combinations of (a) and (b) e.g. a zinc tannate salt. Additionally, the compounds of the present invention or, preferably, a relatively insoluble salt such as those just described, can be formulated in a gel, for example, an aluminum monostearate gel with, e.g. sesame oil, suitable for injection. Particularly preferred salts are zinc salts, zinc tannate salts, pamoate salts, and the like. Another type of slow release depot formulation for injection would contain the compound or salt dispersed for encapsulated in a slow degrading, non-toxic, non-antigenic polymer such as a polylactic acid/polyglycolic acid polymer for example as described in U.S. Pat. No. 3,773,919. The compounds or, preferably, relatively insoluble salts such as those described above can also be formulated in cholesterol matrix silastic pellets, particularly for use in animals. Additional slow release, depot or implant formulations, e.g. gas or liquid liposomes are known in the literature (U.S. Pat. No. 5,770,222 and "Sustained and Controlled Release Drug Delivery Systems", J. R. Robinson ed., Marcel Dekker, Inc., N.Y., 1978).

Abbreviations:

| | |
|---|---|
| BSA | bovine serum albumin |
| EIA | enzyme immunoassay |
| FBS | fetal bovine serum |
| $H_2O_2$ | hydrogen peroxide |
| HRP | horseradish peroxidase |
| Ig | immunoglobulin |
| IL-6 | Interleukin-6 |
| IP | intraperitoneal |
| IV | intravenous |
| Mab | monoclonal antibody |
| OD | optical density |
| OPD | o-Phenylenediamine dihydrochloride |
| PEG | polyethylene glycol |
| PSA | penicillin, streptomycin, amphotericin |
| RT | room temperature |
| SQ | subcutaneous |
| v/v | volume per volume |
| w/v | weight per volume |

EXAMPLE 1

Affinity and Quantitation ELISAs

Affinity ELISA with IL-6

Nunc-Immuno MaxiSorp 96 well plates were coated with 100 µl of 2 µg/ml, 0.2 µg/ml, 0.02 µg/ml or 0.002 µg/ml IL-6 in coating solution; covered with plate sealer and incubated at 4° C. overnight. Plates were emptied and the residual liquid tapped out on paper towels. 200 µl washing solution (0.05% Tween-20 in PBS) was added and shaken at 200 RPM for 5 min at room temperature. The plates were emptied and residual liquid tapped out on paper towels. 200 µl blocking solution (2% Carnation milk in PBS) was added and shaken at 200 RPM for one hour at room temperature. Plates were emptied and residual liquid tapped out on paper towels. 100 µl of diluted samples for ELISA was used. The samples were shaken at 200 RPM for one hour at room temperature; plates emptied and residual liquid tapped out on paper towels. 200 µl washing solution (0.05% Tween-20 in PBS) was added, shaken at 200 RPM for 5 min at room temperature; plates emptied and residual liquid tapped out on paper towels. This process was repeated three times. 100 µl of 1:2500 dilution of anti-human IgG conjugated with HRP diluted in block solution (2% Carnation milk in PBS) was added for 001 samples. 100 µl of 1:2500 dilution of anti-rabbit IgG conjugated with HRP diluted in block solution (2% Carnation milk in PBS) was added for control antibody. The contents were shaken at 200 RPM for one hour at room temperature, plates emptied and residue liquid tapped out on paper towels. 200 µl washing solution (0.05% Tween-20 in PBS) was added, shaken at 200 RPM for 5 min at room temperature; plates emptied and residual liquid tapped out on paper towels. This process was repeated three times. 100 µl TMB substrate solution was added, and incubated at room temperature. The reaction was stopped with 1 N HCl, and the plate read at 450 nm.

Affinity ELISA with biotinylated IL-6

Nunc-Immuno MaxiSorp 96 well plates were coated with 100 µl of 10 µg/ml affinity purified Fc-specific goat anti-human IgG in coating solution. Plates were covered with plate sealer and incubated at 4° C. overnight. Emptied plate and tapped out residual liquid on paper towels. Added 200 µl washing solution (0.05% Tween-20 in PBS). Shaken at 200 RPM for 5 min at room temperature. Emptied plate and tapped out residual liquid on paper towels. Added 200 µl blocking solution (2% Carnation milk in PBS). Shaken at 200 RPM for one hour at room temperature. Emptied plate and tapped out residual liquid on paper towels. Used 100 µl of diluted sample for ELISA. Shaken at 200 RPM for one hour at room temperature. Emptied plate and tapped out residual liquid on paper towels. Added 200 µl washing solution (0.05% Tween-20 in PBS). Shaken at 200 RPM for 5 min at room temperature. Emptied plate and tapped out residual liquid on paper towels. Repeated three times. Added 100 µl of 2 µg/ml, 0.2 µg/ml, 0.02 µg/ml or 0.002 µg/ml of biotinylated IL-6 diluted in PBS. Shaken at 200 RPM for one hour at room temperature. Emptied plate and tapped out residue liquid on paper towels. Added 200 µl washing solution (0.05% Tween-20 in PBS). Shaken at 200 RPM for 5 min at room temperature. Emptied plate and tapped out residual liquid on paper towels. Repeated three times. Added 100 µl of 1:2000 dilution of anti-biotin antibody conjugated with HRP diluted in block solution (2% Carnation milk in PBS). Shaken at 200 RPM for one hour at room Temperature. Emptied plate and tapped out residue liquid on paper towels. Added 100 µl TMB substrate solution. Incubated at room temperature. Stopped the reaction with 1 N HCl. Read plates at 450 nm.

Quantitation ELISA

This ELISA was used for determining the expression level of antibodies in cell culture supernatant. Nunc-Immuno MaxiSorp 96 well plates (Nalge Nunc) were coated with 100 µl of 10 µg/ml affinity purified Fc-specific goat anti-human IgG in coating solution. Covered with plate sealer and incubated at 4° C. overnight. Emptied plate and tapped out residual liquid on paper towels. Added 200 µl washing solution (0.05% Tween-20 in PBS). Shaken at 200 RPM for 5 min at room temperature. Emptied plate and tapped out residual liquid on paper towels. Added 200 µl blocking solution (2% Carnation milk in PBS). Shaken at 200 RPM for one hour at room temperature. Emptied plate and tapped out residual liquid on paper towels. Used 100 µl of diluted sample for ELISA. 20 ng/ml of human IgG and 1:2 dilution thereafter was used for standards. Supernatant from transfection (50 ng-200 ng/ml) was diluted from none to 1:10 for assay. Shaken at 200 RPM for one hour at room temperature. Emptied plate and tapped out residual liquid on paper towels. Added 200 washing solution (0.05% Tween-20 in PBS). Shaken at 200 RPM for 5 min at room temperature. Emptied plate and tapped out residual liquid on paper towels. Repeated three times. Added 100 µl of 1:2500 or 1:5000 dilution of goat anti-human IgG conjugated with HRP diluted in block solution (2% Carnation milk in PBS). Shaken at 200 RPM for one hour at room temperature. Emptied plate and tapped out residue liquid on paper towels. Added 100 µl TMB substrate solution (Sigma). Incubated at room temperature. Stopped the reaction with 1 N HCl. Read plates at 450 nm.

Specific Activity.

Figure 29:
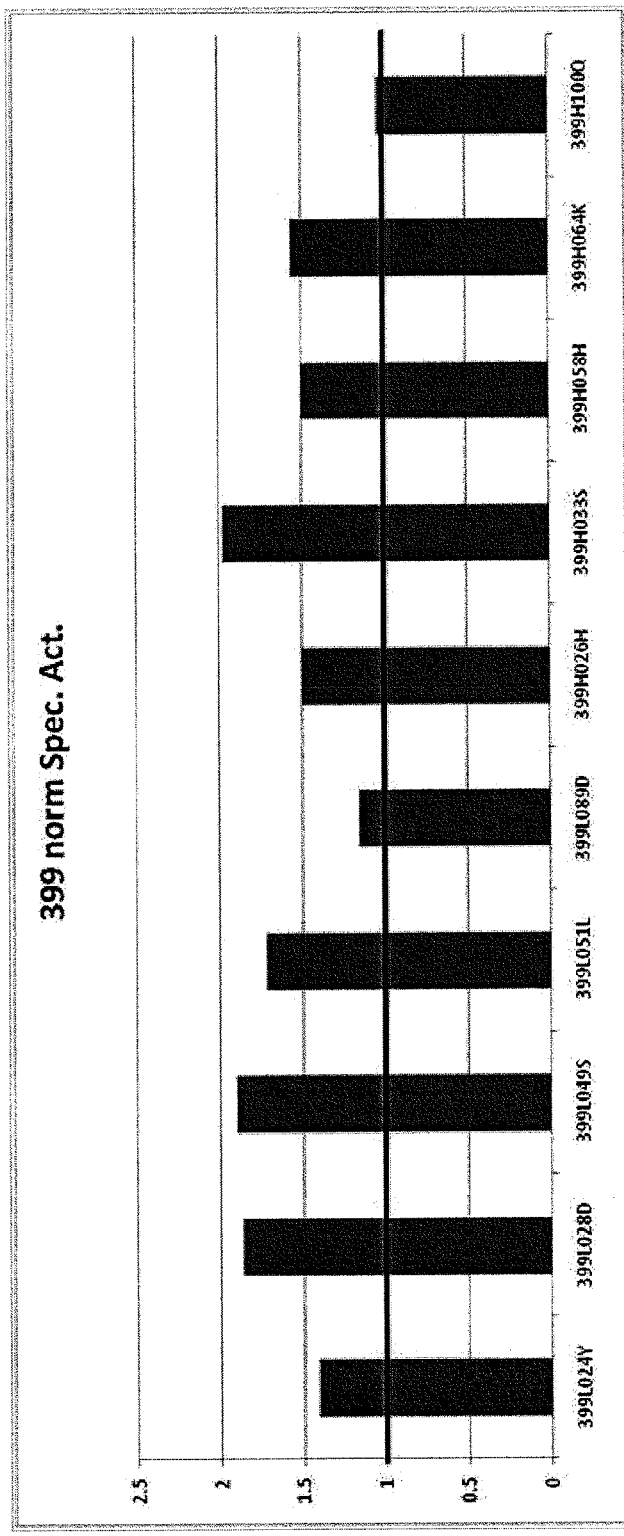
FIG. 29 shows the relative specific activity of the top 10 hits from BA399 affinity maturation by comprehensive positional evolution (CPE). The relative specific activity for each clone is normalized to that of Anti-IL-6 Ab BA399, which is shown as the black horizontal line.
Figure 32:
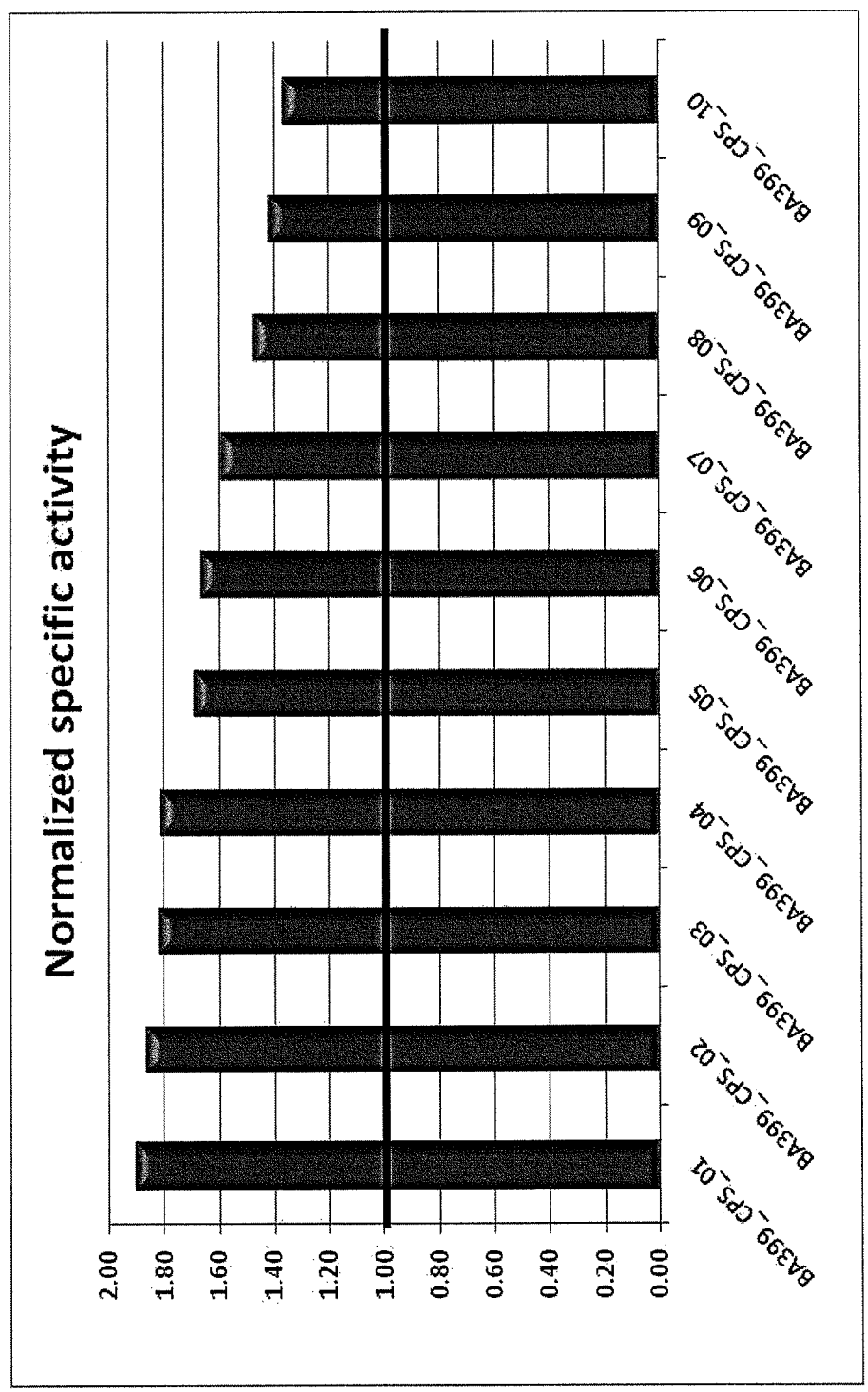
FIG. 32 shows normalized specific activity of the top 10 hits from BA399 affinity maturation by combinatorial protein synthesis (CPS). The relative specific activity for each clone is normalized to that of Anti-IL-6 Ab BA399, shown as a horizontal black line.

The Specific ELISA activity for each anti-IL-6 Mab is calculated as the value of Affinity ELISA divided by the value of Quantitation ELISA. FIG. 29 shows the normalized specific activity for the top 10 CPE hits from affinity maturation. FIG. 32 shows the normalized specific activity for the top 10 CPS hits. Specific ELISA activity of the clones is divided by the specific activity of clone BA399. The normalized specific activity of BA399 is 1 (horizontal black line).

Functional ELISA of 001

This ELISA was used to compare the affinity of antibodies in cell culture supernatant. Nunc Immuno-MaxiSorp 96 well plates were coated with 100 uL 2 µg/ml of 001 IL-6 antigen and incubated overnight at 4° C. Plates were decanted, washed (0.05% Tween-20 in PBS) and blocked for 1 h at room temperature with 2% Carnation non-fat milk in PBS. 20 ng/ml of anti-001 control antibody and 1:2 dilution thereafter was used as standards. Duplicates of 100 uL supernatant from transfection was diluted from none to 1:50 for assays (50 ng-200 ng/ml) and added to plates for 1 h at room temperature. Plates were decanted and washed 3 times. Added to each well 100 µl of 1:5000 dilution of goat anti-human IgG conjugated with HRP diluted in block solution (2% Carnation milk in PBS) which was shaken at 200 RPM for one hour at room temperature. Decanted and washed plate. Added 100 µl TMB substrate solution (Sigma) and incubated at room temperature; checking every 2-5 minutes. Stopped the reaction with 1 N HCl. Read plates at 450 nm.

EXAMPLE 2

Competition ELISA to Confirm Epitope Overlapping Between BA001 and Anti-IL-6 Antibodies of the Invention Coated Nunc-Immuno MaxiSorp 96 well plates with 100 µl of 0.2 µg/ml IL-6 in coating solution (prepared enough wells for the experiment). Covered with plate sealer and incubate at 4° C. overnight. Emptied plate and tapped out residual liquid on paper towels. Added 200 µl washing solution (0.05% Tween-20 in PBS). Plates were shaken at 200 RPM for 5 min at room temperature. Emptied plate and tapped out residual liquid on paper towels. Added 200 µl blocking solution (2% Carnation milk in PBS). Plates were shaken at 200 RPM for one hour at room temperature. Emptied plate and tapped out residual liquid on paper towels. Added 100 ul of 0.05 µg/ml of biotinylated 001 diluted in PBS with 0 µg/ml, 0.005 µg/ml, 0.05 µg/ml, 0.5 µg/ml, 5 µg/ml of purified 001 antibody (prepared two reactions for each purified 001 antibody amount). Also added 100 µl of 0.05 µg/ml of biotinylated 001 diluted in PBS with 0 µg/ml, 0.005 µg/ml, 0.05 µg/ml, 0.5 µg/ml, 5 µg/ml of non-anti-IL6 antibody (any anti-mouse IgG or other negative control antibody) (prepared two reactions for each purified 001 antibody amount). Plates were shaken at 200 RPM for one hour at room temperature. Emptied plate and tapped out residue liquid on paper towels. Added 200 µl washing solution (0.05% Tween-20 in PBS). Plates were shaken at 200 RPM for 5 min at room temperature. Emptied plate and tapped out residual liquid on paper towels. Repeated three times. Added 100 µl of 1:2000 dilution of anti-biotin antibody conjugated with HRP diluted in block solution (2% Carnation milk in PBS). Plates were shaken at 200 RPM for one hour at room temperature. Emptied plates and tapped out residue liquid on paper towels. Added 100 µl TMB substrate solution. Incubated at room temperature. Stopped the reaction with 1 N HCl. Read plates at 450 nm. Results are set forth in FIG. 10. As shown all of the Anti-IL-6 Abs of the present invention reduce binding of BA001 to human IL6. This indicates that the novel humanized antibodies bind to the same region as BA001.

EXAMPLE 3

CHO-S Cells Transfection

One week before transfection, CHO-S cells (Invitrogen) were transferred to monolayer culture in serum supplemented Dulbecco's Modified Eagle Medium (D-MEM) (Invitrogen). One day before transfection, cells are plated $0.4 \times 10^5$ cells in 100 uL of serum supplemented D-MEM per transfection sample in 96 well formats. Prepared DNA-Lipofectamine complexes for each transfection sample. Diluted 0.25 ug of DNA in 25 uL Opti-MEM Reduced Serum Medium and mixed gently, and incubated at room temperature for 5 min. Diluted 0.5 uL Lipofectamine 2000 (Invitrogen) in 25 uL Opti-MEM Reduced Serum Medium. Mixed gently and incubated at room temperature for 5 min. Combined the diluted DNA with the diluted Lipofectamine. Mixed gently and incubated for 20 min at room temperature. Added the 50 uL DNA-Lipofectamine complexes to each well containing cells and medium. Mixed gently by rocking the plate. Incubated the cells at 37 C in a 5% $CO_2$ incubator overnight. Aspirated medium in each well. Added 100 uL of serum supplemented D-MEM to each well. Collected supernatant for ELISA assay and cell lysate for beta-galactosidase assay.

EXAMPLE 4

Antibody Purification from Cell Culture Supernatant

The following buffers were prepared in a standard fashion. Binding buffer 10 mM $Na_2HPO_4/NaH_2PO_4$, pH 7.0. Elution Buffer: 12.5 mM Citric Acid, pH 2.7 (use $Na_3$-citrate). Neutralization Buffer: 0.5 M $Na_2HPO_4/NaH_2PO_4$, pH 8.0. 20% Ethanol and water. All buffers were filtered before use (0.45 µm). Supernatants were purified using an ÄKTA™ FPLC™ system fitted with a HiTrap™ Protein G Sepharose HP (1 mL volume) column. For Sample loading, loading tubes are rinsed with ethanol (20 mL, 5 mL/min), then binding buffer (20 mL, 5 mL/min). Protein G column is attached to system and rinsed with binding buffer (10 mL, 1 mL/mn). The sample is loaded at 1 mL/mn or slower (for overnight loading). After loading, the column is detached and loading tubes are rinsed with water (20 mL, 5 mL/mn) and then 20% ethanol (20 mL, 5 mL/min). For antibody purification, the AKTA system was washed (pump A and all tubing) with binding buffer. Collection tubes were prepared for fraction collection by adding 50 µl Neutralization buffer to each tube. The protein G column was attached to the system. The flow was set to 1 mL/min, and run until baseline was stable. The column valve was switched to position 3. The column was washed with binding buffer (10 mL minimum) until baseline was reached. The pump was stopped and washed with water, then with Elution buffer. The flow was set to 1 mL/min, and run until baseline was stable. The column valve was switched to position 3 and the fraction collector was started (0.5 mL fractions). Fractions were collected until base line was reached at which point the system was stopped. The elution profile was copied to the clipboard and into WORD document. The pump was washed with water; then with binding buffer. The protein G column was washed with binding buffer (10 mL). The pump was washed with 20% Ethanol. The column was washed with 20% Ethanol (20 mL) stored in the coldroom.

EXAMPLE 5

Sapidyne Analysis

The Sapidyne KinExA™ kinetic exclusion assay automated immunoassay system (Sapidyne Instruments, Inc., Boise, Id.) was used to determine equilibrium and rate constants of various antibodies according to the manufacturer's protocols. The Kinetic Exclusion Assay (KinExA) is a method to measure true equilibrium binding affinity and kinetics, in solution phase, on unmodified molecules. See for example, Darling et al., Kinetic Exclusion Assay Technology Characterization of Molecular Interactions, ASSAY and Drug Dev. Technol. 2(6): 2004, which is incorporated herein by reference. Briefly, the KinExA™ system is comprised of a capillary flow/observation cell (inner diameter=1.6 mm) fitted with a microporous screen through which various solutions are drawn under negative pressure. Uniform particles larger than the average pore size of the screen (53 mm) were precoated with antigen and deposited above the screen in a packed bed. Individual solution mixtures of antigen and antibody either at or approaching equilibrium were then drawn through the packed bed of particles. Only those antibodies in each mixture with unoccupied binding sites were available to bind to the antigen coated on the solid phase. Quantification of primary antibody thus captured was achieved by the brief exposure of the particles to a fluorescently labeled anti-species secondary antibody, followed by measurement of the resulting fluorescence from the particles after removal of excess unbound reagents.

The antibodies were reconstituted in sterile 1×PBS, pH 7.4, 0.02% sodium azide, 10 mg/mL BSA. The antigen was IL-6 (21,000 kDa) in four separate vials at 0.5 mg, 1 mg, 0.5 mg and 0.5 mg, was diluted with sterile 1×PBS, pH 7.4, 0.02% sodium azide to 375 ug/mL, 1 mg/mL, 500 ug/mL and 500 ug/mL. The label, Cy5-conjugated AffiniPure goat anti-human IgG (H+L), Cy5, 1.5 µg/mL, was purchased from Jackson ImmunoResearch (West Grove, Pa.). The label was reconstituted in sterile 1×PBS, pH 7.4, 0.02% sodium azide, and diluted to 0.500 mg/mL. The Running Buffer was 1×PBS, pH 7.4, 0.02% sodium azide. The Sample Buffer was 1×PBS, pH 7.4, 0.02% sodium azide, 1 mg/mL Bovine Serum Albumin (BSA). The PMMA beads (Part# 440197/Lot3257) were provided by Sapidyne Instruments, Inc. (Boise, Id.) and coated with capture reagent in the following fashion. Beads were aliquoted dry into 200 mg portions and rocked in 1 mL coating solution (30 ug/mL BAP001 in running buffer) for 2 hours. Beads were then rocked 1 hour in blocking solution (10 mg/mL BSA in running buffer) and stored at 4° C.

For Equilibrium Analysis, PMMA beads coated with IL-6 were used to capture a portion of the free receptor from equilibrated sample of receptor (anti-IL-6 antibody) and ligand (antigen; IL-6). For each data point a fresh column of ligand-coated beads was introduced into the flow cell. The equilibrated sample was rapidly drawn past the column to minimize the contact time with the immobilized ligand. This ensured the contact time with the immobilized ligand does not disrupt the sample equilibrium. The immobilized ligand thus acted as a probe to capture free receptor in solution. Captured antibodies were detected with fluorescently labeled anti-human secondary antibody. Unbound reagents were washed away, leaving a signal that is proportional to free receptor in the equilibrated sample. The fluorescence was converted to voltage that is directly proportional to the amount of free receptor (antibody) in the equilibrated sample. Experiments were run at both high and low concentrations of receptor, then utilized together in an n-curve analysis for optimal results. For the Direct Method of Kinetic Analysis, the same immobilized ligand (IL-6 coated PMMA) was used as the capture reagent for kinetic experiments as for equilibrium experiments. The amount of free receptor (antibody) in the sample was measured pre-equilibrium, yielding data points that monitor the decrease in free receptor (antibody) over time as the sample moves toward equilibrium. FIG. 33 shows a table with data from Sapidyne analysis of the top 10 hits for anti-IL6 antibodies BAP001-clone 1 to BAP001-clone 10 compared to BA003 (CNTO136).

EXAMPLE 6

Biacore (Surface Plasmon Resonance) Affinity Measurement of BA001 and Humanized Derivatives BIAcore 3000, GE Healthcare, was used to determine binding curves and kinetic parameters. An anti-human Fc (1.8 mg/ml) was diluted to a concentration of 50 ug/ml in NaOAc buffer (10 mM, pH 4.8) and coupled to the carboxymethylated dextran matrix of a CM-5 sensor chip using the manufacturer's amine-coupling chemistry as described in the BIAcore systems manual. Using the surface preparation wizard aiming for 10000 RU, the carboxyl groups on the sensor surfaces were first activated with NHS/EDC followed by the addition of the anti-human Fc. The remaining activated groups were blocked by the injection of 1M ethanolamine. Each of the flow cells was coupled individually. Employing these conditions, the four flow cell surfaces containing 7554-9571 RU of anti-human Fc were prepared. In preliminary experiments, it was determine that three injections (15 ul at 30 ul/min) 100 mM $H_3PO_4$/0.05% CHAPS would efficiently remove the bound immunoglobulin and preserve the binding capacity of the immobilized anti-human Fc.

Experiments were performed on the BIAcore 3000 at 25° C. and a flow rate of 30 ul/min. The antibody candidate was dissolved in HBS (10 mM HEPES with 0.15M NaCl, 3.4 mM EDTA, and 0.05% surfactant P20 at pH 7.4) at 5 ug/ml. The analyte, IL-6, was dissolved in HBS at 0.25, 0.125, 0.062, 0.031 and 0.015 ug/ml. 3*30 ul of 5 ug/ml of antibody BA001 was flowed over its respective flow cell followed by injections of 240 ul of each IL-6 concentration at 30 ul/min (association phase) and an uninterrupted 1200 seconds of buffer flow (dissociation phase). The surface of the chip was regenerated by three sequential injections of 15 ul each with 100 m M $H_3PO_4$/0.05% CHAPS. The injections of HBS serve as a reference (blank sensogram) for the subtraction of bulk refractive indices for analysis. Using the 1:1 model in BIAevaluation 4.1, both a local fit and global fit was done for both dissociation (kd, [s−1] and association (ka, [$M^{-1}s^{-1}$]) and the dissociation constant (KD, [M]) calculated (kd/ka).

Analysis was done using BIAeveluation version 3.0. Kinetic constants were derived from sensogram data by fitting the experimental curves to the rate equations derived from models of the interaction mechanisms. A global analysis using a 1:1 binding model with local RUmax fit, the ka, kd, and KD were determined.

The following equations were utilized:

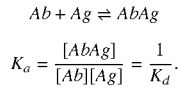

$$Ab + Ag \rightleftharpoons AbAg$$

$$K_a = \frac{[AbAg]}{[Ab][Ag]} = \frac{1}{K_d}.$$

Biacore data for humanized anti-IL6 Mabs before affinity maturation is set forth in FIG. 11. After BA399 affinity maturation was performed on anti-IL-6 Mab BA399; selected clones were tested by Biacore analysis. FIG. 34 shows Biacore data for clones BA399-2, BA399-5, BA-399-9 and BA399-10, respectively.

EXAMPLE 7

Inhibition of Stat3 Phosphorylation in THP-1 Cells

The Stat3 transcription factor is an important cell signaling molecule for many cytokines and growth factor receptors (Heim. The Jak-STAT pathway: cytokine signaling from the receptor to the nucleus. J. Recept. Signal Transduct. Res. 1999. 19(1-4):75-120.) Stat3 is constitutively activated in a number of human tumors and possesses oncogenic potential (Bromberg et al., Stat3 as an oncogene. Cell 1999 98(3):295-303) and anti-apoptotic activities. Stat3 is activated by phosphorylation at Tyr705, which induces dimerization, nuclear translocation and DNA binding (Ihle, Cytokine receptor signaling. Nature 1995, 377(6550):591-4). Transcriptional activation seems to be regulated by phosphorylation at Ser727 through the MAPK or mTOR pathways (Yokogami et al., Serine phosphorylation and maximal activation of Stat3 during CNTF signaling is mediated by rapamycin target mTOR. 2000 Curr Biol. 10(1):47-50).

Inhibition of Stat3 phosphorylation was measured in THP-1 cells. THP-1 (ATCC) cells were utilized according to standard protocols. For each test condition, $2 \times 10^6$ cells were serum starved. Positive controls consisted of THP-1 cells stimulated with human IL-6 (100, 50, 10 ng/ml) with sIL-6R (200 ng/ml). Negative controls consisted of media only. Test samples included 10 mg/ml of either CNTO 136, #399, BA399 clone #2, or BA399 clone #9; each with human IL-6 (100, 50, 10 ng/ml) and with sIL-6R (200 ng/ml). The IL-6, sIL-6R and antibodies were incubated at 37° C. for 15 minutes. The reaction mixture was then added to THP-1 cells. After incubation at 37° C. for 15 minutes, cells were washed with cold PBS and immediately assayed. The phosphorylation level of Stat3 was measured by a Cell Signaling Phosphot-Stat3 Sandwich ELISA kit used according to manufacturer's protocol (e.g. PathScan® Phospho-Stat3 (Tyr705) Sandwich ELISA Kit #7300, Cell Signaling Technology, Inc). The expression level of total Stat3 was measured by Santa Cruz rabbit polyclonal antibody against human Stat 3 (aa 50-240). (Santa Cruz Biotechnology, Inc.) The THP-1 phosphorylation data are shown in FIGS. 35-38. In each Figure, the data are normalized based on Western blot for total Stat3.

Figure 35:
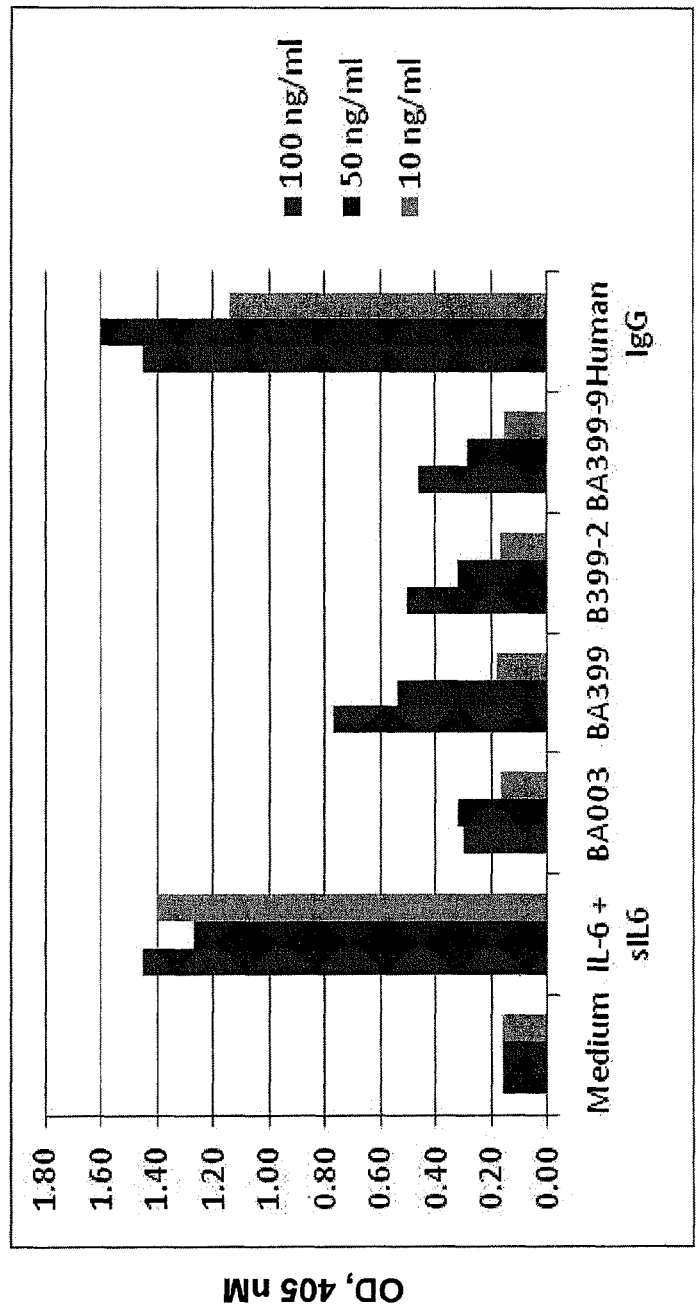
FIG. 35 shows inhibition of IL-6/sIL6R induced Stat3 phosphorylation in THP-1 cells by increasing anti-IL-6 Mab concentration. The data are normalized based on Western blot for total Stat3.

As shown in FIG. 35, each of the anti-IL-6 Mabs BA003 (CNTO 136), BA399, BA399-2 and BA399-9 caused a concentration-dependent decrease in phosphorylation of Stat-3 in IL6/sILR stimulated THP-1 cells compared to positive control.

FIG. 36 shows relative levels of phosphorylation when THP-1 cells are stimulated with 100 ng/mL IL6 and sIL-6R under various conditions (A). Total Stat3 levels by Western blot are shown in (B). Each of the anti-IL-6 Mabs BA003 (CNTO 136), BA399, BA399-2 and BA399-9 caused a significant decrease in phosphorylation of Stat-3 in IL6/sILR stimulated THP-1 cells compared to positive control.

FIG. 37 shows relative levels of phosphorylation when THP-1 cells are stimulated with 10 ng/mL IL6 and sIL-6R under various conditions (A). Total Stat3 levels by Western blot are shown in (B). Each of the anti-IL-6 Mabs BA003 (CNTO 136), BA399, BA399-2 and BA399-5 caused a significant decrease in phosphorylation of Stat-3 in IL6/sILR stimulated THP-1 cells compared to positive control.

FIG. 38 shows relative levels of phosphorylation when THP-1 cells are stimulated with 10 ng/mL IL6 and sIL-6R under various conditions (A). Total Stat3 levels by Western blot are shown in (B). Each of the anti-IL-6 Mabs BA003 (CNTO 136), BA399, BA399-2 and BA399-9 caused a significant decrease in phosphorylation of Stat-3 in IL6/sILR stimulated THP-1 cells compared to positive control.

EXAMPLE 8

Inhibition of Serum Amyloid A Protein Production by HepG2 Cells

Serum amyloid A (SAA) is an acute phase protein whose production is induced by IL-6. Cytokines such as IL-6, IL-1 and TNF are considered mediators of SAA protein synthesis. They stimulate hepatocytes to produce and release SAA into the bloodstream. High levels of SAA are seen in patients with acute and chronic inflammation. Secondary amyloidosis can develop as a result of prolonged or repeated inflammatory conditions in which SAA remains elevated. This progressive, fatal condition is characterized by loss of organ function. Inflammatory disorders such as rheumatoid arthritis, juvenile arthritis, ankylosing spondylitis, familial Mediterranean fever, progressive sclerosis as well as chronic infections such as tuberculosis and osteomyelitis are predisposed to developing amyloidosis (Reinhoff et al., Molecular and cellular biology of serum amyloid A. 1990 Mol. Bio. Med. 7:287-298.)

The ability of the anti-IL6 Mabs to block serum amyloid A protein production in Hep G2 cells stimulated by IL-6/sIL6R with IL-1b was tested as follows. HepG2 cells were seeded $2.25 \times 10^5$ cells/well in 24 well format. Duplicate wells per condition were utilized. Positive controls consisted of human IL-6 (100 ng/ml)+sIL-6R (200 ng/ml)+IL-1b (25 ng/ml). One negative control consisted of media only. Another negative control consisted of human IL-6 (100 ng/ml)+sIL-6R (200 ng/ml). Serial dilutions were made of each of anti-IL6 Mabs CNTO 136, BA399, BA399-2, BA399-9 ($10^{-5}$, $10^{-4}$, $10^{-3}$, $10^{-2}$, $10^{-1}$, 1 mg/ml) with human IL-6 (100 ng/ml) with sIL-6R (200 ng/ml) and IL-1b (25 ng/ml). IL-6, sIL-6R and Mabs were incubated at room temperature for 30 minutes. IL-1b was added to the IL6/antibody mixture. The whole reaction mixture was added to HepG2 cells. Serum Amyloid A (SAA) expression level was measured by Invitrogen human SAA Immunoassay kit according to manufacturers protocol at 24 hours and 48 hours post addition of the reaction mixture. The data are shown in FIGS. 39 and 40.

Figure 39:
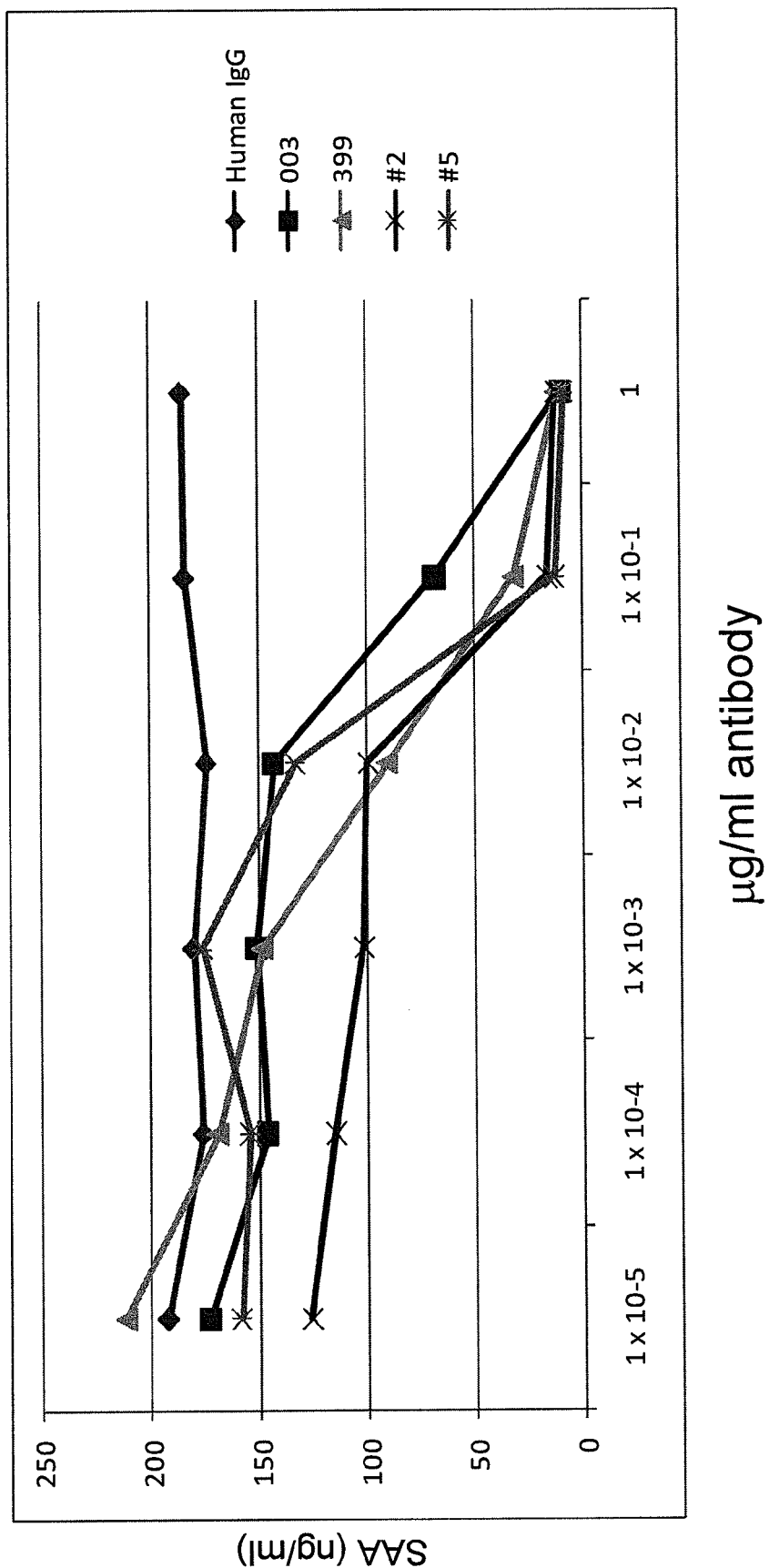
FIG. 39 shows inhibition of serum amyloid A protein production by HepG2 cells stimulated with human IL-6, sIL-6R and IL-1b, by serial dilutions of anti-IL-6 Mabs CNTO136, BA399, BA399-2, BA399-9 at 24 hours.

FIG. 39 shows inhibition of serum amyloid A protein production at 24 hours by HepG2 cells stimulated by human IL-6/sIL-6R and IL-1b by anti-IL-6 Mabs. Each of the anti-IL6 Mabs 003 (CNTO 136), BA399, BA399-2 and BA399-5 inhibited SAA production in a dose-dependent manner. Human IgG is the negative control.

Figure 40:
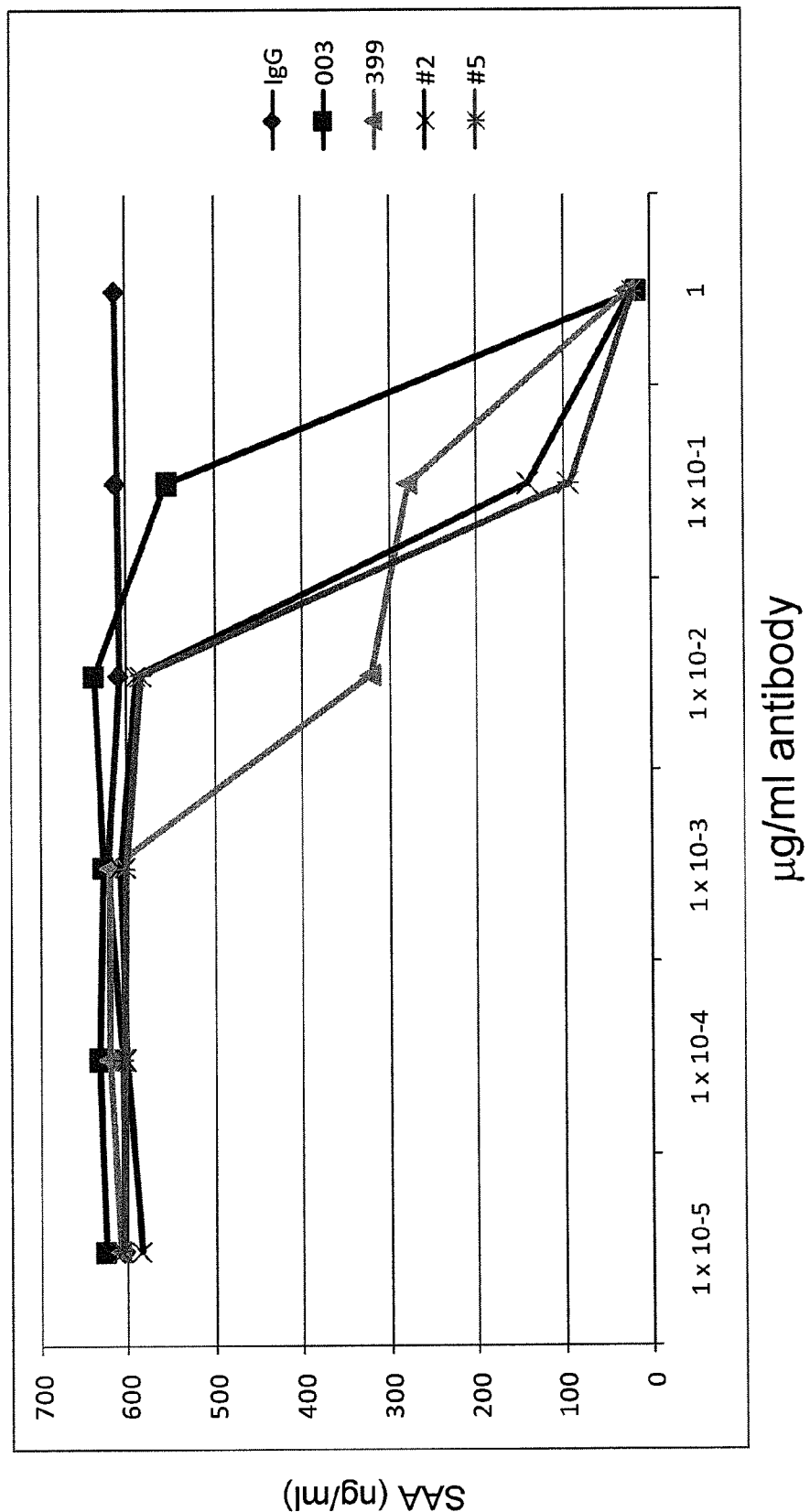
FIG. 40 shows inhibition of serum amyloid A protein production by HepG2 cells stimulated with human IL-6, sIL-6R and IL-1b, by serial dilutions of anti-IL-6 Mabs CNTO136, BA399, BA399-2, BA399-9 at 48 hours.

FIG. 40 shows inhibition of serum amyloid A protein production at 48 hours by HepG2 cells stimulated by human IL-6/sIL-6R and IL-1b by anti-IL-6 Mabs. Each of the anti-IL6 Mabs 003 (CNTO 136), BA399, BA399-2 and BA399-5 inhibited SAA production in a dose-dependent manner. Human IgG is the negative control.

EXAMPLE 9

Cross Reactivity with Monkey IL-6

Figure 41:
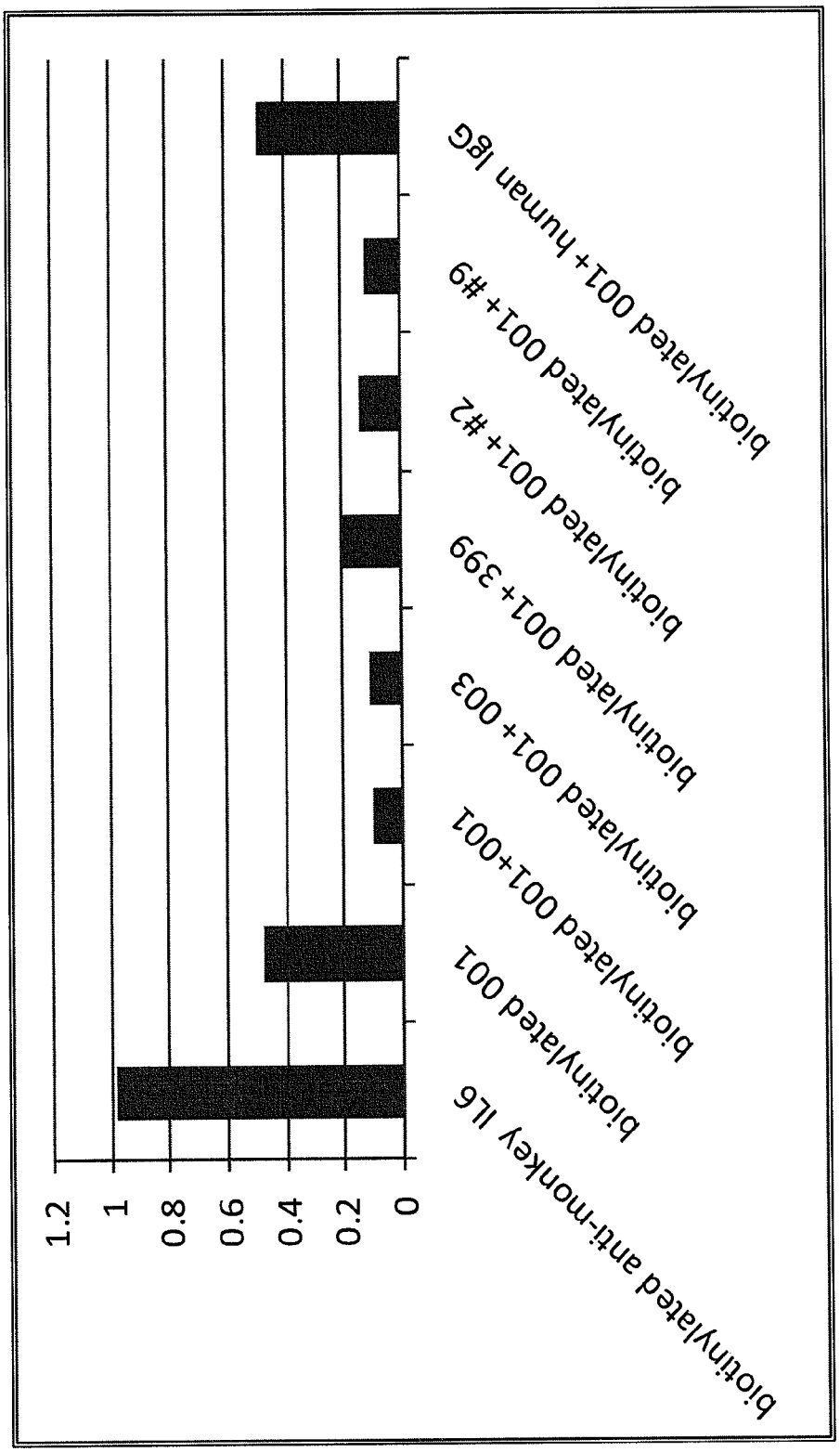
FIG. 41 shows cross reactivity to monkey IL-6 of biotinylated anti-IL-6 Mab 001, and the ability of non-biotinylated humanized anti-IL-6 Mabs BA001, BA003, BA399, BA399-2 and BA399-9 to block binding of biotinylated BA001 to monkey IL-6. Human IgG is used as a non-specific antibody.

ELISA plates were coated with anti-monkey IL-6 antibody. Added 300 pg/mL monkey IL-6. The positive control consisted of biotinylated anti-monkey IL-6. The negative control consisted of buffer only. Test samples of 0.1 mg/mL of biotinylated 001 with each of 5 mg/ml 001, 003, BA399, BA399-2, and BA399-9 along with non-specific human IgG were utilized. The ELISA was performed with Streptavidin-HRP. Data is shown in FIG. 41. Biotinylated anti-IL6 Mab exhibited some cross reactivity with monkey IL-6 which was partially blocked by each of the anti-IL6 humanized Mabs, but not the non-specific human IgG.

EXAMPLE 10

Inhibition of IL-6 Induced DS-1 Cell Proliferation

DS-1 is a B-cell line derived from an immunodeficient patient with intestinal lymphangiectasia and lymphoma. Cell proliferation is increased in response to human IL-6, but not murine IL-6. Despite constitutive IL-6 production, the in vitro growth of DS-1 is dependent on exogenous IL-6. (Bock et al., Characterization of a new IL-6 dependent human B-lymphoma cell line in a long term culture. Cytokine 5(5):480-489 (1993).

Figure 42:
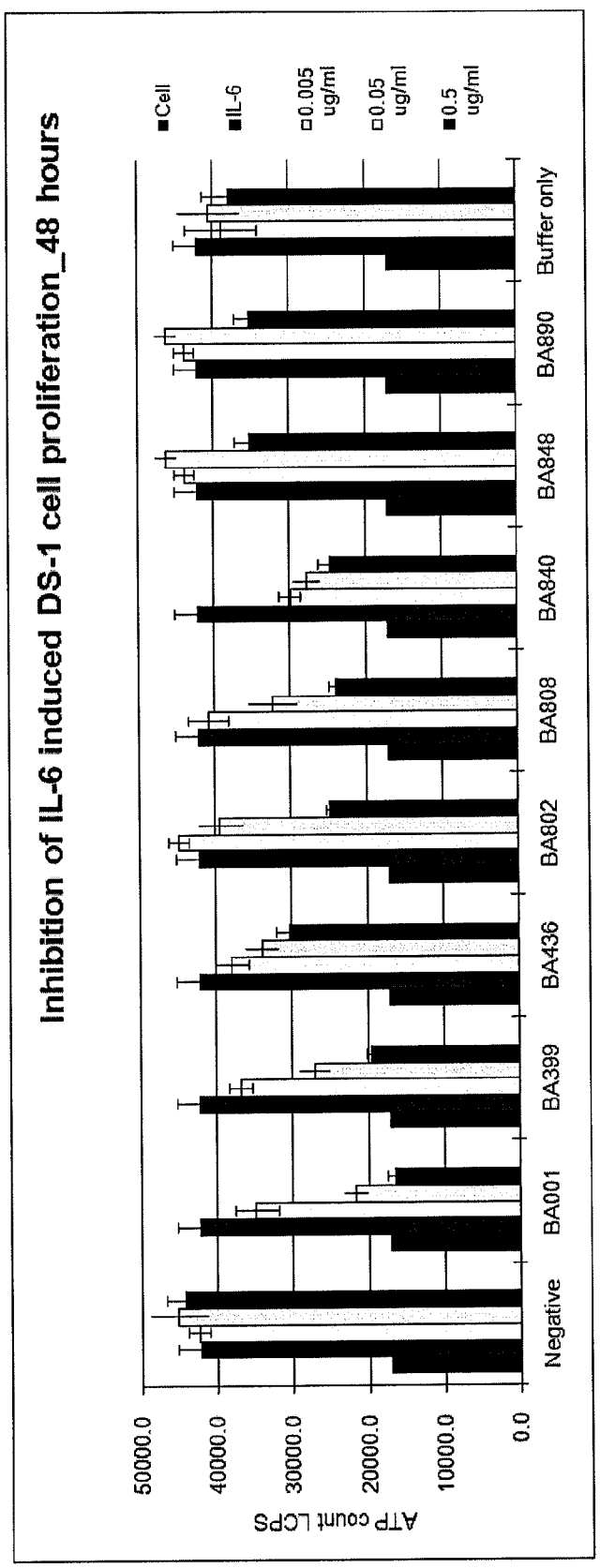
FIG. 42 shows inhibition of IL-6 induced DS-1 cell proliferation at 48 hours by anti-IL-6 Mabs BA001, BA399, BA436, BA802, BA808, BA840, BA848 and BA890.
Figure 43:
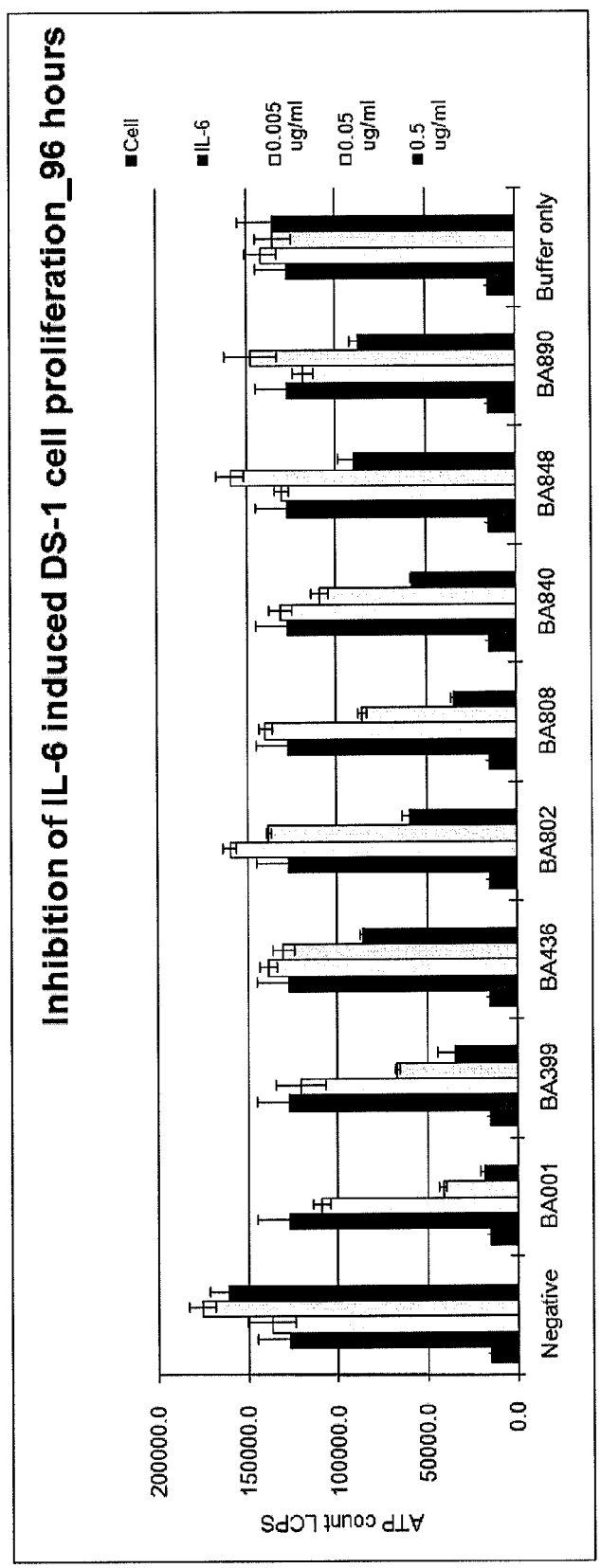
FIG. 43 shows inhibition of IL-6 induced DS-1 cell proliferation at 96 hours by anti-IL-6 Mabs BA001, BA399, BA436, BA802, BA808, BA840, BA848 and BA890.

Briefly, 800 cells were seeded in a 96 well format for each test condition. 10 U/mL human IL-6 and 0, 0.005, 0.05 and 0.5 micrograms/mL CNTO136, BA399 and various anti-IL-6 Mabs were utilized. Cell proliferation was measured using Promega CellTiter-Glo® assay (Promega Corp., Madison, Wis.) was measured at 0, 2, and 4 days post addition of antibodies. Inhibition of IL-6 induced DS-1 cell proliferation at 48 hours and 96 hours is shown in FIGS. 42 and 43, respectively. Several anti-IL-6 Mabs decreased DS-1 cell proliferation at both 48 and 96 hours in a dose-dependent manner, including BA001, BA399, BA436, BA802, BA808 and BA840.

It will be clear that the invention can be practiced otherwise than as particularly described in the foregoing description and examples.

Numerous modifications and variations of the present invention are possible in light of the above teachings and, therefore, are within the scope of the appended claims.

What is claimed is:

1. An isolated antibody or antibody fragment that binds to human IL-6, comprising a heavy chain variable region having the amino acid sequence of SEQ ID NO: 144; a light chain variable region having the amino acid sequence of SEQ ID NO: 76; and a constant region derived from one or more human antibodies.

2. An isolated antibody or antibody fragment that binds to human IL-6, comprising a heavy chain and light chain complementarity determining regions (CDRs) derived by affinity maturation from the variable regions from BA399, and a constant region derived from one or more human antibodies.

3. The antibody or fragment according to claim 1, wherein said antibody or fragment competitively inhibits in vivo the binding to human IL-6 of an anti IL-6 murine antibody.

4. The anti-IL-6 antibody or antibody fragment that binds to human IL-6 according to claim 1, wherein said antibody or antibody fragment binds IL-6 with an affinity ($K_d$) of at least $10^{-9}$ M.

5. The IL-6 antibody or antibody fragment that binds to human IL-6 according to claim 1, wherein said antibody or antibody fragment binds IL-6 with an affinity ($K_d$) of at least $10^{-11}$ M.

6. The IL-6 antibody or antibody fragment that binds to human IL-6, according to claim 1, wherein said antibody or antibody fragment binds with an affinity ($K_d$) of at least $10^{-12}$ M.

7. The IL-6 antibody or antibody fragment that binds to human IL-6 according to claim 1, wherein said antibody or antibody fragment substantially neutralizes at least one activity of at least one IL-6.

8. The IL-6 antibody or antibody fragment that binds to human IL-6 according to claim 7, wherein said activity is at least one selected from the group consisting of inhibition of IL-6 mediated MCP-1 production, inhibition of IL-6 signaling in THP-1 human monocytic leukemia cells, inhibition of IL-6 induced serum amyloid A production from HepG2 cells, and inhibition of rhIL-6 induced cell proliferation.

9. A pharmaceutical composition comprising an isolated IL-6 antibody or antibody fragment that binds to human IL-6 according to claim 1, and a carrier or diluent.

10. The composition according to claim 9, further comprising at least one compound or protein selected from at least one of TNF antagonist, an antirheumatic, a muscle relaxant, a narcotic, a non-steroid anti-inflamatory drug (NSAID), an analgesic, an anesthetic, a sedative, a local anethetic, a neuromuscular blocker, an antimicrobial, an antipsoriatic, a corticosteriod, an anabolic steroid, a diabetes related agent, a mineral, a nutritional, a thyroid agent, a vitamin, a calcium related hormone, an antidiarrheal, an antitussive, an antiemetic, an antiulcer, a laxative, an anticoagulant, an erythropieitin, a filgrastim, a sargramostim, an immunication, an immunoglobulin, an immunosuppressive, a growth hormone, a hormone replacement drug, an estrogen receptor modulator, a mydriatic, a cycloplegic, an alkylating agent, an antimetabolite, a mitotic inhibitor, a radiopharmaceutical, an antidepressant, antimanic agent, an antipsychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog, dornase alpha, a cytokine, a cytokine antagonist, and an anti-TNFα or IL-12/IL-23 monoclonal antibody.

11. An isolated fully human antibody or antibody fragment that binds to human IL-6, wherein said antibody or antibody fragment binds the same epitope or antigenic region as an anti-IL-6 antibody or fragment according to claim 1.

12. A pharmaceutical composition comprising at least one anti-IL-6 antibody or fragment according to claim 1, and at least one carrier selected from sterile water, sterile buffered water, or at least one preservative selected from the group consisting of phenol, m-cresol, p-cresol, o-cresol, chlorocresol, benzyl alcohol, phenylmercuric nitrite, phenoxyethanol, formaldehyde, chlorobutanol, magnesium chloride, alkylparaben, benzalkonium chloride, benzethonium chloride, sodium dehydroacetate and thimerosal, or mixtures thereof, in an aqueous diluent.

13. The composition of claim 12, wherein the concentration of anti-IL-6 antibody or antibody fragment that binds to human IL-6 is about 0.1 mg/ml to about 100 mg/ml.

14. The composition of claim 12, further comprising an isotonicity agent.

15. The composition of claim 12, further comprising a physiologically acceptable buffer.

16. A kit comprising at least one anti-IL-6 antibody or fragment according to claim 1 in lyophilized form in a first container, and an optional second container comprising sterile water, sterile buffered water, or at least one preservative selected from the group consisting of phenol, m-cresol, p-cresol, o-cresol, chlorocresol, benzyl alcohol, phenylmercuric nitrite, phenoxyethanol, formaldehyde, chlorobutanol, magnesium chloride, alkylparaben, benzalkonium chloride, benzethonium chloride, sodium dehydroacetate and thimerosal, or mixtures thereof in an aqueous diluent.

17. The kit of claim 16, wherein the concentration of anti-IL-6 antibody or antibody fragment that binds to human IL-6 is reconstituted to a concentration of about 0.1 mg/ml to about 500 mg/ml.

18. The kit of claim 16, further comprising an isotonicity agent.

19. The kit of claim 16, further comprising a physiologically acceptable buffer.

20. An article of manufacture for human pharmaceutical use, comprising packaging material and a container comprising a solution or a lyophilized form of at least one IL-6 antibody or antibody fragment that binds to human IL-6 according to claim 1.

21. The article of manufacture of claim 20, wherein said container is a glass or plastic container having a stopper for multi-use administration.

22. A method for producing an anti-IL-6 antibody or fragment according to claim 1, comprising expressing said antibody or fragment in an isolated host cell transformed with a nucleotide sequence encoding said antibody or fragment and recovering such antibody or fragment therefrom.

23. The method according to claim 22, wherein said isolated host cell is a mammalian cell, a plant cell or a yeast cell.

24. At least one anti-IL-6 antibody or antibody fragment that binds to human IL-6 produced by a method according to claim 22.

* * * * *

SEQUENCE LISTING

<160> NUMBER OF SEQ ID NOS: 160

<210> SEQ ID NO 1
<211> LENGTH: 100
<212> TYPE: PRT
<213> ORGANISM: Artificial Sequence
<220> FEATURE:
<223> OTHER INFORMATION: Synthetic

<400> SEQUENCE: 1

```
Ala Ile Gln Leu Thr Gln Ser Pro Ser Ser Leu Ser Ala Ser Val Gly
1               5                   10                  15

Asp Arg Val Thr Ile Thr Cys Ser Ala Ser Ser Ser Val Ser Tyr Met
            20                  25                  30

Tyr Trp Tyr Gln Gln Lys Pro Gly Gln Ala Pro Arg Leu Leu Ile Tyr
        35                  40                  45
```

```
Asp Thr Ser Asn Leu Ala Ser Gly Ile Pro Pro Arg Phe Ser Gly Ser
        50                  55                  60

Gly Tyr Gly Thr Asp Phe Thr Leu Thr Ile Asn Asn Ile Glu Ser Glu
 65                  70                  75                  80

Asp Ala Ala Tyr Tyr Phe Cys Gln Gln Trp Ser Gly Tyr Pro Tyr Thr
                85                  90                  95

Phe Gly Gln Gly
            100

<210> SEQ ID NO 2
<211> LENGTH: 300
<212> TYPE: DNA
<213> ORGANISM: Artificial Sequence
<220> FEATURE:
<223> OTHER INFORMATION: Synthetic

<400> SEQUENCE: 2
gccatccagt tgacccagtc tccatcctcc ctgtctgcat ctgtaggaga cagagtcacc      60
atcacttgca gtgccagctc aagtgtaagt tacatgtact ggtaccagca gaaacctggc     120
caggctccca ggctcctcat ctatgacaca tccaacctgg cttctgggat cccacctcga     180
ttcagtggca gcgggtatgg aacagatttt accctcacaa ttaataacat agaatctgag     240
gatgctgcat attacttctg tcagcagtgg agtggttacc catacacgtt cggccaaggg     300

<210> SEQ ID NO 3
<211> LENGTH: 112
<212> TYPE: PRT
<213> ORGANISM: Artificial Sequence
<220> FEATURE:
<223> OTHER INFORMATION: Synthetic

<400> SEQUENCE: 3

Gln Val Gln Leu Val Gln Ser Gly Ala Glu Val Lys Lys Pro Gly Ala
 1               5                  10                  15

Ser Val Lys Val Ser Cys Lys Ala Ser Gly Phe Thr Phe Ser Ser Phe
                20                  25                  30

Ala Met Ser Trp Ile Arg Gln Ser Pro Ser Arg Gly Leu Glu Trp Leu
            35                  40                  45

Gly Glu Ile Ser Ser Gly Gly Ser Tyr Thr Tyr Tyr Pro Asp Thr Val
        50                  55                  60

Thr Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Arg Gly Leu Trp Gly Tyr Tyr Ala Leu Asp Tyr Trp Gly Gln Gly
            100                 105                 110

<210> SEQ ID NO 4
<211> LENGTH: 336
<212> TYPE: DNA
<213> ORGANISM: Artificial Sequence
<220> FEATURE:
<223> OTHER INFORMATION: Synthetic

<400> SEQUENCE: 4
caggttcagc tggtgcagtc tggagctgag gtgaagaagc ctggggcctc agtgaaggtc      60
tcctgcaagg cttctggatt caccttcagt agctttgcca tgtcttggat caggcagtcc     120
ccatcgagag gccttgagtg gctgggtgaa attagtagtg gtgggagtta cacctactat     180
```

```
cctgacactg tgacgggcag attcaccatc tccagagaca acgccaagaa ctcactgtat    240
ctgcaaatga acagcctgag agccgaggac acggctgtgt attactgtgc gagaggttta    300
tgggggtact atgctcttga ctactggggc caggga                              336
```

```
<210> SEQ ID NO 5
<211> LENGTH: 100
<212> TYPE: PRT
<213> ORGANISM: Artificial Sequence
<220> FEATURE:
<223> OTHER INFORMATION: Synthetic

<400> SEQUENCE: 5
```

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Val Ser Tyr Met
            20                  25                  30

Tyr Trp Tyr Gln Gln Lys Pro Gly Gln Ala Pro Arg Leu Leu Ile Tyr
        35                  40                  45

Asp Thr Ser Asn Leu Ala Ser Gly Ile Pro Pro Arg Phe Ser Gly Ser
    50                  55                  60

Gly Tyr Gly Thr Asp Phe Thr Leu Thr Ile Asn Asn Ile Glu Ser Glu
65                  70                  75                  80

Asp Ala Ala Tyr Tyr Phe Cys Gln Gln Trp Ser Gly Tyr Pro Tyr Thr
                85                  90                  95

Phe Gly Gln Gly
            100

```
<210> SEQ ID NO 6
<211> LENGTH: 300
<212> TYPE: DNA
<213> ORGANISM: Artificial Sequence
<220> FEATURE:
<223> OTHER INFORMATION: Synthetic

<400> SEQUENCE: 6
gacatccaga tgacccagtc tccatcctcc ctgtctgcat ctgtaggaga cagagtcacc    60
atcacttgca gtgccagctc aagtgtaagt tacatgtact ggtaccagca gaaacctggc   120
caggctccca ggctcctcat ctatgacaca tccaacctgg cttctgggat cccacctcga   180
ttcagtggca gcgggtatgg aacagatttt accctcacaa ttaataacat agaatctgag   240
gatgctgcat attacttctg tcagcagtgg agtggttacc catacacgtt cggccaaggg   300
```

```
<210> SEQ ID NO 7
<211> LENGTH: 112
<212> TYPE: PRT
<213> ORGANISM: Artificial Sequence
<220> FEATURE:
<223> OTHER INFORMATION: Synthetic

<400> SEQUENCE: 7
```

Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Ser Ser Phe
            20                  25                  30

Ala Met Ser Trp Ile Arg Gln Ser Pro Ser Arg Gly Leu Glu Trp Leu
        35                  40                  45

Gly Glu Ile Ser Ser Gly Gly Ser Tyr Thr Tyr Tyr Pro Asp Thr Val
    50                  55                  60

Thr Gly Arg Phe Thr Ile Ser Arg Asp Asn Ala Lys Asn Ser Leu Tyr

```
                65                  70                  75                  80
Leu Gln Met Asn Ser Leu Arg Ala Glu Asp Thr Ala Val Tyr Tyr Cys
                    85                  90                  95

Ala Arg Gly Leu Trp Gly Tyr Tyr Ala Leu Asp Tyr Trp Gly Gln Gly
                100                 105                 110

<210> SEQ ID NO 8
<211> LENGTH: 336
<212> TYPE: DNA
<213> ORGANISM: Artificial Sequence
<220> FEATURE:
<223> OTHER INFORMATION: Synthetic

<400> SEQUENCE: 8
caggttcagc tggtgcagtc tggagctgag gtgaagaagc ctggggcctc agtgaaggtc      60
tcctgcaagg cttctggatt caccttcagt agctttgcca tgtcttggat caggcagtcc     120
ccatcgagag gccttgagtg gctgggtgaa attagtagtg gtgggagtta cacctactat     180
cctgacactg tgacgggcag attcaccatc tccagagaca cgccaagaa ctcactgtat      240 ctgcaaatga acagcctgag agccgaggac acggctgtgt attactgtgc gagaggttta     300
tgggggtact atgctcttga ctactggggc cagga                                336

<210> SEQ ID NO 9
<211> LENGTH: 100
<212> TYPE: PRT
<213> ORGANISM: Artificial Sequence
<220> FEATURE:
<223> OTHER INFORMATION: Synthetic

<400> SEQUENCE: 9

Glu Ile Val Leu Thr Gln Ser Pro Asp Phe Gln Ser Val Thr Pro Lys
1               5                   10                  15

Glu Lys Val Thr Ile Thr Cys Ser Ala Ser Ser Ser Val Ser Tyr Met
                20                  25                  30

Tyr Trp Tyr Leu Gln Lys Pro Gly Gln Ser Pro Gln Leu Leu Ile Tyr
            35                  40                  45

Asp Thr Ser Asn Leu Ala Ser Gly Val Pro Ser Arg Phe Ser Gly Ser
        50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Gly Tyr Pro Tyr Thr
                85                  90                  95

Phe Gly Gln Gly
            100

<210> SEQ ID NO 10
<211> LENGTH: 300
<212> TYPE: DNA
<213> ORGANISM: Artificial Sequence
<220> FEATURE:
<223> OTHER INFORMATION: Synthetic

<400> SEQUENCE: 10
gaaattgtgc tgactcagtc tccagacttt cagtctgtga ctccaaagga gaaagtcacc      60
atcacctgca gtgccagctc aagtgtaagt tacatgtact ggtacctgca gaagccaggg     120
cagtctccac agctcctgat ctatgacaca tccaacctgg cttctggggt cccatcaagg     180
ttcagcggca gtggatctgg gacagatttc actctcacca tcagcagcct gcagcctgaa     240
gattttgcaa cttattactg tcagcagtgg agtggttacc catacacgtt cggccaaggg     300
```

<210> SEQ ID NO 11
<211> LENGTH: 112
<212> TYPE: PRT
<213> ORGANISM: Artificial Sequence
<220> FEATURE:
<223> OTHER INFORMATION: Synthetic

<400> SEQUENCE: 11

```
Gln Val Gln Leu Val Gln Ser Gly Ala Glu Val Lys Lys Pro Gly Ala
1               5                   10                  15
Ser Val Lys Val Ser Cys Lys Ala Ser Gly Phe Thr Phe Ser Ser Phe
            20                  25                  30
Ala Met Ser Trp Ile Arg Gln Ser Pro Ser Arg Gly Leu Glu Trp Leu
        35                  40                  45
Gly Glu Ile Ser Ser Gly Gly Ser Tyr Thr Tyr Tyr Pro Asp Thr Val
    50                  55                  60
Thr Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Val Tyr Tyr Cys
                85                  90                  95
Ala Arg Gly Leu Trp Gly Tyr Tyr Ala Leu Asp Tyr Trp Gly Gln Gly
            100                 105                 110
```

<210> SEQ ID NO 12
<211> LENGTH: 336
<212> TYPE: DNA
<213> ORGANISM: Artificial Sequence
<220> FEATURE:
<223> OTHER INFORMATION: Synthetic

<400> SEQUENCE: 12

```
caggttcagc tggtgcagtc tggagctgag gtgaagaagc ctggggcctc agtgaaggtc    60
tcctgcaagg cttctggatt caccttcagt agctttgcca tgtcttggat caggcagtcc   120
ccatcgagag gccttgagtg gctgggtgaa attagtagtg gtgggagtta cacctactat   180
cctgacactg tgacgggcag attcaccatc tccagagaca cgccaagaa ctcactgtat    240
ctgcaaatga acagcctgag agccgaggac acggctgtgt attactgtgc gagaggttta   300
tgggggtact atgctcttga ctactggggc caggga                             336
```

<210> SEQ ID NO 13
<211> LENGTH: 100
<212> TYPE: PRT
<213> ORGANISM: Artificial Sequence
<220> FEATURE:
<223> OTHER INFORMATION: Synthetic

<400> SEQUENCE: 13

```
Glu Ile Val Leu Thr Gln Ser Pro Ala Thr Leu Ser Val Ser Pro Gly
1               5                   10                  15
Glu Arg Ala Thr Leu Ser Cys Ser Ala Ser Ser Ser Val Ser Tyr Met
            20                  25                  30
Tyr Trp Tyr Leu Gln Lys Pro Gly Gln Ser Pro Gln Leu Leu Ile Tyr
        35                  40                  45
Asp Thr Ser Asn Leu Ala Ser Gly Ile Pro Pro Arg Phe Ser Gly Ser
    50                  55                  60
Gly Tyr Gly Thr Asp Phe Thr Leu Thr Ile Asn Asn Ile Glu Ser Glu
65                  70                  75                  80
Asp Ala Ala Tyr Tyr Phe Cys Gln Gln Trp Ser Gly Tyr Pro Tyr Thr
```

Phe Gly Gln Gly
        100

<210> SEQ ID NO 14
<211> LENGTH: 300
<212> TYPE: DNA
<213> ORGANISM: Artificial Sequence
<220> FEATURE:
<223> OTHER INFORMATION: Synthetic

<400> SEQUENCE: 14
gaaattgtgt tgacacagtc tccagccacc ctgtctgtgt ctccagggga aagagccacc    60
ctctcctgca gtgccagctc aagtgtaagt tacatgtact ggtacctgca gaagccaggg   120
cagtctccac agctcctgat ctatgacaca tccaacctgg cttctgggat cccacctcga   180
ttcagtggca gcgggtatgg aacagatttt accctcacaa ttaataacat agaatctgag   240
gatgctgcat attacttctg tcagcagtgg agtggttacc catacacgtt cggccaaggg   300

<210> SEQ ID NO 15
<211> LENGTH: 112
<212> TYPE: PRT
<213> ORGANISM: Artificial Sequence
<220> FEATURE:
<223> OTHER INFORMATION: Synthetic

<400> SEQUENCE: 15

Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Ser Ser Phe
            20                  25                  30

Ala Met Ser Trp Ile Arg Gln Ser Pro Ser Arg Gly Leu Glu Trp Leu
        35                  40                  45

Gly Glu Ile Ser Ser Gly Gly Ser Tyr Thr Tyr Tyr Pro Asp Thr Val
    50                  55                  60

Thr Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Trp Gly Tyr Tyr Ala Leu Asp Tyr Trp Gly Gln Gly
            100                 105                 110

<210> SEQ ID NO 16
<211> LENGTH: 336
<212> TYPE: DNA
<213> ORGANISM: Artificial Sequence
<220> FEATURE:
<223> OTHER INFORMATION: Synthetic

<400> SEQUENCE: 16
caggttcagc tggtgcagtc tggagctgag gtgaagaagc ctggggcctc agtgaaggtc    60
tcctgcaagg cttctggatt caccttcagt agctttgcca tgtcttggat caggcagtcc   120
ccatcgagag gccttgagtg gctgggtgaa attagtagtg gtgggagtta cacctactat   180
cctgacactg tgacgggcag attcaccatc tccagagaca acgccaagaa ctcactgtat   240
ctgcaaatga acagcctgag agccgaggac acggctgtgt attactgtgc gagaggttta   300
tgggggtact atgctcttga ctactggggc caggga                            336

<210> SEQ ID NO 17

```
<211> LENGTH: 100
<212> TYPE: PRT
<213> ORGANISM: Artificial Sequence
<220> FEATURE:
<223> OTHER INFORMATION: Synthetic

<400> SEQUENCE: 17
```

Glu Ile Val Leu Thr Gln Ser Pro Asp Phe Gln Ser Val Thr Pro Lys
1               5                   10                  15

Glu Lys Val Thr Ile Thr Cys Ser Ala Ser Ser Val Ser Tyr Met
            20                  25                  30

Tyr Trp Tyr Leu Gln Lys Pro Gly Gln Ser Pro Gln Leu Leu Ile Tyr
            35                  40                  45

Asp Thr Ser Asn Leu Ala Ser Gly Ile Pro Arg Phe Ser Gly Ser
50                  55                  60

Gly Tyr Gly Thr Asp Phe Thr Leu Thr Ile Asn Asn Ile Glu Ser Glu
65                  70                  75                  80

Asp Ala Ala Tyr Tyr Phe Cys Gln Gln Trp Ser Gly Tyr Pro Tyr Thr
                85                  90                  95

Phe Gly Gln Gly
            100

```
<210> SEQ ID NO 18
<211> LENGTH: 300
<212> TYPE: DNA
<213> ORGANISM: Artificial Sequence
<220> FEATURE:
<223> OTHER INFORMATION: Synthetic

<400> SEQUENCE: 18
```
gaaattgtgc tgactcagtc tccagacttt cagtctgtga ctccaaagga gaaagtcacc     60
atcacctgca gtgccagctc aagtgtaagt tacatgtact ggtacctgca gaagccaggg    120
cagtctccac agctcctgat ctatgacaca tccaacctgg cttctgggat cccacctcga    180
ttcagtggca gcgggtatgg aacagatttt accctcacaa ttaataacat agaatctgag    240
gatgctgcat attacttctg tcagcagtgg agtggttacc catacacgtt cggccaaggg    300

```
<210> SEQ ID NO 19
<211> LENGTH: 112
<212> TYPE: PRT
<213> ORGANISM: Artificial Sequence
<220> FEATURE:
<223> OTHER INFORMATION: Synthetic

<400> SEQUENCE: 19
```

Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Ser Ser Phe
            20                  25                  30

Ala Met Ser Trp Ile Arg Gln Pro Pro Gly Lys Gly Leu Glu Trp Ile
            35                  40                  45

Gly Glu Ile Ser Ser Gly Gly Ser Tyr Thr Tyr Tyr Pro Asp Thr Val
50                  55                  60

Thr Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Trp Gly Tyr Tyr Ala Leu Asp Tyr Trp Gly Gln Gly
            100                 105                 110

<210> SEQ ID NO 20
<211> LENGTH: 336
<212> TYPE: DNA
<213> ORGANISM: Artificial Sequence
<220> FEATURE:
<223> OTHER INFORMATION: Synthetic

<400> SEQUENCE: 20

```
caggttcagc tggtgcagtc tggagctgag gtgaagaagc ctggggcctc agtgaaggtc      60
tcctgcaagg cttctggatt caccttcagt agctttgcca tgtcttggat ccgccagccc     120
ccagggaagg gctggagtg gattggtgaa attagtagtg gtgggagtta cacctactat     180
cctgacactg tgacgggcag attcaccatc tccagagaca acgccaagaa ctcactgtat     240
ctgcaaatga acagcctgag agccgaggac acggccgtgt attactgtgc gagaggttta     300
tgggggtact atgctcttga ctactggggc caggga                               336
```

<210> SEQ ID NO 21
<211> LENGTH: 100
<212> TYPE: PRT
<213> ORGANISM: Artificial Sequence
<220> FEATURE:
<223> OTHER INFORMATION: Synthetic

<400> SEQUENCE: 21

```
Ala Ile Gln Leu Thr Gln Ser Pro Ser Ser Leu Ser Ala Ser Val Gly
1               5                   10                  15

Asp Arg Val Thr Ile Thr Cys Ser Ala Ser Ser Val Ser Tyr Met
            20                  25                  30

Tyr Trp Tyr Gln Gln Lys Pro Gly Gln Ala Pro Arg Leu Leu Ile Tyr
        35                  40                  45

Asp Thr Ser Asn Leu Ala Ser Gly Ile Pro Pro Arg Phe Ser Gly Ser
    50                  55                  60

Gly Tyr Gly Thr Asp Phe Thr Leu Thr Ile Asn Asn Ile Glu Ser Glu
65                  70                  75                  80

Asp Ala Ala Tyr Tyr Phe Cys Gln Gln Trp Ser Gly Tyr Pro Tyr Thr
                85                  90                  95

Phe Gly Gln Gly
            100
```

<210> SEQ ID NO 22
<211> LENGTH: 300
<212> TYPE: DNA
<213> ORGANISM: Artificial Sequence
<220> FEATURE:
<223> OTHER INFORMATION: Synthetic

<400> SEQUENCE: 22

```
gccatccagt tgacccagtc tccatcctcc ctgtctgcat ctgtaggaga cagagtcacc      60
atcacttgca gtgccagctc aagtgtaagt tacatgtact ggtaccagca gaaacctggc     120
caggctccca ggctcctcat ctatgacaca tccaacctgg cttctgggat cccacctcga     180
ttcagtggca gcgggtatgg aacagatttt acctcacaa ttaataacat agaatctgag      240
gatgctgcat attacttctg tcagcagtgg agtggttacc catacacgtt cggccaaggg     300
```

<210> SEQ ID NO 23
<211> LENGTH: 112
<212> TYPE: PRT
<213> ORGANISM: Artificial Sequence
<220> FEATURE:
<223> OTHER INFORMATION: Synthetic

<400> SEQUENCE: 23

Glu Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Ser Ser Phe
            20                  25                  30

Ala Met Ser Trp Val Arg Gln Ala Pro Gly Gln Gly Leu Glu Trp Met
        35                  40                  45

Gly Glu Ile Ser Ser Gly Gly Ser Tyr Thr Tyr Tyr Pro Asp Thr Val
50                  55                  60

Thr Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Trp Gly Tyr Tyr Ala Leu Asp Tyr Trp Gly Gln Gly
            100                 105                 110

<210> SEQ ID NO 24
<211> LENGTH: 336
<212> TYPE: DNA
<213> ORGANISM: Artificial Sequence
<220> FEATURE:
<223> OTHER INFORMATION: Synthetic

<400> SEQUENCE: 24
gaggttcagc tggtgcagtc tggagctgag gtgaagaagc ctggggcctc agtgaaggtc    60
tcctgcaagg cttctggatt caccttcagt agctttgcca tgtcttgggt gcgacaggcc   120
cctggacaag gcttgagtg gatgggtgaa attagtagtg gtgggagtta cacctactat    180
cctgacactg tgacgggcag attcaccatc tccagagaca cgccaagaa ctcactgtat    240 ctgcaaatga acagcctgag agccgaggac acggctgtgt attactgtgc gagaggttta   300
tgggggtact atgctcttga ctactggggc caggga                             336

<210> SEQ ID NO 25
<211> LENGTH: 100
<212> TYPE: PRT
<213> ORGANISM: Artificial Sequence
<220> FEATURE:
<223> OTHER INFORMATION: Synthetic

<400> SEQUENCE: 25

Ala Ile Gln Leu Thr Gln Ser Pro Ser Ser Leu Ser Ala Ser Val Gly
1               5                   10                  15

Asp Arg Val Thr Ile Thr Cys Ser Ala Ser Ser Ser Val Ser Tyr Met
            20                  25                  30

Tyr Trp Tyr Gln Gln Lys Pro Gly Gln Ala Pro Arg Leu Leu Ile Tyr
        35                  40                  45

Asp Thr Ser Asn Leu Ala Ser Gly Ile Pro Pro Arg Phe Ser Gly Ser
    50                  55                  60

Gly Tyr Gly Thr Asp Phe Thr Leu Thr Ile Asn Asn Ile Glu Ser Glu
65                  70                  75                  80

Asp Ala Ala Tyr Tyr Phe Cys Gln Gln Trp Ser Gly Tyr Pro Tyr Thr
                85                  90                  95

Phe Gly Gln Gly
            100

<210> SEQ ID NO 26
<211> LENGTH: 300

<212> TYPE: DNA
<213> ORGANISM: Artificial Sequence
<220> FEATURE:
<223> OTHER INFORMATION: Synthetic

<400> SEQUENCE: 26

```
gccatccagt tgacccagtc tccatcctcc ctgtctgcat ctgtaggaga cagagtcacc    60
atcacttgca gtgccagctc aagtgtaagt tacatgtact ggtaccagca gaaacctggc   120
caggctccca ggctcctcat ctatgacaca tccaacctgg cttctgggat cccacctcga   180
ttcagtggca gcgggtatgg aacagatttt accctcacaa ttaataacat agaatctgag   240
gatgctgcat attacttctg tcagcagtgg agtggttacc catacacgtt cggccaaggg   300
```

<210> SEQ ID NO 27
<211> LENGTH: 112
<212> TYPE: PRT
<213> ORGANISM: Artificial Sequence
<220> FEATURE:
<223> OTHER INFORMATION: Synthetic

<400> SEQUENCE: 27

```
Gln Val Gln Leu Val Gln Ser Gly Ala Glu Val Lys Lys Pro Gly Ala
1               5                   10                  15
Ser Val Lys Val Ser Cys Lys Ala Ser Gly Phe Thr Phe Ser Ser Phe
            20                  25                  30
Ala Met Ser Trp Ile Arg Gln Pro Pro Gly Lys Gly Leu Glu Trp Ile
        35                  40                  45
Gly Glu Ile Ser Ser Gly Gly Ser Tyr Thr Tyr Tyr Pro Asp Thr Val
    50                  55                  60
Thr Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Val Tyr Tyr Cys
                85                  90                  95
Ala Arg Gly Leu Trp Gly Tyr Tyr Ala Leu Asp Tyr Trp Gly Gln Gly
            100                 105                 110
```

<210> SEQ ID NO 28
<211> LENGTH: 336
<212> TYPE: DNA
<213> ORGANISM: Artificial Sequence
<220> FEATURE:
<223> OTHER INFORMATION: Synthetic

<400> SEQUENCE: 28

```
caggttcagc tggtgcagtc tggagctgag gtgaagaagc ctggggcctc agtgaaggtc    60
tcctgcaagg cttctggatt caccttcagt agctttgcca tgtcttggat ccgccagccc   120
ccagggaagg gctggagtg gattggtgaa attagtagtg gtgggagtta cacctactat   180
cctgacactg tgacgggcag attcaccatc tccagagaca cgccaagaa ctcactgtat   240
ctgcaaatga acagcctgag agccgaggac acggccgtgt attactgtgc gagaggttta   300
tgggggtact atgctcttga ctactggggc caggga                            336
```

<210> SEQ ID NO 29
<211> LENGTH: 100
<212> TYPE: PRT
<213> ORGANISM: Artificial Sequence
<220> FEATURE:
<223> OTHER INFORMATION: Synthetic

<400> SEQUENCE: 29

```
Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Val Ser Tyr Met
            20                  25                  30

Tyr Trp Tyr Gln Gln Lys Pro Gly Gln Ala Pro Arg Leu Leu Ile Tyr
            35                  40                  45

Asp Thr Ser Asn Leu Ala Ser Gly Ile Pro Pro Arg Phe Ser Gly Ser
            50                  55                  60

Gly Tyr Gly Thr Asp Phe Thr Leu Thr Ile Asn Asn Ile Glu Ser Glu
65              70                  75                  80

Asp Ala Ala Tyr Tyr Phe Cys Gln Gln Trp Ser Gly Tyr Pro Tyr Thr
            85                  90                  95

Phe Gly Gln Gly
            100

<210> SEQ ID NO 30
<211> LENGTH: 300
<212> TYPE: DNA
<213> ORGANISM: Artificial Sequence
<220> FEATURE:
<223> OTHER INFORMATION: Synthetic

<400> SEQUENCE: 30
gacatccaga tgacccagtc tccatcctcc ctgtctgcat ctgtaggaga cagagtcacc      60
atcacttgca gtgccagctc aagtgtaagt tacatgtact ggtaccagca gaaacctggc     120
caggctccca ggctcctcat ctatgacaca tccaacctgg cttctgggat cccacctcga     180
ttcagtggca gcgggtatgg aacagatttt accctcacaa ttaataacat agaatctgag     240
gatgctgcat attacttctg tcagcagtgg agtggttacc catacacgtt cggccaaggg     300

<210> SEQ ID NO 31
<211> LENGTH: 112
<212> TYPE: PRT
<213> ORGANISM: Artificial Sequence
<220> FEATURE:
<223> OTHER INFORMATION: Synthetic

<400> SEQUENCE: 31

Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Ser Ser Phe
            20                  25                  30

Ala Met Ser Trp Val Arg Gln Ala Pro Gly Gln Gly Leu Glu Trp Met
            35                  40                  45

Gly Glu Ile Ser Ser Gly Gly Ser Tyr Thr Tyr Tyr Pro Asp Thr Val
            50                  55                  60

Thr Gly Arg Phe Thr Ile Ser Arg Asp Asn Ala Lys Asn Ser Leu Tyr
65              70                  75                  80

Leu Gln Met Asn Ser Leu Arg Ala Glu Asp Thr Ala Val Tyr Tyr Cys
            85                  90                  95

Ala Arg Gly Leu Trp Gly Tyr Tyr Ala Leu Asp Tyr Trp Gly Gln Gly
            100                 105                 110

<210> SEQ ID NO 32
<211> LENGTH: 336
<212> TYPE: DNA
<213> ORGANISM: Artificial Sequence
<220> FEATURE:
<223> OTHER INFORMATION: Synthetic
```

<400> SEQUENCE: 32

```
caggttcagc tggtgcagtc tggagctgag gtgaagaagc ctggggcctc agtgaaggtc      60
tcctgcaagg cttctggatt caccttcagt agctttgcca tgtcttgggt gcgacaggcc     120
cctggacaag gcttgagtg gatgggtgaa attagtagtg gtgggagtta cacctactat      180
cctgacactg tgacgggcag attcaccatc tccagagaca acgccaagaa ctcactgtat     240
ctgcaaatga acagcctgag agccgaggac acggctgtgt attactgtgc gagaggttta     300
tgggggtact atgctcttga ctactggggc caggga                               336
```

<210> SEQ ID NO 33
<211> LENGTH: 100
<212> TYPE: PRT
<213> ORGANISM: Artificial Sequence
<220> FEATURE:
<223> OTHER INFORMATION: Synthetic

<400> SEQUENCE: 33

```
Gln Ile Val Leu Ile Gln Ser Pro Ala Ile Met Ser Ala Ser Pro Gly
1               5                   10                  15

Glu Lys Val Thr Met Thr Cys Ser Ala Ser Ser Val Ser Tyr Met
            20                  25                  30

Tyr Trp Tyr Gln Gln Lys Pro Gly Ser Ser Pro Arg Leu Leu Ile Tyr
        35                  40                  45

Asp Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Trp Ser Gly Tyr Pro Tyr Thr
                85                  90                  95

Phe Gly Gln Gly
            100
```

<210> SEQ ID NO 34
<211> LENGTH: 300
<212> TYPE: DNA
<213> ORGANISM: Artificial Sequence
<220> FEATURE:
<223> OTHER INFORMATION: Synthetic

<400> SEQUENCE: 34

```
caaattgttc tcatacagtc tccagcaatc atgtctgcat ctccagggga gaaggtcacc      60
atgacctgca gtgccagctc aagtgtaagt tacatgtact ggtaccagca gaagccagga     120
tcctccccca gactcctgat ttatgacaca tccaacctgg cttctggagt ccctgttcgc     180
ttcagtggca gtgggtctgg gacctcttac tctctcacaa tcagccgaat ggaggctgag     240
gatgctgcca cttattactg ccagcagtgg agtggttacc catacacgtt cggccaaggg     300
```

<210> SEQ ID NO 35
<211> LENGTH: 112
<212> TYPE: PRT
<213> ORGANISM: Artificial Sequence
<220> FEATURE:
<223> OTHER INFORMATION: Synthetic

<400> SEQUENCE: 35

```
Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Ser Ser Phe
            20                  25                  30
```

Ala Met Ser Trp Ile Arg Gln Ser Pro Ser Arg Gly Leu Glu Trp Leu
         35                  40                  45

Gly Glu Ile Ser Ser Gly Ser Tyr Thr Tyr Tyr Pro Asp Thr Val
     50                  55                  60

Thr Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Gly Leu Trp Gly Tyr Tyr Ala Leu Asp Tyr Trp Gly Gln Gly
             100                 105                 110

<210> SEQ ID NO 36
<211> LENGTH: 336
<212> TYPE: DNA
<213> ORGANISM: Artificial Sequence
<220> FEATURE:
<223> OTHER INFORMATION: Synthetic

<400> SEQUENCE: 36
caggttcagc tggtgcagtc tggagctgag gtgaagaagc tggggcctc agtgaaggtc      60 tcctgcaagg cttctggatt caccttcagt agctttgcca tgtcttggat caggcagtcc    120
ccatcgagag gccttgagtg gctgggtgaa attagtagtg gtgggagtta cacctactat    180
cctgacactg tgacgggcag attcaccatc tccagagaca acgccaagaa ctcactgtat    240
ctgcaaatga acagcctgag agccgaggac acggctgtgt attactgtgc gagaggttta    300
tgggggtact atgctcttga ctactggggc caggga                              336

<210> SEQ ID NO 37
<211> LENGTH: 300
<212> TYPE: DNA
<213> ORGANISM: Artificial Sequence
<220> FEATURE:
<223> OTHER INFORMATION: Synthetic

<400> SEQUENCE: 37
gccatccagt tgacccagtc tccatcctcc ctgtctgcat ctgtaggaga cagagtcacc     60
atcacttgct atgccagctc aagtgtaagt tacatgtact ggtaccagca gaaacctggc   120
caggctccca ggctcctcat ctatgacaca tccaacctgg cttctgggat cccacctcga   180
ttcagtggca gcgggtatgg aacagatttt accctcacaa ttaataacat agaatctgag   240
gatgctgcat attacttctg tcagcagtgg agtggttacc catacacgtt cggccaaggg   300

<210> SEQ ID NO 38
<211> LENGTH: 300
<212> TYPE: DNA
<213> ORGANISM: Artificial Sequence
<220> FEATURE:
<223> OTHER INFORMATION: Synthetic

<400> SEQUENCE: 38
gccatccagt tgacccagtc tccatcctcc ctgtctgcat ctgtaggaga cagagtcacc     60
atcacttgca gtgccagctc agatgtaagt tacatgtact ggtaccagca gaaacctggc   120
caggctccca ggctcctcat ctatgacaca tccaacctgg cttctgggat cccacctcga   180
ttcagtggca gcgggtatgg aacagatttt accctcacaa ttaataacat agaatctgag   240
gatgctgcat attacttctg tcagcagtgg agtggttacc catacacgtt cggccaaggg   300

<210> SEQ ID NO 39

```
<211> LENGTH: 300
<212> TYPE: DNA
<213> ORGANISM: Artificial Sequence
<220> FEATURE:
<223> OTHER INFORMATION: Synthetic

<400> SEQUENCE: 39
gccatccagt tgacccagtc tccatcctcc ctgtctgcat ctgtaggaga cagagtcacc      60
atcacttgca gtgccagctc aagtgtaagt tacatgtact ggtaccagca gaaacctggc     120
caggctccca ggctcctcat ctattctaca tccaacctgg cttctgggat cccacctcga     180
ttcagtggca gcgggtatgg aacagatttt accctcacaa ttaataacat agaatctgag     240
gatgctgcat attacttctg tcagcagtgg agtggttacc catacacgtt cggccaaggg     300

<210> SEQ ID NO 40
<211> LENGTH: 300
<212> TYPE: DNA
<213> ORGANISM: Artificial Sequence
<220> FEATURE:
<223> OTHER INFORMATION: Synthetic

<400> SEQUENCE: 40
gccatccagt tgacccagtc tccatcctcc ctgtctgcat ctgtaggaga cagagtcacc      60
atcacttgca gtgccagctc aagtgtaagt tacatgtact ggtaccagca gaaacctggc     120
caggctccca ggctcctcat ctatgacaca ttgaacctgg cttctgggat cccacctcga     180
ttcagtggca gcgggtatgg aacagatttt accctcacaa ttaataacat agaatctgag     240
gatgctgcat attacttctg tcagcagtgg agtggttacc catacacgtt cggccaaggg     300

<210> SEQ ID NO 41
<211> LENGTH: 300
<212> TYPE: DNA
<213> ORGANISM: Artificial Sequence
<220> FEATURE:
<223> OTHER INFORMATION: Synthetic

<400> SEQUENCE: 41
gccatccagt tgacccagtc tccatcctcc ctgtctgcat ctgtaggaga cagagtcacc      60
atcacttgca gtgccagctc aagtgtaagt tacatgtact ggtaccagca gaaacctggc     120
caggctccca ggctcctcat ctatgacaca tccaacctgg cttctgggat cccacctcga     180
ttcagtggca gcgggtatgg aacagatttt accctcacaa ttaataacat agaatctgag     240
gatgctgcat attacttctg tcaggattgg agtggttacc catacacgtt cggccaaggg     300

<210> SEQ ID NO 42
<211> LENGTH: 300
<212> TYPE: DNA
<213> ORGANISM: Artificial Sequence
<220> FEATURE:
<223> OTHER INFORMATION: Synthetic

<400> SEQUENCE: 42
gccatccagt tgacccagtc tccatcctcc ctgtctgcat ctgtaggaga cagagtcacc      60
atcacttgct atgccagctc agatgtaagt tacatgtact ggtaccagca gaaacctggc     120
caggctccca ggctcctcat ctatgacaca tccaacctgg cttctgggat cccacctcga     180
ttcagtggca gcgggtatgg aacagatttt accctcacaa ttaataacat agaatctgag     240
gatgctgcat attacttctg tcagcagtgg agtggttacc catacacgtt cggccaaggg     300

<210> SEQ ID NO 43
```

```
<211> LENGTH: 300
<212> TYPE: DNA
<213> ORGANISM: Artificial Sequence
<220> FEATURE:
<223> OTHER INFORMATION: Synthetic

<400> SEQUENCE: 43
gccatccagt tgacccagtc tccatcctcc ctgtctgcat ctgtaggaga cagagtcacc      60
atcacttgct atgccagctc aagtgtaagt tacatgtact ggtaccagca gaaacctggc     120
caggctccca ggctcctcat ctattctaca tccaacctgg cttctgggat cccacctcga     180
ttcagtggca gcgggtatgg aacagatttt accctcacaa ttaataacat agaatctgag     240
gatgctgcat attacttctg tcagcagtgg agtggttacc catacacgtt cggccaaggg     300

<210> SEQ ID NO 44
<211> LENGTH: 300
<212> TYPE: DNA
<213> ORGANISM: Artificial Sequence
<220> FEATURE:
<223> OTHER INFORMATION: Synthetic

<400> SEQUENCE: 44
gccatccagt tgacccagtc tccatcctcc ctgtctgcat ctgtaggaga cagagtcacc      60
atcacttgct atgccagctc aagtgtaagt tacatgtact ggtaccagca gaaacctggc     120
caggctccca ggctcctcat ctatgacaca ttgaacctgg cttctgggat cccacctcga     180
ttcagtggca gcgggtatgg aacagatttt accctcacaa ttaataacat agaatctgag     240
gatgctgcat attacttctg tcagcagtgg agtggttacc catacacgtt cggccaaggg     300

<210> SEQ ID NO 45
<211> LENGTH: 300
<212> TYPE: DNA
<213> ORGANISM: Artificial Sequence
<220> FEATURE:
<223> OTHER INFORMATION: Synthetic

<400> SEQUENCE: 45
gccatccagt tgacccagtc tccatcctcc ctgtctgcat ctgtaggaga cagagtcacc      60
atcacttgct atgccagctc aagtgtaagt tacatgtact ggtaccagca gaaacctggc     120
caggctccca ggctcctcat ctatgacaca tccaacctgg cttctgggat cccacctcga     180
ttcagtggca gcgggtatgg aacagattttt accctcacaa ttaataacat agaatctgag    240
gatgctgcat attacttctg tcaggattgg agtggttacc catacacgtt cggccaaggg     300

<210> SEQ ID NO 46
<211> LENGTH: 300
<212> TYPE: DNA
<213> ORGANISM: Artificial Sequence
<220> FEATURE:
<223> OTHER INFORMATION: Synthetic

<400> SEQUENCE: 46
gccatccagt tgacccagtc tccatcctcc ctgtctgcat ctgtaggaga cagagtcacc      60
atcacttgca gtgccagctc agatgtaagt tacatgtact ggtaccagca gaaacctggc     120
caggctccca ggctcctcat ctattctaca tccaacctgg cttctgggat cccacctcga     180
ttcagtggca gcgggtatgg aacagatttt accctcacaa ttaataacat agaatctgag     240
gatgctgcat attacttctg tcagcagtgg agtggttacc catacacgtt cggccaaggg     300

<210> SEQ ID NO 47
```

```
<211> LENGTH: 300
<212> TYPE: DNA
<213> ORGANISM: Artificial Sequence
<220> FEATURE:
<223> OTHER INFORMATION: Synthetic

<400> SEQUENCE: 47
gccatccagt tgacccagtc tccatcctcc ctgtctgcat ctgtaggaga cagagtcacc    60
atcacttgca gtgccagctc agatgtaagt tacatgtact ggtaccagca gaaacctggc   120
caggctccca ggctcctcat ctatgacaca ttgaacctgg cttctgggat cccacctcga   180
ttcagtggca gcgggtatgg aacagatttt accctcacaa ttaataacat agaatctgag   240
gatgctgcat attacttctg tcagcagtgg agtggttacc catacacgtt cggccaaggg   300

<210> SEQ ID NO 48
<211> LENGTH: 300
<212> TYPE: DNA
<213> ORGANISM: Artificial Sequence
<220> FEATURE:
<223> OTHER INFORMATION: Synthetic

<400> SEQUENCE: 48
gccatccagt tgacccagtc tccatcctcc ctgtctgcat ctgtaggaga cagagtcacc    60
atcacttgca gtgccagctc agatgtaagt tacatgtact ggtaccagca gaaacctggc   120
caggctccca ggctcctcat ctatgacaca tccaacctgg cttctgggat cccacctcga   180
ttcagtggca gcgggtatgg aacagatttt accctcacaa ttaataacat agaatctgag   240
gatgctgcat attacttctg tcaggattgg agtggttacc catacacgtt cggccaaggg   300

<210> SEQ ID NO 49
<211> LENGTH: 300
<212> TYPE: DNA
<213> ORGANISM: Artificial Sequence
<220> FEATURE:
<223> OTHER INFORMATION: Synthetic

<400> SEQUENCE: 49
gccatccagt tgacccagtc tccatcctcc ctgtctgcat ctgtaggaga cagagtcacc    60
atcacttgca gtgccagctc aagtgtaagt tacatgtact ggtaccagca gaaacctggc   120
caggctccca ggctcctcat ctattctaca ttgaacctgg cttctgggat cccacctcga   180
ttcagtggca gcgggtatgg aacagatttt accctcacaa ttaataacat agaatctgag   240
gatgctgcat attacttctg tcagcagtgg agtggttacc catacacgtt cggccaaggg   300

<210> SEQ ID NO 50
<211> LENGTH: 300
<212> TYPE: DNA
<213> ORGANISM: Artificial Sequence
<220> FEATURE:
<223> OTHER INFORMATION: Synthetic

<400> SEQUENCE: 50
gccatccagt tgacccagtc tccatcctcc ctgtctgcat ctgtaggaga cagagtcacc    60
atcacttgca gtgccagctc aagtgtaagt tacatgtact ggtaccagca gaaacctggc   120
caggctccca ggctcctcat ctattctaca tccaacctgg cttctgggat cccacctcga   180
ttcagtggca gcgggtatgg aacagatttt accctcacaa ttaataacat agaatctgag   240
gatgctgcat attacttctg tcaggattgg agtggttacc catacacgtt cggccaaggg   300

<210> SEQ ID NO 51
```

<211> LENGTH: 300
<212> TYPE: DNA
<213> ORGANISM: Artificial Sequence
<220> FEATURE:
<223> OTHER INFORMATION: Synthetic

<400> SEQUENCE: 51

```
gccatccagt tgacccagtc tccatcctcc ctgtctgcat ctgtaggaga cagagtcacc    60
atcacttgca gtgccagctc aagtgtaagt tacatgtact ggtaccagca gaaacctggc   120
caggctccca ggctcctcat ctatgacaca ttgaacctgg cttctgggat cccacctcga   180
ttcagtggca gcgggtatgg aacagatttt accctcacaa ttaataacat agaatctgag   240
gatgctgcat attacttctg tcaggattgg agtggttacc catacacgtt cggccaaggg   300
```

<210> SEQ ID NO 52
<211> LENGTH: 300
<212> TYPE: DNA
<213> ORGANISM: Artificial Sequence
<220> FEATURE:
<223> OTHER INFORMATION: Synthetic

<400> SEQUENCE: 52

```
gccatccagt tgacccagtc tccatcctcc ctgtctgcat ctgtaggaga cagagtcacc    60
atcacttgct atgccagctc agatgtaagt tacatgtact ggtaccagca gaaacctggc   120
caggctccca ggctcctcat ctattctaca tccaacctgg cttctgggat cccacctcga   180
ttcagtggca gcgggtatgg aacagatttt accctcacaa ttaataacat agaatctgag   240
gatgctgcat attacttctg tcagcagtgg agtggttacc catacacgtt cggccaaggg   300
```

<210> SEQ ID NO 53
<211> LENGTH: 300
<212> TYPE: DNA
<213> ORGANISM: Artificial Sequence
<220> FEATURE:
<223> OTHER INFORMATION: Synthetic

<400> SEQUENCE: 53

```
gccatccagt tgacccagtc tccatcctcc ctgtctgcat ctgtaggaga cagagtcacc    60
atcacttgct atgccagctc agatgtaagt tacatgtact ggtaccagca gaaacctggc   120
caggctccca ggctcctcat ctatgacaca ttgaacctgg cttctgggat cccacctcga   180
ttcagtggca gcgggtatgg aacagatttt accctcacaa ttaataacat agaatctgag   240
gatgctgcat attacttctg tcagcagtgg agtggttacc catacacgtt cggccaaggg   300
```

<210> SEQ ID NO 54
<211> LENGTH: 300
<212> TYPE: DNA
<213> ORGANISM: Artificial Sequence
<220> FEATURE:
<223> OTHER INFORMATION: Synthetic

<400> SEQUENCE: 54

```
gccatccagt tgacccagtc tccatcctcc ctgtctgcat ctgtaggaga cagagtcacc    60
atcacttgct atgccagctc agatgtaagt tacatgtact ggtaccagca gaaacctggc   120
caggctccca ggctcctcat ctatgacaca tccaacctgg cttctgggat cccacctcga   180
ttcagtggca gcgggtatgg aacagatttt accctcacaa ttaataacat agaatctgag   240
gatgctgcat attacttctg tcaggattgg agtggttacc catacacgtt cggccaaggg   300
```

<210> SEQ ID NO 55

```
<211> LENGTH: 300
<212> TYPE: DNA
<213> ORGANISM: Artificial Sequence
<220> FEATURE:
<223> OTHER INFORMATION: Synthetic

<400> SEQUENCE: 55
gccatccagt tgacccagtc tccatcctcc ctgtctgcat ctgtaggaga cagagtcacc      60
atcacttgct atgccagctc aagtgtaagt tacatgtact ggtaccagca gaaacctggc     120
caggctccca ggctcctcat ctattctaca ttgaacctgg cttctgggat cccacctcga     180
ttcagtggca gcgggtatgg aacagatttt accctcacaa ttaataacat agaatctgag     240
gatgctgcat attacttctg tcagcagtgg agtggttacc catacacgtt cggccaaggg     300

<210> SEQ ID NO 56
<211> LENGTH: 300
<212> TYPE: DNA
<213> ORGANISM: Artificial Sequence
<220> FEATURE:
<223> OTHER INFORMATION: Synthetic

<400> SEQUENCE: 56
gccatccagt tgacccagtc tccatcctcc ctgtctgcat ctgtaggaga cagagtcacc      60
atcacttgct atgccagctc aagtgtaagt tacatgtact ggtaccagca gaaacctggc     120
caggctccca ggctcctcat ctattctaca tccaacctgg cttctgggat cccacctcga     180
ttcagtggca gcgggtatgg aacagatttt accctcacaa ttaataacat agaatctgag     240
gatgctgcat attacttctg tcaggattgg agtggttacc catacacgtt cggccaaggg     300

<210> SEQ ID NO 57
<211> LENGTH: 300
<212> TYPE: DNA
<213> ORGANISM: Artificial Sequence
<220> FEATURE:
<223> OTHER INFORMATION: Synthetic

<400> SEQUENCE: 57
gccatccagt tgacccagtc tccatcctcc ctgtctgcat ctgtaggaga cagagtcacc      60
atcacttgct atgccagctc aagtgtaagt tacatgtact ggtaccagca gaaacctggc     120
caggctccca ggctcctcat ctatgacaca ttgaacctgg cttctgggat cccacctcga     180
ttcagtggca gcgggtatgg aacagatttt accctcacaa ttaataacat agaatctgag     240
gatgctgcat attacttctg tcaggattgg agtggttacc catacacgtt cggccaaggg     300

<210> SEQ ID NO 58
<211> LENGTH: 300
<212> TYPE: DNA
<213> ORGANISM: Artificial Sequence
<220> FEATURE:
<223> OTHER INFORMATION: Synthetic

<400> SEQUENCE: 58
gccatccagt tgacccagtc tccatcctcc ctgtctgcat ctgtaggaga cagagtcacc      60
atcacttgca gtgccagctc agatgtaagt tacatgtact ggtaccagca gaaacctggc     120
caggctccca ggctcctcat ctattctaca ttgaacctgg cttctgggat cccacctcga     180
ttcagtggca gcgggtatgg aacagatttt accctcacaa ttaataacat agaatctgag     240
gatgctgcat attacttctg tcagcagtgg agtggttacc catacacgtt cggccaaggg     300

<210> SEQ ID NO 59
```

<211> LENGTH: 300
<212> TYPE: DNA
<213> ORGANISM: Artificial Sequence
<220> FEATURE:
<223> OTHER INFORMATION: Synthetic

<400> SEQUENCE: 59

```
gccatccagt tgacccagtc tccatcctcc ctgtctgcat ctgtaggaga cagagtcacc    60
atcacttgca gtgccagctc agatgtaagt tacatgtact ggtaccagca gaaacctggc   120
caggctccca ggctcctcat ctattctaca tccaacctgg cttctgggat cccacctcga   180
ttcagtggca gcgggtatgg aacagatttt accctcacaa ttaataacat agaatctgag   240
gatgctgcat attacttctg tcaggattgg agtggttacc catacacgtt cggccaaggg   300
```

<210> SEQ ID NO 60
<211> LENGTH: 300
<212> TYPE: DNA
<213> ORGANISM: Artificial Sequence
<220> FEATURE:
<223> OTHER INFORMATION: Synthetic

<400> SEQUENCE: 60

```
gccatccagt tgacccagtc tccatcctcc ctgtctgcat ctgtaggaga cagagtcacc    60
atcacttgca gtgccagctc agatgtaagt tacatgtact ggtaccagca gaaacctggc   120
caggctccca ggctcctcat ctatgacaca ttgaacctgg cttctgggat cccacctcga   180
ttcagtggca gcgggtatgg aacagatttt accctcacaa ttaataacat agaatctgag   240
gatgctgcat attacttctg tcaggattgg agtggttacc catacacgtt cggccaaggg   300
```

<210> SEQ ID NO 61
<211> LENGTH: 300
<212> TYPE: DNA
<213> ORGANISM: Artificial Sequence
<220> FEATURE:
<223> OTHER INFORMATION: Synthetic

<400> SEQUENCE: 61

```
gccatccagt tgacccagtc tccatcctcc ctgtctgcat ctgtaggaga cagagtcacc    60
atcacttgca gtgccagctc aagtgtaagt tacatgtact ggtaccagca gaaacctggc   120
caggctccca ggctcctcat ctattctaca ttgaacctgg cttctgggat cccacctcga   180
ttcagtggca gcgggtatgg aacagatttt accctcacaa ttaataacat agaatctgag   240
gatgctgcat attacttctg tcaggattgg agtggttacc catacacgtt cggccaaggg   300
```

<210> SEQ ID NO 62
<211> LENGTH: 300
<212> TYPE: DNA
<213> ORGANISM: Artificial Sequence
<220> FEATURE:
<223> OTHER INFORMATION: Synthetic

<400> SEQUENCE: 62

```
gccatccagt tgacccagtc tccatcctcc ctgtctgcat ctgtaggaga cagagtcacc    60
atcacttgct atgccagctc agatgtaagt tacatgtact ggtaccagca gaaacctggc   120
caggctccca ggctcctcat ctattctaca ttgaacctgg cttctgggat cccacctcga   180
ttcagtggca gcgggtatgg aacagatttt accctcacaa ttaataacat agaatctgag   240
gatgctgcat attacttctg tcagcagtgg agtggttacc catacacgtt cggccaaggg   300
```

<210> SEQ ID NO 63

```
<211> LENGTH: 300
<212> TYPE: DNA
<213> ORGANISM: Artificial Sequence
<220> FEATURE:
<223> OTHER INFORMATION: Synthetic

<400> SEQUENCE: 63
gccatccagt tgacccagtc tccatcctcc ctgtctgcat ctgtaggaga cagagtcacc      60
atcacttgct atgccagctc agatgtaagt tacatgtact ggtaccagca gaaacctggc     120
caggctccca ggctcctcat ctattctaca tccaacctgg cttctgggat cccacctcga     180
ttcagtggca gcgggtatgg aacagatttt accctcacaa ttaataacat agaatctgag     240
gatgctgcat attacttctg tcaggattgg agtggttacc catacacgtt cggccaaggg     300

<210> SEQ ID NO 64
<211> LENGTH: 300
<212> TYPE: DNA
<213> ORGANISM: Artificial Sequence
<220> FEATURE:
<223> OTHER INFORMATION: Synthetic

<400> SEQUENCE: 64
gccatccagt tgacccagtc tccatcctcc ctgtctgcat ctgtaggaga cagagtcacc      60
atcacttgct atgccagctc agatgtaagt tacatgtact ggtaccagca gaaacctggc     120
caggctccca ggctcctcat ctatgacaca ttgaacctgg cttctgggat cccacctcga     180
ttcagtggca gcgggtatgg aacagatttt accctcacaa ttaataacat agaatctgag     240
gatgctgcat attacttctg tcaggattgg agtggttacc catacacgtt cggccaaggg     300

<210> SEQ ID NO 65
<211> LENGTH: 300
<212> TYPE: DNA
<213> ORGANISM: Artificial Sequence
<220> FEATURE:
<223> OTHER INFORMATION: Synthetic

<400> SEQUENCE: 65
gccatccagt tgacccagtc tccatcctcc ctgtctgcat ctgtaggaga cagagtcacc      60
atcacttgct atgccagctc aagtgtaagt tacatgtact ggtaccagca gaaacctggc     120
caggctccca ggctcctcat ctattctaca ttgaacctgg cttctgggat cccacctcga     180
ttcagtggca gcgggtatgg aacagatttt accctcacaa ttaataacat agaatctgag     240
gatgctgcat attacttctg tcaggattgg agtggttacc catacacgtt cggccaaggg     300

<210> SEQ ID NO 66
<211> LENGTH: 300
<212> TYPE: DNA
<213> ORGANISM: Artificial Sequence
<220> FEATURE:
<223> OTHER INFORMATION: Synthetic

<400> SEQUENCE: 66
gccatccagt tgacccagtc tccatcctcc ctgtctgcat ctgtaggaga cagagtcacc      60
atcacttgca gtgccagctc agatgtaagt tacatgtact ggtaccagca gaaacctggc     120
caggctccca ggctcctcat ctattctaca ttgaacctgg cttctgggat cccacctcga     180
ttcagtggca gcgggtatgg aacagatttt accctcacaa ttaataacat agaatctgag     240
gatgctgcat attacttctg tcaggattgg agtggttacc catacacgtt cggccaaggg     300

<210> SEQ ID NO 67
```

<211> LENGTH: 300
<212> TYPE: DNA
<213> ORGANISM: Artificial Sequence
<220> FEATURE:
<223> OTHER INFORMATION: Synthetic

<400> SEQUENCE: 67

```
gccatccagt tgacccagtc tccatcctcc ctgtctgcat ctgtaggaga cagagtcacc    60
atcacttgct atgccagctc agatgtaagt tacatgtact ggtaccagca gaaacctggc   120
caggctccca ggctcctcat ctattctaca ttgaacctgg cttctgggat cccacctcga   180
ttcagtggca gcgggtatgg aacagatttt accctcacaa ttaataacat agaatctgag   240
gatgctgcat attacttctg tcaggattgg agtggttacc catacacgtt cggccaaggg   300
```

<210> SEQ ID NO 68
<211> LENGTH: 100
<212> TYPE: PRT
<213> ORGANISM: Artificial Sequence
<220> FEATURE:
<223> OTHER INFORMATION: Synthetic

<400> SEQUENCE: 68

Ala Ile Gln Leu Thr Gln Ser Pro Ser Ser Leu Ser Ala Ser Val Gly
1               5                   10                  15

Asp Arg Val Thr Ile Thr Cys Tyr Ala Ser Ser Val Ser Tyr Met
            20                  25                  30

Tyr Trp Tyr Gln Gln Lys Pro Gly Gln Ala Pro Arg Leu Leu Ile Tyr
        35                  40                  45

Asp Thr Ser Asn Leu Ala Ser Gly Ile Pro Pro Arg Phe Ser Gly Ser
    50                  55                  60

Gly Tyr Gly Thr Asp Phe Thr Leu Thr Ile Asn Asn Ile Glu Ser Glu
65                  70                  75                  80

Asp Ala Ala Tyr Tyr Phe Cys Gln Gln Trp Ser Gly Tyr Pro Tyr Thr
                85                  90                  95

Phe Gly Gln Gly
            100

<210> SEQ ID NO 69
<211> LENGTH: 100
<212> TYPE: PRT
<213> ORGANISM: Artificial Sequence
<220> FEATURE:
<223> OTHER INFORMATION: Synthetic

<400> SEQUENCE: 69

Ala Ile Gln Leu Thr Gln Ser Pro Ser Ser Leu Ser Ala Ser Val Gly
1               5                   10                  15

Asp Arg Val Thr Ile Thr Cys Ser Ala Ser Ser Asp Val Ser Tyr Met
            20                  25                  30

Tyr Trp Tyr Gln Gln Lys Pro Gly Gln Ala Pro Arg Leu Leu Ile Tyr
        35                  40                  45

Asp Thr Ser Asn Leu Ala Ser Gly Ile Pro Pro Arg Phe Ser Gly Ser
    50                  55                  60

Gly Tyr Gly Thr Asp Phe Thr Leu Thr Ile Asn Asn Ile Glu Ser Glu
65                  70                  75                  80

Asp Ala Ala Tyr Tyr Phe Cys Gln Gln Trp Ser Gly Tyr Pro Tyr Thr
                85                  90                  95

Phe Gly Gln Gly
            100

```
<210> SEQ ID NO 70
<211> LENGTH: 100
<212> TYPE: PRT
<213> ORGANISM: Artificial Sequence
<220> FEATURE:
<223> OTHER INFORMATION: Synthetic

<400> SEQUENCE: 70

Ala Ile Gln Leu Thr Gln Ser Pro Ser Ser Leu Ser Ala Ser Val Gly
1               5                   10                  15

Asp Arg Val Thr Ile Thr Cys Ser Ala Ser Ser Val Ser Tyr Met
            20                  25                  30

Tyr Trp Tyr Gln Gln Lys Pro Gly Gln Ala Pro Arg Leu Leu Ile Tyr
            35                  40                  45

Ser Thr Ser Asn Leu Ala Ser Gly Ile Pro Pro Arg Phe Ser Gly Ser
        50                  55                  60

Gly Tyr Gly Thr Asp Phe Thr Leu Thr Ile Asn Asn Ile Glu Ser Glu
65                  70                  75                  80

Asp Ala Ala Tyr Tyr Phe Cys Gln Gln Trp Ser Gly Tyr Pro Tyr Thr
                85                  90                  95

Phe Gly Gln Gly
            100

<210> SEQ ID NO 71
<211> LENGTH: 100
<212> TYPE: PRT
<213> ORGANISM: Artificial Sequence
<220> FEATURE:
<223> OTHER INFORMATION: Synthetic

<400> SEQUENCE: 71

Ala Ile Gln Leu Thr Gln Ser Pro Ser Ser Leu Ser Ala Ser Val Gly
1               5                   10                  15

Asp Arg Val Thr Ile Thr Cys Ser Ala Ser Ser Val Ser Tyr Met
            20                  25                  30

Tyr Trp Tyr Gln Gln Lys Pro Gly Gln Ala Pro Arg Leu Leu Ile Tyr
            35                  40                  45

Asp Thr Leu Asn Leu Ala Ser Gly Ile Pro Pro Arg Phe Ser Gly Ser
        50                  55                  60

Gly Tyr Gly Thr Asp Phe Thr Leu Thr Ile Asn Asn Ile Glu Ser Glu
65                  70                  75                  80

Asp Ala Ala Tyr Tyr Phe Cys Gln Gln Trp Ser Gly Tyr Pro Tyr Thr
                85                  90                  95

Phe Gly Gln Gly
            100

<210> SEQ ID NO 72
<211> LENGTH: 100
<212> TYPE: PRT
<213> ORGANISM: Artificial Sequence
<220> FEATURE:
<223> OTHER INFORMATION: Synthetic

<400> SEQUENCE: 72

Ala Ile Gln Leu Thr Gln Ser Pro Ser Ser Leu Ser Ala Ser Val Gly
1               5                   10                  15

Asp Arg Val Thr Ile Thr Cys Ser Ala Ser Ser Val Ser Tyr Met
            20                  25                  30

Tyr Trp Tyr Gln Gln Lys Pro Gly Gln Ala Pro Arg Leu Leu Ile Tyr
            35                  40                  45
```

Asp Thr Ser Asn Leu Ala Ser Gly Ile Pro Pro Arg Phe Ser Gly Ser
        50                  55                  60

Gly Tyr Gly Thr Asp Phe Thr Leu Thr Ile Asn Asn Ile Glu Ser Glu
 65                  70                  75                  80

Asp Ala Ala Tyr Tyr Phe Cys Gln Asp Trp Ser Gly Tyr Pro Tyr Thr
                85                  90                  95

Phe Gly Gln Gly
            100

<210> SEQ ID NO 73
<211> LENGTH: 100
<212> TYPE: PRT
<213> ORGANISM: Artificial Sequence
<220> FEATURE:
<223> OTHER INFORMATION: Synthetic

<400> SEQUENCE: 73

Ala Ile Gln Leu Thr Gln Ser Pro Ser Ser Leu Ser Ala Ser Val Gly
 1               5                  10                  15

Asp Arg Val Thr Ile Thr Cys Tyr Ala Ser Ser Asp Val Ser Tyr Met
                20                  25                  30

Tyr Trp Tyr Gln Gln Lys Pro Gly Gln Ala Pro Arg Leu Leu Ile Tyr
            35                  40                  45

Asp Thr Ser Asn Leu Ala Ser Gly Ile Pro Pro Arg Phe Ser Gly Ser
        50                  55                  60

Gly Tyr Gly Thr Asp Phe Thr Leu Thr Ile Asn Asn Ile Glu Ser Glu
 65                  70                  75                  80

Asp Ala Ala Tyr Tyr Phe Cys Gln Gln Trp Ser Gly Tyr Pro Tyr Thr
                85                  90                  95

Phe Gly Gln Gly
            100

<210> SEQ ID NO 74
<211> LENGTH: 100
<212> TYPE: PRT
<213> ORGANISM: Artificial Sequence
<220> FEATURE:
<223> OTHER INFORMATION: Synthetic

<400> SEQUENCE: 74

Ala Ile Gln Leu Thr Gln Ser Pro Ser Ser Leu Ser Ala Ser Val Gly
 1               5                  10                  15

Asp Arg Val Thr Ile Thr Cys Tyr Ala Ser Ser Ser Val Ser Tyr Met
                20                  25                  30

Tyr Trp Tyr Gln Gln Lys Pro Gly Gln Ala Pro Arg Leu Leu Ile Tyr
            35                  40                  45

Ser Thr Ser Asn Leu Ala Ser Gly Ile Pro Pro Arg Phe Ser Gly Ser
        50                  55                  60

Gly Tyr Gly Thr Asp Phe Thr Leu Thr Ile Asn Asn Ile Glu Ser Glu
 65                  70                  75                  80

Asp Ala Ala Tyr Tyr Phe Cys Gln Gln Trp Ser Gly Tyr Pro Tyr Thr
                85                  90                  95

Phe Gly Gln Gly
            100

<210> SEQ ID NO 75
<211> LENGTH: 100
<212> TYPE: PRT
<213> ORGANISM: Artificial Sequence

```
<220> FEATURE:
<223> OTHER INFORMATION: Synthetic

<400> SEQUENCE: 75

Ala Ile Gln Leu Thr Gln Ser Pro Ser Ser Leu Ser Ala Ser Val Gly
1               5                   10                  15

Asp Arg Val Thr Ile Thr Cys Tyr Ala Ser Ser Val Ser Tyr Met
            20                  25                  30

Tyr Trp Tyr Gln Gln Lys Pro Gly Gln Ala Pro Arg Leu Leu Ile Tyr
        35                  40                  45

Asp Thr Leu Asn Leu Ala Ser Gly Ile Pro Pro Arg Phe Ser Gly Ser
    50                  55                  60

Gly Tyr Gly Thr Asp Phe Thr Leu Thr Ile Asn Asn Ile Glu Ser Glu
65                  70                  75                  80

Asp Ala Ala Tyr Tyr Phe Cys Gln Gln Trp Ser Gly Tyr Pro Tyr Thr
                85                  90                  95

Phe Gly Gln Gly
            100

<210> SEQ ID NO 76
<211> LENGTH: 100
<212> TYPE: PRT
<213> ORGANISM: Artificial Sequence
<220> FEATURE:
<223> OTHER INFORMATION: Synthetic

<400> SEQUENCE: 76

Ala Ile Gln Leu Thr Gln Ser Pro Ser Ser Leu Ser Ala Ser Val Gly
1               5                   10                  15

Asp Arg Val Thr Ile Thr Cys Tyr Ala Ser Ser Val Ser Tyr Met
            20                  25                  30

Tyr Trp Tyr Gln Gln Lys Pro Gly Gln Ala Pro Arg Leu Leu Ile Tyr
        35                  40                  45

Asp Thr Ser Asn Leu Ala Ser Gly Ile Pro Pro Arg Phe Ser Gly Ser
    50                  55                  60

Gly Tyr Gly Thr Asp Phe Thr Leu Thr Ile Asn Asn Ile Glu Ser Glu
65                  70                  75                  80

Asp Ala Ala Tyr Tyr Phe Cys Gln Asp Trp Ser Gly Tyr Pro Tyr Thr
                85                  90                  95

Phe Gly Gln Gly
            100

<210> SEQ ID NO 77
<211> LENGTH: 100
<212> TYPE: PRT
<213> ORGANISM: Artificial Sequence
<220> FEATURE:
<223> OTHER INFORMATION: Synthetic

<400> SEQUENCE: 77

Ala Ile Gln Leu Thr Gln Ser Pro Ser Ser Leu Ser Ala Ser Val Gly
1               5                   10                  15

Asp Arg Val Thr Ile Thr Cys Ser Ala Ser Ser Asp Val Ser Tyr Met
            20                  25                  30

Tyr Trp Tyr Gln Gln Lys Pro Gly Gln Ala Pro Arg Leu Leu Ile Tyr
        35                  40                  45

Ser Thr Ser Asn Leu Ala Ser Gly Ile Pro Pro Arg Phe Ser Gly Ser
    50                  55                  60

Gly Tyr Gly Thr Asp Phe Thr Leu Thr Ile Asn Asn Ile Glu Ser Glu
```

```
                65                  70                  75                  80
Asp Ala Ala Tyr Tyr Phe Cys Gln Gln Trp Ser Gly Tyr Pro Tyr Thr
                    85                  90                  95

Phe Gly Gln Gly
            100

<210> SEQ ID NO 78
<211> LENGTH: 100
<212> TYPE: PRT
<213> ORGANISM: Artificial Sequence
<220> FEATURE:
<223> OTHER INFORMATION: Synthetic

<400> SEQUENCE: 78

Ala Ile Gln Leu Thr Gln Ser Pro Ser Ser Leu Ser Ala Ser Val Gly
1               5                   10                  15

Asp Arg Val Thr Ile Thr Cys Ser Ala Ser Ser Asp Val Ser Tyr Met
            20                  25                  30

Tyr Trp Tyr Gln Gln Lys Pro Gly Gln Ala Pro Arg Leu Leu Ile Tyr
        35                  40                  45

Asp Thr Leu Asn Leu Ala Ser Gly Ile Pro Pro Arg Phe Ser Gly Ser
    50                  55                  60

Gly Tyr Gly Thr Asp Phe Thr Leu Thr Ile Asn Asn Ile Glu Ser Glu
65                  70                  75                  80

Asp Ala Ala Tyr Tyr Phe Cys Gln Gln Trp Ser Gly Tyr Pro Tyr Thr
                    85                  90                  95

Phe Gly Gln Gly
            100

<210> SEQ ID NO 79
<211> LENGTH: 100
<212> TYPE: PRT
<213> ORGANISM: Artificial Sequence
<220> FEATURE:
<223> OTHER INFORMATION: Synthetic

<400> SEQUENCE: 79

Ala Ile Gln Leu Thr Gln Ser Pro Ser Ser Leu Ser Ala Ser Val Gly
1               5                   10                  15

Asp Arg Val Thr Ile Thr Cys Ser Ala Ser Ser Asp Val Ser Tyr Met
            20                  25                  30

Tyr Trp Tyr Gln Gln Lys Pro Gly Gln Ala Pro Arg Leu Leu Ile Tyr
        35                  40                  45

Asp Thr Ser Asn Leu Ala Ser Gly Ile Pro Pro Arg Phe Ser Gly Ser
    50                  55                  60

Gly Tyr Gly Thr Asp Phe Thr Leu Thr Ile Asn Asn Ile Glu Ser Glu
65                  70                  75                  80

Asp Ala Ala Tyr Tyr Phe Cys Gln Asp Trp Ser Gly Tyr Pro Tyr Thr
                    85                  90                  95

Phe Gly Gln Gly
            100

<210> SEQ ID NO 80
<211> LENGTH: 100
<212> TYPE: PRT
<213> ORGANISM: Artificial Sequence
<220> FEATURE:
<223> OTHER INFORMATION: Synthetic

<400> SEQUENCE: 80
```

Ala Ile Gln Leu Thr Gln Ser Pro Ser Ser Leu Ser Ala Ser Val Gly
1               5                   10                  15

Asp Arg Val Thr Ile Thr Cys Ser Ala Ser Ser Ser Val Ser Tyr Met
            20                  25                  30

Tyr Trp Tyr Gln Gln Lys Pro Gly Gln Ala Pro Arg Leu Leu Ile Tyr
        35                  40                  45

Ser Thr Leu Asn Leu Ala Ser Gly Ile Pro Pro Arg Phe Ser Gly Ser
    50                  55                  60

Gly Tyr Gly Thr Asp Phe Thr Leu Thr Ile Asn Asn Ile Glu Ser Glu
65                  70                  75                  80

Asp Ala Ala Tyr Tyr Phe Cys Gln Gln Trp Ser Gly Tyr Pro Tyr Thr
                85                  90                  95

Phe Gly Gln Gly
            100

<210> SEQ ID NO 81
<211> LENGTH: 100
<212> TYPE: PRT
<213> ORGANISM: Artificial Sequence
<220> FEATURE:
<223> OTHER INFORMATION: Synthetic

<400> SEQUENCE: 81

Ala Ile Gln Leu Thr Gln Ser Pro Ser Ser Leu Ser Ala Ser Val Gly
1               5                   10                  15

Asp Arg Val Thr Ile Thr Cys Ser Ala Ser Ser Ser Val Ser Tyr Met
            20                  25                  30

Tyr Trp Tyr Gln Gln Lys Pro Gly Gln Ala Pro Arg Leu Leu Ile Tyr
        35                  40                  45

Ser Thr Ser Asn Leu Ala Ser Gly Ile Pro Pro Arg Phe Ser Gly Ser
    50                  55                  60

Gly Tyr Gly Thr Asp Phe Thr Leu Thr Ile Asn Asn Ile Glu Ser Glu
65                  70                  75                  80

Asp Ala Ala Tyr Tyr Phe Cys Gln Asp Trp Ser Gly Tyr Pro Tyr Thr
                85                  90                  95

Phe Gly Gln Gly
            100

<210> SEQ ID NO 82
<211> LENGTH: 100
<212> TYPE: PRT
<213> ORGANISM: Artificial Sequence
<220> FEATURE:
<223> OTHER INFORMATION: Synthetic

<400> SEQUENCE: 82

Ala Ile Gln Leu Thr Gln Ser Pro Ser Ser Leu Ser Ala Ser Val Gly
1               5                   10                  15

Asp Arg Val Thr Ile Thr Cys Ser Ala Ser Ser Ser Val Ser Tyr Met
            20                  25                  30

Tyr Trp Tyr Gln Gln Lys Pro Gly Gln Ala Pro Arg Leu Leu Ile Tyr
        35                  40                  45

Asp Thr Leu Asn Leu Ala Ser Gly Ile Pro Pro Arg Phe Ser Gly Ser
    50                  55                  60

Gly Tyr Gly Thr Asp Phe Thr Leu Thr Ile Asn Asn Ile Glu Ser Glu
65                  70                  75                  80

Asp Ala Ala Tyr Tyr Phe Cys Gln Asp Trp Ser Gly Tyr Pro Tyr Thr
                85                  90                  95

```
Phe Gly Gln Gly
            100

<210> SEQ ID NO 83
<211> LENGTH: 100
<212> TYPE: PRT
<213> ORGANISM: Artificial Sequence
<220> FEATURE:
<223> OTHER INFORMATION: Synthetic

<400> SEQUENCE: 83

Ala Ile Gln Leu Thr Gln Ser Pro Ser Ser Leu Ser Ala Ser Val Gly
1               5                   10                  15

Asp Arg Val Thr Ile Thr Cys Tyr Ala Ser Ser Asp Val Ser Tyr Met
            20                  25                  30

Tyr Trp Tyr Gln Gln Lys Pro Gly Gln Ala Pro Arg Leu Leu Ile Tyr
        35                  40                  45

Ser Thr Ser Asn Leu Ala Ser Gly Ile Pro Pro Arg Phe Ser Gly Ser
    50                  55                  60

Gly Tyr Gly Thr Asp Phe Thr Leu Thr Ile Asn Asn Ile Glu Ser Glu
65                  70                  75                  80

Asp Ala Ala Tyr Tyr Phe Cys Gln Gln Trp Ser Gly Tyr Pro Tyr Thr
                85                  90                  95

Phe Gly Gln Gly
            100

<210> SEQ ID NO 84
<211> LENGTH: 100
<212> TYPE: PRT
<213> ORGANISM: Artificial Sequence
<220> FEATURE:
<223> OTHER INFORMATION: Synthetic

<400> SEQUENCE: 84

Ala Ile Gln Leu Thr Gln Ser Pro Ser Ser Leu Ser Ala Ser Val Gly
1               5                   10                  15

Asp Arg Val Thr Ile Thr Cys Tyr Ala Ser Ser Asp Val Ser Tyr Met
            20                  25                  30

Tyr Trp Tyr Gln Gln Lys Pro Gly Gln Ala Pro Arg Leu Leu Ile Tyr
        35                  40                  45

Asp Thr Leu Asn Leu Ala Ser Gly Ile Pro Pro Arg Phe Ser Gly Ser
    50                  55                  60

Gly Tyr Gly Thr Asp Phe Thr Leu Thr Ile Asn Asn Ile Glu Ser Glu
65                  70                  75                  80

Asp Ala Ala Tyr Tyr Phe Cys Gln Gln Trp Ser Gly Tyr Pro Tyr Thr
                85                  90                  95

Phe Gly Gln Gly
            100

<210> SEQ ID NO 85
<211> LENGTH: 100
<212> TYPE: PRT
<213> ORGANISM: Artificial Sequence
<220> FEATURE:
<223> OTHER INFORMATION: Synthetic

<400> SEQUENCE: 85

Ala Ile Gln Leu Thr Gln Ser Pro Ser Ser Leu Ser Ala Ser Val Gly
1               5                   10                  15

Asp Arg Val Thr Ile Thr Cys Tyr Ala Ser Ser Asp Val Ser Tyr Met
            20                  25                  30
```

-continued

Tyr Trp Tyr Gln Gln Lys Pro Gly Gln Ala Pro Arg Leu Leu Ile Tyr
            35                  40                  45

Asp Thr Ser Asn Leu Ala Ser Gly Ile Pro Pro Arg Phe Ser Gly Ser
 50                  55                  60

Gly Tyr Gly Thr Asp Phe Thr Leu Thr Ile Asn Asn Ile Glu Ser Glu
 65                  70                  75                  80

Asp Ala Ala Tyr Tyr Phe Cys Gln Asp Trp Ser Gly Tyr Pro Tyr Thr
                85                  90                  95

Phe Gly Gln Gly
            100

<210> SEQ ID NO 86
<211> LENGTH: 100
<212> TYPE: PRT
<213> ORGANISM: Artificial Sequence
<220> FEATURE:
<223> OTHER INFORMATION: Synthetic

<400> SEQUENCE: 86

Ala Ile Gln Leu Thr Gln Ser Pro Ser Ser Leu Ser Ala Ser Val Gly
 1               5                  10                  15

Asp Arg Val Thr Ile Thr Cys Tyr Ala Ser Ser Val Ser Tyr Met
            20                  25                  30

Tyr Trp Tyr Gln Gln Lys Pro Gly Gln Ala Pro Arg Leu Leu Ile Tyr
            35                  40                  45

Ser Thr Leu Asn Leu Ala Ser Gly Ile Pro Pro Arg Phe Ser Gly Ser
 50                  55                  60

Gly Tyr Gly Thr Asp Phe Thr Leu Thr Ile Asn Asn Ile Glu Ser Glu
 65                  70                  75                  80

Asp Ala Ala Tyr Tyr Phe Cys Gln Gln Trp Ser Gly Tyr Pro Tyr Thr
                85                  90                  95

Phe Gly Gln Gly
            100

<210> SEQ ID NO 87
<211> LENGTH: 100
<212> TYPE: PRT
<213> ORGANISM: Artificial Sequence
<220> FEATURE:
<223> OTHER INFORMATION: Synthetic

<400> SEQUENCE: 87

Ala Ile Gln Leu Thr Gln Ser Pro Ser Ser Leu Ser Ala Ser Val Gly
 1               5                  10                  15

Asp Arg Val Thr Ile Thr Cys Tyr Ala Ser Ser Val Ser Tyr Met
            20                  25                  30

Tyr Trp Tyr Gln Gln Lys Pro Gly Gln Ala Pro Arg Leu Leu Ile Tyr
            35                  40                  45

Ser Thr Ser Asn Leu Ala Ser Gly Ile Pro Pro Arg Phe Ser Gly Ser
 50                  55                  60

Gly Tyr Gly Thr Asp Phe Thr Leu Thr Ile Asn Asn Ile Glu Ser Glu
 65                  70                  75                  80

Asp Ala Ala Tyr Tyr Phe Cys Gln Asp Trp Ser Gly Tyr Pro Tyr Thr
                85                  90                  95

Phe Gly Gln Gly
            100

<210> SEQ ID NO 88

<211> LENGTH: 100
<212> TYPE: PRT
<213> ORGANISM: Artificial Sequence
<220> FEATURE:
<223> OTHER INFORMATION: Synthetic

<400> SEQUENCE: 88

```
Ala Ile Gln Leu Thr Gln Ser Pro Ser Ser Leu Ser Ala Ser Val Gly
1               5                   10                  15

Asp Arg Val Thr Ile Thr Cys Tyr Ala Ser Ser Val Ser Tyr Met
            20                  25                  30

Tyr Trp Tyr Gln Gln Lys Pro Gly Gln Ala Pro Arg Leu Leu Ile Tyr
        35                  40                  45

Asp Thr Leu Asn Leu Ala Ser Gly Ile Pro Pro Arg Phe Ser Gly Ser
    50                  55                  60

Gly Tyr Gly Thr Asp Phe Thr Leu Thr Ile Asn Asn Ile Glu Ser Glu
65                  70                  75                  80

Asp Ala Ala Tyr Tyr Phe Cys Gln Asp Trp Ser Gly Tyr Pro Tyr Thr
                85                  90                  95

Phe Gly Gln Gly
            100
```

<210> SEQ ID NO 89
<211> LENGTH: 100
<212> TYPE: PRT
<213> ORGANISM: Artificial Sequence
<220> FEATURE:
<223> OTHER INFORMATION: Synthetic

<400> SEQUENCE: 89

```
Ala Ile Gln Leu Thr Gln Ser Pro Ser Ser Leu Ser Ala Ser Val Gly
1               5                   10                  15

Asp Arg Val Thr Ile Thr Cys Ser Ala Ser Ser Asp Val Ser Tyr Met
            20                  25                  30

Tyr Trp Tyr Gln Gln Lys Pro Gly Gln Ala Pro Arg Leu Leu Ile Tyr
        35                  40                  45

Ser Thr Leu Asn Leu Ala Ser Gly Ile Pro Pro Arg Phe Ser Gly Ser
    50                  55                  60

Gly Tyr Gly Thr Asp Phe Thr Leu Thr Ile Asn Asn Ile Glu Ser Glu
65                  70                  75                  80

Asp Ala Ala Tyr Tyr Phe Cys Gln Gln Trp Ser Gly Tyr Pro Tyr Thr
                85                  90                  95

Phe Gly Gln Gly
            100
```

<210> SEQ ID NO 90
<211> LENGTH: 100
<212> TYPE: PRT
<213> ORGANISM: Artificial Sequence
<220> FEATURE:
<223> OTHER INFORMATION: Synthetic

<400> SEQUENCE: 90

```
Ala Ile Gln Leu Thr Gln Ser Pro Ser Ser Leu Ser Ala Ser Val Gly
1               5                   10                  15

Asp Arg Val Thr Ile Thr Cys Ser Ala Ser Ser Asp Val Ser Tyr Met
            20                  25                  30

Tyr Trp Tyr Gln Gln Lys Pro Gly Gln Ala Pro Arg Leu Leu Ile Tyr
        35                  40                  45

Ser Thr Ser Asn Leu Ala Ser Gly Ile Pro Pro Arg Phe Ser Gly Ser
```

```
                 50                  55                  60
Gly Tyr Gly Thr Asp Phe Thr Leu Thr Ile Asn Asn Ile Glu Ser Glu
 65                  70                  75                  80

Asp Ala Ala Tyr Tyr Phe Cys Gln Asp Trp Ser Gly Tyr Pro Tyr Thr
                 85                  90                  95

Phe Gly Gln Gly
            100

<210> SEQ ID NO 91
<211> LENGTH: 100
<212> TYPE: PRT
<213> ORGANISM: Artificial Sequence
<220> FEATURE:
<223> OTHER INFORMATION: Synthetic

<400> SEQUENCE: 91

Ala Ile Gln Leu Thr Gln Ser Pro Ser Ser Leu Ser Ala Ser Val Gly
  1               5                  10                  15

Asp Arg Val Thr Ile Thr Cys Ser Ala Ser Ser Asp Val Ser Tyr Met
                 20                  25                  30

Tyr Trp Tyr Gln Gln Lys Pro Gly Gln Ala Pro Arg Leu Leu Ile Tyr
                 35                  40                  45

Asp Thr Leu Asn Leu Ala Ser Gly Ile Pro Pro Arg Phe Ser Gly Ser
                 50                  55                  60

Gly Tyr Gly Thr Asp Phe Thr Leu Thr Ile Asn Asn Ile Glu Ser Glu
 65                  70                  75                  80

Asp Ala Ala Tyr Tyr Phe Cys Gln Asp Trp Ser Gly Tyr Pro Tyr Thr
                 85                  90                  95

Phe Gly Gln Gly
            100

<210> SEQ ID NO 92
<211> LENGTH: 100
<212> TYPE: PRT
<213> ORGANISM: Artificial Sequence
<220> FEATURE:
<223> OTHER INFORMATION: Synthetic

<400> SEQUENCE: 92

Ala Ile Gln Leu Thr Gln Ser Pro Ser Ser Leu Ser Ala Ser Val Gly
  1               5                  10                  15

Asp Arg Val Thr Ile Thr Cys Ser Ala Ser Ser Ser Val Ser Tyr Met
                 20                  25                  30

Tyr Trp Tyr Gln Gln Lys Pro Gly Gln Ala Pro Arg Leu Leu Ile Tyr
                 35                  40                  45

Ser Thr Leu Asn Leu Ala Ser Gly Ile Pro Pro Arg Phe Ser Gly Ser
                 50                  55                  60

Gly Tyr Gly Thr Asp Phe Thr Leu Thr Ile Asn Asn Ile Glu Ser Glu
 65                  70                  75                  80

Asp Ala Ala Tyr Tyr Phe Cys Gln Asp Trp Ser Gly Tyr Pro Tyr Thr
                 85                  90                  95

Phe Gly Gln Gly
            100

<210> SEQ ID NO 93
<211> LENGTH: 100
<212> TYPE: PRT
<213> ORGANISM: Artificial Sequence
<220> FEATURE:
<223> OTHER INFORMATION: Synthetic
```

<400> SEQUENCE: 93

```
Ala Ile Gln Leu Thr Gln Ser Pro Ser Ser Leu Ser Ala Ser Val Gly
 1               5                  10                  15
Asp Arg Val Thr Ile Thr Cys Tyr Ala Ser Ser Asp Val Ser Tyr Met
            20                  25                  30
Tyr Trp Tyr Gln Gln Lys Pro Gly Gln Ala Pro Arg Leu Leu Ile Tyr
        35                  40                  45
Ser Thr Leu Asn Leu Ala Ser Gly Ile Pro Pro Arg Phe Ser Gly Ser
    50                  55                  60
Gly Tyr Gly Thr Asp Phe Thr Leu Thr Ile Asn Asn Ile Glu Ser Glu
65                  70                  75                  80
Asp Ala Ala Tyr Tyr Phe Cys Gln Gln Trp Ser Gly Tyr Pro Tyr Thr
                85                  90                  95
Phe Gly Gln Gly
            100
```

<210> SEQ ID NO 94
<211> LENGTH: 100
<212> TYPE: PRT
<213> ORGANISM: Artificial Sequence
<220> FEATURE:
<223> OTHER INFORMATION: Synthetic

<400> SEQUENCE: 94

```
Ala Ile Gln Leu Thr Gln Ser Pro Ser Ser Leu Ser Ala Ser Val Gly
 1               5                  10                  15
Asp Arg Val Thr Ile Thr Cys Tyr Ala Ser Ser Asp Val Ser Tyr Met
            20                  25                  30
Tyr Trp Tyr Gln Gln Lys Pro Gly Gln Ala Pro Arg Leu Leu Ile Tyr
        35                  40                  45
Ser Thr Ser Asn Leu Ala Ser Gly Ile Pro Pro Arg Phe Ser Gly Ser
    50                  55                  60
Gly Tyr Gly Thr Asp Phe Thr Leu Thr Ile Asn Asn Ile Glu Ser Glu
65                  70                  75                  80
Asp Ala Ala Tyr Tyr Phe Cys Gln Asp Trp Ser Gly Tyr Pro Tyr Thr
                85                  90                  95
Phe Gly Gln Gly
            100
```

<210> SEQ ID NO 95
<211> LENGTH: 100
<212> TYPE: PRT
<213> ORGANISM: Artificial Sequence
<220> FEATURE:
<223> OTHER INFORMATION: Synthetic

<400> SEQUENCE: 95

```
Ala Ile Gln Leu Thr Gln Ser Pro Ser Ser Leu Ser Ala Ser Val Gly
 1               5                  10                  15
Asp Arg Val Thr Ile Thr Cys Tyr Ala Ser Ser Asp Val Ser Tyr Met
            20                  25                  30
Tyr Trp Tyr Gln Gln Lys Pro Gly Gln Ala Pro Arg Leu Leu Ile Tyr
        35                  40                  45
Asp Thr Leu Asn Leu Ala Ser Gly Ile Pro Pro Arg Phe Ser Gly Ser
    50                  55                  60
Gly Tyr Gly Thr Asp Phe Thr Leu Thr Ile Asn Asn Ile Glu Ser Glu
65                  70                  75                  80
```

-continued

Asp Ala Ala Tyr Tyr Phe Cys Gln Asp Trp Ser Gly Tyr Pro Tyr Thr
                85                  90                  95
Phe Gly Gln Gly
            100

<210> SEQ ID NO 96
<211> LENGTH: 100
<212> TYPE: PRT
<213> ORGANISM: Artificial Sequence
<220> FEATURE:
<223> OTHER INFORMATION: Synthetic

<400> SEQUENCE: 96

Ala Ile Gln Leu Thr Gln Ser Pro Ser Ser Leu Ser Ala Ser Val Gly
1               5                   10                  15
Asp Arg Val Thr Ile Thr Cys Tyr Ala Ser Ser Val Ser Tyr Met
            20                  25                  30
Tyr Trp Tyr Gln Gln Lys Pro Gly Gln Ala Pro Arg Leu Leu Ile Tyr
            35                  40                  45
Ser Thr Leu Asn Leu Ala Ser Gly Ile Pro Pro Arg Phe Ser Gly Ser
        50                  55                  60
Gly Tyr Gly Thr Asp Phe Thr Leu Thr Ile Asn Asn Ile Glu Ser Glu
65                  70                  75                  80
Asp Ala Ala Tyr Tyr Phe Cys Gln Asp Trp Ser Gly Tyr Pro Tyr Thr
                85                  90                  95
Phe Gly Gln Gly
            100

<210> SEQ ID NO 97
<211> LENGTH: 100
<212> TYPE: PRT
<213> ORGANISM: Artificial Sequence
<220> FEATURE:
<223> OTHER INFORMATION: Synthetic

<400> SEQUENCE: 97

Ala Ile Gln Leu Thr Gln Ser Pro Ser Ser Leu Ser Ala Ser Val Gly
1               5                   10                  15
Asp Arg Val Thr Ile Thr Cys Ser Ala Ser Ser Asp Val Ser Tyr Met
            20                  25                  30
Tyr Trp Tyr Gln Gln Lys Pro Gly Gln Ala Pro Arg Leu Leu Ile Tyr
            35                  40                  45
Ser Thr Leu Asn Leu Ala Ser Gly Ile Pro Pro Arg Phe Ser Gly Ser
        50                  55                  60
Gly Tyr Gly Thr Asp Phe Thr Leu Thr Ile Asn Asn Ile Glu Ser Glu
65                  70                  75                  80
Asp Ala Ala Tyr Tyr Phe Cys Gln Asp Trp Ser Gly Tyr Pro Tyr Thr
                85                  90                  95
Phe Gly Gln Gly
            100

<210> SEQ ID NO 98
<211> LENGTH: 100
<212> TYPE: PRT
<213> ORGANISM: Artificial Sequence
<220> FEATURE:
<223> OTHER INFORMATION: Synthetic

<400> SEQUENCE: 98

Ala Ile Gln Leu Thr Gln Ser Pro Ser Ser Leu Ser Ala Ser Val Gly
1               5                   10                  15

Asp Arg Val Thr Ile Thr Cys Tyr Ala Ser Ser Asp Val Ser Tyr Met
            20                  25                  30

Tyr Trp Tyr Gln Gln Lys Pro Gly Gln Ala Pro Arg Leu Leu Ile Tyr
        35                  40                  45

Ser Thr Leu Asn Leu Ala Ser Gly Ile Pro Pro Arg Phe Ser Gly Ser
    50                  55                  60

Gly Tyr Gly Thr Asp Phe Thr Leu Thr Ile Asn Asn Ile Glu Ser Glu
65                  70                  75                  80

Asp Ala Ala Tyr Tyr Phe Cys Gln Asp Trp Ser Gly Tyr Pro Tyr Thr
                85                  90                  95

Phe Gly Gln Gly
            100

<210> SEQ ID NO 99
<211> LENGTH: 336
<212> TYPE: DNA
<213> ORGANISM: Artificial Sequence
<220> FEATURE:
<223> OTHER INFORMATION: Synthetic

<400> SEQUENCE: 99
caggttcagc tggtgcagtc tggagctgag gtgaagaagc ctggggcctc agtgaaggtc      60
tcctgcaagg cttctcattt caccttcagt agctttgcca tgtcttggat caggcagtcc     120
ccatcgagag gccttgagtg gctgggtgaa attagtagtg gtgggagtta cacctactat     180
cctgacactg tgacgggcag attcaccatc tccagagaca cgccaagaa ctcactgtat      240 ctgcaaatga acagcctgag agccgaggac acggctgtgt attactgtgc gagaggttta     300
tgggggtact atgctcttga ctactggggc caggga                               336

<210> SEQ ID NO 100
<211> LENGTH: 336
<212> TYPE: DNA
<213> ORGANISM: Artificial Sequence
<220> FEATURE:
<223> OTHER INFORMATION: Synthetic

<400> SEQUENCE: 100
caggttcagc tggtgcagtc tggagctgag gtgaagaagc ctggggcctc agtgaaggtc      60
tcctgcaagg cttctggatt caccttcagt agcttttcga tgtcttggat caggcagtcc     120
ccatcgagag gccttgagtg gctgggtgaa attagtagtg gtgggagtta cacctactat     180
cctgacactg tgacgggcag attcaccatc tccagagaca cgccaagaa ctcactgtat      240 ctgcaaatga acagcctgag agccgaggac acggctgtgt attactgtgc gagaggttta     300
tgggggtact atgctcttga ctactggggc caggga                               336

<210> SEQ ID NO 101
<211> LENGTH: 336
<212> TYPE: DNA
<213> ORGANISM: Artificial Sequence
<220> FEATURE:
<223> OTHER INFORMATION: Synthetic

<400> SEQUENCE: 101
caggttcagc tggtgcagtc tggagctgag gtgaagaagc ctggggcctc agtgaaggtc      60
tcctgcaagg cttctggatt caccttcagt agctttgcca tgtcttggat caggcagtcc     120
ccatcgagag gccttgagtg gctgggtgaa attagtagtg gtgggagtta ccattactat     180
cctgacactg tgacgggcag attcaccatc tccagagaca cgccaagaa ctcactgtat      240

```
ctgcaaatga acagcctgag agccgaggac acggctgtgt attactgtgc gagaggttta    300
tgggggtact atgctcttga ctactggggc caggga                              336
```

<210> SEQ ID NO 102
<211> LENGTH: 336
<212> TYPE: DNA
<213> ORGANISM: Artificial Sequence
<220> FEATURE:
<223> OTHER INFORMATION: Synthetic

<400> SEQUENCE: 102

```
caggttcagc tggtgcagtc tggagctgag gtgaagaagc ctggggcctc agtgaaggtc    60
tcctgcaagg cttctggatt caccttcagt agctttgcca tgtcttggat caggcagtcc   120
ccatcgagag gccttgagtg gctgggtgaa attagtagtg gtgggagtta cacctactat   180
cctgacacta agacgggcag attcaccatc tccagagaca acgccaagaa ctcactgtat   240
ctgcaaatga acagcctgag agccgaggac acggctgtgt attactgtgc gagaggttta   300
tgggggtact atgctcttga ctactggggc caggga                              336
```

<210> SEQ ID NO 103
<211> LENGTH: 336
<212> TYPE: DNA
<213> ORGANISM: Artificial Sequence
<220> FEATURE:
<223> OTHER INFORMATION: Synthetic

<400> SEQUENCE: 103

```
caggttcagc tggtgcagtc tggagctgag gtgaagaagc ctggggcctc agtgaaggtc    60
tcctgcaagg cttctggatt caccttcagt agctttgcca tgtcttggat caggcagtcc   120
ccatcgagag gccttgagtg gctgggtgaa attagtagtg gtgggagtta cacctactat   180
cctgacactg tgacgggcag attcaccatc tccagagaca acgccaagaa ctcactgtat   240
ctgcaaatga acagcctgag agccgaggac acggctgtgt attactgtgc gagaggtcag   300
tgggggtact atgctcttga ctactggggc caggga                              336
```

<210> SEQ ID NO 104
<211> LENGTH: 336
<212> TYPE: DNA
<213> ORGANISM: Artificial Sequence
<220> FEATURE:
<223> OTHER INFORMATION: Synthetic

<400> SEQUENCE: 104

```
caggttcagc tggtgcagtc tggagctgag gtgaagaagc ctggggcctc agtgaaggtc    60
tcctgcaagg cttctcattt caccttcagt agcttttcga tgtcttggat caggcagtcc   120
ccatcgagag gccttgagtg gctgggtgaa attagtagtg gtgggagtta cacctactat   180
cctgacactg tgacgggcag attcaccatc tccagagaca acgccaagaa ctcactgtat   240
ctgcaaatga acagcctgag agccgaggac acggctgtgt attactgtgc gagaggttta   300
tgggggtact atgctcttga ctactggggc caggga                              336
```

<210> SEQ ID NO 105
<211> LENGTH: 336
<212> TYPE: DNA
<213> ORGANISM: Artificial Sequence
<220> FEATURE:
<223> OTHER INFORMATION: Synthetic

<400> SEQUENCE: 105
caggttcagc tggtgcagtc tggagctgag gtgaagaagc ctggggcctc agtgaaggtc    60
tcctgcaagg cttctcattt caccttcagt agctttgcca tgtcttggat caggcagtcc   120
ccatcgagag gccttgagtg gctgggtgaa attagtagtg gtgggagtta ccattactat   180
cctgacactg tgacgggcag attcaccatc tccagagaca cgccaagaa ctcactgtat    240 ctgcaaatga acagcctgag agccgaggac acggctgtgt attactgtgc gagaggttta   300
tgggggtact atgctcttga ctactggggc caggga                             336

<210> SEQ ID NO 106
<211> LENGTH: 336
<212> TYPE: DNA
<213> ORGANISM: Artificial Sequence
<220> FEATURE:
<223> OTHER INFORMATION: Synthetic

<400> SEQUENCE: 106
caggttcagc tggtgcagtc tggagctgag gtgaagaagc ctggggcctc agtgaaggtc    60
tcctgcaagg cttctcattt caccttcagt agctttgcca tgtcttggat caggcagtcc   120
ccatcgagag gccttgagtg gctgggtgaa attagtagtg gtgggagtta cacctactat   180
cctgacacta agacgggcag attcaccatc tccagagaca cgccaagaa ctcactgtat    240 ctgcaaatga acagcctgag agccgaggac acggctgtgt attactgtgc gagaggttta   300
tgggggtact atgctcttga ctactggggc caggga                             336

<210> SEQ ID NO 107
<211> LENGTH: 336
<212> TYPE: DNA
<213> ORGANISM: Artificial Sequence
<220> FEATURE:
<223> OTHER INFORMATION: Synthetic

<400> SEQUENCE: 107
caggttcagc tggtgcagtc tggagctgag gtgaagaagc ctggggcctc agtgaaggtc    60
tcctgcaagg cttctcattt caccttcagt agctttgcca tgtcttggat caggcagtcc   120
ccatcgagag gccttgagtg gctgggtgaa attagtagtg gtgggagtta cacctactat   180
cctgacactg tgacgggcag attcaccatc tccagagaca cgccaagaa ctcactgtat    240 ctgcaaatga acagcctgag agccgaggac acggctgtgt attactgtgc gagaggtcag   300
tgggggtact atgctcttga ctactggggc caggga                             336

<210> SEQ ID NO 108
<211> LENGTH: 336
<212> TYPE: DNA
<213> ORGANISM: Artificial Sequence
<220> FEATURE:
<223> OTHER INFORMATION: Synthetic

<400> SEQUENCE: 108
caggttcagc tggtgcagtc tggagctgag gtgaagaagc ctggggcctc agtgaaggtc    60
tcctgcaagg cttctggatt caccttcagt agcttttcga tgtcttggat caggcagtcc   120
ccatcgagag gccttgagtg gctgggtgaa attagtagtg gtgggagtta ccattactat   180
cctgacactg tgacgggcag attcaccatc tccagagaca cgccaagaa ctcactgtat    240 ctgcaaatga acagcctgag agccgaggac acggctgtgt attactgtgc gagaggttta   300
tgggggtact atgctcttga ctactggggc caggga                             336

<210> SEQ ID NO 109
<211> LENGTH: 336
<212> TYPE: DNA
<213> ORGANISM: Artificial Sequence
<220> FEATURE:
<223> OTHER INFORMATION: Synthetic

<400> SEQUENCE: 109

```
caggttcagc tggtgcagtc tggagctgag gtgaagaagc ctggggcctc agtgaaggtc     60
tcctgcaagg cttctggatt caccttcagt agcttttcga tgtcttggat caggcagtcc    120
ccatcgagag gccttgagtg gctgggtgaa attagtagtg gtgggagtta cacctactat    180
cctgacacta agacgggcag attcaccatc tccagagaca acgccaagaa ctcactgtat    240
ctgcaaatga acagcctgag agccgaggac acggctgtgt attactgtgc gagaggttta    300
tgggggtact atgctcttga ctactggggc caggga                              336
```

<210> SEQ ID NO 110
<211> LENGTH: 336
<212> TYPE: DNA
<213> ORGANISM: Artificial Sequence
<220> FEATURE:
<223> OTHER INFORMATION: Synthetic

<400> SEQUENCE: 110

```
caggttcagc tggtgcagtc tggagctgag gtgaagaagc ctggggcctc agtgaaggtc     60
tcctgcaagg cttctggatt caccttcagt agcttttcga tgtcttggat caggcagtcc    120
ccatcgagag gccttgagtg gctgggtgaa attagtagtg gtgggagtta cacctactat    180
cctgacactg tgacgggcag attcaccatc tccagagaca acgccaagaa ctcactgtat    240
ctgcaaatga acagcctgag agccgaggac acggctgtgt attactgtgc gagaggtcag    300
tgggggtact atgctcttga ctactggggc caggga                              336
```

<210> SEQ ID NO 111
<211> LENGTH: 336
<212> TYPE: DNA
<213> ORGANISM: Artificial Sequence
<220> FEATURE:
<223> OTHER INFORMATION: Synthetic

<400> SEQUENCE: 111

```
caggttcagc tggtgcagtc tggagctgag gtgaagaagc ctggggcctc agtgaaggtc     60
tcctgcaagg cttctggatt caccttcagt agctttgcca tgtcttggat caggcagtcc    120
ccatcgagag gccttgagtg gctgggtgaa attagtagtg gtgggagtta ccattactat    180
cctgacacta agacgggcag attcaccatc tccagagaca acgccaagaa ctcactgtat    240
ctgcaaatga acagcctgag agccgaggac acggctgtgt attactgtgc gagaggttta    300
tgggggtact atgctcttga ctactggggc caggga                              336
```

<210> SEQ ID NO 112
<211> LENGTH: 336
<212> TYPE: DNA
<213> ORGANISM: Artificial Sequence
<220> FEATURE:
<223> OTHER INFORMATION: Synthetic

<400> SEQUENCE: 112

```
caggttcagc tggtgcagtc tggagctgag gtgaagaagc ctggggcctc agtgaaggtc     60
tcctgcaagg cttctggatt caccttcagt agctttgcca tgtcttggat caggcagtcc    120
ccatcgagag gccttgagtg gctgggtgaa attagtagtg gtgggagtta ccattactat    180
```

```
cctgacactg tgacgggcag attcaccatc tccagagaca acgccaagaa ctcactgtat    240
ctgcaaatga acagcctgag agccgaggac acggctgtgt attactgtgc gagaggtcag    300
tgggggtact atgctcttga ctactggggc caggga                              336
```

<210> SEQ ID NO 113
<211> LENGTH: 336
<212> TYPE: DNA
<213> ORGANISM: Artificial Sequence
<220> FEATURE:
<223> OTHER INFORMATION: Synthetic

<400> SEQUENCE: 113

```
caggttcagc tggtgcagtc tggagctgag gtgaagaagc ctggggcctc agtgaaggtc    60
tcctgcaagg cttctggatt caccttcagt agctttgcca tgtcttggat caggcagtcc   120
ccatcgagag gccttgagtg gctgggtgaa attagtagtg gtgggagtta cacctactat   180
cctgacacta agacgggcag attcaccatc tccagagaca acgccaagaa ctcactgtat   240
ctgcaaatga acagcctgag agccgaggac acggctgtgt attactgtgc gagaggtcag   300
tgggggtact atgctcttga ctactggggc caggga                              336
```

<210> SEQ ID NO 114
<211> LENGTH: 336
<212> TYPE: DNA
<213> ORGANISM: Artificial Sequence
<220> FEATURE:
<223> OTHER INFORMATION: Synthetic

<400> SEQUENCE: 114

```
caggttcagc tggtgcagtc tggagctgag gtgaagaagc ctggggcctc agtgaaggtc    60
tcctgcaagg cttctcattt caccttcagt agcttttcga tgtcttggat caggcagtcc   120
ccatcgagag gccttgagtg gctgggtgaa attagtagtg gtgggagtta ccattactat   180
cctgacactg tgacgggcag attcaccatc tccagagaca acgccaagaa ctcactgtat   240
ctgcaaatga acagcctgag agccgaggac acggctgtgt attactgtgc gagaggttta   300
tgggggtact atgctcttga ctactggggc caggga                              336
```

<210> SEQ ID NO 115
<211> LENGTH: 336
<212> TYPE: DNA
<213> ORGANISM: Artificial Sequence
<220> FEATURE:
<223> OTHER INFORMATION: Synthetic

<400> SEQUENCE: 115

```
caggttcagc tggtgcagtc tggagctgag gtgaagaagc ctggggcctc agtgaaggtc    60
tcctgcaagg cttctcattt caccttcagt agcttttcga tgtcttggat caggcagtcc   120
ccatcgagag gccttgagtg gctgggtgaa attagtagtg gtgggagtta cacctactat   180
cctgacacta agacgggcag attcaccatc tccagagaca acgccaagaa ctcactgtat   240
ctgcaaatga acagcctgag agccgaggac acggctgtgt attactgtgc gagaggttta   300
tgggggtact atgctcttga ctactggggc caggga                              336
```

<210> SEQ ID NO 116
<211> LENGTH: 336
<212> TYPE: DNA
<213> ORGANISM: Artificial Sequence
<220> FEATURE:
<223> OTHER INFORMATION: Synthetic

<400> SEQUENCE: 116

```
caggttcagc tggtgcagtc tggagctgag gtgaagaagc ctggggcctc agtgaaggtc      60
tcctgcaagg cttctcattt caccttcagt agcttttcga tgtcttggat caggcagtcc     120
ccatcgagag gccttgagtg gctgggtgaa attagtagtg gtgggagtta cacctactat     180
cctgacactg tgacgggcag attcaccatc tccagagaca acgccaagaa ctcactgtat     240
ctgcaaatga acagcctgag agccgaggac acggctgtgt attactgtgc gagaggtcag     300
tgggggtact atgctcttga ctactggggc caggga                               336
```

<210> SEQ ID NO 117
<211> LENGTH: 336
<212> TYPE: DNA
<213> ORGANISM: Artificial Sequence
<220> FEATURE:
<223> OTHER INFORMATION: Synthetic

<400> SEQUENCE: 117

```
caggttcagc tggtgcagtc tggagctgag gtgaagaagc ctggggcctc agtgaaggtc      60
tcctgcaagg cttctcattt caccttcagt agctttgcca tgtcttggat caggcagtcc     120
ccatcgagag gccttgagtg gctgggtgaa attagtagtg gtgggagtta ccattactat     180
cctgacacta agacgggcag attcaccatc tccagagaca acgccaagaa ctcactgtat     240
ctgcaaatga acagcctgag agccgaggac acggctgtgt attactgtgc gagaggttta     300
tgggggtact atgctcttga ctactggggc caggga                               336
```

<210> SEQ ID NO 118
<211> LENGTH: 336
<212> TYPE: DNA
<213> ORGANISM: Artificial Sequence
<220> FEATURE:
<223> OTHER INFORMATION: Synthetic

<400> SEQUENCE: 118

```
caggttcagc tggtgcagtc tggagctgag gtgaagaagc ctggggcctc agtgaaggtc      60
tcctgcaagg cttctcattt caccttcagt agctttgcca tgtcttggat caggcagtcc     120
ccatcgagag gccttgagtg gctgggtgaa attagtagtg gtgggagtta ccattactat     180
cctgacactg tgacgggcag attcaccatc tccagagaca acgccaagaa ctcactgtat     240
ctgcaaatga acagcctgag agccgaggac acggctgtgt attactgtgc gagaggtcag     300
tgggggtact atgctcttga ctactggggc caggga                               336
```

<210> SEQ ID NO 119
<211> LENGTH: 336
<212> TYPE: DNA
<213> ORGANISM: Artificial Sequence
<220> FEATURE:
<223> OTHER INFORMATION: Synthetic

<400> SEQUENCE: 119

```
caggttcagc tggtgcagtc tggagctgag gtgaagaagc ctggggcctc agtgaaggtc      60
tcctgcaagg cttctcattt caccttcagt agctttgcca tgtcttggat caggcagtcc     120
ccatcgagag gccttgagtg gctgggtgaa attagtagtg gtgggagtta cacctactat     180
cctgacacta agacgggcag attcaccatc tccagagaca acgccaagaa ctcactgtat     240
ctgcaaatga acagcctgag agccgaggac acggctgtgt attactgtgc gagaggtcag     300
tgggggtact atgctcttga ctactggggc caggga                               336
```

<210> SEQ ID NO 120
<211> LENGTH: 336
<212> TYPE: DNA
<213> ORGANISM: Artificial Sequence
<220> FEATURE:
<223> OTHER INFORMATION: Synthetic

<400> SEQUENCE: 120
caggttcagc tggtgcagtc tggagctgag gtgaagaagc ctggggcctc agtgaaggtc      60
tcctgcaagg cttctggatt caccttcagt agcttttcga tgtcttggat caggcagtcc     120
ccatcgagag gccttgagtg gctgggtgaa attagtagtg gtgggagtta ccattactat     180
cctgacacta agacgggcag attcaccatc tccagagaca acgccaagaa ctcactgtat     240
ctgcaaatga acagcctgag agccgaggac acggctgtgt attactgtgc gagaggttta     300
tgggggtact atgctcttga ctactggggc caggga                               336

<210> SEQ ID NO 121
<211> LENGTH: 336
<212> TYPE: DNA
<213> ORGANISM: Artificial Sequence
<220> FEATURE:
<223> OTHER INFORMATION: Synthetic

<400> SEQUENCE: 121
caggttcagc tggtgcagtc tggagctgag gtgaagaagc ctggggcctc agtgaaggtc      60
tcctgcaagg cttctggatt caccttcagt agcttttcga tgtcttggat caggcagtcc     120
ccatcgagag gccttgagtg gctgggtgaa attagtagtg gtgggagtta ccattactat     180
cctgacactg tgacgggcag attcaccatc tccagagaca acgccaagaa ctcactgtat     240
ctgcaaatga acagcctgag agccgaggac acggctgtgt attactgtgc gagaggtcag     300
tgggggtact atgctcttga ctactggggc caggga                               336

<210> SEQ ID NO 122
<211> LENGTH: 336
<212> TYPE: DNA
<213> ORGANISM: Artificial Sequence
<220> FEATURE:
<223> OTHER INFORMATION: Synthetic

<400> SEQUENCE: 122
caggttcagc tggtgcagtc tggagctgag gtgaagaagc ctggggcctc agtgaaggtc      60
tcctgcaagg cttctggatt caccttcagt agcttttcga tgtcttggat caggcagtcc     120
ccatcgagag gccttgagtg gctgggtgaa attagtagtg gtgggagtta cacctactat     180
cctgacacta agacgggcag attcaccatc tccagagaca acgccaagaa ctcactgtat     240
ctgcaaatga acagcctgag agccgaggac acggctgtgt attactgtgc gagaggtcag     300
tgggggtact atgctcttga ctactggggc caggga                               336

<210> SEQ ID NO 123
<211> LENGTH: 336
<212> TYPE: DNA
<213> ORGANISM: Artificial Sequence
<220> FEATURE:
<223> OTHER INFORMATION: Synthetic

<400> SEQUENCE: 123
caggttcagc tggtgcagtc tggagctgag gtgaagaagc ctggggcctc agtgaaggtc      60
tcctgcaagg cttctggatt caccttcagt agctttgcca tgtcttggat caggcagtcc     120

```
ccatcgagag gccttgagtg gctgggtgaa attagtagtg gtgggagtta ccattactat      180
cctgacacta agacgggcag attcaccatc tccagagaca acgccaagaa ctcactgtat      240
ctgcaaatga acagcctgag agccgaggac acggctgtgt attactgtgc gagaggtcag      300
tgggggtact atgctcttga ctactggggc caggga                                336
```

<210> SEQ ID NO 124
<211> LENGTH: 336
<212> TYPE: DNA
<213> ORGANISM: Artificial Sequence
<220> FEATURE:
<223> OTHER INFORMATION: Synthetic

<400> SEQUENCE: 124

```
caggttcagc tggtgcagtc tggagctgag gtgaagaagc ctggggcctc agtgaaggtc       60
tcctgcaagg cttctcattt caccttcagt agcttttcga tgtcttggat caggcagtcc      120
ccatcgagag gccttgagtg gctgggtgaa attagtagtg gtgggagtta ccattactat      180
cctgacacta agacgggcag attcaccatc tccagagaca acgccaagaa ctcactgtat      240
ctgcaaatga acagcctgag agccgaggac acggctgtgt attactgtgc gagaggttta      300
tgggggtact atgctcttga ctactggggc caggga                                336
```

<210> SEQ ID NO 125
<211> LENGTH: 336
<212> TYPE: DNA
<213> ORGANISM: Artificial Sequence
<220> FEATURE:
<223> OTHER INFORMATION: Synthetic

<400> SEQUENCE: 125

```
caggttcagc tggtgcagtc tggagctgag gtgaagaagc ctggggcctc agtgaaggtc       60
tcctgcaagg cttctcattt caccttcagt agcttttcga tgtcttggat caggcagtcc      120
ccatcgagag gccttgagtg gctgggtgaa attagtagtg gtgggagtta ccattactat      180
cctgacactg tgacgggcag attcaccatc tccagagaca acgccaagaa ctcactgtat      240
ctgcaaatga acagcctgag agccgaggac acggctgtgt attactgtgc gagaggtcag      300
tgggggtact atgctcttga ctactggggc caggga                                336
```

<210> SEQ ID NO 126
<211> LENGTH: 336
<212> TYPE: DNA
<213> ORGANISM: Artificial Sequence
<220> FEATURE:
<223> OTHER INFORMATION: Synthetic

<400> SEQUENCE: 126

```
caggttcagc tggtgcagtc tggagctgag gtgaagaagc ctggggcctc agtgaaggtc       60
tcctgcaagg cttctcattt caccttcagt agcttttcga tgtcttggat caggcagtcc      120
ccatcgagag gccttgagtg gctgggtgaa attagtagtg gtgggagtta cacctactat      180
cctgacacta agacgggcag attcaccatc tccagagaca acgccaagaa ctcactgtat      240
ctgcaaatga acagcctgag agccgaggac acggctgtgt attactgtgc gagaggtcag      300
tgggggtact atgctcttga ctactggggc caggga                                336
```

<210> SEQ ID NO 127
<211> LENGTH: 336
<212> TYPE: DNA
<213> ORGANISM: Artificial Sequence

```
<220> FEATURE:
<223> OTHER INFORMATION: Synthetic

<400> SEQUENCE: 127
caggttcagc tggtgcagtc tggagctgag gtgaagaagc ctggggcctc agtgaaggtc    60
tcctgcaagg cttctcattt caccttcagt agctttgcca tgtcttggat caggcagtcc   120
ccatcgagag gccttgagtg gctgggtgaa attagtagtg gtgggagtta ccattactat   180
cctgacacta agacgggcag attcaccatc tccagagaca acgccaagaa ctcactgtat   240
ctgcaaatga acagcctgag agccgaggac acggctgtgt attactgtgc gagaggtcag   300
tgggggtact atgctcttga ctactggggc caggga                             336

<210> SEQ ID NO 128
<211> LENGTH: 336
<212> TYPE: DNA
<213> ORGANISM: Artificial Sequence
<220> FEATURE:
<223> OTHER INFORMATION: Synthetic

<400> SEQUENCE: 128
caggttcagc tggtgcagtc tggagctgag gtgaagaagc ctggggcctc agtgaaggtc    60
tcctgcaagg cttctggatt caccttcagt agcttttcga tgtcttggat caggcagtcc   120
ccatcgagag gccttgagtg gctgggtgaa attagtagtg gtgggagtta ccattactat   180
cctgacacta agacgggcag attcaccatc tccagagaca acgccaagaa ctcactgtat   240
ctgcaaatga acagcctgag agccgaggac acggctgtgt attactgtgc gagaggtcag   300
tgggggtact atgctcttga ctactggggc caggga                             336

<210> SEQ ID NO 129
<211> LENGTH: 336
<212> TYPE: DNA
<213> ORGANISM: Artificial Sequence
<220> FEATURE:
<223> OTHER INFORMATION: Synthetic

<400> SEQUENCE: 129
caggttcagc tggtgcagtc tggagctgag gtgaagaagc ctggggcctc agtgaaggtc    60
tcctgcaagg cttctcattt caccttcagt agcttttcga tgtcttggat caggcagtcc   120
ccatcgagag gccttgagtg gctgggtgaa attagtagtg gtgggagtta ccattactat   180
cctgacacta agacgggcag attcaccatc tccagagaca acgccaagaa ctcactgtat   240
ctgcaaatga acagcctgag agccgaggac acggctgtgt attactgtgc gagaggtcag   300
tgggggtact atgctcttga ctactggggc caggga                             336

<210> SEQ ID NO 130
<211> LENGTH: 112
<212> TYPE: PRT
<213> ORGANISM: Artificial Sequence
<220> FEATURE:
<223> OTHER INFORMATION: Synthetic

<400> SEQUENCE: 130

Gln Val Gln Leu Val Gln Ser Gly Ala Glu Val Lys Lys Pro Gly Ala
1               5                   10                  15

Ser Val Lys Val Ser Cys Lys Ala Ser His Phe Thr Phe Ser Ser Phe
            20                  25                  30

Ala Met Ser Trp Ile Arg Gln Ser Pro Ser Arg Gly Leu Glu Trp Leu
        35                  40                  45
```

```
Gly Glu Ile Ser Ser Gly Gly Ser Tyr Thr Tyr Tyr Pro Asp Thr Val
            50                  55                  60

Thr Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Arg Gly Leu Trp Gly Tyr Tyr Ala Leu Asp Tyr Trp Gly Gln Gly
               100                 105                 110
```

<210> SEQ ID NO 131
<211> LENGTH: 112
<212> TYPE: PRT
<213> ORGANISM: Artificial Sequence
<220> FEATURE:
<223> OTHER INFORMATION: Synthetic

<400> SEQUENCE: 131

```
Gln Val Gln Leu Val Gln Ser Gly Ala Glu Val Lys Lys Pro Gly Ala
  1               5                  10                  15

Ser Val Lys Val Ser Cys Lys Ala Ser Gly Phe Thr Phe Ser Ser Phe
                 20                  25                  30

Ser Met Ser Trp Ile Arg Gln Ser Pro Ser Arg Gly Leu Glu Trp Leu
            35                  40                  45

Gly Glu Ile Ser Ser Gly Gly Ser Tyr Thr Tyr Tyr Pro Asp Thr Val
            50                  55                  60

Thr Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Arg Gly Leu Trp Gly Tyr Tyr Ala Leu Asp Tyr Trp Gly Gln Gly
               100                 105                 110
```

<210> SEQ ID NO 132
<211> LENGTH: 112
<212> TYPE: PRT
<213> ORGANISM: Artificial Sequence
<220> FEATURE:
<223> OTHER INFORMATION: Synthetic

<400> SEQUENCE: 132

```
Gln Val Gln Leu Val Gln Ser Gly Ala Glu Val Lys Lys Pro Gly Ala
  1               5                  10                  15

Ser Val Lys Val Ser Cys Lys Ala Ser Gly Phe Thr Phe Ser Ser Phe
                 20                  25                  30

Ala Met Ser Trp Ile Arg Gln Ser Pro Ser Arg Gly Leu Glu Trp Leu
            35                  40                  45

Gly Glu Ile Ser Ser Gly Gly Ser Tyr His Tyr Tyr Pro Asp Thr Val
            50                  55                  60

Thr Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Arg Gly Leu Trp Gly Tyr Tyr Ala Leu Asp Tyr Trp Gly Gln Gly
               100                 105                 110
```

<210> SEQ ID NO 133
<211> LENGTH: 112
<212> TYPE: PRT
<213> ORGANISM: Artificial Sequence
<220> FEATURE:

<223> OTHER INFORMATION: Synthetic

<400> SEQUENCE: 133

Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Ser Ser Phe
            20                  25                  30

Ala Met Ser Trp Ile Arg Gln Ser Pro Ser Arg Gly Leu Glu Trp Leu
        35                  40                  45

Gly Glu Ile Ser Ser Gly Gly Ser Tyr Thr Tyr Tyr Pro Asp Thr Lys
    50                  55                  60

Thr Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Trp Gly Tyr Tyr Ala Leu Asp Tyr Trp Gly Gln Gly
            100                 105                 110

<210> SEQ ID NO 134
<211> LENGTH: 112
<212> TYPE: PRT
<213> ORGANISM: Artificial Sequence
<220> FEATURE:
<223> OTHER INFORMATION: Synthetic

<400> SEQUENCE: 134

Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Ser Ser Phe
            20                  25                  30

Ala Met Ser Trp Ile Arg Gln Ser Pro Ser Arg Gly Leu Glu Trp Leu
        35                  40                  45

Gly Glu Ile Ser Ser Gly Gly Ser Tyr Thr Tyr Tyr Pro Asp Thr Val
    50                  55                  60

Thr Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gln Trp Gly Tyr Tyr Ala Leu Asp Tyr Trp Gly Gln Gly
            100                 105                 110

<210> SEQ ID NO 135
<211> LENGTH: 112
<212> TYPE: PRT
<213> ORGANISM: Artificial Sequence
<220> FEATURE:
<223> OTHER INFORMATION: Synthetic

<400> SEQUENCE: 135

Gln Val Gln Leu Val Gln Ser Gly Ala Glu Val Lys Lys Pro Gly Ala
1               5                   10                  15

Ser Val Lys Val Ser Cys Lys Ala Ser His Phe Thr Phe Ser Ser Phe
            20                  25                  30

Ser Met Ser Trp Ile Arg Gln Ser Pro Ser Arg Gly Leu Glu Trp Leu
        35                  40                  45

Gly Glu Ile Ser Ser Gly Gly Ser Tyr Thr Tyr Tyr Pro Asp Thr Val
    50                  55                  60

Thr Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Trp Gly Tyr Tyr Ala Leu Asp Tyr Trp Gly Gln Gly
            100                 105                 110

<210> SEQ ID NO 136
<211> LENGTH: 112
<212> TYPE: PRT
<213> ORGANISM: Artificial Sequence
<220> FEATURE:
<223> OTHER INFORMATION: Synthetic

<400> SEQUENCE: 136

Gln Val Gln Leu Val Gln Ser Gly Ala Glu Val Lys Lys Pro Gly Ala
1               5                   10                  15

Ser Val Lys Val Ser Cys Lys Ala Ser His Phe Thr Phe Ser Ser Phe
            20                  25                  30

Ala Met Ser Trp Ile Arg Gln Ser Pro Ser Arg Gly Leu Glu Trp Leu
        35                  40                  45

Gly Glu Ile Ser Ser Gly Gly Ser Tyr His Tyr Tyr Pro Asp Thr Val
    50                  55                  60

Thr Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Trp Gly Tyr Tyr Ala Leu Asp Tyr Trp Gly Gln Gly
            100                 105                 110

<210> SEQ ID NO 137
<211> LENGTH: 112
<212> TYPE: PRT
<213> ORGANISM: Artificial Sequence
<220> FEATURE:
<223> OTHER INFORMATION: Synthetic

<400> SEQUENCE: 137

Gln Val Gln Leu Val Gln Ser Gly Ala Glu Val Lys Lys Pro Gly Ala
1               5                   10                  15

Ser Val Lys Val Ser Cys Lys Ala Ser His Phe Thr Phe Ser Ser Phe
            20                  25                  30

Ala Met Ser Trp Ile Arg Gln Ser Pro Ser Arg Gly Leu Glu Trp Leu
        35                  40                  45

Gly Glu Ile Ser Ser Gly Gly Ser Tyr Thr Tyr Tyr Pro Asp Thr Lys
    50                  55                  60

Thr Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Trp Gly Tyr Tyr Ala Leu Asp Tyr Trp Gly Gln Gly
            100                 105                 110

<210> SEQ ID NO 138
<211> LENGTH: 112
<212> TYPE: PRT
<213> ORGANISM: Artificial Sequence
<220> FEATURE:
<223> OTHER INFORMATION: Synthetic

<400> SEQUENCE: 138

Gln Val Gln Leu Val Gln Ser Gly Ala Glu Val Lys Lys Pro Gly Ala

```
            1               5                   10                  15
Ser Val Lys Val Ser Cys Lys Ala Ser His Phe Thr Phe Ser Ser Phe
                20                  25                  30

Ala Met Ser Trp Ile Arg Gln Ser Pro Ser Arg Gly Leu Glu Trp Leu
                35                  40                  45

Gly Glu Ile Ser Ser Gly Gly Ser Tyr Thr Tyr Tyr Pro Asp Thr Val
        50                  55                  60

Thr Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gln Trp Gly Tyr Tyr Ala Leu Asp Tyr Trp Gly Gln Gly
                100                 105                 110

<210> SEQ ID NO 139
<211> LENGTH: 112
<212> TYPE: PRT
<213> ORGANISM: Artificial Sequence
<220> FEATURE:
<223> OTHER INFORMATION: Synthetic

<400> SEQUENCE: 139

Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Ser Ser Phe
                20                  25                  30

Ser Met Ser Trp Ile Arg Gln Ser Pro Ser Arg Gly Leu Glu Trp Leu
                35                  40                  45

Gly Glu Ile Ser Ser Gly Gly Ser Tyr His Tyr Tyr Pro Asp Thr Val
        50                  55                  60

Thr Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Trp Gly Tyr Tyr Ala Leu Asp Tyr Trp Gly Gln Gly
                100                 105                 110

<210> SEQ ID NO 140
<211> LENGTH: 112
<212> TYPE: PRT
<213> ORGANISM: Artificial Sequence
<220> FEATURE:
<223> OTHER INFORMATION: Synthetic

<400> SEQUENCE: 140

Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Ser Ser Phe
                20                  25                  30

Ser Met Ser Trp Ile Arg Gln Ser Pro Ser Arg Gly Leu Glu Trp Leu
                35                  40                  45

Gly Glu Ile Ser Ser Gly Gly Ser Tyr Thr Tyr Tyr Pro Asp Thr Lys
        50                  55                  60

Thr Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Trp Gly Tyr Tyr Ala Leu Asp Tyr Trp Gly Gln Gly
```

100           105           110

<210> SEQ ID NO 141
<211> LENGTH: 112
<212> TYPE: PRT
<213> ORGANISM: Artificial Sequence
<220> FEATURE:
<223> OTHER INFORMATION: Synthetic

<400> SEQUENCE: 141

Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Ser Ser Phe
            20                  25                  30

Ser Met Ser Trp Ile Arg Gln Ser Pro Ser Arg Gly Leu Glu Trp Leu
        35                  40                  45

Gly Glu Ile Ser Ser Gly Gly Ser Tyr Thr Tyr Tyr Pro Asp Thr Val
    50                  55                  60

Thr Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gln Trp Gly Tyr Tyr Ala Leu Asp Tyr Trp Gly Gln Gly
            100                 105                 110

<210> SEQ ID NO 142
<211> LENGTH: 112
<212> TYPE: PRT
<213> ORGANISM: Artificial Sequence
<220> FEATURE:
<223> OTHER INFORMATION: Synthetic

<400> SEQUENCE: 142

Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Ser Ser Phe
            20                  25                  30

Ala Met Ser Trp Ile Arg Gln Ser Pro Ser Arg Gly Leu Glu Trp Leu
        35                  40                  45

Gly Glu Ile Ser Ser Gly Gly Ser Tyr His Tyr Tyr Pro Asp Thr Lys
    50                  55                  60

Thr Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Trp Gly Tyr Tyr Ala Leu Asp Tyr Trp Gly Gln Gly
            100                 105                 110

<210> SEQ ID NO 143
<211> LENGTH: 112
<212> TYPE: PRT
<213> ORGANISM: Artificial Sequence
<220> FEATURE:
<223> OTHER INFORMATION: Synthetic

<400> SEQUENCE: 143

Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Ser Ser Phe
            20                  25                  30

```
Ala Met Ser Trp Ile Arg Gln Ser Pro Ser Arg Gly Leu Glu Trp Leu
        35                  40                  45

Gly Glu Ile Ser Ser Gly Gly Ser Tyr His Tyr Tyr Pro Asp Thr Val
    50                  55                  60

Thr Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gln Trp Gly Tyr Tyr Ala Leu Asp Tyr Trp Gly Gln Gly
            100                 105                 110

<210> SEQ ID NO 144
<211> LENGTH: 112
<212> TYPE: PRT
<213> ORGANISM: Artificial Sequence
<220> FEATURE:
<223> OTHER INFORMATION: Synthetic

<400> SEQUENCE: 144

Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Ser Ser Phe
            20                  25                  30

Ala Met Ser Trp Ile Arg Gln Ser Pro Ser Arg Gly Leu Glu Trp Leu
        35                  40                  45

Gly Glu Ile Ser Ser Gly Gly Ser Tyr Thr Tyr Tyr Pro Asp Thr Lys
    50                  55                  60

Thr Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gln Trp Gly Tyr Tyr Ala Leu Asp Tyr Trp Gly Gln Gly
            100                 105                 110

<210> SEQ ID NO 145
<211> LENGTH: 112
<212> TYPE: PRT
<213> ORGANISM: Artificial Sequence
<220> FEATURE:
<223> OTHER INFORMATION: Synthetic

<400> SEQUENCE: 145

Gln Val Gln Leu Val Gln Ser Gly Ala Glu Val Lys Lys Pro Gly Ala
1               5                   10                  15

Ser Val Lys Val Ser Cys Lys Ala Ser His Phe Thr Phe Ser Ser Phe
            20                  25                  30

Ser Met Ser Trp Ile Arg Gln Ser Pro Ser Arg Gly Leu Glu Trp Leu
        35                  40                  45

Gly Glu Ile Ser Ser Gly Gly Ser Tyr His Tyr Tyr Pro Asp Thr Val
    50                  55                  60

Thr Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Trp Gly Tyr Tyr Ala Leu Asp Tyr Trp Gly Gln Gly
            100                 105                 110

<210> SEQ ID NO 146
<211> LENGTH: 112
```

<212> TYPE: PRT
<213> ORGANISM: Artificial Sequence
<220> FEATURE:
<223> OTHER INFORMATION: Synthetic

<400> SEQUENCE: 146

```
Gln Val Gln Leu Val Gln Ser Gly Ala Glu Val Lys Lys Pro Gly Ala
1               5                   10                  15
Ser Val Lys Val Ser Cys Lys Ala Ser His Phe Thr Phe Ser Ser Phe
            20                  25                  30
Ser Met Ser Trp Ile Arg Gln Ser Pro Ser Arg Gly Leu Glu Trp Leu
        35                  40                  45
Gly Glu Ile Ser Ser Gly Gly Ser Tyr Thr Tyr Tyr Pro Asp Thr Lys
    50                  55                  60
Thr Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Val Tyr Tyr Cys
                85                  90                  95
Ala Arg Gly Leu Trp Gly Tyr Tyr Ala Leu Asp Tyr Trp Gly Gln Gly
            100                 105                 110
```

<210> SEQ ID NO 147
<211> LENGTH: 112
<212> TYPE: PRT
<213> ORGANISM: Artificial Sequence
<220> FEATURE:
<223> OTHER INFORMATION: Synthetic

<400> SEQUENCE: 147

```
Gln Val Gln Leu Val Gln Ser Gly Ala Glu Val Lys Lys Pro Gly Ala
1               5                   10                  15
Ser Val Lys Val Ser Cys Lys Ala Ser His Phe Thr Phe Ser Ser Phe
            20                  25                  30
Ser Met Ser Trp Ile Arg Gln Ser Pro Ser Arg Gly Leu Glu Trp Leu
        35                  40                  45
Gly Glu Ile Ser Ser Gly Gly Ser Tyr Thr Tyr Tyr Pro Asp Thr Val
    50                  55                  60
Thr Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Val Tyr Tyr Cys
                85                  90                  95
Ala Arg Gly Gln Trp Gly Tyr Tyr Ala Leu Asp Tyr Trp Gly Gln Gly
            100                 105                 110
```

<210> SEQ ID NO 148
<211> LENGTH: 112
<212> TYPE: PRT
<213> ORGANISM: Artificial Sequence
<220> FEATURE:
<223> OTHER INFORMATION: Synthetic

<400> SEQUENCE: 148

```
Gln Val Gln Leu Val Gln Ser Gly Ala Glu Val Lys Lys Pro Gly Ala
1               5                   10                  15
Ser Val Lys Val Ser Cys Lys Ala Ser His Phe Thr Phe Ser Ser Phe
            20                  25                  30
Ala Met Ser Trp Ile Arg Gln Ser Pro Ser Arg Gly Leu Glu Trp Leu
        35                  40                  45
Gly Glu Ile Ser Ser Gly Gly Ser Tyr His Tyr Tyr Pro Asp Thr Lys
    50                  55                  60
```

-continued

Thr Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Trp Gly Tyr Tyr Ala Leu Asp Tyr Trp Gly Gln Gly
            100                 105                 110

<210> SEQ ID NO 149
<211> LENGTH: 112
<212> TYPE: PRT
<213> ORGANISM: Artificial Sequence
<220> FEATURE:
<223> OTHER INFORMATION: Synthetic

<400> SEQUENCE: 149

Gln Val Gln Leu Val Gln Ser Gly Ala Glu Val Lys Lys Pro Gly Ala
1               5                   10                  15

Ser Val Lys Val Ser Cys Lys Ala Ser His Phe Thr Phe Ser Ser Phe
            20                  25                  30

Ala Met Ser Trp Ile Arg Gln Ser Pro Ser Arg Gly Leu Glu Trp Leu
        35                  40                  45

Gly Glu Ile Ser Ser Gly Gly Ser Tyr His Tyr Tyr Pro Asp Thr Val
    50                  55                  60

Thr Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gln Trp Gly Tyr Tyr Ala Leu Asp Tyr Trp Gly Gln Gly
            100                 105                 110

<210> SEQ ID NO 150
<211> LENGTH: 112
<212> TYPE: PRT
<213> ORGANISM: Artificial Sequence
<220> FEATURE:
<223> OTHER INFORMATION: Synthetic

<400> SEQUENCE: 150

Gln Val Gln Leu Val Gln Ser Gly Ala Glu Val Lys Lys Pro Gly Ala
1               5                   10                  15

Ser Val Lys Val Ser Cys Lys Ala Ser His Phe Thr Phe Ser Ser Phe
            20                  25                  30

Ala Met Ser Trp Ile Arg Gln Ser Pro Ser Arg Gly Leu Glu Trp Leu
        35                  40                  45

Gly Glu Ile Ser Ser Gly Gly Ser Tyr Thr Tyr Tyr Pro Asp Thr Lys
    50                  55                  60

Thr Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gln Trp Gly Tyr Tyr Ala Leu Asp Tyr Trp Gly Gln Gly
            100                 105                 110

<210> SEQ ID NO 151
<211> LENGTH: 112
<212> TYPE: PRT
<213> ORGANISM: Artificial Sequence
<220> FEATURE:
<223> OTHER INFORMATION: Synthetic

<400> SEQUENCE: 151

```
Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Ser Ser Phe
            20                  25                  30

Ser Met Ser Trp Ile Arg Gln Ser Pro Ser Arg Gly Leu Glu Trp Leu
        35                  40                  45

Gly Glu Ile Ser Ser Gly Gly Ser Tyr His Tyr Tyr Pro Asp Thr Lys
    50                  55                  60

Thr Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Trp Gly Tyr Tyr Ala Leu Asp Tyr Trp Gly Gln Gly
            100                 105                 110
```

<210> SEQ ID NO 152
<211> LENGTH: 112
<212> TYPE: PRT
<213> ORGANISM: Artificial Sequence
<220> FEATURE:
<223> OTHER INFORMATION: Synthetic

<400> SEQUENCE: 152

```
Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Ser Ser Phe
            20                  25                  30

Ser Met Ser Trp Ile Arg Gln Ser Pro Ser Arg Gly Leu Glu Trp Leu
        35                  40                  45

Gly Glu Ile Ser Ser Gly Gly Ser Tyr His Tyr Tyr Pro Asp Thr Val
    50                  55                  60

Thr Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gln Trp Gly Tyr Tyr Ala Leu Asp Tyr Trp Gly Gln Gly
            100                 105                 110
```

<210> SEQ ID NO 153
<211> LENGTH: 112
<212> TYPE: PRT
<213> ORGANISM: Artificial Sequence
<220> FEATURE:
<223> OTHER INFORMATION: Synthetic

<400> SEQUENCE: 153

```
Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Ser Ser Phe
            20                  25                  30

Ser Met Ser Trp Ile Arg Gln Ser Pro Ser Arg Gly Leu Glu Trp Leu
        35                  40                  45

Gly Glu Ile Ser Ser Gly Gly Ser Tyr Thr Tyr Tyr Pro Asp Thr Lys
    50                  55                  60

Thr Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
```

Ala Arg Gly Gln Trp Gly Tyr Tyr Ala Leu Asp Tyr Trp Gln Gly
            100                 105                 110

<210> SEQ ID NO 154
<211> LENGTH: 112
<212> TYPE: PRT
<213> ORGANISM: Artificial Sequence
<220> FEATURE:
<223> OTHER INFORMATION: Synthetic

<400> SEQUENCE: 154

Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Ser Ser Phe
                20                  25                  30

Ala Met Ser Trp Ile Arg Gln Ser Pro Ser Arg Gly Leu Glu Trp Leu
            35                  40                  45

Gly Glu Ile Ser Ser Gly Gly Ser Tyr His Tyr Tyr Pro Asp Thr Lys
        50                  55                  60

Thr Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gln Trp Gly Tyr Tyr Ala Leu Asp Tyr Trp Gly Gln Gly
            100                 105                 110

<210> SEQ ID NO 155
<211> LENGTH: 112
<212> TYPE: PRT
<213> ORGANISM: Artificial Sequence
<220> FEATURE:
<223> OTHER INFORMATION: Synthetic

<400> SEQUENCE: 155

Gln Val Gln Leu Val Gln Ser Gly Ala Glu Val Lys Lys Pro Gly Ala
1               5                   10                  15

Ser Val Lys Val Ser Cys Lys Ala Ser His Phe Thr Phe Ser Ser Phe
                20                  25                  30

Ser Met Ser Trp Ile Arg Gln Ser Pro Ser Arg Gly Leu Glu Trp Leu
            35                  40                  45

Gly Glu Ile Ser Ser Gly Gly Ser Tyr His Tyr Tyr Pro Asp Thr Lys
        50                  55                  60

Thr Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Trp Gly Tyr Tyr Ala Leu Asp Tyr Trp Gly Gln Gly
            100                 105                 110

<210> SEQ ID NO 156
<211> LENGTH: 112
<212> TYPE: PRT
<213> ORGANISM: Artificial Sequence
<220> FEATURE:
<223> OTHER INFORMATION: Synthetic

<400> SEQUENCE: 156

Gln Val Gln Leu Val Gln Ser Gly Ala Glu Val Lys Lys Pro Gly Ala
1               5                   10                  15

```
Ser Val Lys Val Ser Cys Lys Ala Ser His Phe Thr Phe Ser Ser Phe
                20                  25                  30

Ser Met Ser Trp Ile Arg Gln Ser Pro Ser Arg Gly Leu Glu Trp Leu
            35                  40                  45

Gly Glu Ile Ser Ser Gly Gly Ser Tyr His Tyr Tyr Pro Asp Thr Val
        50                  55                  60

Thr Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gln Trp Gly Tyr Tyr Ala Leu Asp Tyr Trp Gly Gln Gly
            100                 105                 110
```

<210> SEQ ID NO 157
<211> LENGTH: 112
<212> TYPE: PRT
<213> ORGANISM: Artificial Sequence
<220> FEATURE:
<223> OTHER INFORMATION: Synthetic

<400> SEQUENCE: 157

```
Gln Val Gln Leu Val Gln Ser Gly Ala Glu Val Lys Lys Pro Gly Ala
1               5                   10                  15

Ser Val Lys Val Ser Cys Lys Ala Ser His Phe Thr Phe Ser Ser Phe
                20                  25                  30

Ser Met Ser Trp Ile Arg Gln Ser Pro Ser Arg Gly Leu Glu Trp Leu
            35                  40                  45

Gly Glu Ile Ser Ser Gly Gly Ser Tyr Thr Tyr Tyr Pro Asp Thr Lys
        50                  55                  60

Thr Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gln Trp Gly Tyr Tyr Ala Leu Asp Tyr Trp Gly Gln Gly
            100                 105                 110
```

<210> SEQ ID NO 158
<211> LENGTH: 112
<212> TYPE: PRT
<213> ORGANISM: Artificial Sequence
<220> FEATURE:
<223> OTHER INFORMATION: Synthetic

<400> SEQUENCE: 158

```
Gln Val Gln Leu Val Gln Ser Gly Ala Glu Val Lys Lys Pro Gly Ala
1               5                   10                  15

Ser Val Lys Val Ser Cys Lys Ala Ser His Phe Thr Phe Ser Ser Phe
                20                  25                  30

Ala Met Ser Trp Ile Arg Gln Ser Pro Ser Arg Gly Leu Glu Trp Leu
            35                  40                  45

Gly Glu Ile Ser Ser Gly Gly Ser Tyr His Tyr Tyr Pro Asp Thr Lys
        50                  55                  60

Thr Gly Arg Phe Thr Ile Ser Arg Asp Asn Ala Lys Asn Ser Leu Tyr
65                  70                  75                  80
```

Leu Gln Met Asn Ser Leu Arg Ala Glu Asp Thr Ala Val Tyr Tyr Cys
                85                  90                  95

Ala Arg Gly Gln Trp Gly Tyr Tyr Ala Leu Asp Tyr Trp Gly Gln Gly
            100                 105                 110

<210> SEQ ID NO 159
<211> LENGTH: 112
<212> TYPE: PRT
<213> ORGANISM: Artificial Sequence
<220> FEATURE:
<223> OTHER INFORMATION: Synthetic

<400> SEQUENCE: 159

Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Ser Ser Phe
            20                  25                  30

Ser Met Ser Trp Ile Arg Gln Ser Pro Ser Arg Gly Leu Glu Trp Leu
        35                  40                  45

Gly Glu Ile Ser Ser Gly Gly Ser Tyr His Tyr Tyr Pro Asp Thr Lys
    50                  55                  60

Thr Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gln Trp Gly Tyr Tyr Ala Leu Asp Tyr Trp Gly Gln Gly
            100                 105                 110

<210> SEQ ID NO 160
<211> LENGTH: 112
<212> TYPE: PRT
<213> ORGANISM: Artificial Sequence
<220> FEATURE:
<223> OTHER INFORMATION: Synthetic

<400> SEQUENCE: 160

Gln Val Gln Leu Val Gln Ser Gly Ala Glu Val Lys Lys Pro Gly Ala
1               5                   10                  15

Ser Val Lys Val Ser Cys Lys Ala Ser His Phe Thr Phe Ser Ser Phe
            20                  25                  30

Ser Met Ser Trp Ile Arg Gln Ser Pro Ser Arg Gly Leu Glu Trp Leu
        35                  40                  45

Gly Glu Ile Ser Ser Gly Gly Ser Tyr His Tyr Tyr Pro Asp Thr Lys
    50                  55                  60

Thr Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gln Trp Gly Tyr Tyr Ala Leu Asp Tyr Trp Gly Gln Gly
            100                 105                 110